United States Patent
Wohlfahrt et al.

(10) Patent No.: US 10,118,933 B2
(45) Date of Patent: Nov. 6, 2018

(54) ANDROGEN RECEPTOR MODULATING COMPOUNDS

(71) Applicant: ORION CORPORATION, Espoo (FI)

(72) Inventors: Gerd Wohlfahrt, Helsinki (FI); Olli Törmäkangas, Turku (FI); Harri Salo, Turku (FI); Iisa Höglund, Turku (FI); Arja Karjalainen, Espoo (FI); Pia Koivikko, Littoinen (FI); Patrik Holm, Lielahti TL (FI); Sirpa Rasku, Vantaa (FI); Anniina Vesalainen, Paimio (FI)

(73) Assignee: ORION CORPORATION, Espoo (FI)

(*) Notice: Subject to any disclaimer, the term of this patent is extended or adjusted under 35 U.S.C. 154(b) by 0 days.

(21) Appl. No.: 15/486,995

(22) Filed: Apr. 13, 2017

(65) Prior Publication Data

US 2017/0260206 A1 Sep. 14, 2017

Related U.S. Application Data

(63) Continuation of application No. 14/598,973, filed on Jan. 16, 2015, now Pat. No. 9,657,003, which is a continuation of application No. 13/504,511, filed as application No. PCT/FI2010/000065 on Oct. 27, 2010, now Pat. No. 8,975,254.

(60) Provisional application No. 61/255,159, filed on Oct. 27, 2009.

(51) Int. Cl.
| | |
|---|---|
| C07D 513/04 | (2006.01) |
| C07D 405/12 | (2006.01) |
| C07D 405/14 | (2006.01) |
| C07D 401/14 | (2006.01) |
| C07D 231/14 | (2006.01) |
| C07D 403/12 | (2006.01) |
| C07D 413/14 | (2006.01) |
| C07D 487/04 | (2006.01) |
| C07D 417/12 | (2006.01) |
| C07D 498/04 | (2006.01) |
| C07D 231/12 | (2006.01) |
| C07D 401/12 | (2006.01) |
| C07D 413/12 | (2006.01) |
| C07D 409/14 | (2006.01) |
| C07D 417/14 | (2006.01) |
| C07D 471/04 | (2006.01) |

(52) U.S. Cl.
CPC ......... *C07D 513/04* (2013.01); *C07D 231/12* (2013.01); *C07D 231/14* (2013.01); *C07D 401/12* (2013.01); *C07D 401/14* (2013.01); *C07D 403/12* (2013.01); *C07D 405/12* (2013.01); *C07D 405/14* (2013.01); *C07D 409/14* (2013.01); *C07D 413/12* (2013.01); *C07D 413/14* (2013.01); *C07D 417/12* (2013.01); *C07D 417/14* (2013.01); *C07D 471/04* (2013.01); *C07D 487/04* (2013.01); *C07D 498/04* (2013.01)

(58) Field of Classification Search
None
See application file for complete search history.

(56) References Cited

U.S. PATENT DOCUMENTS

| | | |
|---|---|---|
| 6,087,509 A | 7/2000 | Claussner et al. |
| 6,673,799 B1 | 1/2004 | Taniguchi et al. |
| 7,271,188 B2 | 9/2007 | Tachibana et al. |

FOREIGN PATENT DOCUMENTS

| | | |
|---|---|---|
| EP | 0 100 172 A1 | 2/1984 |
| EP | 1 790 640 A1 | 5/2007 |
| WO | WO 2003/057669 A1 | 7/2003 |
| WO | WO 2003/073999 | 9/2003 |
| WO | WO 2004/099188 A1 | 11/2004 |
| WO | WO 2006/124118 A1 | 11/2006 |
| WO | WO 2006/133567 A1 | 12/2006 |
| WO | WO 2007/005887 | 1/2007 |
| WO | WO 2007/029035 | 3/2007 |
| WO | WO 2007/056155 | 5/2007 |
| WO | WO 2008/062878 | 5/2008 |
| WO | WO 2008/124000 | 10/2008 |
| WO | WO 2009/006404 | 1/2009 |
| WO | WO 2009/028543 A1 | 3/2009 |
| WO | WO 2009/055053 A2 | 4/2009 |
| WO | WO 2009/119880 A1 | 10/2009 |

(Continued)

OTHER PUBLICATIONS

Benckova, M., et al.; "Disubstituted Ureas of the 5-R-2-Furylethylene Type"; Chemical Papers, 50(3); pp. 148-150; Jan. 1, 1996.

(Continued)

*Primary Examiner* — Kamal A Saeed
(74) *Attorney, Agent, or Firm* — Finnegan, Henderson, Farabow, Garrett & Dunner, LLP

(57) ABSTRACT

The present disclosure relates to compounds of formula (I), and pharmaceutically acceptable salts thereof. The present disclosure also relates to compositions and methods of treating comprising compounds of formula (I), and pharmaceutically acceptable salts thereof.

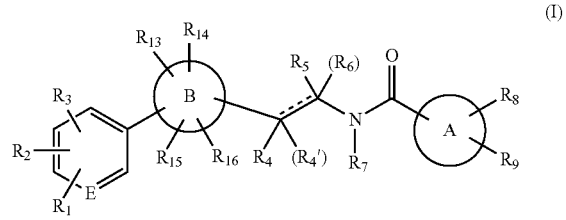

3 Claims, No Drawings

(56) References Cited

FOREIGN PATENT DOCUMENTS

WO    WO 2009/153721    12/2009

OTHER PUBLICATIONS

Database Registry; Chemical Abstracts Service; "1-cycloheptyl-N-[2-[3-(2-methylphenyl)-1-pyrrolidlnyl]ethyl]-1H-1,2,3-Triazole-4-carboxamide"; XP002623902; Nov. 2, 2008.
Database Registry; Chemical Abstracts Service; "N-[2-(2,5-dimethyl-1-phenyl-1H-pyrrol-3-yl)ethyl]-4-phenyl-1-piperazinecarboxamide"; XP002623901; Mar. 2, 2007.
Database Registry; Chemical Abstracts Service; "N-[2-[5-(2-nitrophenyl)-2-furanyl]ethenyl]-4-morpholinecarboxamide"; XP002623903; Aug. 28, 2001.
English abstract of WO 2008/062878, Basic Derwent, Week: 200867, (2012).
International Search Report for International Application No. PCT/FI2010/000065, dated Mar. 17, 2011.
Narayanan, R., et al.; "Selective Androgen Receptor Modulators in Preclinical and Clinical Development"; Nuclear Receptor Signalling, 6, pp. 1-26, (2008).
Office Action from U.S. Appl. No. 13/504,511 dated Nov. 27, 2013.
Office Action from U.S. Appl. No. 13/504,511 dated Jul. 3, 2014.
Notice of Allowance of U.S. Appl. No. 13/504,511 dated Oct. 21, 2014.
Office Action from U.S. Appl. No. 14/598,973 dated Jun. 30, 2016.
Notice of Allowance of U.S. Appl. No. 14/598,973 dated Jan. 18, 2017.

ANDROGEN RECEPTOR MODULATING COMPOUNDS

This is a continuation of pending application Ser. No. 14/598,973, filed Jan. 16, 2015, which is a continuation of prior application Ser. No. 13/504,511, filed Apr. 27, 2012, and issued Mar. 10, 2015, as U.S. Pat. No. 8,975,254, which is a national stage filing under 35 U.S.C. § 371 of International Application No. PCT/FI2010/000065, filed Oct. 27, 2010, which claims the benefit of priority to U.S. Provisional Application No. 61/255,159, filed Oct. 27, 2009, all of which are incorporated herein by reference.

TECHNICAL FIELD

The present invention relates to therapeutically active compounds and pharmaceutically acceptable salts and esters thereof useful in the treatment of nuclear receptor, especially steroid receptor, and in particular androgen receptor (AR) dependent conditions and diseases, and to pharmaceutical compositions containing such compounds. In particular, the invention discloses non-steroidal carboxamide and acyl hydrazone structured compounds having utility as tissue-selective androgen receptor modulators (SARM). The compounds of the invention, which possess AR antagonist activity, are useful for treating patients requiring androgen receptor antagonist therapy. In particular, AR antagonists of the invention are useful in the treatment or prevention of cancer, particularly AR dependent cancer such as prostate cancer, and other diseases where AR antagonism is desired.

BACKGROUND OF THE INVENTION

In recent years, there has been growing interest in the development of nonsteroidal modulators for steroid receptors for therapeutical use. It has been shown that nonsteroidal ligands can achieve better receptor selectivity and better physicochemical, pharmacokinetic and pharmacological properties. For androgen receptor (AR), nonsteroidal antagonists (antiandrogens) are now used clinically to counteract the undesirable actions of excessive androgens.

Androgens, functioning through the AR, are essential for the initiation and progression of prostate cancer. Thus, treatment of advanced prostate cancer involves androgen-ablation therapies, such as surgical castration or hormonal manipulation using gonadotropin-releasing hormone (GnRH) agonists, anti-androgens or both. Although such therapies initially lead to disease regression, eventually all patients progress to a castration resistant late stage that is refractory to current therapies. Castration-resistant prostate cancer (CRPC) is associated with increased levels of AR. First generation anti-androgens such as bicalutamide display agonistic properties in cells engineered to express higher AR levels. In vitro and in vivo, increased AR expression has been shown to confer resistance of prostate cancer cell lines to anti-androgen therapy. To overcome resistance problems, second generation anti-androgens that retain antagonism in cells expressing excess AR may have utility in the treatment of CRPC.

Non-steroidal androgen receptor antagonists have been described earlier e.g. in patent publications EP 100172, EP 1790640, U.S. Pat. No. 6,087,509, U.S. Pat. No. 6,673,799, U.S. Pat. No. 7,271,188, WO 03/057669, WO 2004/099188, WO 2006/133567, WO 2008/124000, WO 2009/028543 and WO 2009/055053.

Related carboxamide structured compounds have been described in WO 2008/062878.

SUMMARY OF THE INVENTION

It has been found that compounds of formula (I) or (I') are potent androgen receptor (AR) modulators, in particular AR antagonists. Compounds of formula (I) or (I') show remarkably high affinity and strong antagonistic activity in androgen receptor. Also in cells which overexpress AR ("AR overexpressing cells") the compounds of the invention possess from high to full AR antagonism while exhibiting only minimal agonism. The compounds of the invention also effectively inhibited proliferation of prostatic cancer cell line. Moreover, the compounds of the invention have low potential for drug-drug interactions, favourable safety profile and sufficient water solubility.

The compounds of the invention are therefore particularly useful as medicaments in the treatment of prostate cancer and other AR dependent conditions and diseases where AR antagonism is desired.

The present invention provides novel carboxamide structured compounds of formula (I)

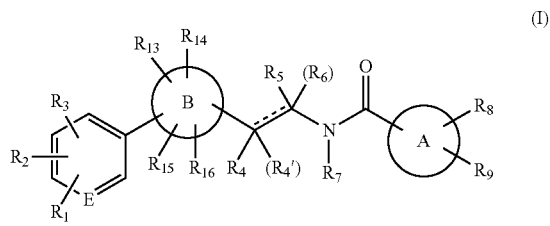

wherein
$R_1$ is hydrogen, halogen, cyano, nitro or optionally substituted 5- or 6-membered heterocyclic ring;
$R_2$ is hydrogen, halogen, cyano, nitro, amino, $C_{1-7}$ alkyl, halo $C_{1-7}$ alkyl, hydroxy $C_{1-7}$ alkyl, thio $C_{1-7}$ alkyl or $C_{1-7}$ alkoxy;
$R_3$ is hydrogen, halogen or $C_{1-7}$ alkyl,
or $R_2$ and $R_3$ together with the carbon atoms to which they are attached form a optionally substituted 5- or 6-membered carbocyclic or heterocyclic ring;
wherein at least two of $R_1$, $R_2$ and $R_3$ are not hydrogen;
$R_4$, $R_4'$, $R_5$, $R_6$ and $R_7$ are, independently, hydrogen, $C_{1-7}$ alkyl, halo $C_{1-7}$ alkyl or hydroxy $C_{1-7}$ alkyl;
ring atom E is C or N;
dashed line means an optional double bond;
A is a 5-12 membered heterocyclic ring;
B is a 5-membered heterocyclic ring wherein 1-3 of the members are heteroatoms selected from N, O and S;
$R_8$ is hydrogen, hydroxy, halogen, nitro, amino, cyano, oxo, $C_{1-7}$ alkyl, $C_{1-7}$ alkoxy, halo $C_{1-7}$ alkyl, hydroxy $C_{1-7}$ alkyl, cyano $C_{1-7}$ alkyl, amino $C_{1-7}$ alkyl, oxo $C_{1-7}$ alkyl, $C_{1-7}$ alkoxy $C_{1-7}$ alkyl, methylsulfonamido $C_{1-7}$ alkyl, oxiran $C_{1-7}$ alkyl, $C_{1-7}$ alkylamino, hydroxy $C_{1-7}$ alkylamino, $C_{1-7}$ alkoxy $C_{1-7}$ alkylamino, $C_{1-7}$ alkylamino $C_{1-7}$ alkyl, hydroxy $C_{1-7}$ alkylamino $C_{1-7}$ alkyl, hydroxyimino $C_{1-7}$ alkyl, halo $C_{1-7}$ alkylhydroxy $C_{1-7}$ alkyl, —C(O)$R_{10}$, —OC(O)$R_{17}$, —NH—C(O)$R_{18}$ or an optionally substituted 5-12 membered carbocyclic or heterocyclic ring, each group optionally linked to A-ring via $C_{1-7}$ alkylene linker;
$R_9$ is hydrogen, halogen, $C_{1-7}$ alkyl, oxo, hydroxy $C_{1-7}$ alkyl, oxo $C_{1-7}$ alkyl or an optionally substituted 5 or 6 membered carbocyclic or heterocyclic ring, each group optionally linked to A-ring via $C_{1-7}$ alkylene linker;

$R_{10}$ is hydrogen, hydroxy, $C_{1-7}$ alkyl, hydroxy $C_{1-7}$ alkyl, halo $C_{1-7}$ alkyl, $C_{1-7}$ alkoxy, $NR_{11}R_{12}$, or an optionally substituted 5-12 membered carbocyclic or heterocyclic ring;

$R_{11}$ is hydrogen, $C_{1-7}$ alkyl, hydroxy $C_{1-7}$ alkyl, amino $C_{1-7}$ alkyl, $C_{1-7}$ alkyl amino $C_{1-7}$ alkyl, $R_{12}$ is hydrogen or $C_{1-7}$ alkyl;

$R_{13}$ and $R_{14}$ are, independently, hydrogen, $C_{1-7}$ alkyl, halogen, cyano or hydroxy $C_{1-7}$ alkyl;

$R_{15}$ and $R_{16}$ are, independently, hydrogen, oxo, thioxo, $C_{1-7}$ alkyl or cyano;

$R_{17}$ is $C_{1-7}$ alkyl, $C_{1-7}$ alkoxy, amino $C_{1-7}$ alkyl or $C_{1-7}$ alkylamino $C_{1-7}$ alkyl;

$R_{18}$ is $C_{1-7}$ alkyl, amino $C_{1-7}$ alkyl or $C_{1-7}$ alkylamino $C_{1-7}$ alkyl;

and pharmaceutically acceptable salts thereof.

In one class of preferred compounds of formula (I) are compounds wherein B is a group of formula (1') the substituents of B being $R_{13}$ and $R_{14}$

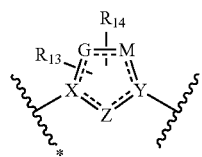

(1')

wherein Z is O, N, C=O or C=S; X is C or N; Y is C or N; G is CH, C=O or C=S and M is CH or O; a dashed line means an optional double bond, the asterisk denotes the point of attachment to the ring, and $R_{13}$ and $R_{14}$ are as defined above for compounds of formula (I).

In another class of preferred compounds of formula (I) are compounds wherein B is a group of formula (2'), (3') or (4') the substituents of B being $R_{13}$ and $R_{14}$ which are again as defined above for compounds of formula (I), and the asterisk denotes the point of attachment to the ring.

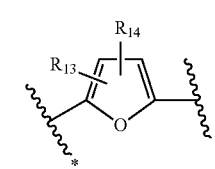

(2')

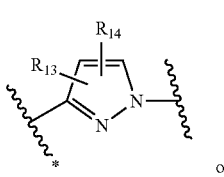

(3')

or

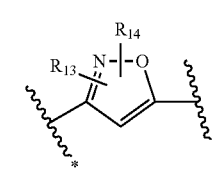

(4')

In another class of preferred compounds of formula (I) are compounds of formula (II), wherein $R_1$, $R_2$, $R_3$, $R_4$, $R_4'$, $R_5$, $R_6$, $R_7$, $R_8$, $R_9$ $R_{13}$, $R_{14}$, A, E, Z, X, Y, G and M are as defined above for compounds of formula (I).

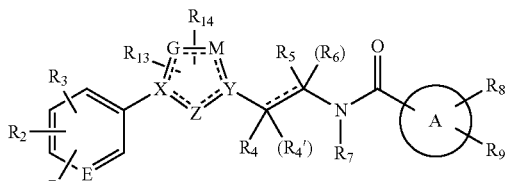

(II)

In one class of preferred compounds of formula (I) are compounds of formula (III), wherein $R_1$, $R_2$, $R_3$, $R_4$, $R_4'$, $R_5$, $R_6$, $R_7$, $R_8$, $R_9$ $R_{13}$, $R_{14}$, A and E are as defined above for compounds of formula (I).

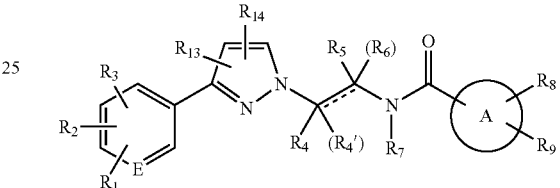

(III)

In other class of preferred compounds of formula (I) are compounds of formula (IV), wherein $R_1$, $R_2$, $R_3$, $R_4$, $R_4'$, $R_5$, $R_6$, $R_7$, $R_8$, $R_9$ $R_{13}$, $R_{14}$, A and E are as defined above for compounds of formula (I).

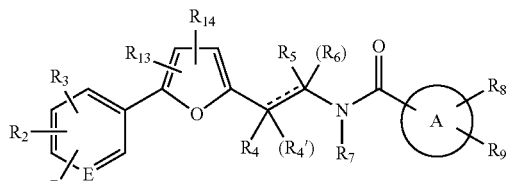

(IV)

In other class of preferred compounds of formula (I) are compounds of formula (V), wherein $R_1$, $R_2$, $R_3$, $R_4$, $R_4'$, $R_5$, $R_6$, $R_7$, $R_8$, $R_9$ $R_{13}$, $R_{14}$, A and E are as defined above for compounds of formula (I).

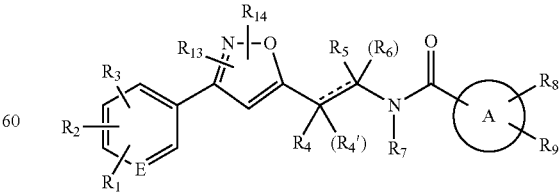

(V)

In other class of preferred compounds of formula (I) are compounds of formula (VI), wherein $R_1$ is halogen, methyl, cyano, nitro or trifluoromethyl; $R_2$ is cyano, halogen or nitro;

$R_3$ is hydrogen, halogen or methyl; $R_4$ is hydrogen or methyl; $R_5$ is hydrogen or $C_{1-3}$ alkyl; A, $R_8$, and $R_9$ are as defined above for compounds of formula (I).

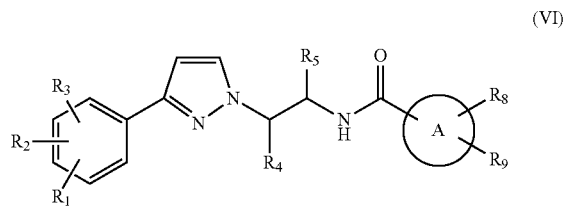

(VI)

One preferred subclass of compounds of formula (VI) are compounds, wherein $R_1$ is halogen, $R_2$ is cyano; $R_3$ is hydrogen, halogen or methyl; $R_4$ is hydrogen, $R_5$ is methyl, and A, $R_8$, and $R_9$ are as defined above for compounds of formula (I).

On the other aspect, the present invention provides the use of carboxamide structured and acyl hydrazone structured compounds of formula (I')

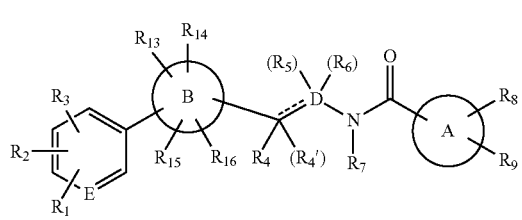

(I')

wherein $R_1$ is hydrogen, halogen, cyano, nitro or optionally substituted 5- or 6-membered heterocyclic ring;

$R_2$ is hydrogen, halogen, cyano, nitro, amino, $C_{1-7}$ alkyl, halo $C_{1-7}$ alkyl, hydroxy $C_{1-7}$ alkyl, thio $C_{1-7}$ alkyl or $C_{1-7}$ alkoxy;

$R_3$ is hydrogen, halogen or $C_{1-7}$ alkyl, or $R_2$ and $R_3$ together with the carbon atoms to which they are attached form a optionally substituted 5- or 6-membered carbocyclic or heterocyclic ring;

wherein at least two of $R_1$, $R_2$ and $R_3$ are not hydrogen;

$R_4$, $R_4'$, $R_5$, $R_6$ and $R_7$ are, independently, hydrogen, $C_{1-7}$ alkyl, halo $C_{1-7}$ alkyl or hydroxy $C_{1-7}$ alkyl;

ring atom E is C or N;

D is C or N;

dashed line means an optional double bond;

A is a 5-12 membered heterocyclic ring;

B is a 5-membered heterocyclic ring wherein 1-3 of the members are heteroatoms selected from N, O and S;

$R_8$ is hydrogen, hydroxy, halogen, nitro, amino, cyano, oxo, $C_{1-7}$ alkyl, $C_{1-7}$ alkoxy, halo $C_{1-7}$ alkyl, hydroxy $C_{1-7}$ alkyl, cyano $C_{1-7}$ alkyl, amino $C_{1-7}$ alkyl, $C_{1-7}$ alkoxy $C_{1-7}$ alkyl, methylsulfonamido $C_{1-7}$ alkyl, oxiran $C_{1-7}$ alkyl, $C_{1-7}$ alkylamino, hydroxy $C_{1-7}$ alkylamino, $C_{1-7}$ alkoxy $C_{1-7}$ alkylamino, $C_{1-7}$ alkylamino $C_{1-7}$ alkyl, hydroxy $C_{1-7}$ alkylamino $C_{1-7}$ alkyl, hydroxyimino $C_{1-7}$ alkyl, halo $C_{1-7}$ alkylhydroxy $C_{1-7}$ alkyl, —C(O)$R_{10}$, —OC(O)$R_{17}$, —NH—C(O)$R_{18}$ or an optionally substituted 5-12 membered carbocyclic or heterocyclic ring, each group optionally linked to A-ring via $C_{1-7}$ alkylene linker;

$R_9$ is hydrogen, halogen, $C_{1-7}$ alkyl, oxo, or an optionally substituted 5 or 6 membered carbocyclic or heterocyclic ring, each group optionally linked to A-ring via $C_{1-7}$ alkylene linker;

$R_{10}$ is hydrogen, hydroxy, $C_{1-7}$ alkyl, hydroxy $C_{1-7}$ alkyl, halo $C_{1-7}$ alkyl, $C_{1-7}$ alkoxy, $NR_{11}R_{12}$, or an optionally substituted 5-12 membered carbocyclic or heterocyclic ring;

$R_{11}$ is hydrogen, $C_{1-7}$ alkyl, hydroxy $C_{1-7}$ alkyl, amino $C_{1-7}$ alkyl, $C_{1-7}$ alkyl amino $C_{1-7}$ alkyl, $R_{12}$ is hydrogen or $C_{1-7}$ alkyl;

$R_{13}$ and $R_{14}$ are, independently, hydrogen, $C_{1-7}$ alkyl, halogen, cyano, halogen $C_{1-7}$ alkyl or hydroxy $C_{1-7}$ alkyl;

$R_{15}$ and $R_{16}$ are, independently, hydrogen, oxo, thioxo, $C_{1-7}$ alkyl or cyano;

$R_{17}$ is $C_{1-7}$ alkyl, $C_{1-7}$ alkoxy, amino $C_{1-7}$ alkyl or $C_{1-7}$ alkylamino $C_{1-7}$ alkyl;

$R_{18}$ is $C_{1-7}$ alkyl, amino $C_{1-7}$ alkyl or $C_{1-7}$ alkylamino $C_{1-7}$ alkyl;

and pharmaceutically acceptable salts thereof;

in the manufacture of a medicament for the prevention or treatment of androgen receptor (AR) dependent disorders.

In one class of preferred compounds of formula (I') are compounds of formula (II'), wherein $R_1$, $R_2$, $R_3$, $R_4$, $R_4'$, $R_5$, $R_6$, $R_7$, $R_8$, $R_9$ $R_{13}$, $R_{14}$, A, E, D, Z, X, Y, G and M are as defined above for compounds of formula (I')

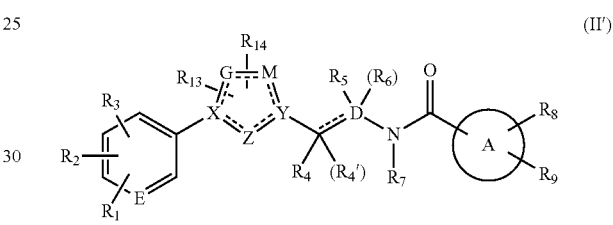

(II')

One particular class of compounds of formula (I') are acyl hydrazone compounds of formula (III'), wherein $R_1$, $R_2$, $R_3$, $R_4$, $R_7$, $R_8$, $R_9$ $R_{13}$, $R_{14}$, $R_{15}$, $R_{16}$, A, B and E are as defined above as defined above for compounds of formula (I').

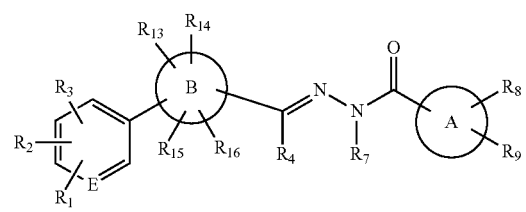

(III')

Another particular class of compounds of formula (I') are acyl hydrazone compounds of formula (IV'), wherein $R_1$, $R_2$, $R_3$, $R_4$, $R_7$, $R_8$, $R_9$ $R_{13}$, $R_{14}$, $R_{15}$, $R_{16}$, A, E, Z, X, Y, G and M are as defined above for compounds of formula (I')

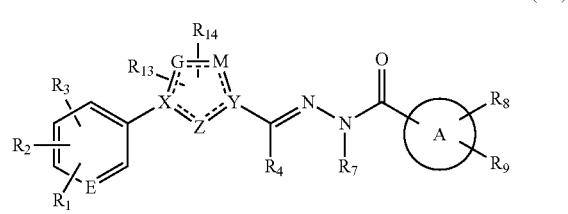

(IV')

Another particular class of compounds of formula (I') or (III') are acyl hydrazone compounds wherein B is a group of formula (2'), (3') or (4') as defined above.
In another class of preferred compounds are compounds of formula (I), (II), (III), (IV), (V), (VI), (I'), (II'), (III') or (IV') wherein A is any one of the following groups or tautomers thereof:
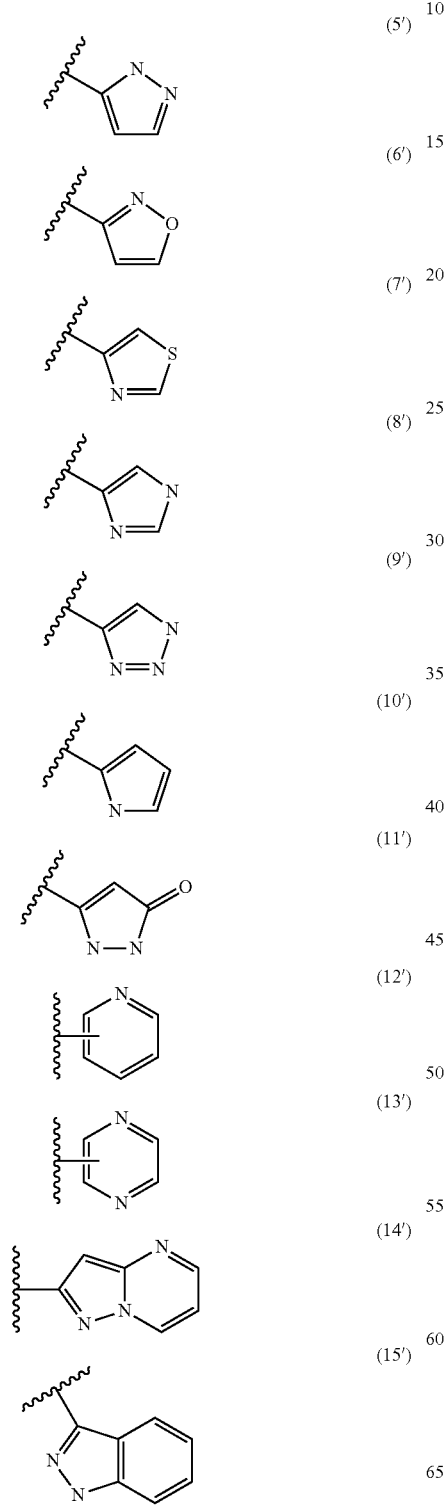
-continued
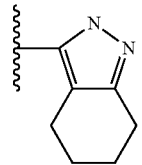
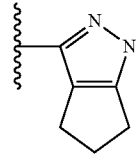
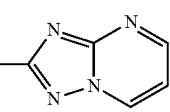
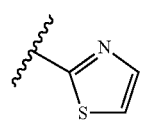
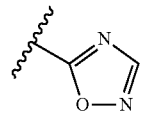
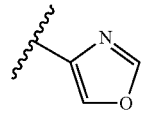
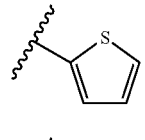
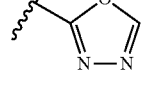
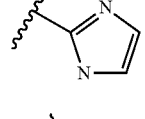
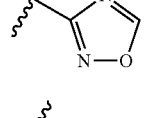
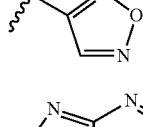
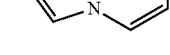

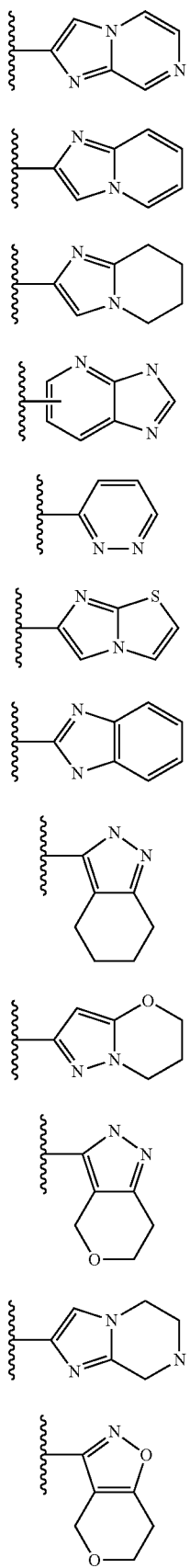

(28')
(29')
(30')
(31')
(32')
(33')
(34')
(35')
(36')
(37')
(38')
(39')

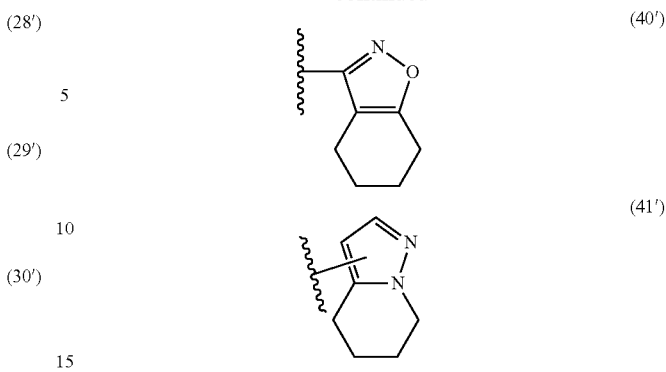

(40')
(41')

wherein each of the above rings are substituted by $R_8$ and $R_9$ as defined above. Preferred are compounds of formula (I), (II), (III), (IV), (V), (VI), (I'), (II'), (III') or (IV') wherein A is any one of groups (5'), (6'), (7'), (8'), (12'), (20'), (21'), (27') and (28') or tautomers thereof. One subclass of above preferred compounds is a class of compounds wherein $R_8$ is hydrogen, $C_{1-7}$ alkyl, hydroxy $C_{1-7}$ alkyl, halogen, pyridinyl, pyrazolyl, imidazolyl, furanyl, —C(O)$R_{10}$ or —OC(O)$R_{17}$, wherein $R_{10}$ is $C_{1-7}$ alkyl, $R_{17}$ is $C_{1-7}$ alkyl, and $R_9$ is hydrogen, halogen or $C_{1-7}$ alkyl, and wherein pyridinyl, pyrazolyl, imidazolyl, furanyl, —C(O)$R_{10}$, or —OC(O)$R_{17}$ groups may be linked to A-ring via $C_{1-7}$ alkylene linker. Preferred compounds of the above subclass are compounds wherein $R_1$ is halogen, $R_2$ is cyano; $R_3$ is hydrogen, halogen or methyl; $R_4$ is hydrogen, and $R_5$ is methyl.

Still another class of preferred compounds are compounds of formula (I), (I') or (III') wherein
ring atom E is C,
$R_1$ is halogen, $C_{1-7}$ alkyl, cyano, nitro or halo $C_{1-7}$ alkyl,
$R_2$ is cyano, halogen or nitro,
$R_3$ is hydrogen, halogen or $C_{1-7}$ alkyl,
A is any one of groups (5'), (6'), (7'), (8'), (12'), (20'), (21'), (27') and (28') or tautomers thereof,
B is a group of formula (2'), (3') or (4') substituted by $R_{13}$ and $R_{14}$, which are hydrogen,
$R_4$ (and $R_4'$ if applicable) is hydrogen or methyl,
$R_5$ is hydrogen or $C_{1-7}$ alkyl,
$R_6$ (if applicable) is hydrogen,
$R_8$ is hydrogen, $C_{1-7}$ alkyl, hydroxy $C_{1-7}$ alkyl, halogen, hydroxyimino $C_{1-7}$ alkyl, a 5 or 6 membered heterocyclic ring or —C(O)$R_{10}$ wherein $R_{10}$ is $C_{1-7}$ alkyl, and
$R_9$ is hydrogen, halogen or $C_{1-7}$ alkyl.

The present invention provides further a method for the treatment or prevention of androgen receptor (AR) dependent conditions, comprising administering to a subject in need thereof a therapeutically effective amount of a compound of formula (I) or (I'). For example, the AR dependent condition to be treated is cancer, particularly AR dependent cancer such as prostate cancer, benign prostatic hyperplasia, androgenic alopecia and acne. According to one embodiment of the invention, the AR dependent condition to be treated is castration-resistant prostate cancer (CRPC).

The present invention also provides a pharmaceutical composition comprising a compound of formula (I) together with a pharmaceutically acceptable carrier.

DETAILED DESCRIPTION OF THE INVENTION

The compounds of the invention can be prepared by a variety of synthetic routes analogously to the methods known in the literature using suitable starting materials. For example, compounds of formula (I) wherein $R_4$, $R_4'$, $R_6$, and $R_7$ are hydrogen, and $R_1$, $R_2$, $R_3$, $R_5$, $R_8$, $R_9$ $R_{13}$, $R_{14}$, $R_{15}$, $R_{16}$, A, B and E are as defined above for compounds of formula (I) can be prepared e.g. analogously or according to the reaction Scheme 1. Some compounds included in the formula (I) can be obtained by converting the functional groups of the other compounds of formula (I) obtained in accordance with Scheme 1, by well known reaction steps such as oxidation, reduction, hydrolysis, acylation, alkylation, amidation, amination and others.

Scheme 1

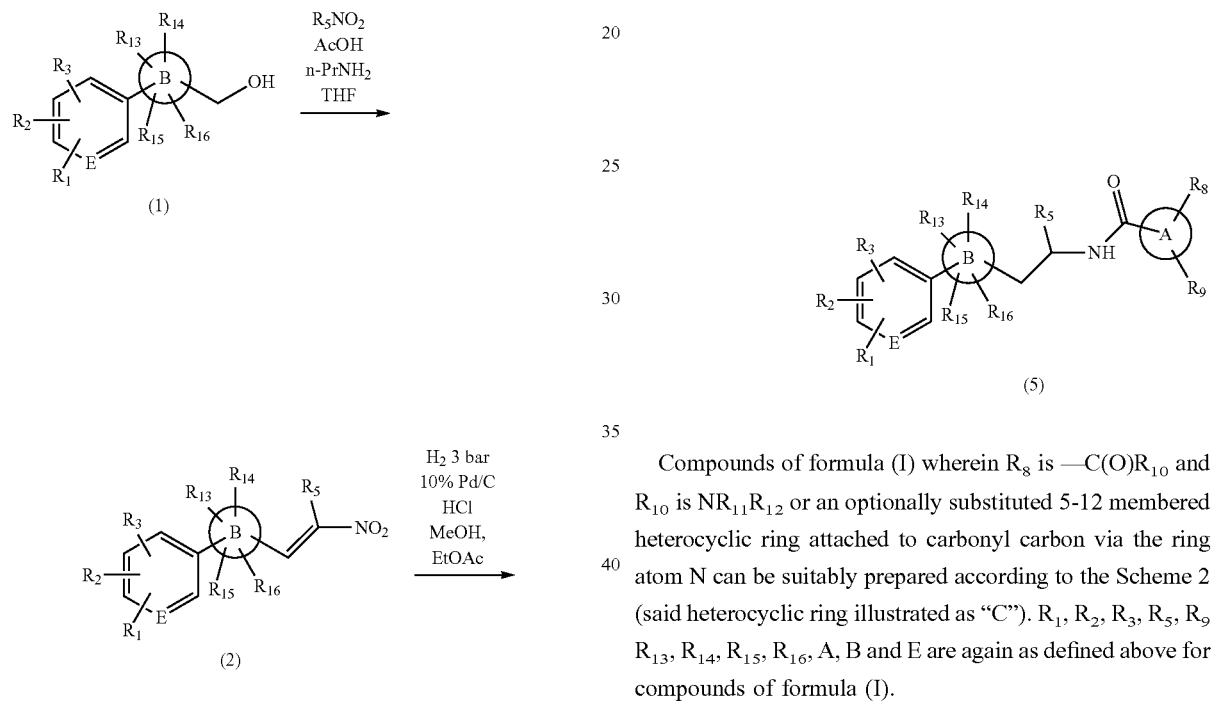

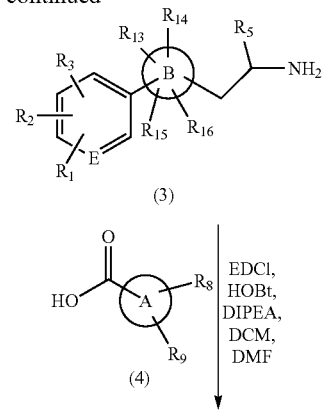

Compounds of formula (I) wherein $R_8$ is —C(O)$R_{10}$ and $R_{10}$ is $NR_{11}R_{12}$ or an optionally substituted 5-12 membered heterocyclic ring attached to carbonyl carbon via the ring atom N can be suitably prepared according to the Scheme 2 (said heterocyclic ring illustrated as "C"). $R_1$, $R_2$, $R_3$, $R_5$, $R_9$ $R_{13}$, $R_{14}$, $R_{15}$, $R_{16}$, A, B and E are again as defined above for compounds of formula (I).

Scheme 2

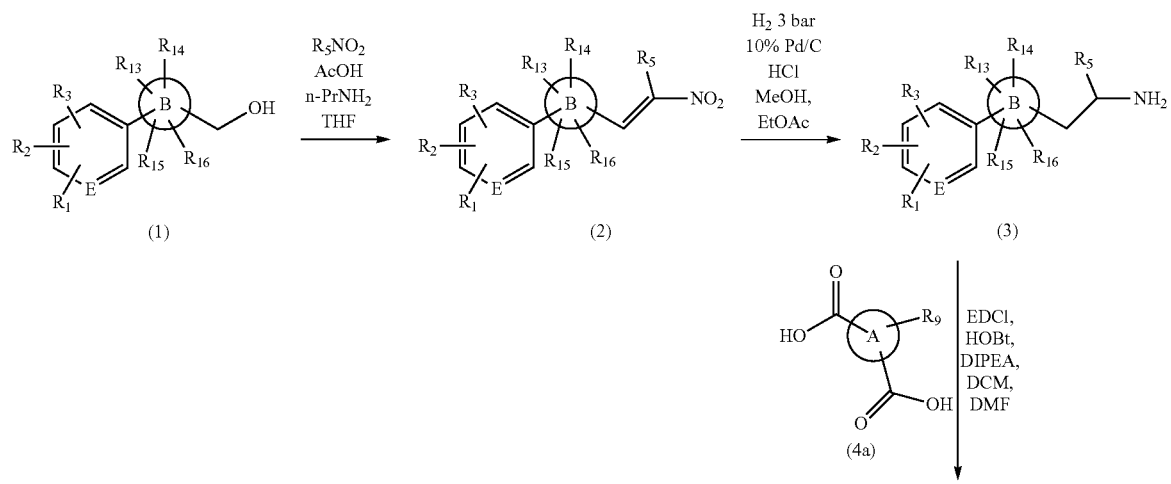

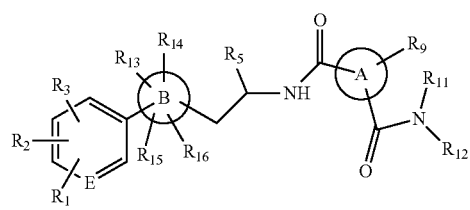

(8)

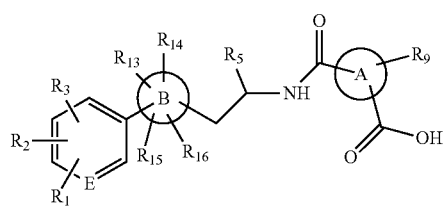

(5a)

-continued $$\underset{(6)}{\overset{H}{\underset{R_{11}}{N}}\underset{R_{12}}{\overset{}{N}}}$$

EDCl, HOBt,
DIPEA
DCM, DMF

EDCl, HOBt,
DIPEA
DCM, DMF

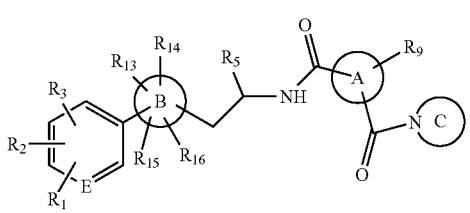

(9)

Compounds of formula (I) wherein B is a pyrazole ring (3') can be suitably prepared from the intermediate compound of formula (16) using the methods of Scheme 1 or 2.

The intermediate compound of formula (16) can be suitably prepared according to Scheme 3, wherein $R_1$, $R_2$, $R_3$, $R_5$, $R_6$ and E are as defined above for compounds of formula (I).

Scheme 3

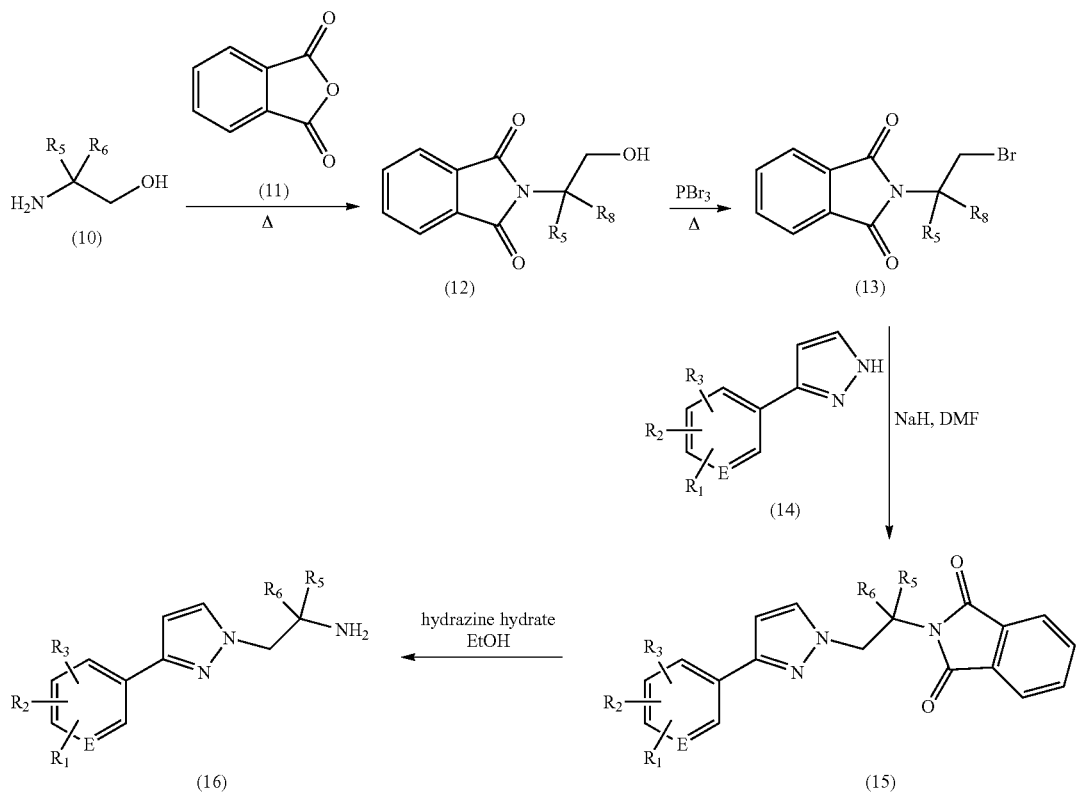

Optically active enantiomers or diastereomers of compounds of formula (I) can be prepared e.g. by using suitable optically active starting materials. For example, optically active enantiomers of compounds of formula (I) can be prepared from optically active intermediate compounds of formula (16a) using the methods of Scheme 1 or 2. The optically active intermediate compound of formula (16a) can be suitably prepared according to Scheme 4 or Scheme 5, wherein $R_1$, $R_2$, $R_3$, $R_4$, $R'_4$, $R_5$, $R_6$ and E are as defined above for compounds of formula (I).

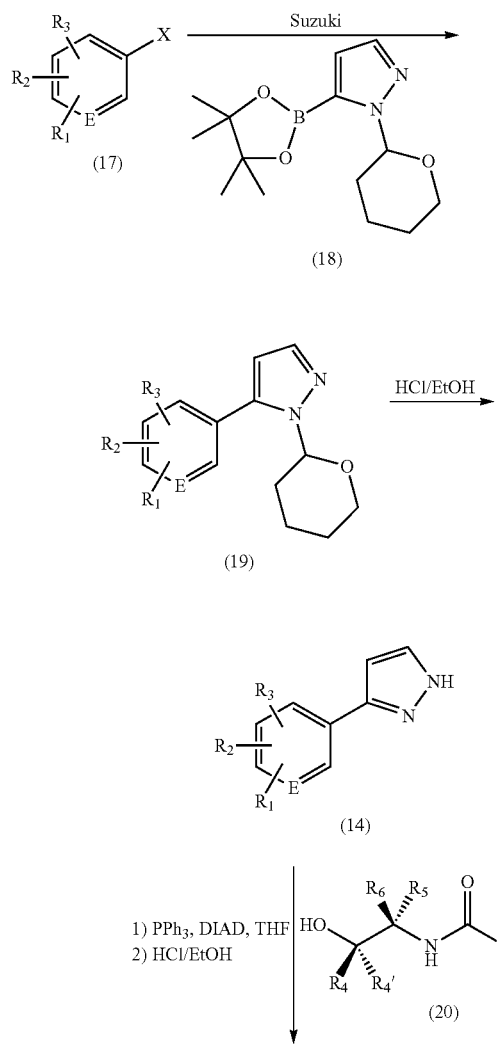

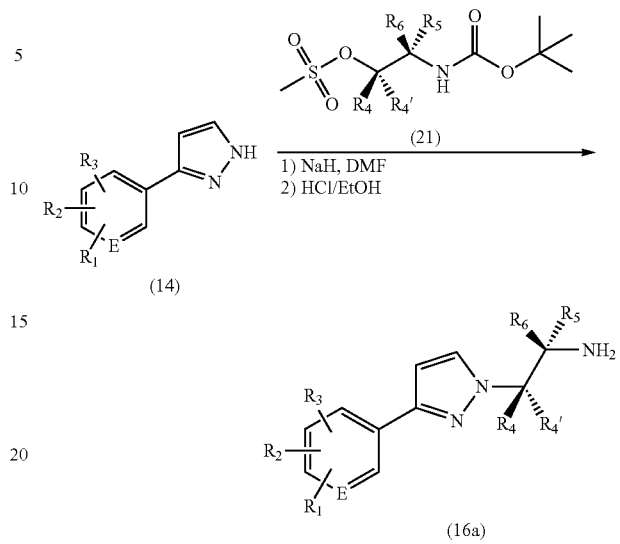

Alternatively, the intermediate compound of formula (16) can be prepared according to Scheme 6, wherein $R_1$, $R_2$, $R_3$, $R_4$, $R'_4$, $R_5$, $R_6$ and E are as defined above for compounds of formula (I) and Tr is a trityl (triphenyl methyl) group.

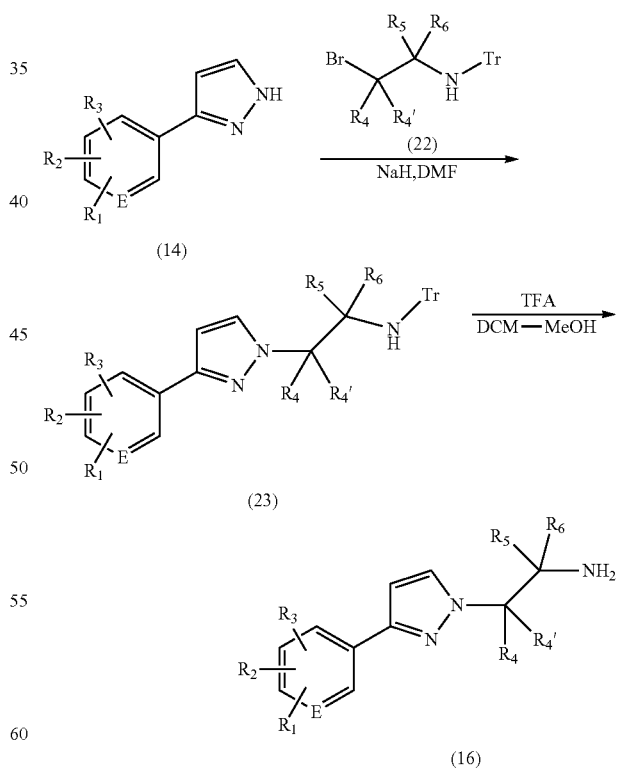

Compounds of formula (I) having the optional double bond can be suitably prepared according to Scheme 7, wherein $R_1$, $R_2$, $R_3$, $R_5$, $R_8$, $R_9$, $R_{13}$, $R_{14}$, $R_{15}$, $R_{16}$, A, B and E are as defined above for compounds of formula (I).

Scheme 7

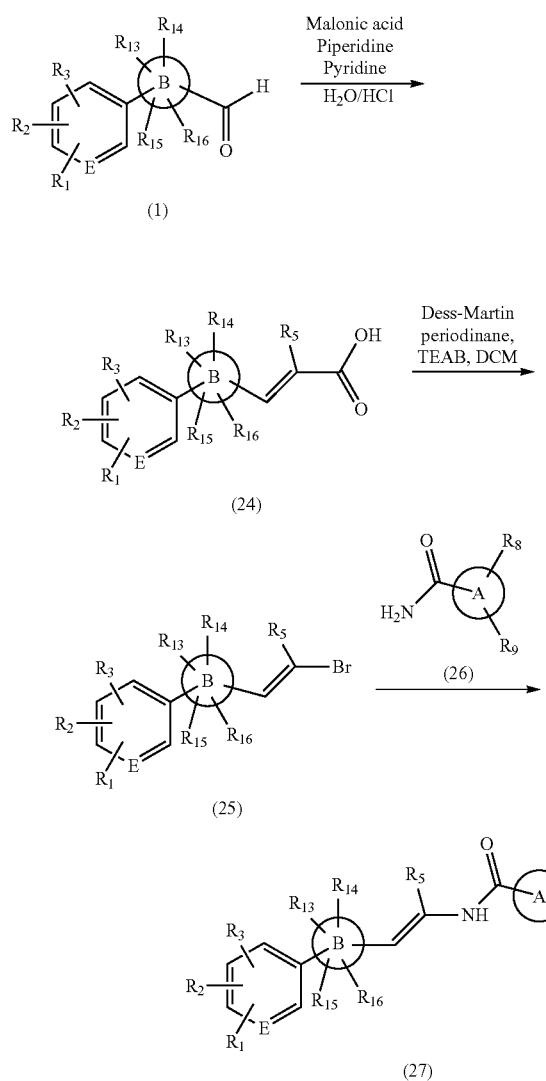

Acyl hydrazone compounds of formula (I'), wherein D is N, are commercially available or can be prepared, for example, according to Scheme 8, wherein $R_1$, $R_2$, $R_3$, $R_4$, $R_8$, $R_9$, $R_{13}$, $R_{14}$, $R_{15}$, $R_{16}$, A, B and E are as defined above for compounds of formula (I'). Some compounds included in the formula (I') can be obtained by converting the functional groups of the other compounds of formula (I') obtained in accordance with Scheme 8, by well known reaction steps such as oxidation, reduction, hydrolysis, acylation, alkylation, amidation, amination and others.

Scheme 8

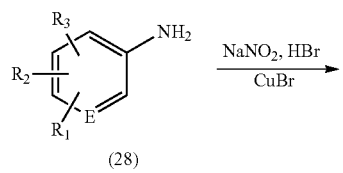

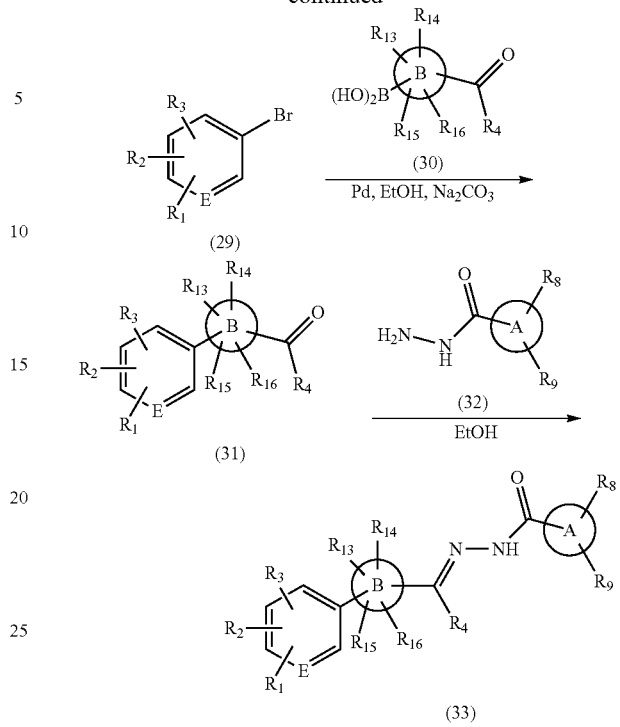

The starting materials of the above Schemes are commercially available or can be prepared according to known methods.

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The definition of formula (I) above is inclusive of all the possible isotopes and stereoisomers of the compounds, including geometric isomers, e.g. Z and E isomers (cis and trans isomers), and optical isomers, e.g. diastereomers and enantiomers, and all prodrug esters, e.g. phosphate esters and carbonate esters. Furthermore, the invention includes in its scope both the individual isomers and any mixtures thereof, e.g. racemic mixtures.

In one embodiment, the term "isomer" is meant to encompass optical isomers of the compounds of the invention. It will be appreciated by those skilled in the art that the compounds of the present invention contain at least one chiral center. Accordingly, the compounds of the invention may exist in optically active or racemic forms. It is to be understood that the present invention encompasses any racemic or optically active form, or mixtures thereof. In one embodiment, the compounds of the invention are the pure (R)-isomers. In another embodiment, the compounds of the invention are the pure (S)-isomers. In another embodiment, the compounds of the invention are a mixture of the (R) and the (S) isomers. In another embodiment, the compounds of the invention are a racemic mixture comprising an equal amount of the (R) and the (S) isomers. The compounds of the invention may contain two chiral centers. In such case, according to one embodiment of the invention, the compounds of the invention are pure diastereomers. According to other embodiment of the invention, the compounds of the invention are a mixture of several diastereomers. The individual isomers may be obtained using the corresponding isomeric forms of the starting material or they may be separated after the preparation of the end compound according to conventional separation methods. For the separation of optical isomers, e.g. enantiomers or diastereomers, from the mixture thereof the conventional resolution methods, e.g. fractional crystallisation, may be used.

The terms employed herein have the following meanings:

The term "halo" or "halogen", as employed herein as such or as part of another group, refers to chlorine, bromine, fluorine or iodine.

The term "$C_{1-7}$ alkyl", as employed herein as such or as part of another group, refers to a saturated or unsaturated straight, branched or cyclized chain radical having 1 to 7 carbon atoms. Representative examples of $C_{1-7}$ alkyl include, but are not limited to, methyl, ethyl, ethenyl, n-propyl, isopropyl, propenyl, n-butyl, isobutyl, sec-butyl, tert-butyl, n-pentyl, isopentyl, neopentyl, n-hexyl, cyclopentyl, cyclohexyl and the like.

The term "$C_{1-7}$ alkylene linker" means a saturated or unsaturated straight, branched or cyclized $C_{1-7}$ alkyl chain which connects two groups together. Examples of $C_{1-7}$ alkylene linker are methylene (—CH$_2$—) and ethylene (—CH$_2$—CH$_2$—) chains.

The term "hydroxy", as employed herein as such or as part of another group, refers to an —OH group.

The term "cyano", as employed herein as such or as part of another group, refers to a —CN group.

The term "hydroxy $C_{1-7}$ alkyl", as employed herein, refers to at least one hydroxy group, as defined herein, appended to the parent molecular moiety through an $C_{1-7}$ alkyl group, as defined herein. Representative examples of hydroxy $C_{1-7}$ alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl, 1-methyl-1-hydroxypropyl, and the like.

The term "halo $C_{1-7}$ alkyl", as employed herein, refers to at least one halogen, as defined herein, appended to the parent molecular moiety through a $C_{1-7}$ alkyl group, as defined herein. Representative examples of halo $C_{1-7}$ alkyl include, but are not limited to, fluoromethyl, difluoromethyl, trifluoromethyl, 2-chloroethyl, 3-bromopropyl, and the like.

The term "$C_{1-7}$ alkoxy", as employed herein as such or as part of another group, refers to —O—$C_{1-7}$ alkyl wherein $C_{1-7}$ alkyl is as defined herein. Representative examples of $C_{1-7}$ alkoxy include, but are not limited to methoxy, ethoxy, propoxy, butoxy, isobutoxy, sec-butoxy, tert-butoxy, and the like.

The term "thio $C_{1-7}$ alkyl", as employed herein, refers to —S—$C_{1-7}$ alkyl, wherein $C_{1-7}$ alkyl is as defined herein. Representative examples of thio $C_{1-7}$ alkyl include, but are not limited to thiomethyl (—SCH$_3$), thioethyl, and the like.

The term "oxo" means a double-bonded group (═O) attached as a substituent.

The term "thioxo" means a double-bonded group (═S) attached as a substituent.

The term "amino", as employed herein as such or as part of another group, refers to a —NH$_2$ group.

The term "$C_{1-7}$ acyl" as employed herein by itself or as part of another group refers to $C_{1-7}$ alkylcarbonyl group, and examples thereof include acetyl, propanoyl, isopropanoyl, butanoyl, sec-butanoyl, tert-butanoyl and pentanoyl.

The term "amino $C_{1-7}$ alkyl", as employed herein, refers to at least one amino group, as defined herein, appended to the parent molecular moiety through an $C_{1-7}$ alkyl group, as defined herein. Representative examples of amino $C_{1-7}$ alkyl include, but are not limited to, aminomethyl, 2-aminoethyl, 1-aminoethyl, 2,2-diaminoethyl, 3-aminopropyl, 2-aminopropyl, 4-aminobutyl, 1-methyl-1-aminoethyl, and the like.

The term "$C_{1-7}$ alkylamino", as employed herein as such or as part of another group, refers to one or two $C_{1-7}$ alkyl group(s), as defined herein, appended to the parent molecular moiety through an amino group, as defined herein. Representative examples of $C_{1-7}$ alkylamino include, but are not limited to methylamino, ethylamino, propylamino, butylamino, dimethylamino, diethylamino, N-ethyl-N-methylamino, and the like.

The term "$C_{1-7}$ alkylamino $C_{1-7}$ alkyl", as employed herein, refers to $C_{1-7}$ alkylamino group, as defined herein, appended to the parent molecular moiety through a $C_{1-7}$ alkyl group, as defined herein. Representative examples of $C_{1-7}$ alkylamino $C_{1-7}$ alkyl include, but are not limited to, N,N-dimethylaminomethyl, N,N-diethylaminomethyl, N-methylaminoethyl, N-methylaminopropyl, N-ethyl-N-methylaminomethyl, and the like.

The term "hydroxy $C_{1-7}$ alkylamino $C_{1-7}$ alkyl", as employed herein, refers to hydroxy $C_{1-7}$ alkylamino group, as defined herein, appended to the parent molecular moiety through a $C_{1-7}$ alkyl group, as defined herein. Representative examples of $C_{1-7}$ alkylamino $C_{1-7}$ alkyl include, but are not limited to, N-hydroxymethylaminoethyl, N-ethyl-N-hydroxymethylaminomethyl, and the like.

The term "$C_{1-7}$ alkoxy $C_{1-7}$ alkyl", as employed herein, refers to at least one $C_{1-7}$ alkoxy group, as defined herein, appended to the parent molecular moiety through a $C_{1-7}$ alkyl group, as defined herein. Representative examples of $C_{1-7}$ alkoxy $C_{1-7}$ alkyl include, but are not limited to methoxymethyl, ethoxymethyl, 2-methoxyethyl, 2-ethoxyethyl, 3,3-dimethoxypropyl, 2,4-dimethoxybutyl and the like.

The term "imino $C_{1-7}$ alkyl", as employed herein, refers to at least one imino group (═NH) appended to the parent molecular moiety through a $C_{1-7}$ alkyl group, as defined herein.

The term "hydroxyimino $C_{1-7}$ alkyl", as employed herein, refers to ═N—OH group appended to the parent molecular moiety through a $C_{1-7}$ alkyl group, as defined herein.

The term "5- or 6-membered heterocyclic ring" as employed herein, refers to a saturated, partially saturated or aromatic ring with 5 or 6 ring atoms, of which 1-3 atoms are heteroatoms selected from a group consisting of N, O and S. Representative examples of 5- or 6-membered heterocyclic ring include, but are not limited to, pyrazolyl, furanyl, piperazinyl, piperidinyl, pyridinyl rings and the like.

The term "5- or 6-membered carbocyclic ring" as employed herein, refers to a saturated, partially saturated or aromatic ring with 5 or 6 ring atoms consisting of carbon atoms only. Representative examples of 5- or 6-membered carbocyclic ring include, but are not limited to, phenyl and cyclohexyl rings and the like.

The term "5-12 membered heterocyclic ring" as employed herein, refers to a monocyclic or bicyclic saturated, partially saturated or aromatic ring with 5 to 12 ring atoms, of which 1-4 atoms are heteroatoms selected from a group consisting of N, O and S. Representative examples of 5-12 membered heterocyclic ring include, but are not limited to, pyrazolyl, furanyl, piperazinyl, piperidinyl, pyridinyl, morpholinyl, pyrazinyl, indazolyl, imidazolyl, pyrazolo[1,5-a]pyrimidinyl, isoxazolyl and thiazolyl rings and the like.

The term "5-12 membered carbocyclic ring" as employed herein, refers to a saturated, partially saturated or aromatic ring with 5 to 12 ring atoms consisting of carbon atoms only. Representative examples of 5-12 membered carbocyclic ring include, but are not limited to, phenyl, naphtyl and cyclohexyl rings and the like.

The term "optionally substituted" as used herein in connection with various residues refers to halogen substituents, such as fluorine, chlorine, bromine, iodine, or $C_{1-7}$ alkyl, hydroxy, amino, halo $C_{1-7}$ alkyl, hydroxy $C_{1-7}$ alkyl, $C_{1-7}$ alkoxy, $C_1$-$C_7$ acyl, $C_{1-7}$ alkylamino, amino $C_{1-7}$ alkyl, methylsulfonyl, nitro, cyano, thiol, or 5- or 6-membered carbocyclic or heterocyclic ring substituents. Preferred substituents are halogen, $C_{1-7}$ alkyl, hydroxy $C_{1-7}$ alkyl, $C_1$-$C_7$ acyl, pyridinyl, morpholinyl and benzyl substituents.

The "optionally substituted" groups may contain 1 to 3, preferably 1 or 2, most preferably 1 of the above mentioned substituents.

Examples of preferred compounds of formula (I) include
N-(2-(5-(3,4-dichlorophenyl)furan-2-yl)ethyl)-3-(morpholine-4-carbonyl)-1H-pyrazole-5-carboxamide;
(S/R)—N-(1-(5-(3,4-dichlorophenyl)furan-2-yl)propan-2-yl)-3-(pyridin-4-yl)-1H-pyrazole-5-carboxamide;
(S)—N-(1-(3-(4-cyano-3-methylphenyl)-1H-pyrazol-1-yl)propan-2-yl)-3-(furan-2-yl)-1H-pyrazole-5-carboxamide;
(S)-3-acetyl-N-(1-(3-(3-chloro-4-cyanophenyl)-1H-pyrazol-1-yl)propan-2-yl)-1H-pyrazole-5-carboxamide;
N-(2-(3-(3-chloro-4-cyanophenyl)-1H-pyrazol-1-yl)ethyl)-5-(1-methyl-1H-pyrazol-4-yl)isoxazole-3-carboxamide;
(S)—N-(1-(3-(3-chloro-4-cyanophenyl)-1H-pyrazol-1-yl)propan-2-yl)-5-(1-methyl-1H-pyrazol-4-yl)isoxazole-3-carboxamide;
N-(2-(3-(3,4-dicyanophenyl)-1H-pyrazol-1-yl)ethyl)-3-(pyridin-3-yl)-1H-pyrazole-5-carboxamide;
(R)-3-acetyl-N-(1-(3-(3-chloro-4-cyanophenyl)-1H-pyrazol-1-yl)propan-2-yl)-1H-pyrazole-5-carboxamide;
N—((S)-1-(3-(3-chloro-4-cyanophenyl)-1H-pyrazol-1-yl)propan-2-yl)-3-(1-hydroxyethyl)-1H-pyrazole-5-carboxamide;
(S)-2-amino-N-(1-(3-(3-chloro-4-cyanophenyl)-1H-pyrazol-1-yl)propan-2-yl)thiazole-4-carboxamide;
(R)-3-acetyl-N-(1-(3-(3-chloro-4-cyanophenyl)-1H-pyrazol-1-yl)butan-2-yl)-1H-pyrazole-5-carboxamide;
(R)—N-(1-(3-(3-chloro-4-cyanophenyl)-1H-pyrazol-1-yl)propan-2-yl)thiazole-4-carboxamide;
(S)—N-(1-(3-(3-chloro-4-cyanophenyl)-1H-pyrazol-1-yl)propan-2-yl)-3-(pyridin-3-yl)-1H-pyrazole-5-carboxamide;
(S)—N-(1-(3-(3-chloro-4-cyanophenyl)-1H-pyrazol-1-yl)propan-2-yl)thiazole-4-carboxamide;
N-(2-(3-(3-chloro-4-cyanophenyl)-1H-pyrazol-1-yl)ethyl)-3-(furan-2-yl)-1H-pyrazole-5-carboxamide;
3-tert-butyl-N-(1-(5-(4-cyano-3-(trifluoromethyl)phenyl)furan-2-yl)propan-2-yl)-1H-pyrazole-5-carboxamide;
3-tert-butyl-N-(2-(5-(3-chloro-cyano-2-methylphenyl)furan-2-yl)ethyl)-1H-pyrazole-5-carboxamide;
N-(2-(3-(3-chloro-4-cyanophenyl)-1H-pyrazol-1-yl)ethyl)-5-(pyridin-3-yl)-1H-pyrazole-3-carboxamide;
(S)-5-acetyl-N-(1-(3-(4-cyano-3,5-difluorophenyl)-1H-pyrazol-1-yl)propan-2-yl)-1H-pyrazole-3-carboxamide;
(R)—N-(1-(3-(4-cyano-3-(trifluoromethyl)phenyl)-1H-pyrazol-1-yl)propan-2-yl)-3-(furan-2-yl)-1H-pyrazole-5-carboxamide;
(S)-3-acetyl-N-(1-(3-(3-chloro-4-cyano-2-methylphenyl)-1H-pyrazol-1-yl)propan-2-yl)-1H-pyrazole-5-carboxamide;
N—((S)-1-(3-(3-chloro-4-cyano-2-methylphenyl)-1H-pyrazol-1-yl)propan-2-yl)-3-(1-hydroxyethyl)-1H-pyrazole-5-carboxamide;
(S)—N-(1-(3-(3-chloro-4-cyano-2-methyl phenyl)-1H-pyrazol-1-yl)propan-2-yl)-5-methylisoxazole-3-carboxamide;
(S)—N-(1-(3-(3-chloro-4-cyano-2-methyl phenyl)-1H-pyrazol-1-yl)propan-2-yl)thiazole-4-carboxamide;
(S)—N-(1-(3-(3-chloro-4-cyano-2-methylphenyl)-1H-pyrazol-1-yl)propan-2-yl)-5-(trifluoromethyl)-1H-pyrazole-3-carboxamide;
(S)—N-(1-(3-(3-chloro-4-cyano-2-methylphenyl)-1H-pyrazol-1-yl)propan-2-yl)-3-(furan-2-yl)-1H-pyrazole-5-carboxamide;
(R)—N-(1-(3-(3-chloro-4-cyano-2-methylphenyl)-1H-pyrazol-1-yl)propan-2-yl)-5-(pyridin-3-yl)-1H-pyrazole-3-carboxamide;
(R)—N-(1-(3-(3-chloro-4-cyano-2-methylphenyl)-1H-pyrazol-1-yl)propan-2-yl)-3-(furan-2-yl)-1H-pyrazole-5-carboxamide;
(S)—N-(1-(3-(3-chloro-4-cyanophenyl)-1H-pyrazol-1-yl)propan-2-yl)-5-(2-methylthiazol-4-yl)-1H-pyrazole-3-carboxamide;
(S)—N-(1-(3-(3-chloro-4-cyanophenyl)-1H-pyrazol-1-yl)propan-2-yl)-3-methyl-1,2,4-oxadiazole-5-carboxamide;
(R)—N-(1-(3-(3-chloro-4-cyanophenyl)-1H-pyrazol-1-yl)propan-2-yl)-2-morpholinothiazole-4-carboxamide;
(S)—N-(1-(3-(3-chloro-4-cyanophenyl)-1H-pyrazol-1-yl)propan-2-yl)-2-(1H-pyrazol-4-yl)thiazole-4-carboxamide;
(S)—N-{1-[3-(3-chloro-4-cyanophenyl)-1H-pyrazol-1-yl]propan-2-yl}-2-methyl-1H-imidazole-4-carboxamide;
N—((S)-1-(3-(3-chloro-4-cyanophenyl)-1H-pyrazol-1-yl)propan-2-yl)-5-(1-hydroxyethyl)isoxazole-3-carboxamide;
(S)—N-(1-(3-(3-chloro-4-cyanophenyl)-1H-pyrazol-1-yl)propan-2-yl)-3-ethyl-1,2,4-oxadiazole-5-carboxamide;
N—((S)-1-(3-(3-chloro-4-cyano-2-methylphenyl)-1H-pyrazol-1-yl)propan-2-yl)-2-(1-hydroxyethyl)thiazole-4-carboxamide;
(R)—N-(2-(3-(4-cyano-3,5-difluorophenyl)-1H-pyrazol-1-yl)propyl)-2-(cyanomethyl)thiazole-4-carboxamide;
(S)—N-{1-[3-(3-chloro-4-cyano-5-fluorophenyl)-1H-pyrazol-1-yl]propan-2-yl}-2-methyl-1H-imidazole-4-carboxamide;
(S)—N-(1-(3-(3-chloro-4-cyano-5-fluorophenyl)-1H-pyrazol-1-yl)propan-2-yl)imidazo[1,2-a]pyrimidine-2-carboxamide;
(S)-3-acetyl-N-(2-(3-(4-cyano-3,5-difluorophenyl)-1H-pyrazol-1-yl)propyl)-1H-pyrazole-5-carboxamide;
(S)—N-(1-(3-(3-chloro-4-cyanophenyl)-1H-pyrazol-1-yl)propan-2-yl)-2,4,6,7-tetrahydropyrano[4,3-c]pyrazole-3-carboxamide;

Compounds of the invention may be administered to a patient in therapeutically effective amounts which range usually from about 0.1 to about 5000 mg, preferably from about 1 to about 2000 mg, per day depending on the age, weight, ethnic group, condition of the patient, condition to be treated, administration route and the androgen (AR) modulator used. The compounds of the invention can be formulated into dosage forms using the principles known in the art. It can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 1 to about 85%, per weight of the total composition.

The present invention will be explained in more detail by the following examples. The examples are meant only for illustrating purposes and do not limit the scope of the invention defined in claims.

EXPERIMENTS

Experiment 1

AR binding affinity (Ki) of the test compound was measured.

AR antagonism of the test compound was measured as $IC_{50}$ value (nM) to human AR in hAR/HEK293 cells.

AR agonism of the test compound in AR overexpressing hAR/HEK293 cells was measured as % of testosterone-induced AR activity at 10 uM concentration.

The $IC_{50}$ value of the test compound for inhibition of mibolerone-induced VCaP cell proliferation was measured.

Bicalutamide was used as a reference compound in the measurements.

Methods

Androgen Receptor Binding Assay

Androgen receptor (AR) binding affinities of test compounds were studied in cytosolic lysates obtained from ventral prostates of castrated rats by competition binding assay (Schilling K. and Liao S., The Prostate, 1984; 5(6): 581-588). Cytosol preparations and 1 nM [3H]mibolerone were incubated with increasing concentrations of test compounds. To determine non-specific binding, parallel incubations were carried out using excess of unlabelled testosterone. After incubation, bound and free steroids were separated by treatment with dextran-coated charcoal suspension. Bound radioactivity was determined by counting of supernatant fraction in scintillation fluid. Radioactivity was measured using a Microbeta counter. All data points were done as quadrublicates. Dissociation constant of [3H]mibolerone for rat androgen receptor was determined by saturation binding assay obtained from ventral prostates of castrated rats essentially as described (Isomaa V. et al., Endocrinology, 1982; 111(3):833-843).

Analysis of Data

For analysis of saturation binding affinity, one site binding equation (hyperbola) was used $$\text{Specific binding} = \frac{B_{max} * X}{Kd + X}$$

where
$B_{max}$=the maximum specific binding
Kd=the equilibrium dissociation constant
X=radioligand concentration Equilibrium dissociation constant (Ki) was calculated using the equation of Cheng and Prusoff:

$$K_i = \frac{IC50}{1 + \frac{[radioligand]}{K_d}}$$

where
[radioligand]=the concentration of free radioligand
$K_d$=the dissociation constant of the radioligand for the receptor
IC50=$IC_{50}$ value measured in a competition radioligand binding assay AR Antagonism Antagonism of test compounds for AR was measured by reporter gene assay in human embryonic kidney (HEK293) cells stably transfected with an expression vector encoding full-length human AR and androgen responsive luciferase reporter gene construct (hAR/HEK293 cells). To determine antagonism for hAR, the cells were treated simultaneously with increasing concentrations of the test compound and submaximal concentration of testosterone (usually 0.45 nM). The final DMSO concentration was 1%. All test compounds were studied in triplicates. The cells were incubated for 24 before measurement of luciferase activity using Luciferase Assay System (Promega Corporation).

Agonism of test compounds in AR overexpressing cells was measured by reporter gene assay in HEK293 cells stably transfected with an expression vector encoding full-length human AR and androgen responsive luciferase reporter gene construct. A clone expressing high levels of androgen receptor (5 times more than AR levels in AR-HEK293 cells) was selected to study agonism in AR overexpressing cells. To determine agonism, the cells were treated with increasing concentrations of the test compound. The final DMSO concentration was 1%. The test compounds were studied in triplicates and luciferase activity was determined as described above.

Cell Proliferation Assays

The ability of test compounds to inhibit prostate cancer cell growth was studied by measuring inhibition of cell proliferation using androgen-sensitive VCaP prostate cancer cell line. Cells were seeded at a density of 50 000 cells/well in a 96-well plate in the appropriate culture medium (phenol red-free RPMI-1640 supplemented with 10% charcoal stripped FBS and 4 mM Glutamax+100 IU penicillin, 100 IU streptomycin). The cells were allowed to attach for 2-3 days and were subsequently treated with the test compounds in the presence of mibolerone (a concentration capable of inducing submaximal increase in cell proliferation, usually 0.1 nM) for 4-5 days. Cell proliferation was measured using WST-1 Cell Proliferation Assay (Roche).

TABLE 1

AR binding affinity, AR antagonism, AR agonism in AR overexpressing cells and inhibition of VCaP cell proliferation

| Compound of Example No. | AR binding affinity Ki (nM) | AR antagonism $IC_{50}$(nM) | Agonism in AR overexpressing cells (%) | Inhibition of VCaP cell proliferation $IC_{50}$ (nM) |
|---|---|---|---|---|
| 8 | 62 | 606 | 0 | 1600 |
| 32 | 6 | 34 | 39 | 560 |
| 34 | 16 | 172 | 39 | 600 |
| 52 | 27 | 149 | 40 | 450 |
| 56 | 14 | 96 | 27 | 400 |
| 53 | 18 | 88 | 24 | 500 |
| 91 | 13 | 54 | 18 | 330 |

TABLE 1-continued

AR binding affinity, AR antagonism, AR agonism in AR overexpressing cells and inhibition of VCaP cell proliferation

| Compound of Example No. | AR binding affinity Ki (nM) | AR antagonism IC$_{50}$(nM) | Agonism in AR overexpressing cells (%) | Inhibition of VCaP cell proliferation IC$_{50}$ (nM) |
|---|---|---|---|---|
| 94 | 8 | 57 | 18 | 790 |
| 103 | 17 | 71 | 19 | 230 |
| 124 | 38 | 133 | 5 | 430 |
| 132 | 29 | 93 | 21 | 210 |
| 186 | 3 | 11 | >20 | 310 |
| 206 | 12 | 29 | >20 | 490 |
| 219 | 40 | 146 | 0 | 1400 |
| 222 | 12 | 33 | 20 | 250 |
| 248 | 31 | 190 | 7 | 490 |
| 249 | 16 | 42 | 34 | 320 |
| 324 | 25 | 128 | 16 | 1000 |
| 338 | 14 | 42 | 25 | 340 |
| Bicalutamide | 40 | 228 | 70 | 2000-3000 |

EXAMPLES

The end products of the following Examples were prepared as a mixture of diastereomers unless otherwise indicated.

Example 1

5-(Piperazine-1-carbonyl)-2H-pyrazole-3-carboxylic Acid {2-[5-(3,4-dichloro-phenyl)furan-2-yl]ethyl}amide a) 2-(3,4-Dichlorophenyl)-5-((E)-2-nitrovinyl)furan A stirred solution of acetic acid (1.4 ml, 1.46 g, 24.3 mmol) in methanol (3.5 ml) under nitrogen atmosphere at 0° C. was treated dropwise with n-propylamine (2.0 ml, 1.42 g, 24.0 mmol). The resulting n-propylammonium acetate solution was stirred at 0° C. for 5 min, then added dropwise to a stirred solution of 5-(3,4-di-chlorophenyl)furfural (10.04 g, 41.6 mmol) in nitromethane (6.8 ml, 7.61 g, 124.7 mmol) at 0° C. The resulting mixture was stirred at 0° C. for 30 min. Then the cooling bath was removed, and stirring was continued at RT. From time to time, 10 ml of THF was added five times. After stirring overnight THF was evaporated and water was added. A solid was filtrated, washed with water and heptane to afford 11.46 g of 2-(3,4-dichlorophenyl)-5-((E)-2-nitrovinyl)furan. $^1$H NMR (400 MHz, DMSO-d$_6$): 7.38 (1H, d), 7.43 (1H, d), 7.76 (1H, d), 7.95 (1H, dd), 8.03 (1H, d), 8.19 (1H, d), 8.31 (1H, d)

b) 2-[5-(3,4-Dichlorophenyl)furan-2-yl]ethylamine Hydrochloride 2-(3,4-Dichlorophenyl)-5-((E)-2-nitrovinyl)furan (5.73 g, 20.2 mmol) was dissolved into the mixture of dry methanol (90 ml) and dry ethyl acetate (70 ml). Then, 14.3 ml of 10 w-% HCl-methanol and 2.4 g of 10% palladium on carbon were added. 2-(3,4-Dichlorophenyl)-5-((E)-2-nitrovinyl) furan was hydrogenated at 3 atm at RT for about 4 h. The catalyst was removed by filtrating through Celite®. Removal of solvent under reduced pressure gave a raw product which was purified by flash chromatography on silica gel using CH$_2$Cl$_2$/MeOH (98:2-80:20) as a gradient eluent. $^1$H NMR (400 MHz, DMSO-d$_6$): 3.04 (2H, m), 3.14 (2H, m), 6.43 (1H, d), 7.07 (1H, d), 7.67 (2H, s), 7.93 (1H, s), 8.19 (3H, broad s).

c) 5-{2-[5-(3,4-Dichlorophenyl)furan-2-yl]ethylcarbamoyl}-1H-pyrazole-3-carboxylic Acid 3,5-Pyrazoledicarboxylic acid monohydrate (8.02 g, 46.1 mmol) was dissolved in the mixture of dry DMF (35 ml), dry DCM (35 ml) and DIPEA (7.9 ml). 1-(3-Dimethylaminopropyl)-3-ethylcarbodiimide hydrochloride (EDCI, 3.37 g, 17.6 mmol), HOBt (2.28 g, 16.9 mmol), and DIPEA (3 ml, 2.23 g, 17.3 mmol) were added at RT. The solution was mixed for 10 min. Then, 2-[5-(3,4-dichlorophenyl)furan-2-yl]ethylamine hydrochloride (3.46 g, 11.8 mmol) dissolved in the mixture of dry DCM (35 ml) and DIPEA (2.0 ml, 1.48 g, 11.5 mmol) was dropped to the solution at RT. After stirring overnight water was added. The product was extracted into ethyl acetate. The organic phase was washed with water, dried and evaporated. The crude product was purified by flash chromatography using DCM as an eluent. The product was triturated in hot methanol. $^1$H NMR (400 MHz, DMSO-d$_6$): 2.95 (2H, t), 3.56 (2H, m), 6.33 (1H, d), 7.01 (1H, d), about 7.03 (1H, broad s), 7.61 (1H, distorted dd), 7.63 (1H, distorted d), 7.83 (1H, d), about 8.45 (1H, broad s), about 14.05 (1H, broad s).

d) 5-(Piperazine-1-carbonyl)-2H-pyrazole-3-carboxylic Acid {2-[5-(3,4-dichlorophenyl)furan-2-yl] ethyl}amide 5-{2-[5-(3,4-Dichlorophenyl)furan-2-yl]ethylcarbamoyl}-1H-pyrazole-3-carboxylic acid (0.30 g, 0.76 mmol) was dissolved in the mixture of dry DMF (3 ml) and dry DCM (3 ml). EDCI (0.22 g, 1.2 mmol), HOBt (0.16 g, 1.2 mmol), and DIPEA (0.2 ml, 0.15 g, 1.2 mmol) were added at RT. After stirring for 15 min piperazine (0.10 g, 1.2 mmol) in dry DCM (2 ml) was dropped to the solution at RT. Then the solution was stirred overnight. Water was added and the product was extracted into ethyl acetate. The organic phase was washed with brine and water, dried and evaporated. The crude product was purified by flash chromatography using CH$_2$Cl$_2$-MeOH as a gradient eluent (95:5-50:50). Another purification was made also by flash chromatography using CH$_2$Cl$_2$-MeOH (9:1) as an eluent. $^1$H NMR (400 MHz, CDCl$_3$): 2.94 (4H, m), 3.01 (2H, t), 3.77 (2H, q), about 3.8 (4H, m), 6.20 (1H, d), 6.58 (1H, d), 7.02 (1H, s), 7.21 (1H, broad s), 7.40 (1H, distorted d), 7.43 (1H, distorted dd), 7.75 (1H, d).

Example 2

5-[4-(2-Hydroxyethyl)piperidine-1-carbonyl]-2H-pyrazole-3-carboxylic Acid {2-[5-(3,4-dichlorophenyl)furan-2-yl]ethyl}amide The title compound was prepared as in the previous Example starting from 5-{2-[5-(3,4-dichlorophenyl)furan-2-yl]ethylcarbamoyl}-1H-pyrazole-3-carboxylic acid and 4-piperidine ethanol. The crude product was purified by flash chromatography using CH$_2$Cl$_2$-MeOH as a gradient eluent (100:0-95:5). $^1$H NMR (400 MHz, CDCl$_3$): 1.27 (3H, m), 1.57 (2H, m), 1.85 (3H, m), 2.81 (1H, m), 3.01 (2H, t), about 3.21 (1H, m), 3.76 (4H, m), about 4.41 (1H, m), about 4.67 (1H, m), 6.20 (1H, d), 6.59 (1H, d), 7.02 (1H, s), 7.29

(1H, broad s), 7.40 (1H, distorted d), 7.43 (1H, distorted dd), 7.75 (1H, d), 11.4 (1H, broad s).

Example 3

5-(4-Hydroxypiperidine-1-carbonyl)-2H-pyrazole-3-carboxylic Acid {2-[5-(3,4-dichlorophenyl)furan-2-yl]ethyl}amide The title compound was prepared as in Example 1 starting from 5-{2-[5-(3,4-dichlorophenyl)furan-2-yl]ethylcarbamoyl}-1H-pyrazole-3-carboxylic acid and 4-hydroxypiperidine. The crude product was purified by flash chromatography using $CH_2Cl_2$-MeOH (95:5) as an eluent. $^1H$ NMR (400 MHz, $CDCl_3$): 1.62 (1H, d), 1.65 (2H, m), 1.95 (2H, m), 3.00 (2H, t), about 3.57 (2H, m), 3.77 (2H, q), about 4.1 (3H, m), 6.20 (1H, d), 6.58 (1H, d), 7.03 (1H, s), about 7.6 (1H, broad s), 7.40 (1H, distorted d), 7.43 (1H, distorted dd), 7.74 (1H, d), 11.6 (1H, broad s).

Example 4

5-[4-(2-Hydroxyethyl)piperazine-1-carbonyl]-2H-pyrazole-3-carboxylic Acid {2-[5-(3,4-dichlorophenyl)furan-2-yl]ethyl}amide The title compound was prepared as in Example 1 starting from 5-{2-[5-(3,4-dichlorophenyl)furan-2-yl]ethylcarbamoyl}-1H-pyrazole-3-carboxylic acid and 1-(2-hydroxyethyl)piperazine. The crude product was purified by flash chromatography using $CH_2Cl_2$-MeOH as a gradient eluent (100:0-90:10). $^1H$ NMR (400 MHz, DMSO-$d_6$): 2.40-2.44 (6H, m), 2.95 (2H, t), about 3.5-3.7 (6H, m), about 3.82 (2H, m), 4.41 (1H, t), 6.33 (1H, d), 7.01 (1H, d), about 7.05 (1H, broad s), 7.59 (1H, distorted dd), 7.63 (1H, distorted d), 7.84 (1H, d), about 8.59 (1H, broad s), 13.9 (1H, broad s).

Example 5

5-(4-Acetylpiperazine-1-carbonyl)-2H-pyrazole-3-carboxylic Acid {2-[5-(3,4-dichlorophenyl)furan-2-yl]ethyl}amide The title compound was prepared as in Example 1 starting from 5-{2-[5-(3,4-dichlorophenyl)furan-2-yl]ethylcarbamoyl}-1H-pyrazole-3-carboxylic acid and 1-acetylpiperazine. The crude product was triturated in $CH_2Cl_2$ at room temperature to afford the product. $^1H$ NMR (400 MHz, $CDCl_3$): 2.15 (3H, s), 3.01 (2H, t), 3.58 (2H, m), 3.72 (2H, m), 3.78 (2H, q), 3.84 (4H, m), 6.21 (1H, d), 6.59 (1H, d), 7.04 (1H, s), about 7.28 (1H, broad s), 7.41 (2H, m), 7.74 (1H, s), 11.35 (1H, broad s).

Example 6

5-(4-Morpholin-4-ylpiperidine-1-carbonyl)-2H-pyrazole-3-carboxylic Acid {2-[5-(3,4-dichlorophenyl)furan-2-yl]ethyl}amide The title compound was prepared as in Example 1 starting from 5-{2-[5-(3,4-dichlorophenyl)furan-2-yl]ethylcarbamoyl}-1H-pyrazole-3-carboxylic acid and 4-morpholinopiperidine. The crude product was purified by flash chromatography using $CH_2Cl_2$-MeOH as a gradient eluent (100:0-96:4). $^1H$ NMR (400 MHz, DMSO-$d_6$): about 1.32 (2H, m), about 1.82 (2H, m), 2.45-2.47 (5H, m), about 2.78 (1H, m), 2.95 (2H, t), about 3.11 (1H, m), 3.55-3.57 (6H, m), about 4.45 (1H, m), 6.34 (1H, d), 7.02 (1H, d), about 7.03 (1H, broad s), 7.59 (1H, distorted dd), 7.63 (1H, distorted d), 7.84 (1H, d), 8.6 (1H, broad s), 13.9 (1H, broad s).

Example 7

5-[4-(1-Hydroxyethyl)piperidine-1-carbonyl]-2H-pyrazole-3-carboxylic Acid {2-[5-(3,4-dichlorophenyl)furan-2-yl]ethyl}amide a) 1-(Pyridin-4-yl)ethanol To a stirred solution of 4-acetylpyridine (2.50 g, 20.6 mmol) in methanol (25 ml) sodium borohydride (1.56 g, 41.2 mmol) was added in portions. After stirring overnight at RT water was added and the mixture was evaporated to dryness in vacuo. The product was taken into ethyl acetate. The solvent was evaporated to give 2.53 g of the title compound. $^1H$ NMR (400 MHz, DMSO-$d_6$): 1.32 (3H, d), 4.69-4.75 (1H, m), 5.38 (1H, d), 7.34 (2H, d), 8.49 (2H, d).

b) 1-(Piperidin-4-yl)ethanol 1-(Pyridin-4-yl)ethanol (2.53 g, 20.5 mmol) was dissolved in acetic acid (20 ml) and hydrogenated in the presence of platinum(IV) oxide (0.19 g) at 1 atm at RT. The catalyst was removed by filtration through Celite® and the filtrate was concentrated in vacuo to yield crude 1-(pyridin-4-yl)ethanol as an acetate salt which was triturated in ethyl acetate. The water solution of the acetate salt was made basic (pH>10) with sodium hydroxide and 1-(pyridin-4-yl)ethanol as a base was extracted into ethyl acetate. The extracts were concentrated in vacuo. $^1H$ NMR (400 MHz, DMSO-$d_6$): 1.00 (3H, d), 0.94-1.11 (2H, m), 1.14-1.23 (1H, m), 1.44 (1H, m), 1.66 (1H, m), 2.37 (2H, m), 2.91 (2H, m), 3.30 (1H, quintet), 4.23 (1H, broad s).

c) 5-[4-(1-Hydroxyethyl)piperidine-1-carbonyl]-2H-pyrazole-3-carboxylic Acid {2-[5-(3,4-dichlorophenyl)furan-2-yl]ethyl}amide The title compound was prepared as in Example 1 starting from 5-{2-[5-(3,4-dichlorophenyl)furan-2-yl]ethylcarbamoyl}-1H-pyrazole-3-carboxylic acid and 1-(piperidin-4-yl)ethanol. The crude product was purified by flash chromatography using $CH_2Cl_2$-MeOH as a gradient eluent (100:0-90:10). $^1H$ NMR (400 MHz, $CDCl_3$): 1.22 (3H, d), 1.30-1.41 (3H, m), 1.62 (1H, m), 1.77 (1H, m), 2.00 (1H, m), about 2.78 (1H, m), 3.01 (2H, t), about 3.18 (1H, m), about 3.64 (1H, m), 3.77 (2H, q), about 4.48 (1H, m), about 4.75 (1H, m), 6.20 (1H, d), 6.58 (1H, d), 7.02 (1H, s), about 7.28 (1H, broad s), 7.40 (1H, distorted d), 7.43 (1H, distorted dd), 7.75 (1H, d), 11.44 (1H, broad s).

Example 8

N-(2-(5-(3,4-dichlorophenyl)furan-2-yl)ethyl)-3-(morpholine-4-carbonyl)-1H-pyrazole-5-carboxamide The title compound was prepared as in Example 1 starting from morpholine and 5-{2-[5-(3,4-dichlorophenyl)furan-2-yl]ethylcarbamoyl}-1H-pyrazole-3-carboxylic acid. Crude product was purified by chromatography (CombiFlash, $1^{st}$ column silica, eluent: 0-10% MeOH/DCM; $2^{nd}$ column C-18 RP, eluent: 0-100% MeCN/water) to give 505 mg (17%) of the title compound. $^1$H-NMR (400 MHz; d6-DMSO): δ 2.95

(t, 1H), 3.56 (q, 1H), 3.62 (br s, 6H), 3.90 (br s, 2H), 6.34 (d, 1H), 7.02 (d, 1H), 7.08 (s, 1H), 7.62 (m, 2H), 7.85 (d, 1H), 8.61 (s, 1H), 13.94 (s, 1H).

Example 9

N-(2-(5-(3,4-dichlorophenyl)furan-2-yl)ethyl)-3-(4-methylpiperazine-1-carbonyl)-1H-pyrazole-5-carboxamide The title compound was synthesized as in Example 1 starting from 1-methylpiperazine and 5-{2-[5-(3,4-dichlorophenyl)furan-2-yl]ethylcarbamoyl}-1H-pyrazole-3-carboxylic acid. Crude product was purified by chromatography (CombiFlash, silica column, eluent 0-10% MeOH/DCM) and crystallized from DCM/heptane to give 1.06 g (35%) of the title compound. $^1$H-NMR (400 MHz; d6-DMSO): δ 2.19 (s, 3H), 2.33 (br s, 4H), 2.95 (t, 2H), 3.56 (q, 2H), 3.62 (br s, 2H), 3.85 (br s, 2H), 6.34 (d, 1H), 7.02 (d, 1H), 7.07 (br s, 1H), 7.60 (dd, 1H), 7.63 (d, 1H), 7.84 (d, 1H), 8.61 (s, 1H), 13.92 (s, 1H).

Example 10

5-(2-(5-(3,4-dichlorophenyl)furan-2-yl)ethylcarbamyl)pyrazine-2-carboxylic Acid

Pyrazine-2,5-dicarboxylic acid (0.58 g; 3.42 mmol), anhydrous HOBt (0.69 g; 5.13 mmol) and 1-(3-dimethylaminopropyl)-3-ethylcarbodiimide hydrochloride (0.98 g: 5.13 mmol) were added to 5 ml of DCM. 2-(5-(3,4-dichlorophenyl)furan-2-yl)-ethanamine hydrochloride (1.0 g; 3.42 mmol) and DIPEA (0.89 ml; 5.13 mmol) were dissolved in 5 ml of DCM and added dropwise to the previous mixture. The reaction mixture was stirred overnight after which pyrazine-2,5-dicarboxylic acid (0.58 g; 1.59 mmol) and DIPEA (0.60 ml; 3.42 mmol) were added and the mixture was again stirred for 5 h. Anhydrous HOBt (0.69 g; 5.13 mmol), 1-(3-dimethylaminopropyl)-3-ethylcarbodiimide hydrochloride (0.98 g: 5.13 mmol) and DIPEA (0.89 ml; 5.13 mmol) were again added to drive the reaction to completion. After overnight stirring the mixture was diluted with 20 ml of DCM and washed with 3×10 ml water. The organic phase was dried over $Na_2SO_4$, filtered and used as such without further purification.

Example 11

N-2-(2-(5-(3,4-dichlorophenyl)furan-2-yl)ethyl)-N-5-(2-hydroxyethyl)pyrazine-2,5-dicarboxamide 5-(2-(5-(3,4-dichlorophenyl)furan-2-yl)ethylcarbamoyl) pyrazine-2-carboxylic acid (0.12 g; 0.30 mmol), anhydrous HOBt (0.15 g; 1.1 mmol), 1-(3-dimethylaminopropyl)-3-ethylcarbodiimide hydrochloride (0.085 g: 0.44 mmol) and DIPEA (0.077 ml; 0.44 mmol) were dissolved in 2.5 ml of DCM. To this a solution of 2-aminoethanol (0.018 ml; 0.3 ml) in 2.5 ml of DCM was added and the mixture was stirred overnight. The mixture was diluted with 10 ml of DCM and washed with 3×5 ml water. The water phases were then extracted with EtOAc, the organic phase dried over $Na_2SO_4$, filtered and evaporated to dryness. The product was purified with flash chromatography. The combined fractions gave 6 mg of the product. $^1$H-NMR (400 MHz; d6-DMSO): δ 3.01 (t, 2H), 3.38-3.43 (m, 2H), 3.52-3.57 (m, 2H), 3.64-3.69 (m, 2H), 4.81 (t, 1H), 6.36 (d, 1H), 7.02 (d, 1H), 7.58-7.64 (m, 2H), 7.80 (d, 1H), 8.91-8.94 (t, 1H), 9.19 (d, 1H), 9.21 (d, 1H), 9.26-9.29 (t, 1H).

Example 12

1,5-Dimethyl-1H-pyrazole-3-carboxylic Acid {2-[5-(3,4-dichlorophenyl)furan-2-yl]ethyl}amide 1,5-Dimethyl-1H-pyrazole-3-carboxylic acid (100 mg, 0.71 mmol) was dissolved in dry DMF (2 ml). EDCI (205 mg, 1.1 mmol), HOBt (145 mg, 1.1 mmol) and DIPEA (0.19 ml, 141 mg, 1.1 mmol) were added at RT. The solution was stirred for 30 min. Then, 2-[5-(3,4-dichlorophenyl)furan-2-yl]ethylamine hydrochloride (313 mg, 1.1 mmol) dissolved in the mixture of dry DMF (4 ml) and DIPEA (0.19 ml, 141 mg, 1.1 mmol) was added to the solution at RT. After stirring overnight water was added. The product was extracted into ethyl acetate. The organic phase was washed with water, dried and evaporated. The crude product was purified by flash chromatography using $CH_2Cl_2$-MeOH as a gradient eluent (100:0-95:5). Another purification was done also by flash chromatography using $CH_2Cl_2$-MeOH as a gradient eluent (100:0-99.7:0.3). The product was triturated in heptane-$CH_2Cl_2$ at RT. $^1$H NMR (400 MHz, DMSO-$d_6$): 2.26 (3H, s), 2.92 (2H, t), 3.52 (2H, m), 3.76 (3H, s), 6.31 (1H, d), 6.38 (1H, s), 7.01 (1H, d), 7.60 (1H, distorted dd), 7.64 (1H, distorted d), 7.83 (1H, d), 8.09 (1H, t).

Example 13

5-Furan-2-yl-1-phenyl-1H-pyrazole-3-carboxylic Acid {2-[5-(3,4-dichlorophenyl)furan-2-yl] ethyl}amide The title compound was prepared as in Example 12 starting from 5-(2-furyl)-1-phenyl-1H-pyrazole-3-carboxylic acid and 2-[5-(3,4-dichlorophenyl)furan-2-yl]-ethylamine hydrochloride. The crude product was purified twice by flash chromatography using first $CH_2Cl_2$-MeOH as a gradient eluent (100:0-99:1). Then another purification by flash chromatography was done by using heptane/EtOAc (8:2) as an eluent. $^1$H NMR (400 MHz, DMSO-$d_6$): 2.96 (2H, t), 3.58 (2H, m), 6.16 (1H, d), 6.34 (1H, d), 6.51 (1H, dd), 7.01 (1H, d), 7.07 (1H, s), 7.45-7.48 (2H, m), 7.54-7.56 (4H, m), 7.61 (1H, distorted dd), 7.73 (1H, d), 7.84 (1H, d), 8.49 (1H, t, $^3$J=5.9 Hz).

Example 14

1-Methyl-1H-indazole-3-carboxylic Acid {2-[5-(3,4-dichlorophenyl)furan-2-yl]ethyl}amide The title compound was prepared as in Example 12 starting from N-methyl-indazole-3-carboxylic acid and 2-[5-(3,4-dichlorophenyl)furan-2-yl]ethylamine hydrochloride. The crude product was purified by flash chromatography using heptane/EtOAc as a gradient eluent (9:1-8:2). $^1$H NMR (400 MHz, DMSO-$d_6$): 3.00 (2H, t), 3.64 (2H, m), 4.12 (3H, s), 6.36 (1H, d), 7.01 (1H, d), 7.26 (1H, m), 7.46 (1H, m), 7.600 (1H, s), 7.602 (1H, s), 7.72 (1H, d), 7.83 (1H, s), 8.16 (1H, d), 8.48 (1H, t).

Example 15

1H-Imidazole-4-carboxylic Acid {2-[5-(3,4-dichlorophenyl)furan-2-yl]ethyl}amide

The title compound was prepared as in Example 12 starting from 4-imidazolecarboxylic acid and 2-[5-(3,4-dichlorophenyl)furan-2-yl]ethylamine hydrochloride. The crude product was purified by flash chromatography using $CH_2Cl_2$/MeOH as a gradient eluent (100:0-99.6:0.4). The product was triturated in ethyl acetate. $^1$H NMR (400 MHz, DMSO-$d_6$): 2.93 (2H, t), 3.55 (2H, m), 6.33 (1H, d), 7.01 (1H, d), 7.59 (1H, s), 7.63 (2H, s), 7.71 (1H, s), 7.87 (1H, s), 8.05 (1H, broad s), 12.43 (1H, broad s).

Example 16

2-Methyl-1H-imidazole-4-carboxylic Acid {2-[5-(3, 4-dichlorophenyl)furan-2-yl]ethyl}amide Hydrochloride The title compound was prepared as in Example 12 starting from 2-methyl-1H-imidazole-4-carboxylic acid and 2-[5-(3,4-dichlorophenyl)furan-2-yl]ethylamine hydrochloride. The crude product was purified by flash chromatography using $CH_2Cl_2$/MeOH as a gradient eluent (100:0-97:3). The product was dissolved in DCM, ethyl acetate saturated with hydrogen chloride was added and the precipitated product as a hydrogen chloride salt was filtered. Recrystallization from MeOH/EtOAc. The HCl salt: $^1$H NMR (400 MHz, MeOH-$d_4$): 2.62 (3H, s), 3.02 (1H, t), 3.69 (1H, t), 6.26 (1H, d), 6.76 (1H, d), 7.49 (1H, distorted d), 6.53 (1H, distorted dd), 7.71 (1H, d), 7.82 (1H, s).

Example 17

1H-Indazole-3-carboxylic Acid {2-[5-(3,4-dichlorophenyl)-furan-2-yl]-ethyl}-amide a) (E)-2-(5-(3,4-dichlorophenyl)furan-2-yl)ethenamine To a stirred solution of 5-(3,4-dichlorophenyl)furfural (1.18 g, 4.89 mmol) in acetic acid (30 ml) was added nitromethane (0.535 ml, 9.78 mmol) and ammonium acetate (1.13 g, 14.7 mmol). The reaction mixture was heated at 80° C. for 4.5 h. Cooled reaction mixture was poured onto ice water (30 ml) and thus formed precipitate was filtered, washed with water and dried under vacuum to give 1.15 g (83%) of the title compound. $^1$H-NMR (400 MHz; d6-DMSO): δ 7.37 (d, 1H), 7.43 (d, 1H), 7.76 (d, 1H), 7.95 (dd, 1H), 8.03 (d, 1H), 8.19 (d, 1H), 8.31 (d, 1H).

b) 2-(5-(3,4-dichlorophenyl)furan-2-yl)ethanamine

To a suspension of lithium aluminium hydride (0.939 g, 24.8 mmol) in THF (20 ml) under nitrogen atmosphere at 0° C. was added slowly a solution of (E)-2-(5-(3,4-dichlorophenyl)furan-2-yl)ethenamine in THF (20 ml). Reaction mixture was stirred at RT for 1 h. Some methanol was added slowly to the mixture followed by addition of water. The mixture was evaporated, and the solid residue was extracted with EtOAc (3×). Combined EtOAc fractions were washed with 2M NaOH and brine. Organic phase was dried over $Na_2SO_4$, evaporated and purified by chromatography (CombiFlash, silica column, eluent: 10-20% MeOH/DCM) to give 227 mg (11%) of the title compound. $^1$H-NMR (400 MHz; d6-DMSO): δ 2.74 (t, 2H), 2.85 (t, 2H), 6.29 (d, 1H), 7.03 (d, 1H), 7.62 (dd, 1H), 7.63 (d, 1H), 7.88 (d, 1H).

c) 1H-Indazole-3-carboxylic Acid {2-[5-(3,4-dichlorophenyl)-furan-2-yl]-ethyl}-amide Indazole-3-carboxylic acid (30 mg; 0.182 mmol), DCC (56 mg, 0.273 mmol) and DMAP (2 mg) were dissolved in DCM:DMF (1:1, 4 ml). 2-(5-(3,4-dichloro-phenyl)furan-2-yl)ethanamine (46 mg, 0.182 mmol) was added and the reaction mixture was stirred for overnight at RT. DCM (30 ml) was added and organic layer washed with water (3×15 ml). Combined organic phases were dried over $Na_2SO_4$, evaporated and purified by chromatography (silica column, eluent: 1% MeOH/DCM) to give 25 mg (34%) of the title compound. $^1$H-NMR (400 MHz; d6-DMSO): δ 3.00 (t, 2H), 3.63 (q, 2H), 6.37 (d, 1H), 7.02 (d, 1H), 7.23 (t, 1H), 7.41 (t, 1H), 7.60 (d, 1H), 7.61 (d, 2H), 7.85 (d, 1H), 8.16 (d, 1H), 8.54 (d, 1H), 13.56 (s, 1H).

Example 18

5-Tert-Butyl-2H-pyrazole-3-carboxylic Acid {2-[5-(3,4-dichlorophenyl)-furan-2-yl]-ethyl}-amide The title compound was synthesized as in Example 17 starting from 5-tert-butyl-2H-pyrazole-3-carboxylic acid and 2-(5-(3,4-dichlorophenyl)furan-2-yl)ethanamine. Crude product was purified by chromatography (silica column, eluent: 3% MeOH/DCM) to give 53 mg (33%) of the title compound. $^1$H-NMR (400 MHz; d6-DMSO): δ 1.27 (s, 9H), 2.97 (t, 2H), 3.54 (q, 2H), 6.33 (m, 1H), 6.39 (br s, 1H), 7.02 (d, 1H), 7.62 (m, 2H), 7.86 (d, 1H), 8.20 (s, 1H), 12.88 (s, 1H).

Example 19

3-Tert-butyl-N-(1-(5-(3,4-dichlorophenyl)furan-2-yl)propan-2-yl)-1H-pyrazole-5-carboxamide a) (E)-1-(5-(3,4-dichlorophenyl)furan-2-yl)prop-1-en-2-amine To a stirred solution of 5-(3,4-dichlorophenyl)furfural (1.21 g, 5.0 mmol) in acetic acid (15 ml) was added nitroatehane (0.720 ml, 10.0 mmol) and ammonium acetate (1.16 g, 15.0 mmol). The mixture was stirred at 80° C. overnight. The reaction mixture was poured to ice water. The resulting precipitate was filtered, washed with water and dried under vacuum to obtain 1.38 g (93%) of the title compound. $^1$H-NMR (400 MHz; d6-DMSO): δ 2.62 (s, 3H), 7.37 (d, 1H), 7.46 (d, 1H), 7.79 (m, 2H), 7.98 (s, 1H), 8.09 (d, 1H).

b) 1-(5-(3,4-dichlorophenyl)furan-2-yl)propan-2-amine Hydrochloride

To a solution of (E)-1-(5-(3,4-dichlorophenyl)furan-2-yl) prop-1-en-2-amine (2.72 g, 9.12 mmol) in MeOH (135 ml), EtOAc (100 ml) and 6.5% HCl (g) in MeOH (32 ml) was added 10% Pd/C (1.09 g). The mixture was hydrogenated under pressure (3.3 bar, Parr hydrogenating apparatus) for 7 h. The reaction mixture was filtered through Celite, evaporated and purified by chromatography (CombiFlash, silica column, eluent: 5-20% MeOH/DCM) to yield 0.811 g (29%) of the title compound as an HCl salt. $^1$H-NMR (400 MHz; d6-DMSO): δ 1.21 (d, 3H), 2.90 (dd, 1H), 3.04 (dd, 1H), 3.55 (q, 1H), 6.44 (d, 1H), 7.09 (d, 1H), 7.68 (m, 2H), 7.93 (m, 1H).

c) 3-Tert-butyl-N-(1-(5-(3,4-dichlorophenyl)furan-2-yl)propan-2-yl)-1H-pyrazole-5-carboxamide 5-Tert-butyl-2H-pyrazole-3-carboxylic acid (94 mg; 0.55 mmol) was dissolved in DCM:DMF (4:1, 5 ml). DCC (172 mg; 0.83 mmol) was added. 1-(5-(3,4-dichlorophenyl)furan-2-yl)propan-2-amine (149 mg; 0.55 mmol) was dissolved in 2 ml of DCM and TEA (77 µl, 0.55 mmol) and the resulting solution was added to the reaction mixture. The reaction mixture was stirred overnight at RT. Then DCM (50 ml) was added and organic phase was washed with water (2×30 ml). The organic phase was dried over $Na_2SO_4$, evaporated and purified by chromatography (CombiFlash, $1^{st}$ column silica, eluent: 7.5-100% EtOAc/heptane; $2^{nd}$ column silica, eluent: 0-5% MeOH/DCM) to give 35 mg (15%) of the title compound. $^1$H-NMR (400 MHz; d6-DMSO): δ 1.19 (d, 3H), 1.27 (s, 9H), 2.88 (dd, 1H), 2.98 (dd, 1H), 4.33 (quintet, 1H), 6.29 (d, 1H), 6.33 (s, 1H), 7.00 (d, 1H), 7.60 (m, 2H), 7.83 (d, 1H), 7.89 (d, 1H), 12.84 (s, 1H).

Example 20

N-(2-(5-(3,4-dichlorophenyl)furan-2-yl)ethyl)-3-(pyridin-4-yl)-1H-pyrazole-5-carboxamide To a stirred solution of 5-pyridin-4-yl-4H-pyrazole-3-carboxylic acid (1.78 g, 9.42 mmol) in DCM (10 ml) was added DIPEA (2.46 ml, 14.1 mmol), EDCI (2.71 g, 9.42 mmol) and HOBt (1.91, 14.1 mmol). 2-(5-(3,4-dichlorophenyl)furan-2-yl)-ethanamine hydrochloride (2.75 g, 9.42 mmol) was dissolved in DCM (15 ml) and DIPEA (1.64 ml, 9.42 mmol). The resulting solution was added to the reaction mixture, which was stirred at RT overnight. The reaction mixture was diluted with DCM and washed with saturated aqueous $NaHCO_3$ solution and water. The organic phase was dried over $Na_2SO_4$, evaporated and purified by chromatography (CombiFlash, silica column, eluent 0-15% MeOH/DCM). Product containing fractions were collected, evaporated and crystallized from DCM and re-crystallized from 2% MeOH/DCM and heptane. Thus, 1.18 g (29%) of the title compound was obtained. $^1$H-NMR (400 MHz; d6-DMSO): δ 2.97 (t, 2H), 3.59 (q, 2H), 6.35 (d, 1H), 7.03 (d, 1H), 7.33 (s, 1H), 7.62 (d, 2H), 7.75 (m, 2H), 7.84 (t, 1H), 8.57 (br s, 1H), 8.63 (m, 2H), 13.95 (s, 1H).

Example 21

3-tert-Butyl-N-(2-(5-(3,4-dicyanophenyl)furan-2-yl)ethyl)-1H-pyrazole-5-carboxamide To a stirred solution of 5-tert-Butyl-2H-pyrazole-3-carboxylic acid {2-[5-(3,4-dichloro-phenyl)-furan-2-yl]-ethyl}-amide of Example 18 (128 mg, 0.315 mmol) in DMF/water (99:1, 1 ml) was added zinc cyanide (81 mg, 0.693 mmol), S-Phos (26 mg, 0.063 mmol) and $Pd_2(dba)_3$ (23 mg, 0.025 mmol). The reaction mixture was heated by a microwave reactor at 150° C. for 40 min. 1.0 M NaOH (20 ml) was added and the mixture was extracted with EtOAc (3×20 ml). Combined organic phases were dried over $Na_2SO_4$, evaporated and purified by chromatography (CombiFlash, $1^{st}$ column silica: eluent 0-100% EtOAc/heptane; $2^{nd}$ column C-18 RP: eluent 0-100% MeCN/water) to give 25 mg (20%) of the title compound. $^1$H-NMR (400 MHz; d6-DMSO): δ 1.27 (s, 9H), 2.96 (t, 2H), 3.57 (q, 2H), 6.35 (br s, 1H), 6.44 (d, 1H), 7.31 (d, 1H), 8.07 (dd, 1H), 8.11 (d, 1H), 8.19 (br s, 1H), 8.38 (d, 1H), 12.87 (br s, 1H).

Example 22

N-(2-(5-(3,4-dichlorophenyl)furan-2-yl)ethyl)-3-methyl-1H-pyrazole-5-carboxamide The title compound was prepared using the method of Example 20 starting from 3-methyl-1H-pyrazole-5-carboxylic acid and 2-(5-(3,4-dichlorophenyl)furan-2-yl)ethanamine hydrochloride. Crude product was purified by chromatography (CombiFlash, silica column, eluent: 0-100% EtOAc/heptane) to obtain 301 mg (28%) of the title compound. $^1$H-NMR (400 MHz; d6-DMSO): δ 2.25 (s, 3H), 2.92 (t, 2H), 3.53 (q, 2H), 6.32 (d, 1H), 6.34 (s, 1H), 7.01 (d, 1H), 7.63 (m, 2H), 7.85 (s, 1H), 8.16 (t, 1H), 13.86 (s, 1H).

Example 23

N-(2-(5-(3,4-dicyanophenyl)furan-2-yl)ethyl)-3-methyl-1H-pyrazole-5-carboxamide

The title compound was prepared as in Example 21, but starting from N-(2-(5-(3,4-dichlorophenyl)furan-2-yl)ethyl)-3-methyl-1H-pyrazole-5-carboxamide. Crude product was purified by chromatography (CombiFlash, $1^{st}$ column silica, eluent: 0-10% MeOH/DCM; $2^{nd}$ column C-18 RP, eluent: 0-100% MeCN/water) to obtain 45 mg (16%) of the title compound. $^1$H-NMR (400 MHz; d6-DMSO): δ 2.24 (s, 3H), 2.96 (t, 2H), 3.55 (q, 2H), 6.35 (s, 1H), 6.43 (d, 1H), 7.31 (d, 1H), 8.07 (dd, 1H), 8.12 (d, 1H), 8.20 (br s, 1H), 8.34 (d, 1H), 12.87 (s, 1H).

Example 24

(S/R)—N-(1-(5-(3,4-dichlorophenyl)furan-2-yl)propan-2-yl)-3-methyl-1H-pyrazole-5-carboxamide The title compound was prepared as a racemate using the method of Example 19, but starting from 3-methyl-1H-pyrazole-5-carboxylic acid and 1-(5-(3,4-dichlorophenyl)furan-2-yl)propan-2-amine hydrochloride. Thus, 79 mg (32%) of the title compound was obtained. The enantiomers were separated by chromatography (SFC Minigram, Mettler Toledo) to obtain 16 mg of the other (optical purity 98.8%) (=Compound 24A) and 16 mg of the other (optical purity 98.3%) (=Compound 24B) enantiomer. The absolute configuration of the separated enantiomers was not analysed.
Compound 24A: $^1$H-NMR (400 MHz; $CDCl_3$): δ 1.26 (d, 3H), 2.34 (s, 3H), 2.91 (dd, 1H), 3.01 (dd, 1H), 4.52 (m, 1H), 6.20 (d, 1H), 6.56 (s, 1H), 6.57 (d, 1H), 7.12 (d, 1H), 7.38 (d, 1H), 7.41. (dd, 1H), 7.78 (d, 1H), 10.26 (s, 1H).
Compound 24B: $^1$H-NMR (400 MHz; $CDCl_3$): δ 1.26 (d, 3H), 2.34 (s, 3H), 2.91 (dd, 1H), 3.01 (dd, 1H), 4.52 (m, 1H), 6.20 (d, 1H), 6.56 (s, 1H), 6.57 (d, 1H), 7.12 (d, 1H), 7.38 (d, 1H), 7.41. (dd, 1H), 7.78 (d, 1H), 10.31 (s, 1H).

Example 25

(S/R)—N-(1-(5-(3,4-dichlorophenyl)furan-2-yl)propan-2-yl)-3-(pyridin-4-yl)-1H-pyrazole-5-carboxamide The title compound was prepared as a racemate using the method of Example 19, but starting from 5-pyridin-4-yl-4H-pyrazole-3-carboxylic acid and 1-(5-(3,4-dichlorophenyl)furan-2-yl)propan-2-amine hydrochloride. Thus, 90 mg (31%) of the title compound was obtained. The enantiomers were separated by chromatography (SFC Minigram, Mettler Toledo) to obtain 16 mg of the other (optical purity 100%) (=Compound 25A) and 11 mg of the other (optical purity 100%) (=Compound 25B) enantiomer. The absolute configuration of the separated enantiomers was not analysed.
Compound 25A: $^1$H-NMR (400 MHz; d6-DMSO): δ 1.24 (d, 3H), 2.95 (m, 2H), 4.35 (m, 1H), 6.31 (d, 1H), 7.00 (d, 1H), 7.35 (s, 1H), 7.58 (s, 2H), 7.73 (m, 2H), 7.93 (s, 1H), 8.33 (br s, 1H), 8.63 (d, 2H), 13.88 (s, 1H).

Compound 25B: $^1$H-NMR (400 MHz; d6-DMSO): δ 1.24 (d, 3H), 2.95 (m, 2H), 4.35 (m, 1H), 6.31 (d, 1H), 7.00 (d, 1H), 7.35 (s, 1H), 7.58 (s, 2H), 7.73 (m, 2H), 7.79 (s, 1H), 8.33 (br s, 1H), 8.63 (d, 2H), 13.88 (s, 1H).

Example 26

1-(Pyridin-2-yl)-1H-imidazole-4-carboxylic Acid {2-[5-(3,4-dichlorophenyl)furan-2-yl]ethyl}amide The title compound was synthesized from 1H-Imidazole-4-carboxylic acid {2-[5-(3,4-dichlorophenyl)furan-2-yl]ethyl}amide of Example 15 and 2-bromopyridine by the method described by A. K. Verma et al. Tetrahedron Lett. 48 (2007) 4207. Purification by flash chromatography using CH$_2$Cl$_2$/MeOH as a gradient eluent (100:0-99.9:0.1) gave a product which was triturated in EtOAc at RT to afford the desired product. $^1$H NMR (400 MHz, DMSO-d$_6$): 2.96 (2H, t), 3.59 (2H, m), 6.35 (1H, d), 7.03 (1H, d), 7.44 (1H, m), 7.63 (2H, s), 7.84 (1H, s), 7.95 (1H, distorted d), 8.05 (1H, m), 8.33 (1H, t), 8.43 (1H, d), 8.54 (1H, m), 8.64 (1H, d, $^4$J=1.1 Hz).

Example 27

N-(2-(3-(3,4-dichlorophenyl)-1H-pyrazol-1-yl)ethyl)-3-methyl-1H-pyrazole-5-carboxamide a) 2-(2-(3-(3,4-dichlorophenyl)-1H-pyrazol-1-yl)ethyl)isoindoline-1,3-dione To a cooled (0° C.) suspension of sodium hydride (96 mg, 2.4 mmol) in DMF (1.0 ml) was added 3-(3,4-dichlorophenyl)-1H-pyrazole (0.426 g, 2.0 mmol) as a solution in DMF (2.0 ml). The reaction mixture was stirred at RT for 45 min. To cooled (0° C.) reaction mixture was added N-(2-bromoethyl)phthalimide (0.610 g, 2.4 mmol) as a solution in DMF (1.0 ml). The reaction mixture was stirred at RT overnight. Water (100 ml) was added, and the mixture was extracted with DCM (3×50 ml). Combined organic phases were dried over Na$_2$SO$_4$ and purified by chromatography (CombiFlash, C-18 RP column, eluent: 0-100% MeCN/water) to obtain 0.155 g (20%) of the title compound. $^1$H-NMR (400 MHz; d6-DMSO): δ 3.98 (t, 2H), 4.26 (t, 2H), 6.74 (d, 1H), 7.45 (dd, 1H), 7.50 (d, 1H), 7.55 (d, 1H), 7.82 (m, 5H).

b) 2-(3-(3,4-dichlorophenyl)-1H-pyrazol-1-yl)ethanamine

To a stirred solution of 2-(2-(3-(3,4-dichlorophenyl)-1H-pyrazol-1-yl)ethyl)-isoindoline-1,3-dione (155 mg, 0.40 mmol) in EtOH (4.0 ml) was added hydrazine hydrate (0.194 ml, 4.0 mmol). The reaction mixture was refluxed for 1 h and left to cool down to RT. Water (20 ml) was added and the mixture was extracted with DCM (3×20 ml). Combined organic phases were dried over Na$_2$SO$_4$ and evaporated to yield quantitative amount of the title compound (102 mg, 100%). Product was used in the next step without analysis.

c) N-(2-(3-(3,4-dichlorophenyl)-1H-pyrazol-1-yl)ethyl)-3-methyl-1H-pyrazole-5-carboxamide To a stirred solution of 3-methyl-1H-pyrazole-5-carboxylic acid (104 mg, 0.83 mmol) in DCM (2.0 ml) was added DIPEA (0.144 ml, 0.83 mmol), EDCI (159 mg, 0.83 mmol) and HOBt (112 mg, 0.83 mmol). After 10 min 2-(3-(3,4-dichlorophenyl)-1H-pyrazol-1-yl)ethanamine (102 mg, 0.40 mmol) was added to the reaction mixture as a solution in DCM (2.0 ml). The reaction mixture was stirred at RT overnight. The reaction mixture was diluted with DCM and washed with saturated aqueous NaHCO$_3$ solution and water. The organic phase was dried over Na$_2$SO$_4$, evaporated and purified by chromatography (CombiFlash, 1$^{st}$ column silica, eluent: 0-10% MeOH/DCM; 2$^{nd}$ column C-18 RP, eluent: 0-100% MeCN/water) to obtain 65 mg (45%) of the title compound. 1H-NMR (400 MHz; d6-DMSO): δ 2.24 (s, 3H), 3.64 (q, 2H), 4.31 (t, 2H), 6.36 (s, 1H), 6.81 (d, 1H), 7.65 (d, 1H), 7.77 (d, 1H), 7.80 (dd, 1H), 8.00 (d, 1H), 8.23 (s, 1H), 12.88 (s, 1H).

Example 28

N-(2-(3-(4-cyano-3-methylphenyl)-1H-pyrazol-1-yl)ethyl)-3-(pyridin-4-yl)-1H-pyrazole-5-carboxamide a) 2-methyl-4-(1H-pyrazol-3-yl)benzonitrile The title compound was synthesized using the method of Example 34(b), but starting from 4-bromo-2-methylbenzonitrile and 1-(tetrahydro-2H-pyran-2-yl)-5-(4,4,5,5-tetramethyl-1,3,2-dioxaborolan-2-yl)-1H-pyrazole. 1H-NMR (400 MHz; CDCl$_3$): δ 2.60 (s, 3H), 6.69 (d, 1H), 7.64 (m, 2H), 7.70 (d, 1H), 7.78 (s, 1H), 10.47 (br s, 1H).

b) 4-(1-(2-(1,3-dioxoisoindolin-2-yl)ethyl)-1H-pyrazol-3-yl)-2-methylbenzonitrile 2-Methyl-4-(1H-pyrazol-3-yl)benzonitrile (0.949 g, 5.2 mmol) was reacted with N-(2-bromoethyl)phthalimide (1.58 g, 6.2 mmol) using the method of Example 27(a). Crude product was purified by chromatography (CombiFlash, silica column, eluent: 0-100% EtOAc/heptane) to yield 0.590 g (32%) of the title compound. 1H-NMR (400 MHz; d6-DMSO): δ 2.36 (s, 3H), 3.99 (t, 2H), 4.44 (t, 2H), 6.76 (d, 1H), 7.44 (s, 1H), 7.46 (m, 1H), 7.62 (d, 1H), 7.83 (m, 5H).

c) 4-(1-(2-aminoethyl)-1H-pyrazol-3-yl)-2-methylbenzonitrile 4-(1-(2-(1,3-Dioxoisoindolin-2-yl)ethyl)-1H-pyrazol-3-yl)-2-methylbenzonitrile (0.590 g, 1.66 mmol) was treated with hydrazine hydrate using the method of Example 27(b). Thus, 362 mg (96%) of the title compound was obtained. 1H-NMR (400 MHz; d6-DMSO): δ 2.52 (s, 3H), 2.95 (t, 2H), 4.13 (t, 2H), 6.84 (d, 1H), 7.77 (m, 2H), 7.82 (d, 1H), 7.89 (m, 1H).

d) N-(2-(3-(4-cyano-3-methylphenyl)-1H-pyrazol-1-yl)ethyl)-3-(pyridin-4-yl)-1H-pyrazole-5-carboxamide The title compound was synthesized from 5-pyridin-4-yl-4H-pyrazole-3-carboxylic acid (303 mg, 1.60 mmol) and 4-(1-(2-aminoethyl)-1H-pyrazol-3-yl)-2-methylbenzonitrile (362 mg, 1.60 mmol) using the method of Example 34(d). Crude product was purified by chromatography (CombiFlash, silica column, eluent: 0-20% MeOH/DCM) to obtain 44 mg (6%) of the title compound. 1H-NMR (400 MHz; d6-DMSO): δ 2.49 (s, 3H), 3.71 (q, 2H), 4.37 (t, 2H), 6.84

(d, 1H), 7.31 (s, 1H), 7.74 (m, 2H), 7.70 (s, 1H), 7.79 (dd, 1H), 7.83 (d, 1H), 7.88 (s, 1H), 8.55 (br s, 1H), 8.63 (m, 2H), 13.99 (s, 1H).

Example 29

(S)—N-(1-(3-(4-cyano-3-methylphenyl)-1H-pyrazol-1-yl)propan-2-yl)-3-(pyridin-4-yl)-1H-pyrazole-5-carboxamide a) (S)-4-(1-(2-(1,3-dioxoisoindolin-2-yl)propyl)-1H-pyrazol-3-yl)-2-methylbenzonitrile 2-Methyl-4-(1H-pyrazol-3-yl)benzonitrile (2.35 g, 12.2 mmol) was reacted with (S)-2-(1-bromopropan-2-yl)isoindoline-1,3-dione (3.61 g, 13.5 mmol) using the method of Example 27(a). Crude product was purified by chromatography (CombiFlash, silica column, eluent: 0-100% EtOAc/heptane) to yield 1.15 g (25%) of the title compound. 1H-NMR (400 MHz; CDCl$_3$): δ 1.59 (d, 3H), 2.47 (s, 3H), 4.41 (m, 1H), 4.83 (m, 2H), 6.46 (d, 1H), 7.39 (m, 2H), 7.47 (m, 2H), 7.69 (m, 2H), 7.78 (m, 2H).

b) (S)-4-(1-(2-aminopropyl)-1H-pyrazol-3-yl)-2-methylbenzonitrile (S)-4-(1-(2-(1,3-dioxoisoindolin-2-yl)propyl)-1H-pyrazol-3-yl)-2-methylbenzonitrile (481 mg, 1.3 mmol) was treated with hydrazine hydrate using the method of Example 27(b). Crude product was purified by chromatography (CombiFlash, silica column, eluent: 0-20% MeOH/DCM) to obtain 59 mg (19%) of the title compound. 1H-NMR (400 MHz; d6-DMSO): δ 0.96 (d, 3H), 2.52 (s, 3H), 3.23 (m, 1H), 4.00 (m, 2H), 6.85 (d, 1H), 7.77 (m, 2H), 7.81 (d, 1H), 7.89 (m, 1H).

c) (S)—N-(1-(3-(4-cyano-3-methylphenyl)-1H-pyrazol-1-yl)propan-2-yl)-3-(pyridin-4-yl)-1H-pyrazole-5-carboxamide The title compound was synthesized from 5-pyridin-4-yl-4H-pyrazole-3-carboxylic acid (47 mg, 0.25 mmol) and (S)-4-(1-(2-aminopropyl)-1H-pyrazol-3-yl)-2-methylbenzonitrile (59 mg, 0.25 mmol) using the method of Example 34(d). Crude product was purified by chromatography (CombiFlash, silica column, eluent: 0-20% MeOH/DCM) to obtain 41 mg (40%) of the title compound. 1H-NMR (400 MHz; MeOD): δ 1.24 (d, 3H), 2.52 (s, 3H), 4.32 (m, 2H), 4.53 (m, 1H), 6.59 (d, 1H), 7.15 (m, 1H), 7.36 (s, 2H), 7.53 (d, 1H), 7.58 (m, 2H), 7.70 (m, 2H), 8.53 (br s, 1H), 8.56 (d, 1H).

Example 30

(R)—N-(1-(3-(4-cyano-3-methylphenyl)-1H-pyrazol-1-yl)propan-2-yl)-3-(pyridin-4-yl)-1H-pyrazole-5-carboxamide a) (R)-2-(1-hydroxypropan-2-yl)isoindoline-1,3-dione D-Alaninol (3.90 ml, 50 mmol) and phthalic anhydride (7.41 g, 50 mmol) were heated at 160° C. for 30 min. To cooled reaction mixture was added ice water and DCM. Organic phase was collected and the water phase was extracted with DCM. Combined organic phases were dried over Na$_2$SO$_4$ and evaporated to obtain 8.75 g (85%) of the title compound. 1H-NMR (400 MHz; d6-DMSO): δ 1.32 (d, 3H), 3.54 (m, 1H), 3.84 (m, 1H), 4.26 (m, 1H), 4.91 (m, 1H), 7.84 (m, 4H).

b) (R)-2-(1-bromopropan-2-yl)isoindoline-1,3-dione (R)-2-(1-hydroxypropan-2-yl)isoindoline-1,3-dione (8.75 g, 43 mmol) and phosphorus tribromide (2.73 ml, 29 mmol) were heated at 175° C. for 50 min. To cooled reaction mixture was added ice (50 ml). Thus formed precipitate was filtered, washed with water and dried under vacuum to obtain 11.1 g (97%) of the title compound. 1H-NMR (400 MHz; d6-DMSO): δ 1.50 (d, 3H), 3.85 (m, 1H), 4.01 (m, 1H), 4.49 (m, 1H), 7.88 (m, 4H).

c) (R)-4-(1-(2-(1,3-dioxoisoindolin-2-yl)propyl)-1H-pyrazol-3-yl)-2-methylbenzonitrile 2-Methyl-4-(1H-pyrazol-3-yl)benzonitrile (2.23 g, 12.2 mmol) was reacted with (R)-2-(1-bromopropan-2-yl)isoindoline-1,3-dione (3.92 g, 14.6 mmol) using the method of Example 27(a). Crude product was purified by chromatography (CombiFlash, silica column, eluent: 0-100% EtOAc/heptane) to yield 0.753 g (17%) of the title compound. Product was used in the next step without analysis.

d) (R)-4-(1-(2-aminopropyl)-1H-pyrazol-3-yl)-2-methylbenzonitrile (R)-4-(1-(2-(1,3-dioxoisoindolin-2-yl)propyl)-1H-pyrazol-3-yl)-2-methylbenzonitrile (753 mg, 2.0 mmol) was treated with hydrazine hydrate using the method of Example 27(b). Crude product was purified by chromatography (CombiFlash, silica column, eluent: 0-20% MeOH/DCM) to obtain 82 mg (17%) of the title compound. 1H-NMR (400 MHz; d6-DMSO): δ 0.96 (d, 3H), 2.52 (s, 3H), 3.22 (m, 1H), 3.99 (m, 2H), 6.84 (d, 1H), 7.77 (m, 2H), 7.81 (d, 1H), 7.89 (m, 1H).

e) (R)—N-(1-(3-(4-cyano-3-methylphenyl)-1H-pyrazol-1-yl)propan-2-yl)-3-(pyridin-4-yl)-1H-pyrazole-5-carboxamide The title compound was synthesized from 5-pyridin-4-yl-4H-pyrazole-3-carboxylic acid (13 mg, 0.069 mmol) and (R)-4-(1-(2-aminopropyl)-1H-pyrazol-3-yl)-2-methylbenzonitrile (17 mg, 0.071 mmol) using the method of Example 34(d). Crude product was purified by chromatography (CombiFlash, silica column, eluent: 0-20% MeOH/DCM) to obtain 19 mg (67%) of the title compound. 1H-NMR (400 MHz; d6-DMSO): δ 1.17 (d, 3H), 2.48 (s, 3H), 4.31 (m, 2H), 4.47 (m, 1H), 6.82 (d, 1H), 7.31 (s, 1H), 7.75 (m, 4H), 7.81 (d, 1H), 7.85 (s, 1H), 8.40 (d, 1H), 8.63 (m, 2H), 13.92 (br s, 1H).

Example 31

N-(2-(3-(4-cyano-3-methylphenyl)-1H-pyrazol-1-yl)ethyl)-3-methyl-1H-pyrazole-5-carboxamide The title compound was synthesized as using the method of Example 28(d) starting from 3-methyl-1H-pyrazole-5-carboxylic acid. Crude product was purified by chromatography (CombiFlash, 1$^{st}$ column silica, eluent: 0-15% MeOH/DCM; 2$^{nd}$ column C-18 RP, eluent: 0-100% MeCN/water) to obtain 39 mg (42%) of the title compound. 1H-NMR (400 MHz; d6-DMSO): δ 2.24 (s, 3H), 2.52 (s, 3H), 3.65 (q, 2H), 4.33 (t, 2H), 6.36 (s, 1H), 6.83 (d, 1H), 7.79 (m, 3H), 7.88 (s, 1H), 8.24 (br s, 1H), 12.85 (br s, 1H).

Example 32

(S)—N-(1-(3-(4-cyano-3-methylphenyl)-1H-pyrazol-1-yl)propan-2-yl)-3-(furan-2-yl)-1H-pyrazole-5-carboxamide The title compound was synthesized using the method of Example 29, but replacing 5-pyridin-4-yl-4H-pyrazole-3-carboxylic acid with 5-(2-furyl)-4H-pyrazole-3-carboxylic acid. Crude product was purified by chromatography (CombiFlash, silica column, eluent: 0-100% EtOAc/heptane) to obtain 39 mg (75%) of the title compound. 1H-NMR (400 MHz; d6-DMSO): δ 1.14 (d, 3H), 2.49 (s, 3H), 4.30 (m, 2H), 4.45 (m, 1H), 6.61 (m, 1H), 6.80 (s, 1H), 6.82 (d, 1H), 6.91 (s, 1H), 7.76 (m, 3H), 7.80 (d, 1H), 7.85 (s, 1H), 8.36 (d, 1H), 13.69 (s, 1H).

Example 33

(R)—N-(1-(3-(4-cyano-3-methylphenyl)-1H-pyrazol-1-yl)propan-2-yl)-3-(morpholine-4-carbonyl)-1H-pyrazole-5-carboxamide The title compound was synthesized using the method of Example 30, but replacing 5-pyridin-4-yl-4H-pyrazole-3-carboxylic acid with 3,5-pyrazoledicarboxylic acid. Thus obtained (R)-5-(1-(3-(4-cyano-3-methylphenyl)-1H-pyrazol-1-yl)propan-2-ylcarbamoyl)-1H-pyrazole-3-carboxylic acid was coupled with morpholine according to synthesis of 5-(piperazine-1-carbonyl)-2H-pyrazole-3-carboxylic acid {2-[5-(3,4-dichlorophenyl)furan-2-yl]ethyl}amide, Example 1, but replacing piperazine with morpholine. Crude product was purified by chromatography (CombiFlash, 1$^{st}$ column silica, eluent: 0-10% MeOH/DCM; 2$^{nd}$ column C-18 RP, eluent: 0-100% MeCN/water) to obtain 24 mg (45%) of the title compound. 1H-NMR (400 MHz; CDCl$_3$): δ 1.25 (d, 3H), 2.60 (s, 3H), 3.79 (m, 8H), 4.29 (dd, 1H), 4.42 (dd, 1H), 4.60 (m, 1H), 6.61 (d, 1H), 7.02 (s, 1H), 7.47 (d, 1H), 7.63 (m, 2H), 7.72 (d, 1H), 7.79 (s, 1H), 11.09 (s, 1H).

Example 34

(S)-3-acetyl-N-(1-(3-(3-chloro-4-cyanophenyl)-1H-pyrazol-1-yl)propan-2-yl)-1H-pyrazole-5-carboxamide a) 2-Chloro-4-(1-(tetrahydro-2H-pyran-2-yl)-1H-pyrazol-5-yl)benzonitrile 1-(tetrahydro-2H-pyran-2-yl)-5-(4,4,5,5-tetramethyl-1,3,2-dioxaborolan-2-yl)-1H-pyrazole (6.5 g; 23.28 mmol) and 4-bromo-2-chlorobenzonitrile (4 g; 18.48 mmol) were dissolved in THF (65 ml). To this mixture bis(triphenylphosphine)palladium(II) chloride (0.65 g; 0.92 mmol), sodium carbonate (4.7 g; 44.3 mmol) and 18 ml of water were added and the reaction mixture was stirred at 35° C. for 2.5 h. The solvents were distilled to almost dryness and water (48 ml) was added. After 30 min of stirring the precipitated product was filtered and 32 ml of ethanol was added to the precipitation. The suspension was stirred for 15 min at RT and 30 min at −10° C. before filtering to give 3.7 g of the product. $^1$H-NMR (400 MHz; d6-DMSO): δ 1.63-1.54 (m, 3H), 1.84-1.80 (m, 1H), 1.97-1.94 (m, 1H), 2.39-2.35 (m, 1H), 3.63-3.57 (m, 1H), 3.99 (m, 1H), 5.32-5.27 (m, 1H), 6.72 (d, 1H), 7.65 (d, 1H), 7.72 (m, 1H), 7.92 (d, 1H), 8.14 (d, 1H).

b) 2-Chloro-4-(1H-pyrazol-5-yl)benzonitrile

2-Chloro-4-(1-(tetrahydro-2H-pyran-2-yl)-1H-pyrazol-5-yl)benzonitrile (3.67 g; 12.75 mmol) was added to 8 ml of ethanol under nitrogen atmosphere. 15.5 ml of ~10% HCl (g) in EtOH was slowly added and the temperature was raised to 30° C. where the mixture was stirred for 1 h. The temperature was then lowered to −10° C. and the mixture was again stirred for 30 min after which the product was precipitated as its HCl salt and was filtered and washed twice with 2 ml of ethanol. The product was dried in vacuo at +40° C. Yield 2.8 g. 2-Chloro-4-(1H-pyrazol-5-yl)benzonitrile hydrochloride (2.8 g; 11.47 mmol) was added to a mixture of 8 ml of water and 14 ml of MeOH under nitrogen atmosphere. To this 50% sodium hydroxide (1.5 ml; 28.7 mmol) was added keeping the temperature under 25° C. during the addition. The mixture was stirred for 2 h, the precipitate filtered and washed twice with 3 ml of lukewarm water. The product was dried in vacuo at +40° C. Yield 1.97 g. $^1$H-NMR (400 MHz; d6-DMSO): δ 6.99 (t, 1H), 7.89 (m, 1H), 7.99 (d, 2H), 8.15 (s, 1H), 13.27 (s, 1H).

c) (S)-4-(1-(2-aminopropyl)-1H-pyrazol-3-yl)-2-chlorobenzonitrile

2-Chloro-4-(1H-pyrazol-3-yl)benzonitrile (4.00 g; 19.64 mmol), (S)-tert-butyl-1-hydroxypropan-2-yl carbamate (3.79 g; 21.61 mmol) and triphenylphosphine were dissolved in dry THF under nitrogen atmosphere and stirred. Diisopropylazo-dicarboxylate (7.74 ml; 39.3 mmol) was added dropwise and the reaction flask was cooled by ice bath. The reaction was stirred at RT overnight (18 h) and evaporated to dryness. For Boc deprotection 200 ml of 10% HCl/EtOH solution was added to the evaporation residue, stirred for 20 h at RT and evaporated to dryness. 100 ml of water was added to the evaporation residue and washed with 3×120 ml of DCM to remove reactant residues. pH of water phase was adjusted to ~12 by addition of 2 M NaOH, washed with 3×80 ml of DCM and organic phase dried over Na$_2$SO$_4$. Organic phase was filtered and evaporated to give 2.605 g of the title compound.

d) (S)-3-acetyl-N-(1-(3-(3-chloro-4-cyanophenyl)-1H-pyrazol-1-yl)propan-2-yl)-1H-pyrazole-5-carboxamide 3-Acetyl-1H-pyrazole-5-carboxylic acid (0.59 g; 3.84 mmol) and DIPEA (1.0 ml; 5.75 mmol) were dissolved in 4 ml of dry DCM. Anhydrous HOBt (0.78 g; 5.75 mmol) and EDCI (1.10 g; 5.75 mmol) were added at RT. (S)-4-(1-(2-aminopropyl)-1H-pyrazol-3-yl)-2-chlorobenzonitrile (1.00 g; 3.84 mmol) was dissolved in 4 ml of DCM and the reaction was stirred for overnight at RT. 40 ml of DCM was added and organic layer washed with 3×15 ml of water. Combined water phases were washed with 2×20 ml of DCM. Both organic phases were dried over Na$_2$SO$_4$, filtered and evaporated to dryness. Both crude product fractions were combined and purified by CombiFlash (2% MeOH in DCM). Product fractions were combined and evaporated to give 497 mg of product. $^1$H-NMR (400 MHz; d6-DMSO): δ 1.16 (d, 3H, J=6.7 Hz), 2.49 (s, 3H), 4.31 (m, 2H), 4.46 (sept, 1H, J=6.7 Hz), 6.93 (d, 1H, J=2.4 Hz), 7.31 (s, 1H), 7.81 (d, 1H, J=2.4 Hz), 7.92 (d, 1H, J=7.9 Hz), 7.97 (d, 1H, J=8.1 Hz), 8.03 (d, 1H, J=1.3 Hz), 8.48 (d, 1H, J=8.5 Hz), 14.16 (s, 1H).

Example 35

N-(2-(3-(3-chloro-4-cyanophenyl)-1H-pyrazol-1-yl)ethyl)-5-(morpholine-4-carbonyl)pyrazine-2-carboxamide a) 4-(1-(2-aminoethyl)-1H-pyrazol-3-yl)-2-chlorobenzonitrile The title compound was prepared using the method of Example 34(c) starting from 2.3 g of 2-chloro-4-(1H-pyrazol-5-yl)benzonitrile hydrochloride, 1.7 ml dipea and 1.7 g tert-butyl 2-hydroxyethylcarbamate yielding 2.08 g of the product. $^1$H-NMR (400 MHz; $d_6$-DMSO): δ 1.56 (s, 2H), 2.97 (t, 2H), 4.13-4.17 (t, 2H), 6.97 (s, 1H), 7.87 (d, 1H), 7.93-8.02 (m, 2H), 8.10 (d, 1H).

b) 5-(2-(3-(3-chloro-4-cyanophenyl)-1H-pyrazol-1-yl)ethylcarbamoyl)pyrazine-2-carboxylic Acid Pyrazine-2,5-dicarboxylic acid (0.53 g; 3.18 mmol), anhydrous HOBt (0.43 g; 3.18 mmol), 1-(3-dimethylaminopropyl)-3-ethylcarbodiimide hydrochloride (0.61 g; 3.18 mmol) and DIPEA (0.55 ml; 3.18 mmol) were dissolved in 5 ml of dry DCM. 4-(1-(2-Aminoethyl)-1H-pyrazol-3-yl)-2-chlorobenzonitrile (0.6 g; 2.12 mmol) and DIPEA (0.55 ml; 3.18 mmol) were dissolved in 5 ml of dry DCM and added dropwise to the previous mixture. The reaction mixture was stirred overnight after which pyrazine-2,5-dicarboxylic acid (0.27 g; 1.59 mmol), anhydrous HOBt (0.52 g; 3.81 mmol), 1-(3-dimethylaminopropyl)-3-ethylcarbodiimide hydrochloride (0.41 g: 2.12 mmol) and DIPEA (0.37 ml; 2.12 mmol) were added to drive the reaction to completion. After 2.5 h the mixture was diluted with 20 ml of DCM. After addition of 10 ml of water, the product precipitated and was filtered yielding 0.42 g of crude product which was used without further purification.

c) N-(2-(3-(3-chloro-4-cyanophenyl)-1H-pyrazol-1-yl)ethyl)-5-(morpholine-4-carbonyl)pyrazine-2-carboxamide 5-(2-(3-(3-chloro-4-cyanophenyl)-1H-pyrazol-1-yl)ethylcarbamoyl)pyrazine-2-carboxylic acid (0.11 g; 0.29 mmol), 1-(3-dimethylaminopropyl)-3-ethylcarbodiimide hydrochloride (0.083 g: 0.43 mmol), anhydrous HOBt (0.058 g; 0.43 mmol), dipea (0.075 ml; 0.43 mmol) and morpholine (0.025 g; 0.29 mmol) were dissolved in 5 ml of dry DCM and stirred overnight. The solution was diluted with 10 ml of DCM and washed with 3×5 ml water. The combined water phases were extracted with 2×5 ml DCM and the combined organic phases dried over $Na_2SO_4$, filtered and evaporated to dryness. The product was purified using flash chromatography DCM/MeOH as gradient eluent. Yield 0.06 g. $^1$H-NMR (400 MHz; $d_6$-DMSO): δ 3.45 (t, 2H), 3.56 (t, 2H), 3.69 (s, 4H), 3.76-3.80 (m, 2H), 4.42 (t, 2H), 6.97 (d, 1H), 7.87 (d, 1H), 7.94-8.01 (m, 2H), 8.01 (s, 1H), 8.93 (d, 1H), 9.13 (s, 1H), 9.22-9.25 (t, 1H).

Example 36

N-(2-(3-(3-chloro-4-cyanophenyl)-1H-pyrazol-1-yl)ethyl)-5-oxo-1-phenyl-2,5-dihydro-1H-pyrazole-3-carboxamide a) Methyl 5-oxo-1-phenyl-2,5-dihydro-1H-pyrazole-3-carboxylate Phenylhydrazine (0.5 g; 4.62 mmol), acetylenedicarboxylic acid dimethyl ester (0.66 g; 4.62 mmol) and 4-toluenesulfonic acid pyridine salt (1.16 g; 4.62 mmol) were dissolved in 7 ml of dry THF under nitrogen atmosphere and the solution was stirred for 2 h at RT after which 7 ml of 10% HCl (g) in EtOAc was added and the mixture heated at 67° C. for 5 h. The reaction mixture evaporated to dryness and 6 ml of DCM added to the residue. The organic phase was washed with 8 ml of water and the combined water phases were extracted with 2×6 ml of DCM. The combined organic phases were once more washed with 12 ml of water, dried over $Na_2SO_4$, filtered and evaporated to dryness to give 0.35 g of the product which was used as such without further purification.

b) 5-Oxo-1-phenyl-2,5-dihydro-1H-pyrazole-3-carboxylic Acid

Methyl 5-oxo-1-phenyl-2,5-dihydro-1H-pyrazole-3-carboxylate (0.35 g; 1.60 mmol) in 5 ml of 2M NaOH solution was heated at 60° C. for 2 h after which the reaction mixture was made acidic with 1.5 ml of concentrated HCl which caused the product to form a yellow precipitate. Filtering gave 0.18 g of the product. $^1$H-NMR (400 MHz; $d_6$-DMSO): δ 5.97 (s, 1H), 7.33-7.37 (m, 1H), 7.48-7.52 (m, 2H), 7.74 (m, 2H).

c) N-(2-(3-(3-chloro-4-cyanophenyl)-1H-pyrazol-1-yl)ethyl)-5-oxo-1-phenyl-2,5-dihydro-1H-pyrazole-3-carboxamide 5-Oxo-1-phenyl-2,5-dihydro-1H-pyrazole-3-carboxylic acid (0.05 g; 0.24 mmol), HOBt (0.049 g; 0.37 mmol) and 1-(3-dimethylaminopropyl)-3-ethylcarbodiimide hydrochloride (0.07 g; 0.37 mmol) were added to 2.5 ml of DCM. To this a mixture of 4-(1-(2-aminoethyl)-1H-pyrazol-3-yl)-2-chlorobenzonitrile (0.06 g; 0.24 mmol) and DIPEA (0.064 ml; 0.37 mmol) was added dropwise and the mixture was stirred overnight after which 10 ml of DCM was added. The mixture was washed with 3×5 ml of water and the combined water phases were extracted with 2×5 ml of DCM. The combined organic layers were dried over $Na_2SO_4$, filtered and evaporated to dryness. The product was purified with flash chromatography using DCM/MeOH as gradient eluent. The combined fractions gave 18 mg of the product. $^1$H-NMR (400 MHz; $d_6$-DMSO): δ 1.23 (s, 1H), 3.65-3.70 (m, 2H), 4.37 (t, 2H), 5.83 (s, 1H), 6.97 (d, 1H), 7.31-7.35 (t, 1H), 7.45-7.49 (t, 2H), 7.76 (d, 2H), 7.85-7.89 (m, 2H), 7.94-7.96 (m, 1H), 8.09 (d, 1H), 8.28 (m, 1H).

Example 37

3-Methyl-N-(2-(3-(8-nitroisoquinolin-5-yl)-1H-pyrazol-1-yl)ethyl)-1H-pyrazole-5-carboxamide a) 8-Nitro-5-(1-(tetrahydro-2H-pyran-2-yl)-1H-pyrazol-5-yl)isoquinoline The title compound was prepared using the method of Example 34(a) starting from 0.5 g of 5-bromo-8-nitroisoquinoline. Yield 0.49 g. $^1$H-NMR (400 MHz; d$_6$-DMSO): δ 1.43-1.51 (m, 3H), 1.80-1.89 (m, 2H), 2.32-2.33 (m, 1H), 3.25-3.27 (m, 1H), 3.76-3.78 (m, 1H), 5.06 (d, 1H), 6.65 (d, 1H), 6.68 (d, 1H), 7.78 (d, 1H), 8.02 (d, 1H), 8.54 (d, 1H), 8.72 (d, 1H), 9.84 (s, 1H).

b) 8-Nitro-5-(1H-pyrazol-5-yl)isoquinoline

The title compound was prepared from 8-nitro-5-(1-(tetrahydro-2H-pyran-2-yl)-1H-pyrazol-5-yl)isoquinoline (0.49 g) using the method of Example 34(b). Yield 0.35 g. $^1$H-NMR (400 MHz; d$_6$-DMSO): δ 6.92 (d, 1H), 8.00 (br s, 1H), 8.18 (d, 1H), 8.48 (d, 1H), 8.75 (d, 1H), 8.87 (br s, 1H), 9.84 (s, 1H), 13.50 (br s, 1H).

c) 2-(3-(Isoquinolin-5-yl)-1H-pyrazol-1-yl)ethanamine

To 0.50 g of 8-nitro-5-(1H-pyrazol-5-yl)isoquinoline was added 5 ml of dry DMF and the mixture was stirred at RT for 30 min. To this was added 0.65 g of 2-(tert-butoxycarbonylamino)ethyl methanesulfonate diluted to 1.5 ml of dry DMF and the mixture was microwaved for 30 min at 160° C. After pouring the mixture to water, it was extracted with EtOAc. Combined organic phases were washed with water and brine, dried with Na$_2$SO$_4$ and evaporated. Crude product was purified by CombiFlash (5% MeOH in DCM). Product fractions were combined and evaporated to give 0.59 g of Boc-protected product. For Boc deprotection 8 ml of 10% HCl/EtOH solution was added to the evaporation residue, stirred at RT until disappearance of starting material by TLC. 3 ml of diethylether was added to the mixture and the precipitate was filtered, washed with diethylether and dried to give 0.30 g of the product as HCl-salt. $^1$H-NMR (400 MHz; d$_6$-DMSO): δ 1.57 (br s, 2H), 3.04 (t, 2H), 4.25 (t, 2H), 6.90 (d, 1H), 8.00 (d, 1H), 8.17 (d, 1H), 8.47 (d, 1H), 8.75 (d, 1H), 8.91 (d, 1H), 9.83 (s, 1H).

d) 3-Methyl-N-(2-(3-(8-nitroisoquinolin-5-yl)-1H-pyrazol-1-yl)ethyl)-1H-pyrazole-5-carboxamide The title compound was prepared from 2-(3-(Isoquinolin-5-yl)-1H-pyrazol-1-yl)ethanamine (0.15 g) and 3-methyl-1H-pyrazole-5-carboxylic acid (0.080 g) using the method of Example 34(d). Yield 0.15 g. $^1$H-NMR (400 MHz; d$_6$-DMSO): δ 2.25 (s, 3H), 3.75 (t, 2H), 4.56 (t, 2H), 6.35 (s, 1H), 6.88 (d, 1H), 7.96 (d, 1H), 8.16 (d, 1H), 8.21 (br s, 1H), 8.47 (d, 1H), 8.62 (d, 1H), 8.88 (d, 1H), 9.82 (s, 1H), 12.90 (br s, 1H).

Example 38

3-(Furan-2-yl)-N-(2-(3-(2-methoxy-4-nitrophenyl)-1H-pyrazol-1-yl)ethyl)-1H-pyrazole-5-carboxamide a) 5-(2-Methoxy-4-nitrophenyl)-1-(tetrahydro-2H-pyran-2-yl)-1H-pyrazole The title compound was prepared using the method of Example 34(a) starting from 2.46 g of 1-iodo-2-methoxy-4-nitrobenzene. Yield 1.88 g. $^1$H-NMR (400 MHz; d$_6$-DMSO): δ 1.41-1.63 (m, 3H), 1.80-1.87 (m, 1H), 1.90-1.98 (m, 1H), 2.26-2.38 (m, 1H), 3.35-3.42 (m, 1H), 3.80-3.85 (m, 1H), 3.92 (s, 3H), 5.05 (d, 1H), 6.44 (d, 1H), 7.60 (d, 1H), 7.61 (d, 1H), 7.91 (d, 1H), 7.95 (d, 1H).

b) 5-(2-Methoxy-4-nitrophenyl)-1H-pyrazole

The title compound was prepared from 1.88 g of 5-(2-methoxy-4-nitrophenyl)-1-(tetrahydro-2H-pyran-2-yl)-1H-pyrazole using the method of Example 34(b). Yield 1.32 g. $^1$H-NMR (400 MHz; d$_6$-DMSO): δ 4.02 (s, 3H), 6.90 (d, 1H), 7.82-7.86 (m, 3H), 8.21 (d, 1H), 13.2 (br s, 1H).

c) 2-(3-(2-Methoxy-4-nitrophenyl)-1H-pyrazol-1-yl)ethanamine

The title compound was prepared from 5-(2-Methoxy-4-nitrophenyl)-1H-pyrazole (1.00 g) and 2-(tert-butoxycarbonylamino)ethyl methanesulfonate (1.42 g) using the method of Example 37(c). Yield 0.24 g (as HCl-salt). $^1$H-NMR (400 MHz; d$_6$-DMSO): δ 3.32 (t, 2H), 4.02 (s, 3H), 4.47 (t, 2H), 6.94 (d, 1H), 7.88-7.93 (m, 3H), 8.12 (br s, 2H), 8.22 (d, 1H).

d) 3-(Furan-2-yl)-N-(2-(3-(2-methoxy-4-nitrophenyl)-1H-pyrazol-1-yl)ethyl)-1H-pyrazole-5-carboxamide The title compound was prepared from 2-(3-(2-Methoxy-4-nitrophenyl)-1H-pyrazol-1-yl)ethanamine (0.11 g) and 3-(furan-2-yl)-1H-pyrazole-5-carboxylic acid (0.079 g) using the method of Example 34(d). Yield 0.11 g. $^1$H-NMR (400 MHz; d$_6$-DMSO): δ 3.71 (t, 2H), 4.01 (s, 3H), 4.39 (t, 2H), 6.57-6.68 (m, 2H), 6.85-6.89 (m, 2H), 7.76-7.93 (m, 4H), 8.15-8.22 (m, 1H), 8.53 (br s, 1H), 13.71 (br s, 1H).

Example 39

N-(2-(3-(3-cyano-4-nitrophenyl)-1H-pyrazol-1-yl)ethyl)-3-(pyridin-2-yl)-1H-pyrazole-5-carboxamide a) 2-Nitro-5-(1-(tetrahydro-2H-pyran-2-yl)-1H-pyrazol-5-yl)benzonitrile 5-Chloro-2-nitrobenzonitrile (1.5 g), 1-(tetrahydro-2H-pyran-2-yl)-5-(4,4,5,5-tetramethyl-1,3,2-dioxaborolan-2-yl)-1H-pyrazole (2.74 g), PEPPSI ((1,3-bis(2,6-diisopropylphenyl)imidazol-2-ylidene) (3-chloropyridyl)palladium(ii) dichloride) (0.11 g), K$_2$CO$_3$ (2.27 g) in DMF (30 ml) and water (3 ml) was stirred under argon at 90° C. for 2.5 h. After pouring the mixture to water, it was extracted with EtOAc. Combined organic phases were washed with 5% NaHCO$_3$, water and brine, dried with Na$_2$SO$_4$ and evaporated. The residue was triturated with ethanol. The precipitate was filtered and washed with water. Yield 1.96 g. $^1$H-NMR (400 MHz; d$_6$-DMSO): δ 1.50-1.65 (m, 3H), 1.83-1.87 (m, 1H), 1.95-1.99 (m, 1H), 2.33-2.42 (m, 1H), 3.60-3.67 (m, 1H), 3.95-4.00 (m, 1H), 5.34 (d, 1H), 6.82 (d, 1H), 7.68 (d, 1H), 8.11 (dd, 1H), 8.32 (d, 1H), 8.54 (d, 1H).

b) 2-nitro-5-(1H-pyrazol-5-yl)benzonitrile

The title compound was prepared from 1.96 g of 2-nitro-5-(1-(tetrahydro-2H-pyran-2-yl)-1H-pyrazol-5-yl)benzonitrile using the method of Example 34(b). Yield 1.40 g. $^1$H-NMR (400 MHz; d$_6$-DMSO): δ 7.10 (d, 1H), 7.90 (d, 1H), 8.37 (dd, 1H), 8.43 (d, 1H), 8.54 (d, 1H), 13.4 (br s, 1H).

c) 5-(1-(2-aminoethyl)-1H-pyrazol-3-yl)-2-nitrobenzonitrile

The title compound was prepared from 2-nitro-5-(1H-pyrazol-5-yl)benzonitrile (1.00 g) and 2-(tert-butoxycarbonylamino)ethyl methanesulfonate (1.45 g) using the method of Example 37(c). Yield 0.32 g (as HCl-salt). $^1$H-NMR (400

MHz; d$_6$-DMSO): δ 3.34 (t, 2H), 4.50 (t, 2H), 7.15 (d, 1H), 7.99 (d, 1H), 8.21 (br s, 2H), 8.39 (dd, 1H), 8.45 (d, 1H), 8.61 (d, 1H).

d) N-(2-(3-(3-cyano-4-nitrophenyl)-1H-pyrazol-1-yl)ethyl)-3-(pyridin-2-yl)-1H-pyrazole-5-carboxamide The title compound was prepared from 5-(1-(2-aminoethyl)-1H-pyrazol-3-yl)-2-nitrobenzonitrile (0.10 g) and 3-(pyridin-2-yl)-1H-pyrazole-5-carboxylic acid (0.077 g) using the method of Example 34(d). Yield 0.21 g. $^1$H-NMR (400 MHz; d$_6$-DMSO): δ 3.75 (t, 2H), 4.41 (t, 2H), 7.09 (s, 1H), 7.24-7.39 (m, 2H), 7.82-7.91 (m, 3H), 8.37-8.70 (m, 5H), 13.84 (br s, 1H).

Example 40

N-(2-(3-(3,4-dicyanophenyl)-1H-pyrazol-1-yl)ethyl)-3-(pyridin-2-yl)-1H-pyrazole-5-carboxamide a) 4-(1-(tetrahydro-2H-pyran-2-yl)-1H-pyrazol-5-yl)phthalonitrile The title compound was prepared using the method of Example 34(a) starting from 2.29 g 4-iodophthalonitrile. Yield 2.28 g. $^1$H-NMR (400 MHz; d$_6$-DMSO): δ 1.50-1.65 (m, 3H), 1.82-1.86 (m, 1H), 1.94-1.99 (m, 1H), 2.32-2.41 (m, 1H), 3.58-3.64 (m, 1H), 3.94-3.97 (m, 1H), 5.33 (d, 1H), 6.76 (d, 1H), 7.67 (d, 1H), 8.06 (dd, 1H), 8.29 (d, 1H), 8.31 (d, 1H).

b) 4-(1H-pyrazol-5-yl)phthalonitrile

The title compound was prepared from 2.28 g of 4-(1-(tetrahydro-2H-pyran-2-yl)-1H-pyrazol-5-yl)phthalonitrile using the method of Example 34(b). Yield 1.53 g. $^1$H-NMR (400 MHz; d$_6$-DMSO): δ 7.05 (d, 1H), 7.91 (br s, 1H), 8.16 (d, 1H), 8.34 (dd, 1H), 8.54 (d, 1H), 13.36 (br s, 1H).

c) 4-(1-(2-aminoethyl)-1H-pyrazol-3-yl)phthalonitrile

The title compound was prepared from 4-(1H-pyrazol-5-yl)phthalonitrile (0.38 g) and 2-(tert-butoxycarbonylamino)ethyl methanesulfonate (0.61 g) using the method of Example 37(c). Yield 0.050 g (as HCl-salt). $^1$H-NMR (400 MHz; d$_4$-MeOH): δ 3.50 (t, 2H), 4.54 (t, 2H), 6.94 (d, 1H), 7.81 (d, 1H), 7.98 (d, 1H), 8.28 (dd, 1H), 8.49 (d, 1H).

d) N-(2-(3-(3,4-dicyanophenyl)-1H-pyrazol-1-yl)ethyl)-3-(pyridin-2-yl)-1H-pyrazole-5-carboxamide The title compound was prepared from 4-(1-(2-aminoethyl)-1H-pyrazol-3-yl)phthalonitrile (0.050 g) and 3-(pyridin-2-yl)-1H-pyrazole-5-carboxylic acid (0.042 g) using the method of Example 34(d). Yield 0.062 g. $^1$H-NMR (400 MHz; d$_6$-DMSO): δ 3.72 (t, 2H), 4.40 (t, 2H), 7.01 (s, 1H), 7.27-7.40 (m, 2H), 7.88-7.94 (m, 3H), 8.14 (d, 1H), 8.32 (d, 1H), 8.35-8.65 (m, 3H), 13.9 (br s, 1H).

Example 41

N-(2-(3-(3-methoxy-4-nitrophenyl)-1H-pyrazol-1-yl)ethyl)-5-methyl-1H-pyrazole-3-carboxamide a) 2-(3-(3-methoxy-4-nitrophenyl)-1H-pyrazol-1-yl)ethanamine 5-(3-methoxy-4-nitrophenyl)-1H-pyrazole (0.555 g, 2.53 mmol), tert-butyl 2-hydroxyethylcarbamate (0.449 g, 2.79 mmol) and triphenylphosphine (0.863 g, 3.29 mmol) and THF (20 ml) were mixed. DIAD (0.997 ml, 5.06 mmol) was added. The mixture was stirred for 3 h. 10% EtOH/HCl (50 ml) was added. The mixture was stirred overnight. The solvent was removed by evaporation. Water (20 ml) was added to the residue. This mixture was washed with DCM (2×20 ml). 1 M NaOH was added until pH 14 was reached followed by extraction with DCM (3×20 ml). The organic layers were pooled and evaporated to dryness. Flash chromatography (gradient of DCM:MeOH) gave 97 mg of the title compound. $^1$H-NMR (400 MHz; CDCl$_3$): δ 3.19-3.26 (m, 2H), 4.04 (s, 3H), 4.20-4.28 (m, 2H), 6.63 (m, 1H), 7.38-7.43 (m, 1H), 7.52 (m. 1H), 7.59 (m, 1H), 7.91-7.97 (m, 1H).

b) N-(2-(3-(3-methoxy-4-nitrophenyl)-1H-pyrazol-1-yl)ethyl)-5-methyl-1H-pyrazole-3-carboxamide 3-Methylpyrazole-5-carboxylic acid (70.0 mg, 0.555 mmol), HOBt (85 mg, 0.629 mmol) and PS-carbodiimide (672 mg) were weighed in a glass vial. DCM (4 ml) and DMF (0.4 ml) were added. The mixture was stirred for 10 minutes. 2-(3-(3-methoxy-4-nitrophenyl)-1H-pyrazol-1-yl)ethanamine (97 mg, 0.370 mmol) was added and the mixture was stirred for 24 h. The solids were filtered off. PS-Trisamine (616 mg, 1.849 mmol) was added to the filtrate. The mixture was stirred for 2 h and filtered. The filtrate was concentrated and purified by flash chromatography (gradient of DCM:MeOH) to give 46 mg of the title compound. $^1$H-NMR (400 MHz; CDCl$_3$): δ 2.35 (s, 3H), 3.92, (m, 2H), 4.05, (s, 3H), 4.40, (t, 2H), 6.57 (s, 1H), 6.61 (d, 1H), 7.31 (s, 1H), 7.40-7.43 (m, 1H), 7.47 (d, 1H), 7.62 (d, 1H), 7.96 (d, 1H), 9.94 (s, 1H).

Example 42

N-(2-(3-(3-chloro-4-cyanophenyl)-1H-pyrazol-1-yl)ethyl)-5-(1-methyl-1H-pyrazol-4-yl)isoxazole-3-carboxamide 5-(1-methyl-1H-pyrazol-4-yl)isoxazole-3-carboxylic acid (57.9 mg, 0.3 mmol), HOBt (46 mg, 0.340 mmol) and PS-carbodiimide (364 mg), DCM (4 ml) and DMF (0.4 ml) were mixed in a glass vial. The mixture was shaken for 10 min. 4-(1-(2-aminoethyl)-1H-pyrazol-3-yl)-2-chlorobenzonitrile (49 mg, 0.20 mmol) was added and the mixture was stirred for 24 h. The solids were filtered off. PS-Trisamine (333 mg, 1.0 mmol) was added to the filtrate. The mixture was shaken for 4 h and filtered. The filtrate was concentrated and purified by flash chromatography (gradient of DCM:MeOH) to give 16 mg of the title compound. $^1$H-NMR (400 MHz; d6-DMSO): 3.70 δ (m, 2H), 3.91 (s, 3H), 4.38 (m, 2H), 6.89 (m, 1H), 6.97 (d, 1H), 7.85 (m, 1H), 7.94-8.00 (m, 3H), 8.10 (d, 1H), 8.36 (s, 1H), 8.86-9.13 (m, 1H).

Example 43

(S)—N-(1-(3-(3-chloro-4-cyanophenyl)-1H-pyrazol-1-yl)propan-2-yl)-5-(1-methyl-1H-pyrazol-4-yl)isoxazole-3-carboxamide 5-(1-methyl-1H-pyrazol-4-yl)isoxazole-3-carboxylic acid (57.9 mg, 0.3 mmol), HOBt (46 mg, 0.340 mmol) and PS-carbodiimide (364 mg), DCM (4 ml) and DMF (0.4 ml) were mixed in a glass vial. The mixture was shaken for 10 min. (S)-4-(1-(2-aminopropyl)-1H-pyrazol-3-yl)-2-chlorobenzonitrile (51 mg, 0.2 mmol) was added and the mixture was stirred for 24 h. The solids were filtered off. PS-Trisamine (333 mg, 1.0 mmol) was added to the filtrate. The mixture was shaken for 4 h and filtered. The filtrate was concentrated and purified by flash chromatography (gradient of DCM:MeOH) to give 12 mg of the title compound. $^1$H-NMR (400 MHz; CDCl$_3$): δ 1.25 (d, 3H), 4.00 (s, 3H), 4.23-4.31 (m, 1H), 4.42-4.48 (m, 1H), 4.55-4.66 (m, 1H), 6.63 (d, 1H), 6.66 (s, 1H), 7.50 (d, 1H), 7.69 (d, 1H), 7.79-7.94 (m, 4H), 8.07 (m, 1H).

Example 44

(S)—N-(1-(3-(4-cyano-3-methylphenyl)-1H-pyrazol-1-yl)propan-2-yl)-5-(1-methyl-1H-pyrazol-4-yl)isoxazole-3-carboxamide 5-(1-methyl-1H-pyrazol-4-yl)isoxazole-3-carboxylic acid (57.9 mg, 0.3 mmol), HOBt (46 mg, 0.340 mmol) and PS-carbodiimide (364 mg), DCM (4 ml) and DMF (0.4 ml) were mixed in a glass vial. The mixture was shaken for 10 min. (S)-4-(1-(2-aminopropyl)-1H-pyrazol-3-yl)-2-methylbenzonitrile (48 mg, 0.2 mmol) was added and the mixture was stirred for 24 h. The solids were filtered off. PS-Trisamine (333 mg, 1.0 mmol) was added to the filtrate. The mixture was shaken for 4 h and filtered. The filtrate was concentrated and purified by flash chromatography (gradient of DCM:MeOH) to give 15 mg of the title compound. $^1$H-NMR (400 MHz; CDCl$_3$): δ 1.25 (d, 3H), 4.00 (s, 3H), 4.23-4.28 (m, 1H), 4.42-4.49 (m, 1H), 4.55-4.66 (m, 1H), 6.62 (d, 1H), 6.67 (s, 1H), 7.49 (d, 1H), 7.63 (d, 1H), 7.72-7.75 (m, 1H), 7.81 (m, 2H), 7.96 (s, 1H), 8.14 (m, 1H).

Example 45

N-(1-(3-(3-chloro-4-cyanophenyl)-1H-pyrazol-1-yl)-3-methylbutan-2-yl)-3-(pyridin-3-yl)-1H-pyrazole-5-carboxamide a) 4-(1-(2-amino-3-methylbutyl)-1H-pyrazol-3-yl)-2-chlorobenzonitrile The title compound was prepared using the method of Example 34(c) starting from 2-chloro-4-(1H-pyrazol-3-yl)benzonitrile (0.2 g; 0.98 mmol) and tert-butyl 1-hydroxy-3-methylbutan-2-ylcarbamate (0.22 g; m 1.09 mmol). Yield 22%. $^1$H-NMR (400 MHz; CDCl$_3$): δ 1.02 (m, 6H), 1.71 (m, 1H), 3.14 (m, 1H), 3.95 (m, 1H), 4.27 (m, 1H), 6.61 (d, 1H), 7.51 (d, 1H), 7.66 (d, 1H), 7.77 (dd, 1H), 7.97 (s, 1H).

b) N-(1-(3-(3-chloro-4-cyanophenyl)-1H-pyrazol-1-yl)-3-methylbutan-2-yl)-3-(pyridin-3-yl)-1H-pyrazole-5-carboxamide The title compound was prepared using the method of Example 34(d) starting from 4-(1-(2-amino-3-methylbutyl)-1H-pyrazol-3-yl)-2-chlorobenzonitrile (0.060 g; 0.21 mmol) and 5-(pyridin-3-yl)-1H-pyrazole-3-carboxylic acid (0.039 g; 0.21 mmol). The crude product was purified by flash chromatography using cyanocolumn and EtOAc/heptane as eluent. Yield 12%. $^1$H-NMR (400 MHz; MeOD): δ 1.14 (m, 6H), 1.95 (m, 1H), 4.35 (m, 2H), 4.55 (m, 1H), 6.71 (s, 1H), 7.02 (m, 1H), 7.53 (m, 1H), 7.72 (m, 3H), 7.95 (s, 1H), 8.25 (m, 1H), 8.54 (m, 1H), 8.88 (m, 1H).

Example 46

N-(2-(3-(3-chloro-4-cyanophenyl)-1H-pyrazol-1-yl)ethyl)pyrazolo[1,5-a]pyrimidine-2-carboxamide The title compound was prepared using the method of Example 34 (d) starting from pyrazolo[1,5-a]pyrimidine-2-carboxylic acid (0.16 g; 0.97 mmol) and 4-(1-(2-aminoethyl)-1H-pyrazol-3-yl)-2-chlorobenzonitrile (0.20 g; 0.81 mmol). Yield 12%. $^1$H-NMR (400 MHz; d$_6$-DMSO): δ 3.75 (q, 2H), 4.41 (t, 2H), 6.96 (d, 1H), 7.03 (s, 1H), 7.19 (m, 1H), 7.86 (d, 1H), 7.97 (m, 2H), 8.06 (s, 1H), 8.64 (m, 1H), 8.71 (m, 1H), 9.09 (d, 1H).

Example 47

N-(2-(3-(4-cyano-3-nitrophenyl)-1H-pyrazol-1-yl)ethyl)-3-(pyridin-2-yl)-1H-pyrazole-5-carboxamide a) 2-Nitro-4-(1-(tetrahydro-2H-pyran-2-yl)-1H-pyrazol-5-yl)benzonitrile The title compound was prepared from 4-chloro-2-nitrobenzonitrile (1.50 g) and 1-(tetrahydro-2H-pyran-2-yl)-5-(4,4,5,5-tetramethyl-1,3,2-dioxa-borolan-2-yl)-1H-pyrazole (2.74 g) using the method of Example 39(a). Yield 1.75 g. $^1$H-NMR (400 MHz; d$_6$-DMSO): δ 1.57 (m, 3H), 1.84 (m, 1H), 1.97 (m, 1H), 2.38-2.47 (m, 1H), 3.68-3.75 (m, 1H), 4.03 (m, 1H), 5.33 (dd, 1H), 6.84 (d, 1H), 7.69 (d, 1H), 8.13 (dd, 1H), 8.31 (d, 1H), 8.60 (d, 1H).

b) 2-Nitro-4-(1H-pyrazol-5-yl)benzonitrile

The title compound was prepared from 1.53 g of 2-nitro-4-(1-(tetrahydro-2H-pyran-2-yl)-1H-pyrazol-5-yl)benzonitrile using the method of Example 34(b). Yield 1.0 g. $^1$H-NMR (400 MHz; d$_6$-DMSO): δ 7.09 (d, 1H), 7.92 (s, 1H), 8.19 (d, 1H), 8.37 (dd, 1H), 8.73 (d, 1H), 13.40 (br s, 1H).

c) 2-(tert-Butoxycarbonylamino)ethyl methanesulfonate tert-Butyl N-(2-hydroxyethyl)carbamate (6.0 g), triethylamine (5.68 ml) were dissolved in DCM (50 ml) and methanesulfonyl chloride (3.02 ml) was added dropwise to the reaction mixture at 0° C. The mixture was stirred for 30 min at 0° C. and stirring was continued for 2 h at RT. Water was added and the mixture was extracted with DCM. Combined organic phases were washed with water and brine, dried with Na$_2$SO$_4$ and evaporated. The product was stored under nitrogen. Yield 8.64 g. $^1$H-NMR (400 MHz; d$_6$-DMSO): δ 1.39 (s, 9H), 3.16 (s, 3H), 3.23 (q, 2H), 4.16 (t, 2H), 7.04 (br s, 1H).

d) tert-Butyl 2-(3-(4-cyano-3-nitrophenyl)-1H-pyrazol-1-yl)ethylcarbamate

2-Nitro-4-(1H-pyrazol-5-yl)benzonitrile (1.0 g), DMF (10 ml) and sodium hydride (60% in oil, 0.24 g) were stirred for 30 min at RT. 2-(tert-Butoxycarbonyl-amino)ethyl methanesulfonate (1.45 g) in DMF (3.3 ml) was added and the mixture was microwaved for 30 min at 160° C. (Biotage Initiator Sixty operating at 2.45 GHz). After pouring the mixture to water, it was extracted with EtOAc. Combined organic phases were washed with water and brine, dried with Na$_2$SO$_4$ and evaporated. The product was triturated with IPA and filtered. Yield 0.92 g. $^1$H-NMR (400 MHz; d$_6$-DMSO): δ 1.35 (s, 9H), 3.38 (m, 2H), 4.24 (t, 2H), 6.92 (m, 1H), 7.06 (d, 1H), 7.85 (d, 1H), 8.19 (d, 1H), 8.33 (dd, 1H), 8.70 (d, 1H).

e) 4-(1-(2-Aminoethyl)-1H-pyrazol-3-yl)-2-nitrobenzonitrile

To a solution of tert-butyl 2-(3-(4-cyano-3-nitrophenyl)-1H-pyrazol-1-yl)-ethylcarbamate (0.92 g) in DCM (3 ml) 17% HCl-ethanol solution (10 ml) was added and the mixture was stirred at RT until disappearance of the starting material. The precipitate was filtrated, washed with diethylether and dried to give 0.70 g of the product as HCl-salt. $^1$H-NMR (400 MHz; d$_6$-DMSO): δ 3.31 (m, 2H), 4.50 (t, 2H), 7.12 (d, 1H), 7.99 (d, 1H), 8.19 (d, 1H), 8.27-8.35 (m, 3H), 8.37 (dd, 1H), 8.73 (d, 1H).

f) N-(2-(3-(4-cyano-3-nitrophenyl)-1H-pyrazol-1-yl) ethyl)-3-(pyridin-2-yl)-1H-pyrazole-5-carboxamide The title compound was prepared from 4-(1-(2-aminoethyl)-1H-pyrazol-3-yl)-2-nitrobenzonitrile (300 mg) and 3-(pyridine-2-yl)-1H-pyrazole-5-carboxylic acid (161 mg) using the method of Example 34(d). Yield 166 mg. $^1$H-NMR (400 MHz; d6-DMSO): δ 3.75 (q, 2H), 4.43 (t, 2H), 7.09 (d, 1H), 7.31 (br. s, 1H), 7.39 (m, 1H), 7.88-7.96 (m, 3H), 8.20 (d, 1H), 8.37 (dd, 1H), 8.47-8.57 (m, 1H), 8.64 (m, 1H), 8.71 (d, 1H), 13.90 (m, 1H).

Example 48

3-acetyl-N-(2-(3-(4-cyano-3-nitrophenyl)-1H-pyrazol-1-yl)ethyl)-1H-pyrazole-5-carboxamide The title compound was prepared from 4-(1-(2-aminoethyl)-1H-pyrazol-3-yl)-2-nitrobenzonitrile (150 mg) and 3-acetyl-1H-pyrazole-5-carboxylic acid (94 mg) using the method of Example 34(d). Yield 84 mg. $^1$H-NMR (400 MHz; d6-DMSO): δ 3.30 (s, 3H), 3.71 (q, 2H), 4.39 (t, 2H), 7.05 (d, 1H), 7.27 (br. s, 1H), 7.88 (d, 1H), 8.18 (d, 1H), 8.33 (d, 1H), 8.45-8.75 (m, 1H), 8.66 (d, 1H), 14.16 (s, 1H).

Example 49

N-(2-(3-(4-cyano-3-nitrophenyl)-1H-pyrazol-1-yl) ethyl)-5-methylisoxazole-3-carboxamide The title compound was prepared from 4-(1-(2-aminoethyl)-1H-pyrazol-3-yl)-2-nitrobenzonitrile (150 mg) and 5-methylisoxazole-3-carboxylic acid (89 mg) using the method of Example 34(d). Yield 9 mg. $^1$H-NMR (400 MHz; d6-DMSO): δ 2.44 (s, 3H), 3.70 (q, 2H), 4.40 (t, 2H), 6.48 (d, 1H), 7.05 (d, 1H), 7.88 (d, 1H), 8.18 (d, 1H), 8.32 (dd, 1H), 8.67 (d, 1H), 8.79 (m, 1H).

Example 50. N-(2-(3-(4-cyano-3-nitrophenyl)-1H-pyrazol-1-yl)ethyl)-5-(pyridin-3-yl)-1H-pyrazole-3-carboxamide The title compound was prepared from 4-(1-(2-aminoethyl)-1H-pyrazol-3-yl)-2-nitrobenzonitrile (50 mg) and 3-(pyridin-3-yl)-1H-pyrazole-5-carboxylic acid (44 mg) using the method of Example 34(d). Yield 27 mg. $^1$H-NMR (400 MHz; d6-DMSO): δ 3.74 (m, 2H), 4.42 (t, 2H), 7.07 (d, 1H), 7.17-7.28 (m, 1H), 7.50 (m, 1H), 7.90 (s, 1H), 8.05-8.20 (m, 2H), 8.31-8.42 (m, 1H), 8.52-8.59 (m, 1H), 8.69 (d, 1H), 8.92-9.04 (m, 1H), 13.79 (s, 1H).

Example 51

3-Acetyl-N-(2-(3-(3,4-dicyanophenyl)-1H-pyrazol-1-yl)ethyl)-1H-pyrazole-5-carboxamide The title compound was prepared from 4-(1-(2-aminoethyl)-1H-pyrazol-3-yl)-phthalonitrile (50 mg) and 3-acetyl-1H-pyrazole-5-carboxylic acid (34 mg) using the method of Example 34(d). Yield 43 mg. $^1$H-NMR (400 MHz; d6-DMSO): δ 2.49 (s, 3H), 3.70 (m, 2H), 4.37 (t, 2H), 7.00 (d, 1H), 7.27 (s, 1H), 7.86 (d, 1H), 8.13 (d, 1H), 8.28 (d, 1H), 8.45 (d, 1H), 8.63 (br s, 1H), 14.05 (br s, 1H).

Example 52

N-(2-(3-(3,4-dicyanophenyl)-1H-pyrazol-1-yl) ethyl)-3-(pyridin-3-yl)-1H-pyrazole-5-carboxamide The title compound was prepared from 4-(1-(2-aminoethyl)-1H-pyrazol-3-yl)-phthalonitrile (50 mg) and 3-(pyridin-3-yl)-1H-pyrazole-5-carboxylic acid (42 mg) using the method of Example 34(d). Yield 39 mg. $^1$H-NMR (400 MHz; d6-DMSO): δ 3.73 (q, 2H), 4.40 (t, 2H), 7.02 (d, 1H), 7.21 (s, 1H), 7.49 (m, 1H), 7.88 (s, 1H), 8.11-8.16 (m, 2H), 8.30 (dd, 1H), 8.40-8.58 (m, 1H), 8.48 (d, 1H), 8.56 (d, 1H), 8.99 (s, 1H), 13.78 (br s, 1H).

Example 53

N-(2-(3-(4-cyano-3-methylphenyl)-1H-pyrazol-1-yl) ethyl)-3-(pyridin-3-yl)-1H-pyrazole-5-carboxamide The title compound was prepared using the method of Example 31 using 5-pyridin-3-yl-4H-pyrazole-3-carboxylic acid (0.46 g; 2.43 mmol), 4-(1-(2-amino-ethyl)-1H-pyrazol-3-yl)-2-methylbenzonitrile (0.50 g; 2.21 mmol), HOBt (0.45 g; 3.31 mmol), EDCI (0.64 g; 3.31 mmol) and 0.58 ml (3.31 mmol) of DIPEA as starting materials. After workup the product was precipitated out from DCM to give 0.56 g (64%) of the title compound. $^1$H-NMR (400 MHz; d6-DMSO): δ 3.67-3.76 (m, 2H), 4.33-4.41 (m, 2H), 6.85 (d, 1H), 7.22 (s, 1H), 7.49 (dd, 1H), 7.74-7.82 (m, 2H), 7.83 (d, 1H), 7.88 (broad s, 1H), 8.10-8.18 (m, 1H), 8.44-8.58 (m, 2H), 9.00 (broad s, 1H), 13.82 (s, 1H).

Example 54

3-Acetyl-N-(2-(3-(3-chloro-4-cyanophenyl)-1H-pyrazol-1-yl)ethyl)-1H-pyrazole-5-carboxamide 3-Acetyl-1H-pyrazole-5-carboxylic acid (0.469 g; 3.04 mmol) and 0.8 ml of DIPEA were dissolved in 3 ml of dry DCM under nitrogen. HOBt (0.616 g; 4.56 mmol) and EDCI (0.874 g; 4.56 mmol) were added. 4-(1-(2-aminoethyl)-1H-pyrazol-3-yl)-2-chlorobenzonitrile (0.75 g; 3.04 mmol) was added in 4.5 ml of DCM and stirred overnight at RT. 60 ml of DCM was added and washed with 3×17 ml of water. Combined water phases were washed with 2×30 ml of DCM. All DCM washes were combined and dried over Na$_2$SO$_4$, filtered and evaporated. Product was purified by trituration in 2 ml of EtOH to give the title compound. $^1$H-NMR (400 MHz; d6-DMSO): δ 2.49 (s, 3H), 3.70 (m, 2H), 4.37 (m, 2H), 6.95 (d, 1H), 7.28 (s, 1H), 7.84 (d, 1H), 7.94, (dd, 1H), 7.98 (d, 1H), 8.07 (d, 1H), 8.64 (broad s, 1H), 14.19 (s, 1H).

Example 55

(R)-3-acetyl-N-(1-(3-(3-chloro-4-cyanophenyl)-1H-pyrazol-1-yl)propan-2-yl)-1H-pyrazole-5-carboxamide a) (R)-4-(1-(2-aminopropyl)-1H-pyrazol-3-yl)-2-chlorobenzonitrile The title compound was prepared with the Mitsunobu reaction using the method of Example 3(c) starting from 2-chloro-4-(1H-pyrazol-5-yl)-benzonitrile (2.00 g, 9.82 mmol) and (R)-tert-butyl 1-hydroxypropan-2-ylcarbamate (1.893 g, 10.80 mmol). After Boc removal and workups 0.434 g (17%) of the title compound was obtained. ¹H-NMR (400 MHz; d6-DMSO): δ 0.97 (d, 3H), 2.96 (m, 2H), 4.15 (m, 2H), 6.98 (d, 1H), 7.86 (d, 1H), 7.92-8.00 (m, 2H), 8.11 (d, 1H).

b) (R)-3-acetyl-N-(1-(3-(3-chloro-4-cyanophenyl)-1H-pyrazol-1-yl)propan-2-yl)-1H-pyrazole-5-carboxamide The title compound was prepared using the method of Example 34(d). (R)-4-(1-(2-amino-propyl)-1H-pyrazol-3-yl)-2-chlorobenzonitrile (1.00 g, 3.84 mmol), 3-acetyl-1H-pyrazole-5-carboxylic acid (0.591 g; 3.84 mmol), 1.0 ml of DIPEA were dissolved in 3 ml of dry DCM under nitrogen. HOBt (0.777 g; 5.75 mmol) and EDCI (1.103 g; 5.75 mmol) were added and the reaction stirred at RT overnight. The crude product (576 mg) was crystallized from 4 ml of EtOH to obtain 164 mg (11%) of the title compound. ¹H-NMR (400 MHz; d6-DMSO): δ 1.16 (d, 3H), 2.49 (s, 3H), 4.34-4.38 (m, 2H), 4.40-4.53 (m, 1H), 6.93 (d, 1H), 7.31 (m, 1H), 7.81 (d, 1H), 7.85-8.09 (m, 3H), 8.48 (broad s, 1H), 14.15 (s, 1H).

Example 56

N—((S)-1-(3-(3-chloro-4-cyanophenyl)-1H-pyrazol-1-yl)-propan-2-yl)-3-(1-hydroxyethyl)-1H-pyrazole-5-carboxamide (S)-3-acetyl-N-(1-(3-(3-chloro-4-cyanophenyl)-1H-pyrazol-1-yl)propan-2-yl)-1H-pyrazole-5-carboxamide (100 mg; 0.25 mmol) and 5 ml of EtOH were put to reaction flask and sodium borohydride (19 mg; 0.5 mmol) was added slowly as EtOH suspension. The reaction was stirred overnight to completion. 0.5 ml of water and 1 ml of 0.5M HCl were added dropwise. The solution was evaporated to dryness, 20 ml of DCM was added and washed with 10 ml of 1 M NaHCO₃ and 10 ml of water followed with drying over Na₂SO₄. After filtration and evaporation 76 mg (76%) of pure title compound was obtained. 1H-NMR (400 MHz; d6-DMSO): δ 1.11 (d, 3H), 1.38 (d, 3H), 4.22-4.48 (m, 3H), 4.74-4.84 (m, 1H), 4.41 (d, 1H), 6.40 (s, 1H), 6.94 (d, 1H), 7.81 (d, 1H), 7.92-8.05 (m, 2H), 8.09 (d, 1H), 8.20 (d, 1H), 13.04 (s, 1H).

Example 57

(S)-2-amino-N-(1-(3-(3-chloro-4-cyanophenyl)-1H-pyrazol-1-yl)propan-2-yl)thiazole-4-carboxamide The compound was prepared using the method of Example 34(d). (S)-4-(1-(2-amino-propyl)-1H-pyrazol-3-yl)-2-chlorobenzonitrile (1.00 g; 3.84 mmol), 2-aminothiazole-4-carboxylic acid (0.66 g; 4.66 mmol), 1.00 ml of DIPEA, HOBt (0.26 g; 1.9 mmol) and EDCI (1.10 g; 5.75 mmol) were used as starting materials. Purification by isopropanol:toluene crystallization afforded 0.93 g (63%) of the title compound. ¹H-NMR (400 MHz; d6-DMSO): δ 1.10 (d, 3H), 4.22-4.45 (m, 3H), 6.96 (d, 1H), 7.04 (broad s, 2H), 7.15 (s, 1H), 7.82 (d, 1H), 7.90 (d, 1H), 7.97 (s, 1H), 8.08 (s, 1H).

Example 58

(R)-3-acetyl-N-(1-(3-(3-chloro-4-cyanophenyl)-1H-pyrazol-1-yl)butan-2-yl)-1H-pyrazole-5-carboxamide a) (R)-4-(1-(2-aminobutyl)-1H-pyrazol-3-yl)-2-chlorobenzonitrile hydrochloride The Mitsunobu reaction was conducted as described in Example 3(c) using 2-chloro-4-(1H-pyrazol-5-yl)benzonitrile (0.60 g, 2.95 mmol) and (R)-tert-butyl 1-hydroxybutan-2-ylcarbamate (0.61 g, 3.24 mmol) as starting materials. 0.249 g (31%) of the title compound was obtained after workup. ¹H-NMR (400 MHz; d6-DMSO): δ 0.91 (t, 3H), 1.22 (d, 3H), 3.33 (broad s, NH₂HCl overlapping with water) 3.99 (dd, 1H), 4.12 (dd, 1H), 4.44-4.86 (m, 1H), 6.97 (d, 1H), 7.86 (d, 1H), 7.92-7.99 (m, 2H), 8.11 (d, 1H).

b) (R)-3-acetyl-N-(1-(3-(3-chloro-4-cyanophenyl)-1H-pyrazol-1-yl)butan-2-yl)-1H-pyrazole-5-carboxamide The compound was prepared using the method of Example 34(d). The reaction was conducted in 4 ml of DCM at RT overnight using (R)-4-(1-(2-aminobutyl)-1H-pyrazol-3-yl)-2-chlorobenzonitrile (0.249 g; 0.91 mmol), 3-acetyl-1H-pyrazole-5-carboxylic acid (0.140 g; 0.91 mmol), 0.24 ml of DIPEA, HOBt (0.184 g; 1.36 mmol) and EDCI (0.261 g; 1.36 mmol) as starting materials. Purification was done by EtOH trituration. ¹H-NMR (400 MHz; d6-DMSO): δ 0.90 (t, 3H), 1.42-1.67 (m, 2H), 2.51 (s, 3H), 4.19-4.42 (m, 3H), 6.91 (d, 1H), 7.32 (s, 1H), 7.79 (d, 1H), 7.85-8.07 (m, 3H), 8.38 (d, 1H), 14.14 (s, 1H).

Example 59

(R)—N-(1-(3-(3-chloro-4-cyanophenyl)-1H-pyrazol-1-yl)propan-2-yl)thiazole-4-carboxamide The title compound was prepared using the method of Example 54 but starting from 1,3-thiazole-4-carboxylic acid (149 mg; 1.51 mmol) and (S)-4-(1-(2-aminopropyl)-1H-pyrazol-3-yl)-2-chlorobenzonitrile (300 mg; 1.51 mmol). Crude product was purified by EtOH trituration to obtain 84 mg (20%) of the title compound. ¹H-NMR (400 MHz; d6-DMSO): δ 1.12 (d, 3H), 4.30-4.53 (m, 3H), 6.95 (d, 1H), 7.86 (d, 1H), 7.95-8.04 (m, 2H), 8.15 (s, 1H), 8.28 (d, 1H), 8.77 (d, 1H), 9.23 (d, 1H).

Example 60

(S)—N-(1-(3-(3-chloro-4-cyanophenyl)-1H-pyrazol-1-yl)propan-2-yl)-3-(4-methylpiperazine-1-carbonyl)-1H-pyrazole-5-carboxamide a) (S)-5-(1-(3-(3-chloro-4-cyanophenyl)-1H-pyrazol-1-yl)propan-2-yl-carbamoyl)-1H-pyrazole-3-carboxylic Acid The title compound was prepared using the method of Example 54 but starting from 3,5-pyrazoledicarboxylic acid monohydrate (0.60 g; 3.84 mmol) and (S)-4-(1-(2-amino-propyl)-1H-pyrazol-3-yl)-2-chlorobenzonitrile (1.0 g; 3.84 mmol). Crude product was purified by chromatography (CombiFlash, silica column, eluent: 0-100% MeOH/DCM) to obtain 29 mg (36%) of the title compound. $^1$H-NMR (400 MHz; d6-DMSO): δ 1.14 (s, 3H), 4.30-4.50 (m, 3H), 6.93 (d, 1H), 7.83 (s, 1H), 7.85-8.05 (m, 2H), 8.04 (s, 1H), 8.35-8.65 (m, 1H), 14.06 (s, 1H), 14.24 (s, 1H).

b) (S)—N-(1-(3-(3-chloro-4-cyanophenyl)-1H-pyrazol-1-yl)propan-2-yl)-3-(4-methylpiperazine-1-carbonyl)-1H-pyrazole-5-carboxamide 1-Methylpiperazine (126 mg; 1.25 mmol) and (S)-5-(1-(3-(3-chloro-4-cyanophenyl)-1H-pyrazol-1-yl)propan-2-yl-carbamoyl)-1H-pyrazole-3-carboxylic acid (50 mg; 1.25 mmol), HOBt (254 mg; 1.88 mmol), DIPEA (0.33 ml; 1.88 mmol) and EDCI (361 mg; 1.88 mmol) were dissolved in 15 ml of DCM and stirred at RT overnight. 50 ml of DCM was added and washed with 3×15 ml of water. Combined water phases were washed with 2×20 mol of DCM, all organic phases were combined and dried over Na$_2$SO$_4$. Crude product was purified by chromatography (CombiFlash, silica column, eluent: 0-20% MeOH/DCM) to obtain 75 mg (12%) of the title compound. $^1$H-NMR (400 MHz; d1-CDCl3): δ 3.90-3.96 (m, 2H), 4.41 (t, 2H), 6.51-6.53 (m, 1H), 6.61 (d, 1H), 6.66 (d, 1H), 6.95 (s, 1H), 7.48-7.50 (m, 2H), 7.61 (broad s, 1H), 7.68 (d, 1H), 7.76-7.79 (m, 1H), 8.11 (s, 1H), 10.45 (broad s, 1H).

Example 61

(S)—N-(1-(3-(3-chloro-4-cyanophenyl)-1H-pyrazol-1-yl)propan-2-yl)-3-(pyridin-3-yl)-1H-pyrazole-5-carboxamide The title compound was prepared using the method of Example 54 but starting from 5-pyridin-3-yl-4H-pyrazole-3-carboxylic acid (181 mg; 0.96 mmol) and (S)-4-(1-(2-aminopropyl)-1H-pyrazol-3-yl)-2-chlorobenzonitrile (250 mg; 0.96 mmol). The product precipitated out from DCM during workup and after filtration and drying 110 mg (27%) of pure title compound was obtained. $^1$H-NMR (400 MHz; d6-DMSO): δ 1.17 (s, 3H), 4.20-4.60 (m, 3H), 7.05-7.36 (m, 1H), 7.40-7.65 (m, 1H), 7.80-8.60 (m, 7H), 8.85-9.07 (m, 1H), 13.76 (s, 1H).

Example 62

(S)—N-(1-(3-(3-chloro-4-cyanophenyl)-1H-pyrazol-1-yl)propan-2-yl)thiazole-4-carboxamide The title compound was prepared using the method of Example 54 but starting from thiazole-4-carboxylic acid (50 mg; 0.38 mmol) and (S)-4-(1-(2-amino-propyl)-1H-pyrazol-3-yl)-2-chlorobenzonitrile (100 mg; 0.38 mmol). Crude product was purified by chromatography (CombiFlash, silica C18 column, eluent: 0-100% ACN/water) to obtain 63 mg (44%) of the title compound. $^1$H-NMR (400 MHz; d6-DMSO): δ 1.12 (d, 3H), 4.30-4.52 (m, 3H), 6.95 (d, 1H), 7.85 (d, 1H), 7.95-8.04 (m, 2H), 8.14 (s, 1H), 8.27 (d, 1H), 8.77 (d, 1H), 9.22 (d, 1H).

Example 63

N-(1-(3-(4-cyano-3-methylphenyl)-1H-pyrazol-1-yl)-2-methylpropan-2-yl)-3-(furan-2-yl)-1H-pyrazole-5-carboxamide a) 2-(1-hydroxy-2-methylpropan-2-yl)isoindoline-1,3-dione 2-Amino-2-methyl-1-propanol (4.46 g, 50 mmol) and phthalic anhydride (7.41 g, 50 mmol) were heated at 170° C. for 30 minutes. Icewater was added to the cooled reaction mixture and then the mixture was extracted three times with DCM. Organic phase was dried over Na$_2$SO$_4$, filtered and evaporated to dryness. Crude product was purified by CombiFlash (column: silica, eluent: 0-10% MeOH in DCM) to obtain 3.611 g (33%) of the title compound. LC-MS: M+1=220.

b) 4-(1-(2-(1,3-dioxoisoindolin-2-yl)-2-methylpropyl)-1H-pyrazol-3-yl)-2-methylbenzonitrile 2-(1-hydroxy-2-methylpropan-2-yl)isoindoline-1,3-dione (1.10 g; 5 mmol) and 2-methyl-4-(1H-pyrazol-3-yl)benzonitrile (0.366 g; 2.0 mmol) were dissolved in 5 ml of THF under nitrogen atmosphere. Triphenylphosphine (1.05 g; 4.0 mmol) and DIAD (0.79 ml; 4.0 mmol) were added and the reaction stirred at RT over the weekend. Additional triphenylphosphine (0.525 g; 2.0 mmol) and DIAD (0.39 ml; 2.0 mmol) were added and the mixture was stirred at RT for 2 days and then refluxed for 2 hours. Solvent was evaporated, 50 ml of water was added and the mixture was washed with 3×50 ml of DCM, dried over Na$_2$SO$_4$, filtered and evaporated to dryness. The crude mixture was purified twice by CombiFlash (column: silica, eluent 0-100% EtOAc in heptane) to obtain 125 mg (16%) of the title product. $^1$H-NMR (400 MHz; CDCl$_3$): δ 1.56 (s, 6H), 2.60 (s, 3H), 4.2-4.38 (m, 2H), 6.50 (d, 1H), 7.33-7.87 (m, 8H).

c) 4-(1-(2-amino-2-methylpropyl)-1H-pyrazol-3-yl)-2-methylbenzonitrile 4-(1-(2-(1,3-dioxoisoindolin-2-yl)-2-methylpropyl)-1H-pyrazol-3-yl)-2-methylbenzonitrile (0.125 g; 0.33 mmol) and hydrazine hydrate (65%) (0.16 ml; 3.3 mmol) were agitated in 2 ml of EtOH and refluxed for 30 min and then for 2 days at RT. Solvent was evaporated, 5 ml of water added and the mixture was washed with 3×10 ml of 2% MeOH/DCM, dried over Na$_2$SO$_4$, filtered and evaporated to dryness. The reaction was uncomplete and the same amounts of reagents were loaded and 5 drops of DMF. The reaction was refluxed without progress and re-extracted like previously to obtain 80 mg of the product mixture containing 21% of the title compound based on LC-MS analysis.

d) N-(1-(3-(4-cyano-3-methylphenyl)-1H-pyrazol-1-yl)-2-methylpropan-2-yl)-3-(furan-2-yl)-1H-pyrazole-5-carboxamide The title compound was prepared using the method of Example 54 but starting from 5-(2-furyl)-4H-pyrazole-3-carboxylic acid (56 mg; 0.32 mmol) and 4-(1-(2-amino-2-methylpropyl)-1H-pyrazol-3-yl)-2-methylbenzonitrile (80 mg; 0.32 mmol). Crude product was purified by chromatography (CombiFlash, silica-C18 column, eluent: 0-100% ACN/water) to obtain 16 mg of the product which was further purified by preparative HPLC (Waters Deltaprep 4000, SymmPrep 56.2, 25-80% ACN/AcONH$_4$) to obtain 5.3 mg of the title compound. $^1$H-NMR (400 MHz; d1-CDCl3): δ 1.52 (s, 6H), 2.54 (s, 3H), 4.50 (s, 2H), 6.52 (dd, 1H), 6.57 (d, 1H), 6.64 (d, 1H), 6.90 (s, 1H), 7.44 (d, 1H), 7.48 (d, 1H), 7.59 (d, 1H), 7.70 (dd, 1H), 7.75 (d, 1H), 10.31 (broad s, 1H).

Example 64

N-(2-(3-(3-chloro-4-cyanophenyl)-1H-pyrazol-1-yl)ethyl)-3-(furan-2-yl)-1H-pyrazole-5-carboxamide The title compound was prepared using the method of Example 54 but starting from 5-(2-furyl)-4H-pyrazole-3-carboxylic acid (36 mg; 0.20 mmol) and 4-(1-(2-aminoethyl)-1H-pyrazol-3-yl)-2-chlorobenzonitrile (50 mg; 0.20 mmol). Crude product was purified by chromatography (CombiFlash, silica column, eluent: 0-100% MeOH/DCM) to obtain 29 mg (36%) of the title compound. $^1$H-NMR (400 MHz; d1-CDCl3): δ 3.90-3.96 (m, 2H), 4.41 (t, 2H), 6.51-6.53 (m, 1H), 6.61 (d, 1H), 6.66 (d, 1H), 6.95 (s, 1H), 7.48-7.50 (m, 2H), 7.61 (broad s, 1H), 7.68 (d, 1H), 7.76-7.79 (m, 1H), 8.11 (s, 1H), 10.45 (broad s, 1H).

Example 65

N-(2-(3-(3-chloro-4-cyanophenyl)-1H-pyrazol-1-yl)ethyl)-3-(pyridin-2-yl)-1H-pyrazole-5-carboxamide The title compound was prepared using the method of Example 53 but starting from 5-pyridin-2-yl-4H-pyrazole-3-carboxylic acid (38 mg; 0.20 mmol) and 4-(1-(2-aminoethyl)-1H-pyrazol-3-yl)-2-chlorobenzonitrile (50 mg; 0.20 mmol). Crude product was purified by chromatography (CombiFlash, silica column, eluent: 0-100% MeOH/DCM) to obtain 19 mg (23%) of the title compound. $^1$H-NMR (400 MHz; d6-DMSO): δ 3.70-3.74 (m, 2H), 4.38 (t, 2H), 6.96 (d, 1H), 7.23-7.40 (m, 2H), 7.82-8.02 (m, 5H), 8.09 (s, 1H), 8.48, (broad s, 1H), 8.62 (d, 1H), 13.89 (broad s, 1H).

Example 66

3-acetyl-N-(2-(5-(3,4-dichlorophenyl)furan-2-yl)ethyl)-1H-pyrazole-5-carboxamide The title compound was prepared using the method of Example 20 but starting from 3-acetyl-1H-pyrazole-5-carboxylic acid (215 mg; 1.37 mmol) and 2-(5-(3,4-dichlorophenyl)furan-2-yl)ethanamine hydrochloride (400 mg; 1.37 mmol). Crude product was purified by chromatography (CombiFlash, silica column, eluent: 0-100% EtOAc/heptane) to obtain 267 mg (50%) of the title compound. $^1$H-NMR (400 MHz; d6-DMSO): δ 2.50 (s, 3H—overlapping with DMSO), 2.93 (t, 2H), 3.54-3.60 (m, 2H), 6.33 (d, 1H), 7.02 (d, 1H), 7.30 (s, 1H), 7.58-7.64 (m, 2H), 7.82 (d, 1H), 8.65 (broad s, 1H), 14.21 (s, 1H).

Example 67

(E/Z)—N-(2-(5-(3,4-dichlorophenyl)furan-2-yl)ethyl)-3-(1-(hydroxyimino)ethyl)-1H-pyrazole-5-carboxamide 3-Acetyl-N-(2-(5-(3,4-dichlorophenyl)furan-2-yl)ethyl)-1H-pyrazole-5-carboxamide (40 mg; 0.10 mmol) was dissolved in 5 ml of EtOH. Anhydrous NaAc (10 mg; 0.12 mmol) and hydroxylamine hydrochloride (8.5 mg; 0.12 mmol) was added. The reaction mixture was stirred at RT for 3 days until complete. The reaction mixture was evaporated to dryness and dissolved in 10 ml of EtOAc and washed 2×2 ml of water. After Na$_2$SO$_4$ drying and evaporation 34 mg (82%) of the title compound was obtained as a mixture of E and Z isomers (1H-NMR/~1:1). $^1$H-NMR (400 MHz; d1-CDCl$_3$): δ 2.23/2.26 (s, 3H), 2.98-3.05 (m, 2H), 3.72-3.82 (m, 2H), 6.19-6.32 (m, 1H), 6.57-6.62 (m, 1H), 7.01 (d, 1H), 7.00/7.05 (s, 1H), 7.20-7.45 (m, 5H), 7.80/7.86 (t, 1H), 13.86 (s, 1H).

Example 68

N-(2-(5-(3,4-dichlorophenyl)furan-2-yl)ethyl)-3-(1-(2-hydroxyethylamino)ethyl)-1H-pyrazole-5-carboxamide 3-Acetyl-N-(2-(5-(3,4-dichlorophenyl)furan-2-yl)ethyl)-1H-pyrazole-5-carboxamide (78 mg; 0.20 mmol) and 2-aminoethanol (10 mg; 0.17 mmol) were dissolved in 5 ml of dry toluene and 5 ml of dry THF and stirred for 6.5 h at 75° C. under nitrogen atmosphere and then overnight at RT. Sodium tetrahydroborate (18.8 mg; 0.50 mmol) was added, stirred for 3 days at RT and then 4.5 h at 75° C. 10 mg of sodium tetrahydroborate was added and the mixture was heated for 5 h at 50° C. to complete the reaction. 0.1 ml of water was added at 0° C. and pH adjusted to 1 with 1 M HCl. Solution was evaporated to dryness, 15 ml of DCM was added and the mixture was washed with 10 ml of water. pH was adjusted to 12 with 1 M NaOH and 15 ml of DCM was added. After Na$_2$SO$_4$ drying the compound was purified by chromatography (CombiFlash, Silica column, 2.5-10% MeOH/DCM) to obtain 19 mg (26%) of the title compound. $^1$H-NMR (400 MHz; d1-CDCl$_3$): δ 1.43 (d, 3H), 2.55-2.70 (m, 1H), 2.74-2.85 (m, 1H), 2.97 (t, 2H), 3.60-3.76 (m, 4H), 4.02-4.12 (m, 1H), 6.16 (d, 1H), 6.53 (d, 1H), 6.65 (s, 1H), 7.33-7.41 (m, 3H), 7.67 (d, 1H).

Example 69

N-(2-(5-(3,4-dichlorophenyl)furan-2-yl)ethyl)-3-(1-hydroxyethyl)-1H-pyrazole-5-carboxamide The title compound was isolated as a side product in the preparation of N-(2-(5-(3,4-dichlorophenyl)furan-2-yl)ethyl)-3-(1-(2-hydroxyethylamino)ethyl)-1H-pyrazole-5-carboxamide by a direct reduction of staring material 3-acetyl-N-(2-(5-(3,4-dichlorophenyl)furan-2-yl)ethyl)-1H-pyrazole-5-carboxamide. After chromatographic purification (CombiFlash, Silica column, 2.5-10% MeOH/DCM) 21 mg (32%) of the title compound was obtained. $^1$H-NMR (400 MHz; d6-DMSO): δ 1.38 (d, 3H), 2.93 (t, 2H), 3.54 (q, 2H), 4.70-4.85 (m, 1H), 5.42 (s, 1H), 6.33 (d, 1H), 6.43 (s, 1H), 7.02 (d, 1H), 7.55-7.68 (m, 2H), 7.87 (d, 1H), 8.19 (broad s, 1H), 13.03 (s, 1H).

Example 70

N-(2-(5-(3,4-dichlorophenyl)furan-2-yl)ethyl)pyrazolo[1,5-a]pyrimidine-2-carboxamide The title compound was prepared using the method of Example 20 but starting from pyrazolo[1,5-a]pyrimidinecarboxylic acid (82 mg; 0.5 mmol) and 2-(5-(3,4-dichlorophenyl)furan-2-yl)ethanamine hydrochloride (146 mg; 0.5 mmol). Crude product was purified by chromatography (CombiFlash, silica column, eluent: 0-20% DCM/MeOH) to obtain 107 mg of the title compound. The product was further purified by trituration in toluene to give 55 mg of pure product (27%). $^1$H-NMR (400 MHz; d1-CDCl$_3$): δ 3.06 (t, 2H), 3.83 (m, 2H), 6.233 (d, 1H), 6.61 (d, 1H), 6.93 (dd, 1H), 7.35-7.41 (m, 2H), 7.44 (dd, 1H), 7.70 (d, 1H), 8.55 (dd, 1H), 8.57-8.60 (m, 1H).

Example 71

N-(2-(3-(5-chloro-6-cyanopyridin-3-yl)-1H-pyrazol-1-yl)ethyl)-5-(pyrin-3-yl)-1H-pyrazole-3-carboxamide a) 3-amino-5-bromopicolinonitrile Iron powder (5.0 g, 90 mmol) was added to a solution 5-bromo-3-nitropyridine-2-carbonitrile (4.56 g, 20 mmol) in glacial acetic acid (125 ml). The suspension was stirred for 2 h at 80° C. The cooled mixture was filtered through a short plug of Celite and washed with EtOAc. Solvents were evaporated, the residue was dissolved in EtOAc and neutralised with 20% aqueous K$_2$CO$_3$. Phases were separated and organic phase was washed with water and brine, dried over anhydrous Na$_2$SO$_4$, filtered and evaporated. Crude product was purified by CombiFlash (DCM-MeOH, gradient elution). Product fractions were combined and evaporated to produce 1.67 g of product. $^1$H-NMR (400 MHz; d6-DMSO): δ 6.55 (s, 2H), 7.46 (d, 1H, J=2.0 Hz), 7.94 (d, 1H, J=1.9 Hz).

b) 5-bromo-3-chloropicolinonitrile

Sodium nitrite (0.7 g, 10.15 mmol) was added to a cooled suspension of 3-amino-5-bromopicolinonitrile (1.67 g, 8.43 g) in 37% hydrochloric acid (14 ml, 169 mmol) and water (4.5 ml) and stirred for 1 h at 0-5° C. Copper powder (0.134 g, 2.11 mmol) was added and the mixture refluxed for 1 h. The mixture was cooled, quenched with ice water and basified with 48% NaOH. The mixture was extracted with EtOAc. The organic phase was washed with water and brine, dried over anhydrous Na$_2$SO$_4$, filtered and evaporated to give 1.21 g of the product. $^1$H-NMR (400 MHz; d6-DMSO): δ 8.75 (d, 1H, J=1.9 Hz), 8.90 (d, 1H, J=1.9 Hz).

c) 3-chloro-5-(1-(tetrahydro-2H-pyran-2-yl)-1H-pyrazol-5-yl)picolinonitrile 5-bromo3-chloropiconilonitrile (1.68 g, 7.73 mmol) and 1-(tetrahydro-2H-pyran-2-yl)-5-(4,4,5,5-tetramethyl-1,3,2-dioxaborolan-2-yl)1-H-pyrazole (2.47 g, 8.88 mmol) were dissolved in ethylene glycol dimethyl ether (25 ml) under nitrogen atmosphere. Bis(triphenylphosphine)palladium chloride (0.38 g, 0.541 mmol) and 2 M Na$_2$CO$_3$ (7.73 ml, 15.45 ml) were added and the mixture was stirred under nitrogen atmosphere at 80° C. for 3.5 h. Solvents were evaporated and the residue was treated with water and extracted with EtOAc. The organic phase was washed with water and brine, dried over anhydrous Na$_2$SO$_4$, filtered and evaporated. Crude product was purified by trituration with EtOAc to give 1.11 g of the product. $^1$H-NMR (400 MHz; d6-DMSO): δ 1.52-1.63 (m, 3H), 1.86 (m, 1H), 1.96 (m, 1H), 2.35 (m, 1H), 3.60 (m, 1H), 3.94 (m, 1H), 5.39 (dd, 1H), 6.84 (d, 1H), 7.69 (d, 1H), 8.39 (d, 1H), 8.87 (d, 1H).

d) 3-chloro-5-(1H-pyrazol-5-yl)picolinonitrile

4 M hydrogen chloride in dioxane (1.1 ml, 4.40 mmol) was added to a solution of 3-chloro-5-(1-(tetrahydro-2H-pyran-2-yl)-1H-pyrazol-5-yl)picolinonitrile (1.1 g, 3.81 mmol) in absolute ethanol (15 ml) and stirred at RT for 3 h. Solvents were evaporated and water was added to the residue. The mixture was neutralised with saturated NaHCO$_3$ and extracted with EtOAc. The organic phase was dried over anhydrous Na$_2$SO$_4$, filtered and evaporated to give 0.796 g of the product. $^1$H-NMR (400 MHz; d6-DMSO): δ 7.10 (d, 1H), 7.92 (d, 1H), 8.58 (d, 1H), 9.17 (d, 1H), 13.4 (bs, 1H).

e) 3-chloro-5-(1-(2-tritylamino)ethyl)1-H-pyrazol-3-yl)pivolinonitrile 3-chloro-5-(1H-pyrazol-5-yl)picolinonitrile (0.34 g, 1.662 mmol) was added to a cooled (0-5° C.) suspension of 60% sodium hydride in mineral oil (0.116 g, 2.91 mmol, washed with heptane) in dry DMF (8 ml) and stirred at RT for 1 h. The mixture was cooled to 0-5° C. and a solution of 2-bromo-N-tritylethanamine (1.00 g, 2.73 mmol, prepared as in EP 435749) in dry DMF (4 ml) was gradually added and stirred at RT for 3 h. The mixture was filtered, water and EtOAc were added to the filtrate and phases were separated. The water phase was extracted with EtOAc, organic phases were washed with water and brine, dried over anhydrous Na$_2$SO$_4$, filtered and evaporated. Crude product was purified by trituration with heptane-EtOAc to give 0.56 g of the product. $^1$H-NMR (400 MHz; d6-DMSO): δ 2.38 (m, 2H), 2.97 (t, 1H), 4.29 (t, 2H), 7.1-7.3 (m, 16H), 7.98 (d, 1H), 8.53 (d, 1H), 9.13 (d, 1H).

f) 5-(1-(2-aminoethyl)-1H-pyrazol-3-yl)-3-chloropiconilonitrile

TFA (3.0 ml, 40.4 mmol) was added to a cooled solution of 3-chloro-5-(1-(2-tritylamino)ethyl)1-H-pyrazol-3-yl)pivolinonitrile (0.475 g, 0.969 mmol) in DCM-MeOH (1:1, 6 ml). The mixture was stirred at RT for 48 h after which solvents were evaporated. Water and ether were added and the phases were separated. The aqueous phase was basified with 2M NaOH and extracted with DCM. Combined organic phases were dried over anhydrous Na$_2$SO$_4$, filtered and evaporated to give 0.187 g of product. $^1$H-NMR (400 MHz; d6-DMSO): δ 2.97 (t, 2H), 4.17 (t, 2H), 7.07 (d, 1H), 7.91 (d, 1H), 8.54 (d, 1H), 9.13 (d, 1H).

g) N-(2-(3-(5-chloro-6-cyanopyridin-3-yl)-1H-pyrazol-1-yl)ethyl)-5-(pyrin-3-yl)-1H-pyrazole-3-carboxamide HOBt hydrate (67 mg, 0.437 mmol), 1-(3-dimethylaminopropyl)-3-ethylcarbodiimide hydrochloride (84 mg, 0.436 mmol) and DIPEA (0.19 ml, 1.09 mmol) were added to a solution of 5-pyridin-3-yl-4H-pyrazole-3-carboxylic acid in DCM (6 ml) and stirred at RT for 15 min. 5-(1-(2-aminoethyl)-1H-pyrazol-3-yl)-3-chloropiconilonitrile was added and stirring continued overnight. Solvent was evaporated, water was added and extracted with EtOAc. The organic phase was washed with brine, dried over anhydrous Na$_2$SO$_4$, filtered and evaporated to give 94 mg of the product. $^1$H-NMR (400 MHz; d6-DMSO): δ 3.73 (q, 2H), 4.41 (t, 2H), 7.07 (d, 1H), 7.21 (d, 1H), 7.49 (dd, 1H), 7.91 (d, 1H), 8.13 (bs, 1H), 8.52 (d, 1H), 8.55 (dd, 1H), 8.99 (bs, 1H), 9.13 (d, 1H), 13.8 (bs, 1H).

Example 72

3-Tert-butyl-N-(1-(5-(4-cyano-3-(trifluoromethyl)phenyl)furan-2-yl)propan-2-yl)-1H-pyrazole-5-carboxamide a) (E)-2-(4-chloro-3-(trifluoromethyl)phenyl)-5-(2-nitroprop-1-enyl)furan 5-(4-chloro-3-(trifluoromethyl)phenyl)furan-2-carbaldehyde (4.00 g, 14.5 mmol), nitroethane (3.00 ml, 40.7 mmol), n-butylamine (1.7 ml, 17.5 mmol) and acetic acid (7.5 ml) were mixed and heated up to 80° C. for 2 h. After cooling to RT the mixture was filtered. The precipitate was crystallized from ethanol affording 2.58 g of the title product. $^1$H-NMR (400 MHz; d6-DMSO): δ 2.62 (s, 3H), 7.39 (d, 1H), 7.57 (d, 1H), 7.87 (m, 1H), 8.00 (s, 1H), 8.11 (m, 1H), 8.22 (m, 1H).

b) 1-(5-(4-chloro-3-(trifluoromethyl)phenyl)furan-2-yl)propan-2-amine (E)-2-(4-chloro-3-(trifluoromethyl)phenyl)-5-(2-nitroprop-1-enyl)furan (2.58 g, 7.78 mmol) was mixed with diethyl ether (54 ml) and toluene (25 ml) and added drop wise to a cooled (−20° C.) solution of lithium aluminium hydride (2.5 g, 65.9 mmol) in diethyl ether (11 ml). The mixture was allowed to warm up to 0° C. and stirred for 3 h and then at RT for additional 1 h stirring. Then the mixture was cooled again and 2.5 ml of water was added at −30° C. and then 2.5 ml of 15% aqueous NaOH solution. An additional 7.5 ml of water was added and the solution was allowed to warm to RT. MgSO$_4$ was added and the mixture was stirred and filtered, precipitate was washed with toluene and diethyl ether and the filtrate was evaporated to dryness. After CombiFlash purification with DCM:MeOH as eluent system, the pooled fractions afforded 1.13 g of the title compound. $^1$H-NMR (400 MHz; d6-DMSO): δ 1.01 (d, 3H), 2.63 (m, 2H), 3.11-3.15 (m, 1H) 6.28 (d, 1H), 7.07 (d, 1H), 7.68 (d, 1H), 7.87 (m, 1H), 7.95 (m, 1H).

c) 3-tert-butyl-N-(1-(5-(4-chloro-3-(trifluoromethyl)phenyl)furan-2-yl)propan-2-yl)-1H-pyrazole-5-carboxamide 3-tert-butyl-N-(1-(5-(4-chloro-3-(trifluoromethyl)phenyl)furan-2-yl)propan-2-yl)-1H-pyrazole-5-carboxamide was prepared from 1-(5-(4-chloro-3-(trifluoromethyl)-phenyl)furan-2-yl)propan-2-amine (0.500 g, 1.651 mmol), 3-tert-butyl-1H-pyrazole-5-carboxylic acid (0.306 g, 1.817 mmol), HOBt (0.246 g, 1.817 mmol), DIPEA (0.576 ml, 3.303 mmol) and EDCI (0.349 g, 1.817 mmol) using the method of Example 1(d) producing 0.692 g of the title compound. $^1$H-NMR (400 MHz; d6-DMSO): δ 1.19 (d, 3H), 1.26 (s, 9H), 2.87-2.92 (m, 1H), 2.96-3.00 (m, 1H), 4.29-4.37 (m, 1H), 6.29-6.32 (m, 1H), 7.04-7.10 (m, 1H), 7.57-7.73 (m, 1H), 7.88-7.98 (m, 3H), 12.84 (m, 1H).

d) 3-tert-butyl-N-(1-(5-(4-cyano-3-(trifluoromethyl)phenyl)furan-2-yl)propan-2-yl)-1H-pyrazole-5-carboxamide 3-tert-butyl-N-(1-(5-(4-chloro-3-(trifluoromethyl)phenyl)furan-2-yl)propan-2-yl)-1H-pyrazole-5-carboxamide (0.615 g, 1.355 mmol) was weighed into a reaction vial (Biotage) and 11.6 ml of DMF was added. Zinc cyanide (0.350 g, 2.981 mmol), S-Phos (0.112 g, 0.271 mmol) and Pd$_2$(dba)$_3$ (0.100 g, 0.108 mmol) were added. The reaction vial was flushed with nitrogen, capped and heated for 30 min at 150° C. in microwave oven. The mixture was allowed to cool to RT and 30 ml of 1 M NaOH was added. The mixture was extracted with EtOAc for three times and the combined organic layers were washed with water, dried with Na$_2$SO$_4$, filtered and evaporated to dryness. CombiFlash purification afforded 0.094 g of the title product. $^1$H-NMR (400 MHz; CDCl$_3$): δ 1.29 (d, 3H), 1.33 (s, 9H), 3.00 (d, 2H), 4.49-4.56 (m, 1H), 6.31 (d, 1H), 6.58 (s, 1H), 6.84 (d, 1H), 7.11 (m, 1H), 7.78 (m, 1H), 7.85 (m, 1H), 7.95 (m, 1H).

Example 73

(E)-N-(2-(5-(4-cyano-3-(trifluoromethyl)phenyl)furan-2-yl)vinyl)picolinamide a) (E)-3-(5-(4-chloro-3-(trifluoromethyl)phenyl)furan-2-yl)acrylic Acid 5-(4-chloro-3-(trifluoromethyl)phenyl)furan-2-carbaldehyde (3.32 g, 13.4 mmol) was dissolved in pyridine (16.6 ml) and piperidine (0.66 ml) was added. Malonic acid (1.67 g, 1.61 mmol) was added and the reaction mixture was refluxed for 4 h. Cooled reaction mixture was poured into a solution of ice (100 ml) water (100 ml) and conc. HCl (100 ml). The precipitate was filtered and washed with cold water and recrystallised from ethanol to afford 2.55 g of the title compound. $^1$H-NMR (400 MHz; d6-DMSO): δ 6.44 (d, 1H), 7.08 (d, 1H), 7.40 (m, 1H), 7.43 (d, 1H), 7.81 (d, 1H), 8.14 (m, 1H), 8.21 (m, 1H), 12.44 (m, 1H).

b) (E)-2-(2-bromovinyl)-5-(4-chloro-3-(trifluoromethyl)phenyl)furan (E)-3-(5-(4-chloro-3-(trifluoromethyl)phenyl)furan-2-yl)acrylic acid (2.55 g, 8.06 mmol) was added to a stirred solution of Dess-Martin periodinane (18.40 ml, 59.07 mmol) and TEAB (1.84 g, 8.86 mmol) in 12.1 ml of dry DCM. After 1.5 h of stirring at RT, the reaction mixture was diluted with DCM (60 ml) and extracted two times with sodium bisulfite (aq. 10%) solution, two times with saturated aqueous NaHCO$_3$ solution, two times with water and finally once with brine. Organic layer was dried with Na$_2$SO$_4$, filtered and evaporated to dryness affording 2.44 g of the title compound. $^1$H-NMR (400 MHz; d6-DMSO): δ 6.43 (d, 1H), 7.08 (d, 1H), 7.67 (m, 2H), 7.93 (m, 1H), 8.17 (m, 2H).

c) (E)-N-(2-(5-(4-chloro-3-(trifluoromethyl)phenyl)furan-2-yl)vinyl)picolinamide (E)-2-(2-bromovinyl)-5-(4-chloro-3-(trifluoromethyl)phenyl)furan (0.501 g, 1.378 mmol) in toluene (2.4 ml) was added to a mixture of copper(I) iodide (0.014 g, 0.069 mmol), potassium carbonate (0.381 g, 2.756 mmol), picolinamide (0.202 g, 1.654 mmol) and N,N'-dimethylethylene diamine (0.0149 ml, 0.0138 mmol) under nitrogen. The reaction mixture was refluxed for 7.5 h and allowed to cool to RT. It was then filtrated through a layer of silica and the filter cake was washed with EtOAc. The filtrate was evaporated to dryness and purified with CombiFlash using heptane-DCM as eluent system affording 0.046 g of the title compound. $^1$H-NMR (400 MHz; d6-DMSO): δ 6.54 (d, 1H), 6.70 (d, 1H), 7.26 (d, 1H), 7.61-7.70 (m, 2H), 7.77 (d, 1H), 7.99-8.02 (m, 1H), 8.04-8.09 (m, 2H), 8.13 (m, 1H), 8.74 (m, 1H), 11.20 (d, 1H).

d) (E)-N-(2-(5-(4-cyano-3-(trifluoromethyl)phenyl) furan-2-yl)vinyl)picolinamide (E)-N-(2-(5-(4-chloro-3-(trifluoromethyl)phenyl)furan-2-yl)vinyl)picolinamide (0.046 g, 0.012 mmol) was treated with zinc cyanide (0.041 g, 0.026 mmol), S-Phos (0.010 g, 0.002 mmol) and $Pd_2(dba)_3$ (0.009 g, 0.001 mmol) using the method of Example 72(d). Preparative TLC-purification afforded 0.011 g of the title compound. $^1$H-NMR (400 MHz; d6-DMSO): δ 6.63 (d, 1H), 6.73 (d, 1H), 7.52 (d, 1H), 7.68-7.76 (m, 2H), 8.05-8.21 (m, 5H), 8.75 (d, 1H), 11.26 (d, 1H).

Example 74

3-tert-butyl-N-(2-(5-(3-chloro-4-cyano-2-methylphenyl)furan-2-yl)ethyl)-1H-pyrazole-5-carboxamide a) 3-tert-butyl-N-(2-(furan-2-yl)ethyl)-1H-pyrazole-5-carboxamide 2-(furan-2-yl)ethanamine (0.81 g, 7.30 mmol) was added to a premixed (10 min) solution of 3-tert-butyl-1H-pyrazole-5-carboxylic acid (0.61 g, 3.60 mmol), DCC (1.51 g, 7.30 mmol) and HOBt (0.99 g, 7.30 mmol) in DCM:DMF-solution (10 ml, 2:9, v/v). After stirring for 15 h at RT the reaction mixture was filtered through a pad of Celite and the filtrate was washed two times with water, evaporated to dryness and purified with CombiFlash to afford 0.36 g of the title compound. $^1$H-NMR (400 MHz; d6-DMSO): δ 1.27 (s, 9H), 2.84 (t, 2H), 3.46 (m, 2H), 6.17 (m, 1H), 6.35 (m, 2H), 7.52 (m, 1H), 8.08 (m, 1H), 12.89 (m, 1H).

b) 3-tert-butyl-N-(2-(5-(3-chloro-4-cyano-2-methylphenyl)furan-2-yl)ethyl)-1H-pyrazole-5-carboxamide 4-amino-2-chloro-3-methylbenzonitrile (0.200 g, 1.20 mmol) was added to a solution of water (2 ml) and conc. HCl (2 ml) and the mixture was stirred vigorously, heated to 80° C. for 15 min and then cooled to −10° C. Sodium nitrite (0.091 g, 1.32 mmol) was dissolved in 0.5 ml of water and added drop wise to the cooled reaction mixture. After 40 min, the mixture was filtered and 3-tert-butyl-N-(2-(furan-2-yl)ethyl)-1H-pyrazole-5-carboxamide (0.345 g, 1.32 mmol) dissolved in acetone (3 ml) was added to the filtrate. Then, a solution of iron (II) chloride tetra hydrate in water (3 ml) was added portion wise and the mixture was stirred for 15 h at RT. Water (25 ml) was added to the reaction mixture and extracted three times with EtOAc. The combined organic layers were washed with saturated aqueous $NaHCO_3$ and water and dried with $Na_2SO_4$, filtered and evaporated to dryness. CombiFlash purification afforded 0.013 g of the title compound. $^1$H-NMR (400 MHz; d6-DMSO): δ 1.34 (s, 9H), 3.03 (t, 2H), 3.77 (m, 2H), 6.28 (d, 1H), 6.62 (m, 2H), 7.12 (m, 1H), 7.50 (d, 1H), 7.65 (d, 1H).

Example 75

(R)—N-(1-(3-(3-chloro-4-cyanophenyl)-1H-pyrazol-1-yl)propan-2-yl)-5-methoxythiazole-2-carboxamide a) Ethyl 5-methoxythiazole-2-carboxylate

A mixture of ethyl 2-(2-methoxy-2-oxoethylamino)-2-oxoacetate (1.00 g, 5.29 mmol) and phosphorus pentasulfide (1.29 g, 5.82 mmol) in chloroform (20 ml) was stirred at 60° C. for 7 h. To the cooled reaction mixture DCM (100 ml) was added and the mixture was washed with water (50 ml) and brine (50 ml). Organic phase was dried over $Na_2SO_4$ and evaporated. Evaporation residual was dissolved in dry MeCN (10 ml) and phosphorus pentoxide (0.75 g, 5.29 mml) was added and the mixture was heated to reflux for 4.5 h. To the cooled reaction mixture water (35 ml) was added and the mixture was extracted with EtOAc (3×50 ml). Combined organic fractions were dried over $Na_2SO_4$ and evaporated to give crude product, which was purified twice by CombiFlash (1$^{st}$ column: silica, eluent: 0-100% EtOAc in heptane; 2$^{nd}$ column: C-18, eluent: 0-100% MeCN in water) to yield 73 mg (7%) of the title compound. $^1$H-NMR (400 MHz; $CDCl_3$): δ 1.42 (t, 3H), 4.01 (s, 3H), 4.43 (q, 2H), 7.30 (s, 1H).

b) 5-methoxythiazole-2-carboxylic Acid

To a solution of ethyl 5-methoxythiazole-2-carboxylate (73 mg, 0.39 mmol) in THF (1 ml) 1 M LiOH-solution (0.78 ml, 0.78 mmol) was added. Reaction mixture was stirred at RT for 1 h. Reaction was quenched by adding 1 M HCl solution until pH was about 5. Solvents were evaporated and thus obtained crude title compound was used without purification. $^1$H-NMR (400 MHz; d6-DMSO): δ 3.88 (s, 3H), 7.12 (s, 1H).

c) (R)—N-(1-(3-(3-chloro-4-cyanophenyl)-1H-pyrazol-1-yl)propan-2-yl)-5-methoxythiazole-2-carboxamide (R)-4-(1-(2-aminopropyl)-1H-pyrazol-3-yl)-2-chlorobenzonitrile (86 mg, 0.33 mmol) was coupled with 5-methoxythiazole-2-carboxylic acid (90 mg, 0.40 mmol) using the method of Example 34(d). Crude product was purified by CombiFlash (column: silica, eluent: 0-10% MeOH in DCM) to yield 12 mg (9%) of the title compound. $^1$H-NMR (400 MHz; $CDCl_3$): δ 1.23 (d, 3H), 3.99 (s, 3H), 4.26 (dd, 1H), 4.40-4.46 (m, 1H), 4.49-4.59 (m, 1H), 6.63 (d, 1H), 7.22 (s, 1H), 7.49 (d, 1H), 7.68 (d, 1H), 7.78 (dd, 1H), 8.10 (broad d, 1H) overlapping with 8.13 (d, 1H).

Example 76

N-(2-(3-(3-chloro-4-cyanophenyl)-1H-pyrazol-1-yl) ethyl)-5-(pyridin-3-yl)-1H-pyrazole-3-carboxamide The title compound was prepared from 4-(1-(2-aminoethyl)-1H-pyrazol-3-yl)-2-chlorobenzonitrile (0.361 g, 1.463 mmol), 5-Pyridin-3-yl-4H-pyrazole-3-carboxylic acid (0.305 g, 1.610 mmol), DIPEA (0.382 ml, 2.195 mmol), HOBt (0.297 g, 2.195 mmol) and EDCI (0.421 g, 2.195 mmol) using the method of Example 75(b) affording 0.022 g of the title compound. $^1$H-NMR (400 MHz; d6-DMSO): δ 3.71 (m, 2H), 4.38 (t, 2H), 6.97 (m, 1H), 7.23 (m, 1H), 7.48 (m, 1H), 7.86 (m, 2H), 7.97 (m, 1H), 8.09 (m, 1H), 8.17 (m, 1H), 8.40-8.71 (m, 2H), 8.98 (m, 1H), 13.82 (m, 1H).

Example 77

(S)—N-(1-(3-(3-chloro-4-cyanophenyl)-1H-pyrazol-1-yl)propan-2-yl)-5-(2-hydroxypropan-2-yl)isoxazole-3-carboxamide a) 5-(2-hydroxypropan-2-yl)isoxazole-3-carboxylic Acid

Ethyl 5-(2-hydroxypropan-2-yl)isoxazole-3-carboxylate (0.436 g, 2.189 mmol) was dissolved in methanol (20 ml).

A solution of cesium carbonate (1.426 g, 4.38 mmol) in 20 ml of water was added and the reaction mixture was stirred at RT for 18 h. Solvents were evaporated and the residue was taken into a mixture of ethyl acetate and water, pH was adjusted to 2.5 with 10% citric acid solution and the layers were separated. Water layer was extracted three times with ethyl acetate and the combined organic layers were dried with $Na_2SO_4$, filtered and evaporated affording 0.246 g of the title compound. $^1$H-NMR (400 MHz; d6-DMSO): δ 1.49 (s, 6H), 5.75 (m, 1H), 6.60 (s, 1H).

b) (S)—N-(1-(3-(3-chloro-4-cyanophenyl)-1H-pyrazol-1-yl)propan-2-yl)-5-(2-hydroxypropan-2-yl)isoxazole-3-carboxamide 5-(2-hydroxypropan-2-yl)isoxazole-3-carboxylic acid (0.088 g, 0.515 mmol) and DIPEA (0.090 ml, 0.515 mmol) were dissolved in 5 ml of dry DCM. Anhydrous HOBt (0.070 g, 0.515 mmol), and EDCI (0.099 g, 0.515 mmol) were added. After stirring at RT for 30 min the (S)-4-(1-(2-aminopropyl)-1H-pyrazol-3-yl)-2-chlorobenzonitrile (0.112 g, 0.430 mmol) dissolved in 1 ml of dry DMF was added to the reaction mixture. After overnight stirring at RT a mixture of 5-(2-hydroxypropan-2-yl)isoxazole-3-carboxylic acid (0.088 g, 0.515 mmol), DIPEA (0.090 ml, 0.515 mmol), anhydrous HOBt (0.070 g, 0.515 mmol) and EDCI (0.099 g, 0.515 mmol) dissolved in 5 ml of dry DCM was added to the reaction mixture. After 3 h the solvents were evaporated and the residue was purified by CombiFlash using MeOH in DCM as an eluent. Product fractions were combined and evaporated to give 58 mg of the product. $^1$H-NMR (400 MHz; CDCl$_3$): δ 1.23 (d, 3H), 1.65 (s, 6H), 4.26 (m, 1H), 4.43 (m, 1H), 4.58 (m, 1H), 6.60 (s, 1H), 6.63 (d, 1H), 7.49 (d, 1H), 7.68 (d, 1H), 7.83 (d, 1H), 7.90 (d, 1H), 8.07 (d, 1H).

Example 78

(S)-5-acetyl-N-(1-(3-(4-cyano-3,5-difluorophenyl)-1H-pyrazol-1-yl)propan-2-yl)-1H-pyrazole-3-carboxamide a) 2,6-difluoro-4-(1-(tetrahydro-2H-pyran-2-yl)-1H-pyrazol-5-yl)benzonitrile The title compound was prepared from 4-bromo-2,6-difluorobenzonitrile (2.5 g, 11.47 mmol) and 1-(tetrahydro-2H-pyran-2-yl)-5-(4,4,5,5-tetramethyl-1,3,2-dioxaborolan-2-yl)-1H-pyrazole (3.51 g, 12.61 mmol) using the method of Example 34(a) producing 3.61 g of title compound. $^1$H-NMR (400 MHz; d6-DMSO): δ 1.52-1.67 (m, 3H), 1.81-1.87 (m, 1H), 1.95-1.99 (m, 1H), 2.33-2.41 (m, 1H), 3.59-3.65 (m, 1H), 3.94-3.98 (m, 1H), 5.36-5.39 (m, 1H), 6.77 (d, 1H), 7.62 (s, 1H), 7.64 (s, 1H), 7.66 (d, 1H).

b) 2,6-difluoro-4-(1H-pyrazol-5-yl)benzonitrile

The title compound was prepared from 2,6-difluoro-4-(1-(tetrahydro-2H-pyran-2-yl)-1H-pyrazol-5-yl)benzonitrile (3.32 g, 11.48 mmol) using the method of Example 34(b) affording 2.38 g of the product. $^1$H-NMR (400 MHz; d6-DMSO): δ 7.04 (m, 1H), 7.83 (s, 1H), 7.86 (s, 1H), 7.91 (m, 1H), 13.37 (s, 1H).

c) (S)-4-(1-(2-aminopropyl)-1H-pyrazol-3-yl)-2,6-difluorobenzonitrile

The title compound was prepared from 2,6-difluoro-4-(1H-pyrazol-5-yl)-benzonitrile (1.39 g, 6.78 mmol) and (S)-tert-butyl 1-hydroxypropan-2-ylcarbamate (1.423 g, 8.12 mmol), triphenylphosphine (2.129 g, 8.12 mmol) and DIAD (1.578 ml, 8.12 mmol) using the method of Example 34(c) affording 0.70 g of the title compound. $^1$H-NMR (400 MHz; d6-DMSO): δ 0.95 (d, 3H), 3.22 (m, 1H), 4.01 (m, 2H), 7.02 (d, 1H), 7.78 (m, 1H), 7.81 (m, 1H), 7.88 (d, 1H).

d) (S)-5-acetyl-N-(1-(3-(4-cyano-3,5-difluorophenyl)-1H-pyrazol-1-yl)propan-2-yl)-1H-pyrazole-3-carboxamide The title compound was prepared from (S)-4-(1-(2-aminopropyl)-1H-pyrazol-3-yl)-2,6-difluorobenzonitrile (0.7 g, 2.67 mmol), 3-acetyl-1H-pyrazole-5-carboxylic acid (0.494 g, 3.20 mmol), HOBt (0.433 g, 3.20 mmol), DIPEA (0.558 ml, 3.20 mmol) and EDCI (0.614 g, 3.20 mmol) using the method of Example 34(d) producing 0.29 g of the title compound. $^1$H-NMR (400 MHz; d6-DMSO): δ 1.17 (m, 3H), 4.32 (m, 2H), 4.44 (m, 1H), 6.97 (m, 1H), 7.31 (m, 1H), 7.71 (m, 2H), 7.83 (m, 1H), 8.44 (m, 1H), 14.15 (m, 1H).

Example 79

N-(2-(3-(4-cyano-3, 5-difluorophenyl)-1H-pyrazol-1-yl)ethyl)-5-(pyridin-3-yl)-1H-pyrazole-3-carboxamide a) 4-(1-(2-aminoethyl)-1H-pyrazol-3-yl)-2,6-difluorobenzonitrile The title compound was prepared from 2,6-difluoro-4-(1H-pyrazol-5-yl)-benzonitrile (1.50 g, 7.31 mmol) and tert-butyl N-(2-hydroxyethyl)carbamate (0.96 ml, 6.09 mmol), triphenylphosphine (1.918 g, 7.31 mmol) and DIAD (1.200 ml, 6.09 mmol) using the method of Example 34 (c) affording 0.30 g of the title compound. $^1$H-NMR (400 MHz; d6-DMSO): δ 1.60 (m, 2H), 2.94 (t, 2H), 4.14 (t, 2H), 7.01 (d, 1H), 7.79 (m, 2H), 7.88 (d, 1H).

b) N-(2-(3-(4-cyano-3,5-difluorophenyl)-1H-pyrazol-1-yl)ethyl)-5-(pyridin-3-yl)-1H-pyrazole-3-carboxamide The title compound was prepared from 4-(1-(2-aminoethyl)-1H-pyrazol-3-yl)-2,6-difluorobenzonitrile (0.3 g, 0.773 mmol), 5-pyridin-3-yl-4H-pyrazole-3-carboxylic acid (0.161 g, 0.851 mmol), DIPEA (0.202 ml, 1.160 mmol), HOBt (0.157 g, 1.160 mmol) and EDCI (0.222 g, 1.160 mmol) using the method of Example 34(d) affording 0.06 g of the title compound. $^1$H-NMR (400 MHz; d6-DMSO): δ 3.70 (t, 2H), 4.39 (t, 2H), 7.01 (d, 1H), 7.79 (m, 2H), 7.88 (d, 1H).

Example 80

5-(1H-imidazol-4-yl)-1-methyl-N-(2-(3-(4-nitro-3-(trifluoromethyl)phenyl)-1H-pyrazol-1-yl)ethyl)-1H-pyrazole-3-carboxamide a) 5-(4-Nitro-3-(trifluoromethyl)phenyl)-1-(tetrahydro-2H-pyran-2-yl)-1H-pyrazole The title compound was prepared from 5-bromo-2-nitrobenzotrifluoride (5 g, 18.52 mmol) and 1-(tetrahydro-2H-pyran-2-yl)-5-(4,4,5,5-tetramethyl-1,3,2-dioxaborolan-2-yl)-1H-pyrazole (5.67 g, 20.37 mmol) using the method of Example 34(a). Reaction afforded 3.90 g of the title compound. ¹H-NMR (400 MHz; d6-DMSO): δ 1.49-1.68 (m, 3H), 1.82 (m, 1H), 1.94 (m, 1H), 2.38 (m, 1H), 3.61 (m, 1H), 3.99 (d, 1H), 5.31 (m, 1H), 6.78 (d, 1H), 7.66 (d, 1H), 8.10 (m, 1H), 8.19 (m, 1H), 8.32 (d, 1H).

b) 5-(4-nitro-3-(trifluoromethyl)phenyl)-1H-pyrazole

The title compound was prepared from 5-(4-Nitro-3-(trifluoromethyl)phenyl)-1-(tetrahydro-2H-pyran-2-yl)-1H-pyrazole (2.693 g, 7.89 mmol) using the method of Example 34(b) affording 1.69 g of the title compound. ¹H-NMR (400 MHz; d6-DMSO): δ 7.08 (m, 1H), 7.92 (m, 1H), 8.22 (d, 1H), 8.35 (m, 1H), 8.38 (m, 1H), 13.45 (m, 1H).

c) 2-(3-(4-nitro-3-(trifluoromethyl)phenyl)-1H-pyrazol-1-yl)ethanamine

The title compound was prepared from 5-(4-nitro-3-(trifluoromethyl)phenyl)-1H-pyrazole (1.69 g, 6.57 mmol) and tert-butyl 2-hydroxyethylcarbamate (1.059 g, 6.57 mmol) using the method of Example 34(c) to afford 1.24 g of the title compound. ¹H-NMR (400 MHz; d6-DMSO): δ 3.33 (m, 2H), 4.53 (t, 2H), 7.13 (d, 1H), 8.00 (d, 1H), 8.38 (m, 1H), 13.45 (m, 1H).

d) 5-(1H-imidazol-4-yl)-1-methyl-N-(2-(3-(4-nitro-3-(trifluoromethyl)phenyl)-1H-pyrazol-1-yl)ethyl)-1H-pyrazole-3-carboxamide The title compound was prepared from 2-(3-(4-nitro-3-(trifluoromethyl)phenyl)-1H-pyrazol-1-yl)ethanamine (0.062 g, 0.208 mmol) and 5-(1H-imidazol-4-yl)-1-methyl-1H-pyrazole-3-carboxylic acid (0.05 g, 0.260 mmol) HOBt (0.035 g, 0.260 mmol), DIPEA (0.091 ml, 0.520 mmol) and EDCI (0.050 g, 0.260 mmol) using the method of Example 34(d) to afford 0.128 g of the title compound. ¹H-NMR (400 MHz; d6-DMSO): δ 3.71 (m, 3H), 4.40 (t, 2H), 7.04 (s, 1H), 7.05 (d, 1H), 7.88 (d, 1H), 8.03 (s, 1H), 8.22 (m, 1H), 8.31-8.33 (m, 2H), 8.40 (t, 1H), 9.03 (m, 1H).

Example 81

N-(2-(3-(4-cyano-3-nitrophenyl)-1H-pyrazol-1-yl)ethyl)-3-(1-(hydroxyimino)-ethyl)-1H-pyrazole-5-carboxamide a) 2-Nitro-4-(1-(tetrahydro-2H-pyran-2-yl)-1H-pyrazol-5-yl)benzonitrile The title compound was prepared from 4-chloro-2-nitrobenzonitrile (3.00 g, 16.43 mmol) and 1-(tetrahydro-2H-pyran-2-yl)-5-(4,4,5,5-tetramethyl-1,3,2-dioxaborolan-2-yl)-1H-pyrazole (5.48 g, 19.72 mmol) using the method of Example 34(a) affording 1.26 g of the title compound. ¹H-NMR (400 MHz; d6-DMSO): δ 1.56-1.62 (m, 3H), 1.81-1.85 (m, 1H), 1.95-1.99 (m, 1H), 2.33-2.47 (m, 1H), 3.68-3.75 (m, 1H), 4.01-4.04 (m, 1H), 5.31-5.34 (m, 1H), 6.84 (d, 1H), 7.69 (d, 1H), 8.13 (m, 1H), 8.32 (d, 1H), 8.60 (d, 1H).

b) 2-Nitro-4-(1H-pyrazol-5-yl)benzonitrile

The title compound was prepared from 2-Nitro-4-(1-(tetrahydro-2H-pyran-2-yl)-1H-pyrazol-5-yl)benzonitrile (1.26 g, 4.22 mmol) using the method of Example 34(b) affording 0.828 g of the title compound. ¹H-NMR (400 MHz; d6-DMSO): δ 7.09 (m, 1H), 7.94 (m, 1H), 8.20 (d, 1H), 8.37 (d, 1H), 8.73 (s, 1H), 13.39 (s, 1H).

c) 4-(1-(2-Aminoethyl)-1H-pyrazol-3-yl)-2-nitrobenzonitrile

The title compound was prepared from 2-nitro-4-(1H-pyrazol-5-yl)benzonitrile (0.828 g, 3.87 mmol) and tert-butyl 2-hydroxyethylcarbamate (0.748 g, 4.64 mmol) using the method of Example 34(c) affording 0.633 g of the title compound. ¹H-NMR (400 MHz; d6-DMSO): δ 3.21-3.29 (m, 2H), 4.02-4.04 (m, 2H), 7.02 (d, 1H), 7.88 (d, 1H), 8.13 (d, 1H), 8.29 (m, 1H), 8.50 (d, 1H).

d) 5-Acetyl-N-(2-(3-(4-cyano-3-nitrophenyl)-1H-pyrazol-1-yl)ethyl)-1H-pyrazole-3-carboxamide The title compound was prepared from 4-(1-(2-aminoethyl)-1H-pyrazol-3-yl)-2-nitrobenzonitrile (0.50 g, 1.94 mmol), 3-acetyl-1H-pyrazole-5-carboxylic acid (0.30 g, 1.94 mmol), HOBt (0.31 g, 2.33 mmol), DIPEA (0.41 ml, 2.33 mmol) and EDCI (0.44 g, 2.33 mmol) using the method of Example 34(d) producing 0.56 g of the title compound. ¹H-NMR (400 MHz; d6-DMSO): δ 2.48 (s, 3H), 3.69-3.73 (m, 2H), 4.39 (t, 2H), 7.05 (d, 1H), 7.30 (s, 1H), 7.88 (d, 1H), 8.18 (d, 1H), 8.32 (d, 1H), 8.66 (d, 1H), 14.16 (s, 1H).

e) N-(2-(3-(4-Cyano-3-nitrophenyl)-1H-pyrazol-1-yl)ethyl)-3-(1-(hydroxy-imino)ethyl)-1H-pyrazole-5-carboxamide 5-Acetyl-N-(2-(3-(4-cyano-3-nitrophenyl)-1H-pyrazol-1-yl)ethyl)-1H-pyrazole-3-carboxamide (0.17 g, 0.43 mmol) was dissolved in ethanol (15 ml). Sodium acetate (0.071 g, 0.86 mmol) and hydroxylamine hydrochloride (0.060 g, 0.86 mmol) was added and the reaction mixture was stirred at RT for 1.5 h. After addition of pyridine (5 ml) stirring was continued for 65 h. The reaction mixture was evaporated to dryness, co-evaporated two times with toluene and dissolved the residue in ethyl acetate. It was then washed two times with water, dried with Na₂SO₄ and purified with Combi-Flash using DCM and methanol as eluents affording 0.034 g of the title compound. ¹H-NMR (400 MHz; d6-DMSO): δ 2.11-2.15 (m, 3H), 3.68-3.71 (m, 2H), 4.39 (t, 2H), 7.05-7.06 (m, 1H), 7.88 (d, 1H), 8.17-8.20 (m, 1H), 8.32-8.35 (m, 1H), 8.68 (d, 1H).

Example 82

(R)—N-(1-(3-(4-cyano-3-(trifluoromethyl)phenyl)-1H-pyrazol-1-yl)propan-2-yl)-3-(furan-2-yl)-1H-pyrazole-5-carboxamide a) 4-(1-(tetrahydro-2H-pyran-2-yl)-1H-pyrazol-5-yl)-2-(trifluoromethyl)-benzonitrile The title compound was prepared from 4-iodo-2-(trifluoromethyl) benzonitrile (5.97 g, 22.6 mmol) using the method of Example 34(a) affording 5.34 g of the title compound after column purification.

b) 4-(1H-pyrazol-5-yl)-2-(trifluoromethyl)benzonitrile

The title compound was prepared from 4-(1-(tetrahydro-2H-pyran-2-yl)-1H-pyrazol-5-yl)-2-(trifluoromethyl)benzonitrile using the method of Example 34(b) affording 3.94 g of the title compound. $^{1}$H-NMR (400 MHz; d6-DMSO): δ 7.07 (m, 1H), 7.91 (m, 1H), 8.19 (d, 1H), 8.31 (d, 1H), 8.35 (s, 1H), 13.33 (s, 1H).

c) (R)-2-(1-bromopropan-2-yl)isoindoline-1,3-dione (R)-2-(1-hydroxypropan-2-yl)isoindoline-1,3-dione (1.3 g, 50.0 mmol) was heated to reflux with phosphorustribromide (9.2 ml, 34 mmol) for 30 min. The reaction mixture was cooled to RT and ice was added to the reaction mixture. After stirring the mixture was filtered and the precipitate was washed with cold water and dried in vacuum to afford 12.37 g of the title compound.

d) (R)-4-(1-(2-(1,3-dioxoisoindolin-2-yl)propyl)-1H-pyrazol-3-yl)-2-(trifluoromethyl)benzonitrile 4-(1H-pyrazol-5-yl)-2-(trifluoromethyl)benzonitrile (1.0 g, 4.22 mmol) and (R)-2-(1-bromopropan-2-yl)isoindoline-1,3-dione (1.35 g, 5.06 mmol) were weighed into a microreaction vial and DMF (10 ml) was added. Then, potassium carbonate (1.165 g, 8.43 mmol), copper(I) iodide (0.040 g, 0.21 mmol) and N, N'-dimethyl-ethylenediamine (0.004 ml, 0.042 mmol) were added and the reaction vial was capped under nitrogen and was heated in the microwave oven (Biotage) at 160° C. for 30 min. The mixture was then poured into water and extracted with DCM and 2% MeOH/DCM. Organic layers were combined, dried with Na$_2$SO$_4$, filtered and evaporated to dryness. CombiFlash purifications using normal and reversed phase columns afforded 0.199 g of the title compound. $^{1}$H-NMR (400 MHz; d6-DMSO): δ 1.54 (m, 3H), 4.55-4.65 (m, 3H), 6.95 (d, 1H), 7.77 (m, 4H), 7.82 (m, 1H), 7.86-7.89 (m, 2H), 8.01 (d, 1H).

e) (R)-4-(1-(2-aminopropyl)-1H-pyrazol-3-yl)-2-(trifluoromethyl)benzonitrile (R)-4-(1-(2-(1,3-dioxoisoindolin-2-yl)propyl)-1H-pyrazol-3-yl)-2-(trifluoro-methyl)benzonitrile (0.199 g, 0.469 mmol) was mixed with ethanol (15 ml). Hydrazine hydrate (0.227 ml, 4.69 mmol) was added and the mixture was refluxed for 3 h. After cooling to RT the precipitate was filtered and washed with ethanol. The filtrate was purified with CombiFlash using DCM and methanol as eluents. Drying in the vacuum afforded 0.080 g of the title product. $^{1}$H-NMR (400 MHz; d6-DMSO): δ 0.96 (d, 3H), 3.21-3.29 (m, 2H), 4.01-4.03 (m, 2H), 7.05 (d, 1H), 7.88 (d, 2H), 8.18 (d, 1H), 8.26-8.28 (m, 1H), 8.31 (s, 1H).

f) (R)—N-(1-(3-(4-cyano-3-(trifluoromethyl)phenyl)-1H-pyrazol-1-yl)propan-2-yl)-3-(furan-2-yl)-1H-pyrazole-5-carboxamide (The title compound was prepared from (R)-4-(1-(2-aminopropyl)-1H-pyrazol-3-yl)-2-(trifluoromethyl)benzonitrile (0.080 g, 0.272 mg) and 3-(furan-2-yl)-1H-pyrazole-5-carboxylic acid (0.053 g, 0.299 mmol) using the method of Example 34(d) affording 0.092 g of the title compound. $^{1}$H-NMR (400 MHz; d6-DMSO): δ 1.17 (d, 3H), 4.30-4.39 (m, 2H), 4.42-4.51 (m, 1H), 6.61 (m, 1H), 7.03 (d, 1H), 7.76 (m, 1H), 7.86 (d, 1H), 8.17 (d, 1H), 8.27 (d, 1H), 8.34-8.36 (m, 1H), 13.69 (m, 1H).

Example 83

(S)-3-acetyl-N-(1-(3-(3-chloro-4-cyano-2-methyl-phenyl)-1H-pyrazol-1-yl)-propan-2-yl)-1H-pyrazole-5-carboxamide a) 2-chloro-3-methyl-4-(1-(tetrahydro-2H-pyran-2-yl)-1H-pyrazol-5-yl)-benzonitrile The title compound was prepared from 2-chloro-4-iodo-3-methylbenzonitrile (3.52 g, 12.68 mmol) and 1-(tetrahydro-2H-pyran-2-yl)-3-(4,4,5,5-tetramethyl-1,3,2-dioxaborolan-2-yl)-1H-pyrazole (3.88 g, 13.95 mmol) using the method of Example 34(a) affording 2.62 g of the title compound.

b) 2-chloro-3-methyl-4-(1H-pyrazol-3-yl)benzonitrile

The title compound was prepared from 2-chloro-3-methyl-4-(1-(tetrahydro-2H-pyran-2-yl)-1H-pyrazol-5-yl) benzonitrile (2.62 g, 8.68 mmol) using the method of Example 34(b) affording 1.66 g of the title compound. $^{1}$H-NMR (400 MHz; d6-DMSO): δ 6.66 (t, 1H), 7.69 (d, 1H), 7.84 (d, 1H), 7.90 (m, 1H), 13.25 (m, 1H).

c) (S)-2-(tert-butoxycarbonylamino)propyl methanesulfonate (S)-tert-Butyl 1-hydroxypropan-2-ylcarbamate (10.25 g, 58.5 mmol) was dissolved DCM (20 ml). Triethylamine (12.23 ml, 87.7 mmol) was added and the solution was cooled to 0° C. under nitrogen. Methanesulfonylchloride (5.0 ml, 64.3 mmol) was diluted with DCM (5 ml) and added drop wise to the reaction mixture keeping the temperature under 10° C. After addition, the reaction mixture was allowed to warm up to RT and stirring was continued for 36 h. Next, the reaction mixture was diluted with DCM (150 ml) and washed several times with NaHCO$_3$-solution and water, the organic layer dried with Na$_2$SO$_4$, filtered and evaporated affording 8.78 g of the title compound. $^{1}$H-NMR (400 MHz; d6-DMSO): δ 1.06 (d, 3H), 1.38 (s, 9H), 3.16 (s, 3H), 3.75 (m, 1H), 4.04 (m, 2H), 6.93 (m, 1H).

d) (S)-tert-butyl 1-(3-(3-chloro-4-cyano-2-methyl-phenyl)-1H-pyrazol-1-yl)propan-2-ylcarbamate 2-Chloro-3-methyl-4-(1H-pyrazol-3-yl)benzonitrile (1.96 g, 8.96 mmol) was dissolved in toluene (20 ml). To this solution an aqueous solution of NaOH (1M, 20 ml) and tetrabutylammonium bromide (0.58 g, 1.79 mmol) was added, respectively. (S)-2-(tert-butoxycarbonylamino)propyl methanesulfonate (4.54 g, 17.92 mmol) was dissolved in toluene (20 ml) and added to the reaction mixture. After 96 h of vigorous stirring at RT the reaction mixture was diluted with toluene and washed several times with water, dried with Na$_2$SO$_4$, filtered and evaporated. After CombiFlash purification using heptane/EtOAc as eluents, 1.85 g of the product was collected. $^{1}$H-NMR (400 MHz; d6-DMSO): δ 1.02 (d, 3H), 1.31 (s, 9H), 2.57 (s, 3H), 3.91 (m, 1H), 4.13 (m, 2H), 6.62 (m, 1H), 6.87 (d, 1H), 7.66 (d, 1H), 7.79 (d, 1H), 7.84 (d, 1H).

e) (S)-4-(1-(2-aminopropyl)-1H-pyrazol-3-yl)-2-chloro-3-methylbenzonitrile (S)-tert-butyl 1-(3-(3-chloro-4-cyano-2-methylphenyl)-1H-pyrazol-1-yl)propan-2-yl carbamate (1.85 g, 4.96 mmol)

was dissolved in a mixture of DCM:TFA:water (8:1.5:0.5, v:v:v, 20 ml) and stirred at RT for 22 h. The reaction mixture was then diluted with DCM to 50 ml and washed with NaHCO₃, brine and water, and the organic layer was dried with Na₂SO₄, filtered and evaporated to dryness affording 1.19 g of the title compound. ¹H-NMR (400 MHz; d6-DMSO): δ 0.96 (d, 3H), 2.57 (s, 3H), 3.23 (m, 1H), 4.02 (d, 2H), 6.64 (d, 1H), 7.67 (d, 1H), 7.83 (d, 1H), 7.87 (d, 1H).

f) (S)-3-acetyl-N-(1-(3-(3-chloro-4-cyano-2-methylphenyl)-1H-pyrazol-1-yl)propan-2-yl)-1H-pyrazole-5-carboxamide The title compound was prepared from (S)-4-(1-(2-aminopropyl)-1H-pyrazol-3-yl)-2-chloro-3-methylbenzonitrile (0.2 g, 0.728 mmol), 3-acetyl-1H-pyrazole-5-carboxylic acid (0.112 g, 0.728 mmol), HOBt (0.128 g, 0.946 mmol), DIPEA (0.165 ml, 0.946 mmol) and EDCI (0.181 g, 0.946 mmol) using the method of Example 34(d) affording 0.117 g of the title compound. ¹H-NMR (400 MHz; CDCl₃): δ 1.27 (d, 3H), 2.54 (s, 3H), 2.55 (s, 3H), 4.31 (m, 1H), 4.44 (m, 1H), 4.62 (m, 1H), 6.44 (d, 1H), 7.51 (d, 1H), 7.54 (s, 2H), 11.14 (m, 1H).

Example 84

N—((S)-1-(3-(3-chloro-4-cyano-2-methylphenyl)-1H-pyrazol-1-yl)propan-2-yl)-3-(1-hydroxyethyl)-1H-pyrazole-5-carboxamide (S)-3-acetyl-N-(1-(3-(3-chloro-4-cyano-2-methylphenyl)-1H-pyrazol-1-yl)-propan-2-yl)-1H-pyrazole-5-carboxamide (0.04 g, 0.097 mmol) as prepared in the previous Example was added in ethanol (5 ml). Solid sodium borohydride (0.018 g, 0.487 mmol) was added to the mixture and it was refluxed for 15 min under nitrogen. To the cooled solution a portion of 10 ml of saturated ammonium chloride was added and the mixture was extracted several times with DCM. The organic extracts were combined and washed with water, dried with Na₂SO₄, filtered and evaporated to dryness affording 0.040 g of the title compound. ¹H-NMR (400 MHz; CDCl₃): δ 1.25 (m, 3H), 1.51 (m, 3H), 2.49 (d, 3H), 3.72 (m, 1H), 4.29 (m, 1H), 4.41 (m, 1H), 4.61 (m, 1H), 4.99 (m, 1H), 6.42 (d, 1H), 6.56 (s, 1H), 7.43-7.50 (m, 3H), 7.53 (d, 1H).

Example 85

(S)—N-(1-(3-(3-chloro-4-cyano-2-methylphenyl)-1H-pyrazol-1-yl)propan-2-yl)-5-methylisoxazole-3-carboxamide The title compound was prepared from (S)-4-(1-(2-aminopropyl)-1H-pyrazol-3-yl)-2-chloro-3-methylbenzonitrile (0.2 g, 0.728 mmol), 5-methylisoxazole-3-carboxylic acid (0.120 g, 0.946 mmol), HOBt (0.128 g, 0.946 mmol), DIPEA (0.165 ml, 0.946 mmol) and EDCI (0.181 g, 0.946 mmol) using DCM as solvent using the method of Example 34(d) affording 0.114 g of the title compound. ¹H-NMR (400 MHz; CDCl₃): δ 1.26 (m, 3H), 2.48 (d, 3H), 2.56 (m, 3H), 4.29 (m, 1H), 4.43 (m, 1H), 4.59 (m, 1H), 6.41 (d, 1H), 6.44 (d, 1H), 7.44 (m, 1H), 7.50 (d, 1H), 7.56 (d, 1H), 7.62 (d, 1H).

Example 86

(S)—N-(1-(3-(3-chloro-4-cyano-2-methylphenyl)-1H-pyrazol-1-yl)propan-2-yl)thiazole-4-carboxamide The title compound was prepared from (S)-4-(1-(2-aminopropyl)-1H-pyrazol-3-yl)-2-chloro-3-methylbenzonitrile (0.2 g, 0.728 mmol), 1,3-thiazole-4-carboxylic acid (0.113 g, 0.874 mmol), HOBt (0.118 g, 0.874 mmol), DIPEA (0.152 ml, 0.874 mmol) and EDCI (0.167 g, 0.874 mmol) using DCM as solvent using the method of Example 34(d) affording 0.88 g of the title compound. ¹H-NMR (400 MHz; d6-DMSO): δ 1.16 (d, 3H), 2.51 (s, 3H), 4.37 (m, 2H), 6.61 (d, 1H), 7.67 (d, 1H), 7.83-7.85 (m, 2H), 8.27 (d, 1H), 8.56 (d, 1H), 9.20 (d, 1H).

Example 87

(S)—N-(1-(3-(3-chloro-4-cyano-2-methylphenyl)-1H-pyrazol-1-yl)propan-2-yl)-5-(trifluoromethyl)-1H-pyrazole-3-carboxamide The title compound was prepared from (S)-4-(1-(2-aminopropyl)-1H-pyrazol-3-yl)-2-chloro-3-methylbenzonitrile (0.15 g, 0.546 mmol), 5-trifluoromethyl-1H-pyrazole-3-carboxylic acid (0.108 g, 0.601 mmol), HOBt (0.111 g, 0.819 mmol), DIPEA (0.143 ml, 0.819 mmol) and EDCI (0.157 g, 0.819 mmol) using DCM as solvent using the method of Example 34(d) affording 0.098 g of the title compound. ¹H-NMR (400 MHz; d6-DMSO): δ 1.18 (d, 3H), 2.48 (s, 3H), 4.30 (m, 2H), 4.46 (m, 1H), 6.60 (d, 1H), 7.21 (m, 1H), 7.60 (d, 1H), 7.79 (d, 1H), 7.85 (d, 1H), 8.51 (m, 1H), 14.39 (m, 1H).

Example 88

(S)—N-(1-(3-(3-chloro-4-cyano-2-methylphenyl)-1H-pyrazol-1-yl)propan-2-yl)-3-(furan-2-yl)-1H-pyrazole-5-carboxamide The title compound was prepared from (S)-4-(1-(2-aminopropyl)-1H-pyrazol-3-yl)-2-chloro-3-methylbenzonitrile (0.059 g, 0.331 mmol), 3-(furan-2-yl)-1H-pyrazole-5-carboxylic acid (0.091 g, 0.331 mmol), HOBt (0.068 g, 0.497 mmol), DIPEA (0.087 ml, 0.497 mmol) and EDCI (0.096 g, 0.497 mmol) using DCM as solvent using the method of Example 34(d) affording 0.065 g of the title compound. ¹H-NMR (400 MHz; d6-DMSO): δ 1.16 (d, 3H), 2.53 (s, 3H), 4.28-4.38 (m, 2H), 4.43-4.51 (m, 1H), 6.60 (d, 2H), 6.81-6.91 (m, 2H), 7.66 (d, 1H), 7.77 (s, 1H), 7.82 (d, 1H), 7.85 (m, 1H), 8.31 (m, 1H), 13.69 (m, 1H).

Example 89

(R)—N-(1-(3-(3-chloro-4-cyano-2-methylphenyl)-1H-pyrazol-1-yl)propan-2-yl)-5-(pyridin-3-yl)-1H-pyrazole-3-carboxamide a) (R)-2-(tert-butoxycarbonylamino)propyl methanesulfonate The title compound was prepared from (R)-tert-butyl 1-hydroxypropan-2-ylcarbamate (9.45 g, 53.9 mmol) using the method of Example 83(c) affording 11.48 g of the title compound. ¹H-NMR (400 MHz; d6-DMSO): δ 1.06 (d, 3H), 1.38 (s, 9H), 3.16 (s, 3H), 3.74 (m, 1H), 4.04 (d, 2H), 6.94 (m, 1H).

b) (R)-tert-Butyl 1-(3-(3-chloro-4-cyano-2-methyl-phenyl)-1H-pyrazol-1-yl)propan-2-ylcarbamate 2-chloro-3-methyl-4-(1H-pyrazol-3-yl)benzonitrile (0.5 g, 2.297 mmol) was dissolved in dry acetonitrile (5 ml) under nitrogen and cooled to 0° C. Sodium ethoxide (0.313 g, 4.59 mmol) was added and the reaction mixture was stirred for 25 min and allowed to warm up to RT. (R)-2-(tert-butoxycarbonylamino)propyl methanesulfonate (0.582 g, 2.297 mmol) was dissolved in 5 ml of dry acetonitrile and added dropwise to the reaction mixture. The reaction mixture was refluxed for 15 h and then the solvents were evaporated. The residue was taken into EtOAc, washed several times with saturated aqueous NaHCO₃ and water, dried with Na₂SO₄ and evaporated to dryness. CombiFlash purification afforded 0.437 g of the title compound using heptane/EtOAc-system as an eluent. ¹H-NMR (400 MHz; d6-DMSO): δ 1.02 (d, 3H), 1.31 (s, 9H), 2.57 (s, 3H), 3.91 (m, 1H), 4.13 (m, 2H), 6.62 (m, 1H), 6.87 (d, 1H), 7.66 (d, 1H), 7.78 (d, 1H), 7.83 (d, 1H).

c) (R)-4-(1-(2-aminopropyl)-1H-pyrazol-3-yl)-2-chloro-3-methylbenzonitrile

The title compound was prepared from (R)-tert-butyl 1-(3-(3-chloro-4-cyano-2-methylphenyl)-1H-pyrazol-1-yl)propan-2-ylcarbamate (0.437 g, 1.166 mmol) using the method of Example 83(e) affording 0.306 g of the title compound. ¹H-NMR (400 MHz; d6-DMSO): δ 0.96 (d, 3H), 2.57 (s, 3H), 3.18-3.26 (m, 1H), 4.01 (d, 2H), 6.64 (d, 1H), 7.67 (d, 1H), 7.83 (d, 1H), 7.86 (d, 1H).

d) (R)—N-(1-(3-(3-chloro-4-cyano-2-methylphenyl)-1H-pyrazol-1-yl)propan-2-yl)-5-(pyridin-3-yl)-1H-pyrazole-3-carboxamide The title compound was prepared from (R)-4-(1-(2-aminopropyl)-1H-pyrazol-3-yl)-2-chloro-3-methylbenzonitrile (0.3 g, 1.092 mmol), 5-pyridin-3-yl-4H-pyrazole-3-carboxylic acid (0.227 g, 1.201 mmol), DIPEA (0.285 ml, 1.638 mmol), HOBt (0.221 g, 1.638 mmol) and EDCI (0.314 g, 1.638 mmol) using the method of Example 34(d) affording 0.214 g of the title compound. ¹H-NMR (400 MHz; d6-DMSO): δ 1.15-1.21 (m, 3H), 2.54 (s, 3H), 4.28-4.41 (m, 2H), 4.45-4.54 (m, 2H), 6.61 (d, 1H), 7.22 (d, 1H), 7.45-7.52 (m, 1H), 7.62-7.70 (m, 1H), 7.76-1.86 (m, 2H), 8.09-8.18 (m, 1H), 8.25-8.47 (m, 1H), 8.53-8.57 (m, 1H), 8.99 (d, 1H).

Example 90

(R)—N-(1-(3-(3-chloro-4-cyano-2-methylphenyl)-1H-pyrazol-1-yl)propan-2-yl)-3-(furan-2-yl)-1H-pyrazole-5-carboxamide The title compound was prepared from (R)-4-(1-(2-aminopropyl)-1H-pyrazol-3-yl)-2-chloro-3-methylbenzonitrile (0.077 g, 0.280 mmol), 3-(furan-2-yl)-1H-pyrazole-5-carboxylic acid (0.055 g, 0.308 mmol), DIPEA (0.073 ml, 0.420 mmol), HOBt (0.057 g, 0.420 mmol) and EDCI (0.081 g, 0.420 mmol) using the method of Example 34(d) affording 0.090 g of the title compound. ¹H-NMR (400 MHz; d6-DMSO): δ 1.15-1.17 (m, 3H), 2.52 (s, 3H), 4.32-4.35 (m, 2H), 4.44-4.51 (m, 1H), 6.61 (d, 2H), 7.65-7.67 (m, 1H), 7.75-7.79 (m, 1H), 7.82 (d, 1H), 7.84 (d, 1H), 8.30 (m, 2H), 8.35 (m, 2H), 13.69 (m, 1H).

Example 91

(S)—N-(1-(3-(3-chloro-4-cyanophenyl)-1H-pyrazol-1-yl)propan-2-yl)-3-ethyl-1,2,4-oxadiazole-5-carboxamide (S)-4-(1-(2-aminopropyl)-1H-pyrazol-3-yl)-2-chlorobenzonitrile (200 mg, 0.77 mmol) was coupled with 3-ethyl-1,2,4-oxadiazole-5-carboxylic acid (131 mg, 0.92 mmol) using the method of Example 34(d). Crude product was suspended in MeCN and the precipitation was filtered to yield 34 mg (11%) of the title compound. Filtrate was purified by CombiFlash (column: C-18, eluent: 0-100% MeCN) to yield additional 118 mg (40%) of title product. Combined total yield was 152 mg (51%). ¹H-NMR (400 MHz; d6-DMSO): δ 1.18 (d, 3H), 1.26 (t, 3H), 2.81 (q, 2H), 4.31-4.37 (m, 2H), 4.40-4.52 (m, 1H), 6.95 (d, 1H), 7.85 (d, 1H), 7.92 (dd, 1H), 7.97 (d, 1H), 8.06 (d, 1H), 9.39 (broad d, 1H).

Example 92

(E)-4-(5-(((3-tert-butyl-1H-pyrazole-5-carbonyl)diazenyl)methyl)-furan-2-yl)-2-(trifluoromethyl)benzonitrile a) 4-bromo-2-(trifluoromethyl)-benzonitrile To the cooled and vigorously stirred suspension of 4-amino-2-(trifluoro-methyl)benzonitrile (5.00 g, 26.8 mmol) in 25 ml of concentrated hydrogen bromide a solution of sodium nitrite (1.85 g, 26.8 mmol) in 10 ml of water was added dropwise while keeping the temperature below 5° C. during the addition. This mixture was then poured into a solution of copper(I)bromide (3.85 g, 26.8 mmol) in 30 ml of concentrated hydrogen bromide and stirred at RT for two hours. The reaction mixture was then poured into an ice-water (300 ml) mixture and extracted four times with ethyl acetate. The combined extracts were washed with saturated sodium bicarbonate and water, dried and evaporated to dryness. Combiflash purification using heptane/ethyl acetate as eluent system afforded 5.1 g of the title product. ¹H-NMR (400 MHz; d6-DMSO): δ 8.13 (d, 1H), 8.18 (d, 1H), 8.27 (s, 1H)

b) 4-(5-formylfuran-2-yl)-2-(trifluoromethyl)benzonitrile

To the stirred solution of 5-formylfuran-3-boronic acid (0.31 g, 2.2 mmol), palladium (10%) in carbon (0.090 g) and sodium carbonate (0.85 g, 8.0 mmol) in ethanol (10 ml) was added a solution of 4-bromo-2-(trifluoromethyl)benzonitrile (0.50 g, 0.19 mmol) in ethanol (10 ml) under nitrogen atmosphere. The reaction mixture was refluxed for two hours, and then cooled to RT and diluted with ethanol. The mixture was filtered through a pad of Celite, washed with ethanol and the filtrate was evaporated to dryness. Combiflash purification using heptane/ethyl acetate as eluent system afforded 0.20 g of the title compound. ¹H-NMR (400 MHz; d6-DMSO): δ 7.73 (d, 1H), 7.76 (d, 1H), 8.31 (m, 1H), 8.33 (m, 1H), 8.39 (m, 1H), 9.71 (s, 1H).

c) (E)-4-(5-(((3-tert-butyl-1H-pyrazole-5-carbonyl) diazenyl)methyl)furan-2-yl)-2-(trifluoromethyl)benzonitrile To the solution of 3-tert-butyl-1H-pyrazole-5-carbohydrazide (0.076 g, 0.41 mmol) in 10 ml of ethanol 4-(5-formylfuran-2-yl)-2-(trifluoromethyl)benzonitrile (0.10 g, 0.37 mmol) was added and the mixture was stirred at RT for 36 h. The solvent was evaporated and the residue purified with Combiflash using DCM/methanol as eluent system affording fractions containing the title compound. After treatment of these fractions with DCM the product precipitated out producing 0.048 g of title compound. $^1$H-NMR (400 MHz; d6-DMSO): δ 1.31 (s, 9H), 6.55 (m, 1H), 7.12 (d, 1H), 7.65 (d, 1H), 8.24 (m, 2H), 8.28 (m, 1H), 8.48 (m, 1H), 11.82 (m, 1H), 13.07 (m, 1H).

Example 93

Pyridine-2-carboxylic acid{1-[5-(3,4-dichlorophenyl)furan-2-yl]-meth-(E)-ylidene}hydrazide and Pyridine-2-carboxylic Acid{1-[5-(3,4-dichlorophenyl)furan-2-yl]meth-(Z)-ylidene}hydrazide A stirred solution of 2-picolinyl hydrazide (0.29 g, 2.11 mmol) and 5-(3,4-dichlorophenyl)furfural (0.45 g, 1.87 mmol) in ethanol (24 ml) was refluxed for 2.5 h under nitrogen atmosphere. Then the solution was cooled and stirring was continued at 0° C. A precipitated solid was filtered and washed with icecold ethanol to afford the mixture of pyridine-2-carboxylic acid {1-[5-(3,4-dichlorophenyl)furan-2-yl]meth-(Z)-ylidene}hydrazide and pyridine-2-carboxylic acid {1-[5-(3,4-dichlorophenyl)-furan-2-yl]meth-(E)-ylidene}hydrazide (Z:E 33:67). The isomers were purified and separated by flash chromatography on silica gel using first heptane/EtOAc (33:67-0:100) as a gradient eluent to afford the Z isomer and then CH$_2$Cl$_2$/MeOH (99.5:0.5) as an eluent to afford the E isomer.

Pyridine-2-carboxylic acid-{1-[5-(3,4-Dichlorophenyl) furan-2-yl]meth-(Z)-ylidene}-hydrazide: $^1$H NMR (400 MHz, DMSO-d$_6$): 7.24 (1H, d), 7.49 (1H, d), 7.61 (1H, s), 7.75-7.80 (1H, m), 7.96 (1H, d), 8.12-8.24 (3H, m), 8.27 (1H, d), 8.87 (1H, m), 12.71 (1H, s).

Pyridine-2-carboxylic acid-{1-[5-(3,4-Dichlorophenyl) furan-2-yl]meth-(E)-ylidene}-hydrazide: $^1$H NMR (400 MHz, DMSO-d$_6$): 7.08 (1H, d), 7.33 (1H, d), 7.67-7.70 (1H, m), 7.74 (1H, distorted d), 7.79 (1H, distorted dd), 8.04 (1H, d), 8.07 (1H, td), 8.14 (1H, distorted d), 8.59 (1H, s), 8.73 (1H, d), 12.29 (1H, s).

Example 94

(S)—N-(1-(3-(3-chloro-4-cyanophenyl)-1H-pyrazol-1-yl)propan-2-yl)-5-(2-methylthiazol-4-yl)-1H-pyrazole-3-carboxamide a) Methyl 3-(2-methylthiazol-4-yl)-1H-pyrazole-5-carboxylate

Methyl 3-acetyl-1H-pyrazole-5-carboxylate (100 mg, 0.595 mmol) was refluxed with bromine (143 mg, 0.892 mmol) in chloroform. Solvent was evaporated and thus obtained methyl 3-(2,2-dibromoacetyl)-1H-pyrazole-5-carboxylate (191 mg, 0.586 mmol) was treated with thioacetamide (44 mg, 0.586 mmol) in refluxing methanol. Solvent was evaporated and the residue was dissolved in DCM and washed with water. Organic phase was dried over Na$_2$SO$_4$, filtered and evaporated to give 133 mg (102%) of the title compound. $^1$H-NMR (400 MHz; d6-DMSO): δ 2.71 (s, 3H), 3.83 (s, 3H), 7.10 (s, 1H), 7.90 (s, 1H) 14.0 (broad s, 1H).

b) 3-(2-methylthiazol-4-yl)-1H-pyrazole-5-carboxylic Acid

A solution of methyl 3-(2-methylthiazol-4-yl)-1H-pyrazole-5-carboxylate (0.586 mmol) in 5 ml of THF and 1 ml of MeOH was treated with 2 ml of 1 M NaOH-solution at RT over three nights. Solvent was evaporated and the residue was taken up in water and washed with DCM. 1 M HCl was added to the water phase until pH was 5. The water phase was washed twice with DCM and neutralized by 1 M sodiumbicarbonate solution. The water phase was evaporated from toluene and the evaporation residual suspended to EtOH. Thus obtained solid was filtered to give 151 mg (123%) of the title compound. $^1$H-NMR (400 MHz; d6-DMSO): δ 2.69 (s, 3H), 6.68 (s, 1H), 7.60 (s, 1H), 12.89 (bs, 1H).

c) (S)—N-(1-(3-(3-chloro-4-cyanophenyl)-1H-pyrazol-1-yl)propan-2-yl)-5-(2-methylthiazol-4-yl)-1H-pyrazole-3-carboxamide 3-(2-Methylthiazol-4-yl)-1H-pyrazole-5-carboxylic acid (0.586 mmol) was coupled with (S)-4-(1-(2-aminopropyl)-1H-pyrazol-3-yl)-2-chlorobenzonitrile using the method of Example 34(d). Crude product was purified by CombiFlash (silica column, eluent: 50-100% EtOAc in heptane) to obtain 24 mg (18%) of the title compound $^1$H-NMR (400 MHz; CDCl$_3$): δ 1.24 (d, 3H), 2.77 (s, 3H), 4.28 (dd, 1H), 4.44 (dd, 1H), 4.55-4.67 (m, 1H), 6.59 (d, 1H), 7.06 (s, 1H), 7.38 (s, 1H), 7.49 (d, 1H), 7.60 (d, 1H), 7.74 (dd, 1H), 7.82 (d, 1H), 8.06 (d, 1H), 11.75 (bs, 1H).

Example 95

1-(5-((S)-1-(3-(3-chloro-4-cyanophenyl)-1H-pyrazol-1-yl)propan-2-ylcarbamoyl)-1H-pyrazol-3-yl) ethyl 2-(dimethylamino)acetate A solution of N—((S)-1-(3-(3-chloro-4-cyanophenyl)-1H-pyrazol-1-yl)propan-2-yl)-3-(1-hydroxyethyl)-1H-pyrazole-5-carboxamide of Example 56 (90 mg, 0.225 mmol) in 2 ml of DCM was added to a suspension of N,N-dimethylglycine (47 mg, 0.45 mmol), DIPEA (0.13 ml; 0.75 mmol), anhydrous HOBt (61 mg, 0.45 mmol) and EDCI (87 mg, 0.45 mmol) in 2 ml of DCM. The reaction mixture was stirred at RT over three nights. The mixture was diluted with DCM and washed with water. Organic phase was dried over Na$_2$SO$_4$, filtered and evaporated. Crude product was purified twice by CombiFlash (1$^{st}$ column: silica, eluent: 0-10% MeOH in DCM; 2$^{nd}$ column: alumina, eluent: 0-10% MeOH in DCM) to obtain 26 mg (36%) of the title compound. $^1$H-NMR (400 MHz; CDCl3): δ 1.22 (d, 3H), 1.66 (d, 3H), 2.35 (d, 6H), 3.20 (d, 2H), 4.25-4.33 (m, 1H), 4.37-4.45 (m, 1H), 4.52-4.64 (m, 1H), 6.00 (q, 1H), 6.60 (m, 1H), 6.80 (s, 1H), 7.50 (dd, 1H), 7.67 (m, 1H), 7.74-7.87 (m, 2H), 8.09 (d, 1H), 11.6 (bs, 1H).

Example 96

(S)—N-(1-(3-(3-chloro-4-cyanophenyl)-1H-pyrazol-1-yl)propan-2-yl)-6-(1H-pyrazol-1-yl)pyridazine-3-carboxamide 6-(1H-pyrazol-1-yl)pyridazine-3-carboxylic acid (100 mg, 0.53 mmol) was coupled with (S)-4-(1-(2-aminopropyl)-1H-pyrazol-3-yl)-2-chlorobenzonitrile as described in Example 34(d). Crude product was purified twice by CombiFlash (1$^{st}$ column: silica, eluent: 0-100% EtOAc in heptane; 2$^{nd}$ column: silica, eluent: 0-15% MeOH in DCM) to obtain 54 mg (26%) of the title compound. $^1$H-NMR (400 MHz; DMSO): δ 1.23 (d, 3H), 4.35-4.50 (m, 2H), 4.51-4.64 (m, 1H), 6.75 (dd, 1H), 6.94 (d, 1H), 7.87 (d, 1H), 7.92-7.98 (m, 2H), 8.03 (dd, 2H), 8.30 (m, 2H), 8.87 (d, 1H), 9.38 (d, 1H).

Example 97

(S)—N-(1-(3-(3-chloro-4-cyanophenyl)-1H-pyrazol-1-yl)propan-2-yl)-2-(2-(dimethylamino)acetamido)thiazole-4-carboxamide A solution of (S)-2-amino-N-(1-(3-(3-chloro-4-cyanophenyl)-1H-pyrazol-1-yl)propan-2-yl)thiazole-4-carboxamide of Example 57 (46 mg, 0.12 mmol) in 1 ml of DCM was added to a suspension of N,N-dimethylglycine (25 mg, 0.24 mmol), DIPEA (0.041 ml; 0.24 mmol), anhydrous HOBt (32 mg, 0.24 mmol) and EDCI (46 mg, 0.24 mmol) in 1 ml of DCM. The reaction mixture was stirred at RT over two nights. N,N-dimethylglycine (25 mg), DIPEA (0.021 ml), anhydrous HOBt (16 mg) and EDCI (23 mg) were added to the reaction mixture, and stirring was continued overnight. N,N-dimethylglycine (25 mg), DIPEA (0.082 ml) and EDCI (46 mg) were added twice the following two days. Three days after last addition of reagents the reaction was quenched by adding DCM and washing with water. Organic phase was dried over Na$_2$SO$_4$, filtered and evaporated. Crude product was purified twice by CombiFlash (1$^{st}$ column: silica, eluent: 0-10% MeOH in DCM; 2$^{nd}$ column: silica, eluent: 20-100% EtOAc in heptane) to obtain 3.2 mg (6%) of the title compound. $^1$H-NMR (400 MHz; CDCl$_3$): δ 1.26 (d, 3H), 2.42 (s, 6H), 3.25 (s, 2H), 4.32 (dd, 1H), 4.42 (dd, 1H), 4.53-4.63 (m, 1H), 6.62 (d, 1H), 7.49 (d, 1H), 7.62 (d, 1H), 7.68 (d, 1H), 7.78 (s, 1H), 7.82 (dd, 1H), 7.96 (d, 1H).

Example 98

(S)—N-(1-(3-(3-chloro-4-cyanophenyl)-1H-pyrazol-1-yl)propan-2-yl)-2-(cyanomethyl)thiazole-4-carboxamide 2-(Cyanomethyl)thiazole-4-carboxylic acid (280 mg, 0.10 mmol) was coupled with (S)-4-(1-(2-aminopropyl)-1H-pyrazol-3-yl)-2-chlorobenzonitrile using the method of Example 34(d). Crude product was purified twice by CombiFlash (1$^{st}$ column: silica, eluent: 0-100% EtOAc in heptane; 2$^{nd}$ column: C-18 silica, eluent: 0-100% MeCN in water) to obtain 4.9 mg (1%) of the title compound. $^1$H-NMR (400 MHz; CDCl$_3$): δ 1.26 (d, 3H), 4.13 (s, 2H), 4.31 (dd, 1H), 4.43 (dd, 1H), 4.55-4.67 (m, 1H), 6.63 (d, 1H), 7.49 (d, 1H), 7.70 (d, 1H), 7.79 (dd, 1H), 7.84 (d, 1H), 7.97 (d, 1H), 8.12 (d, 1H).

Example 99

(S)-3-acetyl-N-(1-(3-(3-chloro-4-cyanophenyl)-1H-pyrazol-1-yl)butan-2-yl)-1H-pyrazole-5-carboxamide a) (S)-4-(1-(2-aminobutyl)-1H-pyrazol-3-yl)-2-chlorobenzonitrile 2-Chloro-4-(1H-pyrazol-3-yl)benzonitrile (1.06 g, 4.40 mmol), N-Boc-(S)-(−)-2-amino-1-butanol (1.0 g, 5.28 mmol) and triphenylphosphine (1.73 g, 6.61 mmol) were dissolved in 15 ml of dry THF under nitrogen atmosphere. DIAD (1.73 ml; 8.81 mmol) was added slowly by syringe to cooled (0° C.) reaction mixture. After being stirred overnight at RT, the reaction mixture was evaporated to dryness. The evaporation residue was dissolved in 20 ml of 10% HCl (g)/EtOH-solution and stirred at RT overnight to induce Boc-deprotection. Solvents were evaporated and the evaporation residue was taken up in water and brine. Thus obtained solution was washed twice with DCM, made alkaline (pH-12) by adding 2 M NaOH-solution, and extracted twice with DCM. The latter organic extracts were combined, dried over Na$_2$SO$_4$, filtered and evaporated to give 568 mg (47%) of the title compound. $^1$H-NMR (400 MHz; d6-DMSO): δ. 0.87-0.94 (m, 3H), 1.10-1.45 (m, 2H), 2.97-3.05 (m. 1H), 4.01 (dd, 1H), 4.13 (dd, 1H), 4.68-4.86 (m, 1H), 6.97 (d, 1H), 7.86 (d, 1H), 7.95 (dd, 1H), 7.97 (dd, 1H), 8.10-8.12 (m, 1H). MS [M+1]: m/z [274.8+1].

b) (S)-3-acetyl-N-(1-(3-(3-chloro-4-cyanophenyl)-1H-pyrazol-1-yl)butan-2-yl)-1H-pyrazole-5-carboxamide (S)-4-(1-(2-aminobutyl)-1H-pyrazol-3-yl)-2-chlorobenzonitrile (100 mg, 0.73 mmol) was coupled with 3-acetyl-1H-pyrazole-5-carboxylic acid (123 mg, 0.80 mmol) using the method of Example 34(d). Crude product was purified twice by CombiFlash (1$^{st}$ column: silica, eluent: 0-10% MeOH in DCM; 2$^{nd}$ column: C-18 silica, eluent: 0-100% MeCN in water) to obtain 72 mg (24%) of the title compound. $^1$H-NMR (400 MHz; d6-CDCl3/MeOD): δ 1.03 (t, 3H), 1.50-1.73 (m, 2H), 2.54 (s, 3H), 4.30-4.46 (m, 3H), 6.63 (d, 1H), 7.42 (s, 2H), 7.57 (d, 1H), 7.73 (d, 1H), 7.84 (d, 1H), 7.93 (s, 1H).

Example 100

(R)—N-(1-(3-(3-chloro-4-cyanophenyl)-1H-pyrazol-1-yl)propan-2-yl)-5-methylthiazole-2-carboxamide 5-Methyl-1,3-thiazole-2-carboxylic acid (55 mg, 0.38 mmol) was coupled with (R)-4-(1-(2-aminopropyl)-1H-pyrazol-3-yl)-2-chlorobenzonitrile (100 mg, 0.38 mmol) using the method of Example 34(d). Crude product was purified by CombiFlash (column: C-18 silica, eluent: 0-100% MeCN in water) to obtain 80 mg (54%) of the title compound. $^1$H-NMR (400 MHz; CDCl$_3$): δ 1.24 (d, 3H), 2.55 (d, 3H), 4.26 (dd, 1H), 4.45 (dd, 1H), 4.51-4.62 (m, 1H), 6.63 (d, 1H), 7.49 (d, 1H), 7.60 (dd, 1H), 7.68 (d, 1H), 7.79 (dd, 1H), 8.13 (d, 1H), 8.24 (d, 1H).

Example 101

(S)—N-(1-(3-(3-chloro-4-cyanophenyl)-1H-pyrazol-1-yl)propan-2-yl)-1,2,5-oxadiazole-3-carboxamide To a solution of 1,2,5-oxadiazole-3-carboxylic acid (66 mg, 0.58 mmol) in 5 ml of DCM were added anhydrous HOBt (88 mg, 0.65 mmol) and PS-carbodiimide (590 mg, 0.77 mmol). After 10 min (S)-4-(1-(2-aminopropyl)-1H-pyrazol-3-yl)-2-chlorobenzonitrile (100 mg, 0.38 mmol) was added and the reaction mixture was stirred at RT overnight. Resin was filtered and washed twice with DCM. Filtrate was washed with 10% citric acid, 1 M NaHCO$_3$-solution, brine and water. Organic phase was dried over Na$_2$SO$_4$, filtered and evaporated to give 111 mg (81%) of the title compound. $^1$H-NMR (400 MHz; CDCl$_3$): δ 1.25 (d, 3H), 4.25 (dd, 1H), 4.48 (dd, 1H), 4.58-4.70 (m, 1H), 6.66 (d, 1H), 7.51 (d, 1H), 7.71 (dd, 1H), 7.83 (dd, 1H), 8.01 (dd, 1H), 8.31 (d, 1H), 8.65 (s, 1H).

Example 102

N—((S)-1-(3-(3-chloro-4-cyanophenyl)-1H-pyrazol-1-yl)butan-2-yl)-3-(1-hydroxyethyl)-1H-pyrazole-5-carboxamide To a cooled (0° C.) solution of sodium borohydride (12 mg, 0.32 mmol) in 2 ml of dry EtOH was added (S)-3-acetyl-N-(1-(3-(3-chloro-4-cyanophenyl)-1H-pyrazol-1-yl)butan-2-yl)-1H-pyrazole-5-carboxamide of Example 99 (66 mg, 0.16 mmol) as a solution in 3 ml of dry EtOH. Reaction mixture was stirred at RT overnight before being quenched by adding some water and 0.5 M HCl until pH was acidic. Solvents were evaporated and the evaporation residual was taken up in 5% MeOH in DCM, washed with 1 M NaHCO$_3$ solution and water. Organic phase was dried over Na$_2$SO$_4$, filtered and evaporated to yield 64 mg (96%) of the title compound. $^1$H-NMR (400 MHz; CDCl$_3$/MeOD): δ 1.00 (t, 3H), 1.48-1.65 (m, 5H), 4.29-4.43 (m, 3H), 4.94 (q, 1H), 6.59-6.62 (m, 2H), 7.52 (d, 1H), 7.67-7.72 (m, 1H), 7.78-7.82 (m, 1H), 7.99-8.01 (m, 1H).

Example 103

(S)—N-(1-(3-(3-chloro-4-cyanophenyl)-1H-pyrazol-1-yl)propan-2-yl)-3-methyl-1,2,4-oxadiazole-5-carboxamide (S)-4-(1-(2-aminopropyl)-1H-pyrazol-3-yl)-2-chlorobenzonitrile (219 mg, 0.84 mmol) was coupled with 3-methyl-1,2,4-oxadiazole-5-carboxylic acid using the method of Example 34(d). Crude product was suspended in MeCN and MeOH. Suspension was filtered to give 16 mg (5%) the title compound as a colourless solid. Filtrate was purified by CombiFlash (column: C-18 silica, eluent: 0-100% MeCN in water). Fractions containing the title compound were combined and suspended in MeCN. Suspension was filtered to give 9 mg (3%) the title compound. $^1$H-NMR (400 MHz; d6-DMSO): δ 1.19 (d, 3H), 2.44 (s, 3H), 4.34 (d, 2H), 4.39-4.53 (m, 1H), 6.95 (d, 1H), 7.84 (d, 1H), 7.92 (dd, 1H), 7.98 (d, 1H), 8.06 (d, 1H), 9.42 (d, 1H).

Example 104

N—((R)-1-(3-(3-chloro-4-cyanophenyl)-1H-pyrazol-1-yl)butan-2-yl)-3-(1-hydroxyethyl)-1H-pyrazole-5-carboxamide a) (R)-4-(1-(2-aminobutyl)-1H-pyrazol-3-yl)-2-chlorobenzonitrile 2-Chloro-4-(1H-pyrazol-3-yl)benzonitrile (3.00 g, 13.3 mmol) was reacted with N-Boc-(R)-(+)-2-amino-1-butanol (2.76 g, 14.6 mmol) in the presence of triphenylphosphine and DIAD using the method of Example 99. After Boc-deprotection 1.48 g (41%) of the title compound was obtained. $^1$H-NMR (400 MHz; d6-DMSO): δ. 0.87-0.94 (m, 3H), 1.11-1.40 (m, 2H), 2.97-3.06 (m, 1H), 4.01 (dd, 1H), 4.13 (dd, 1H), 4.68-4.84 (m, 1H), 6.96 (d, 1H), 7.86 (d, 1H), 7.94 (dd, 1H), 7.97 (dd, 1H), 8.09-8.11 (m, 1H). MS [M+1]: m/z [274.8+1].

b) (R)-3-acetyl-N-(1-(3-(3-chloro-4-cyanophenyl)-1H-pyrazol-1-yl)butan-2-yl)-1H-pyrazole-5-carboxamide (R)-4-(1-(2-aminobutyl)-1H-pyrazol-3-yl)-2-chlorobenzonitrile (300 mg, 1.1 mmol) was coupled with 3-acetyl-1H-pyrazole-5-carboxylic acid (202 mg, 1.3 mmol) using the method of Example 34(d). Crude product was purified by CombiFlash (column: C-18 silica, eluent: 0-100% MeCN in water) to obtain 225 mg (50%) of the title compound. $^1$H-NMR (400 MHz; d6-DMSO): δ 0.90 (t, 3H), 1.43-1.65 (m, 2H), 2.49 (s, 3H), 4.22-4.41 (m, 3H), 6.91 (d, 1H), 7.32 (s, 1H), 7.79 (d, 1H), 7.86-8.05 (m, 3H), 8.38 (d, 1H), 14.1 (bs, 1H).

c) N—((R)-1-(3-(3-chloro-4-cyanophenyl)-1H-pyrazol-1-yl)butan-2-yl)-3-(1-hydroxyethyl)-1H-pyrazole-5-carboxamide (R)-3-acetyl-N-(1-(3-(3-chloro-4-cyanophenyl)-1H-pyrazol-1-yl)butan-2-yl)-1H-pyrazole-5-carboxamide (225 mg, 0.55 mmol) was treated with sodium borohydride using the method of Example 102. Thus, 192 mg (85%) of title compound was obtained. $^1$H-NMR (400 MHz; CDCl$_3$/MeOD): δ 1.00 (t, 3H), 1.46-1.67 (m, 5H), 4.28-4.44 (m, 3H), 4.94 (q, 1H), 7.61 (m, 2H), 7.53 (d, 1H), 7.69 (d, 1H), 7.80 (d, 1H), 8.00 (d, 1H).

Example 105

(S)-3-acetyl-N-(1-(3-(4-cyano-3-(methylthio)phenyl)-1H-pyrazol-1-yl)propan-2-yl)-1H-pyrazole-5-carboxamide (S)-5-acetyl-N-(1-(3-(3-chloro-4-cyanophenyl)-1H-pyrazol-1-yl)propan-2-yl)-1H-pyrazole-3-carboxamide (64 mg, 0.16 mmol) was placed into a microwave vial. DMF (1 ml) and sodium thiomethoxide (12.4 mg, 0.18 mmol) were added and the reaction mixture was heated in microwave reactor at 150° C. Sodium thiomethoxide was added after 30, 30 and 20 min of heating (12.4 mg, 5.6 mg and 5.6 mg, respectively). After total of 90 min of heating DMF was evaporated, and the evaporation residual was taken up in DCM and washed with water. Organic phase was dried over Na$_2$SO$_4$, filtered and evaporated. Thus obtained crude product was suspended in MeCN. Suspension was filtered to give 9 mg (14%) of the title compound as a colourless solid. Filtrate was purified by CombiFlash (column: C-18 silica, eluent: 0-100% MeCN in water) to yield 13 mg (20%) of the title compound. $^1$H-NMR (400 MHz; d6-DMSO): δ 1.11-1.20 (m, 3H), 2.49 (s, 3H, overlap with DMSO) 2.57-2.64 (m, 3H), 4.20-4.55 (m, 3H), 6.91 (s, 1H), 7.31 (s, 1H), 7.62-7.89 (m, 4H), 8.47 (dd, 1H), 14.2 (d, 1H).

Example 106

(S)-5-acetyl-N-(1-(3-(4-cyano-3-iodophenyl)-1H-pyrazol-2-yl)propan-2-yl)-1H-pyrazole-3-carboxamide a) 2-nitro-4-(1-(tetrahydro-2H-pyran-2-yl)-1H-pyrazol-5-yl)benzonitrile To a solution of 4-chloro-2-nitrobenzonitrile (15 g, 82 mmol) and 1-(tetrahydro-2H-pyran-2-yl)-5-(4,4,5,5-tetramethyl-1,3,2-dioxaborolan-2-yl)-1H-pyrazole (27.4 g, 99 mmol) in 300 ml of DMF were added bis(triphenylphosphine)palladium (II) chloride (1.12 g; 1.64 mmol), sodium carbonate (22.7 g; 0.16 mol) and water (30 ml). The reaction mixture was heated at 90° C. for 4.5 h, cooled and poured into 500 ml of water. The water phase was extracted twice with EtOAc, and the combined organic fractions were washed with saturated NaHCO$_3$— solution and brine, dried over Na$_2$SO$_4$ and evaporated. The evaporation residual was suspended to EtOH (100 ml) and the remaining solids were filtered to give 17.7 g (72%) of the title compound. $^1$H-NMR (400 MHz; d6-DMSO): δ 1.52-1.68 (m, 3H), 1.78-1.87 (m, 1H), 1.91-2.00 (m, 1H), 2.31-2.47 (m, 1H), 3.67-3.76 (m, 1H), 3.99-4.06 (m, 1H), 5.32 (dd, 1H), 6.84 (d, 1H), 7.69 (d, 1H), 8.13 (dd, 1H), 8.32 (d, 1H), 8.60 (d, 1H).

b) 2-nitro-4-(1H-pyrazol-5-yl)benzonitrile

To a solution of 2-nitro-4-(1-(tetrahydro-2H-pyran-2-yl)-1H-pyrazol-5-yl)-benzonitrile (17.7 g, 59 mmol) in EtOH (440 ml) was added 44 ml of concentrated HCl. The reaction mixture was stirred at RT for 1.5 h. The mixture was poured into water (1 l), and 2 M NaOH-solution was added until pH was 12. Thus resulting precipitate was filtered, washed with water and dried to give 11.7 g (92%) of the title compound. $^1$H-NMR (400 MHz; d6-DMSO): δ 7.09 (d, 1H), 7.91 (d, 1H), 8.20 (d, 1H), 8.37 (dd, 1H), 8.73 (d, 1H), 13.4 (bs, 1H).

c) (S)-4-(1-(2-aminopropyl)-1H-pyrazol-3-yl)-2-nitrobenzonitrile (S)-4-(1-(2-aminopropyl)-1H-pyrazol-3-yl)-2-nitrobenzonitrile was prepared from 2-nitro-4-(1H-pyrazol-5-yl)benzonitrile (2.0 g, 9.3 mmol) using the method of Example 34(d). Thus, 1.6 g (71%) of the title compound was obtained. $^1$H-NMR (400 MHz; d6-DMSO): δ 0.98 (d, 3H), 3.25-3.33 (m, 1H), 4.01-4.11 (m, 2H), 7.08 (d, 1H), 7.90 (d, 1H), 8.18 (d, 1H), 8.34 (dd, 1H), 8.69 (d, 1H).

d) (S)-3-acetyl-N-(1-(3-(4-cyano-3-nitrophenyl)-1H-pyrazol-1-yl)propan-2-yl)-1H-pyrazole-5-carboxamide (S)-4-(1-(2-aminopropyl)-1H-pyrazol-3-yl)-2-nitrobenzonitrile (400 mg, 1.48 mmol) was coupled with 3-acetyl-1H-pyrazole-5-carboxylic acid (250 mg, 1.62 mmol) using the method of Example 34(d). Crude product was purified by CombiFlash (column: silica, eluent: 0-10% MeOH in DCM) to yield 295 mg (49%) of the title compound. $^1$H-NMR (400 MHz; d6-DMSO): δ 1.18 (d, 3H), 2.49 (s, 3H), 4.26-4.55 (m, 3H), 7.04 (d, 1H), 7.30 (s, 1H), 7.86 (d, 1H), 8.18 (d, 1H), 8.31 (d, 1H), 8.50 (d, 1H), 8.63 (s, 1H), 14.1 (bs, 1H).

e) (S)-3-acetyl-N-(1-(3-(4-cyano-3-nitrophenyl)-1H-pyrazol-1-yl)propan-2-yl)-1H-pyrazole-5-carboxamide Tin(II) chloride dihydrate (490 mg, 2.17 mmol) was added to a cooled (0° C.) solution of (S)-4-(1-(2-aminopropyl)-1H-pyrazol-3-yl)-2-nitrobenzonitrile (295 mg, 0.72 mmol) in conc. HCl (2 ml). Reaction mixture was stirred at RT overnight. Small volume of 1 M NaOH was added until precipitate was formed. Solids were filtered, washed with water and dried to yield 0.263 g (96 5) of the title compound. $^1$H-NMR (400 MHz; d6-DMSO): δ 1.14 (d, 3H), 2.50 (s, 3H), 4.27 (m, 2H), 4.45 (m, 1H), 6.62 (d, 1H), 7.01 (dd, 1H), 7.27 (d, 1H), 7.32 (s, 1H), 7.38 (d, 1H), 7.75 (d, 1H), 8.51 (d, 1H).

f) (S)-5-acetyl-N-(1-(3-(4-cyano-3-iodophenyl)-1H-pyrazol-1-yl)propan-2-yl)-1H-pyrazole-3-carboxamide Sodium nitrite (50 mg, 0.73 mmol) in 1 ml of water was added slowly to a solution of (S)-3-acetyl-N-(1-(3-(4-cyano-3-nitrophenyl)-1H-pyrazol-1-yl)propan-2-yl)-1H-pyrazole-5-carboxamide (250 mg, 0.66 mmol) in water (2 ml), sulfuric acid (71 µl, 1.33 mmol) and MeCN (3 ml) at 0° C. After 15 min potassium iodide (0.22 g, 1.32 mmol) in 1 ml of water was added. Reaction mixture was stirred at RT for 2 h and then poured into 10 ml of water. Thus resulting precipitate was filtered and washed with 10% sodium bisulfite solution and water. Crude product was purified by CombiFlash (column: silica, eluent: 3-10% MeOH in DCM) to yield 75 mg (23%) of the title compound. $^1$H-NMR (400 MHz; MeOD): δ 1.27 (d, 3H), 2.55 (s, 3H), 4.35 (m, 1H), 4.39 (m, 1H), 4.57 (m, 1H), 6.63 (d, 1H), 7.28 (br s, 1H), 7.42 (s, 1H), 7.57 (d, 1H), 7.66 (d, 1H), 7.93 (br s, 1H), 8.35 (s, 1H).

Example 107

N—((S)-1-(3-(4-cyano-3-iodophenyl)-1H-pyrazol-1-yl)propan-2-yl)-3-(1-hydroxyethyl)-1H-pyrazole-5-carboxamide N—((S)-1-(3-(4-cyano-3-iodophenyl)-1H-pyrazol-1-yl)propan-2-yl)-3-(1-hydroxyethyl)-1H-pyrazole-5-carboxamide (65 mg, 0.13 mmol) was treated with sodium borohydride using the method of Example 102. Crude product was suspended in small volume of MeCN and the remaining solids were filtered to yield 19 mg (29%) of the title compound. $^1$H-NMR (400 MHz; MeOD/CDCl3): δ 1.05 (d, 3H), 1.33 (d, 3H), 4.12-4.19 (m, 1H), 4.28-4.40 (m, 1H), 4.70-4.79 (m, 1H), 6.38-6.48 (m, 2H), 7.36-7.40 (m, 1H), 7.44-7.45 (m, 1H), 7.69-7.75 (m, 1H), 8.18-8.82 (m, 1H).

Example 108

(R)-3-acetyl-N-(1-(3-(6-cyano-5-nitropyridin-3-yl)-1H-pyrazol-1-yl)propan-2-yl)-1H-pyrazole-5-carboxamide a) 3-nitro-5-(1-(tetrahydro-2H-pyran-2-yl)-1H-pyrazol-5-yl)picolinonitrile To a solution of 5-bromo-3-nitropyridine-2-carbonitrile (2.00 g, 8.77 mmol) and 1-(tetrahydro-2H-pyran-2-yl)-5-(4,4,5,5-tetramethyl-1,3,2-dioxaborolan-2-yl)-1H-pyrazole (2.68 g, 9.65 mmol) in 10 ml of ethylene glycol dimethyl ether were added bis(triphenylphosphine)palladium(II) chloride (0.31 g; 0.44 mmol) and 9 ml of 2 M sodium carbonate-solution. The reaction mixture was heated at 50° C. for 2 h. Cooled reaction mixture was filtered, the solids were washed with water and dried in vacuum to give 2.77 g (105%) of the title compound. $^1$H-NMR (400 MHz; d6-DMSO): δ 1.50-1.66 (m, 3H), 1.81-2.04 (m, 2H), 2.29-2.47 (m, 1H), 3.66-3.79 (m, 1H), 3.97-4.07 (m, 1H), 5.37 (dd, 1H), 6.99 (d, 1H), 7.74 (d, 1H), 8.92 (s, 1H), 9.25 (s, 1H).

b) 3-nitro-5-(1H-pyrazol-5-yl)picolinonitrile

3-Nitro-5-(1-(tetrahydro-2H-pyran-2-yl)-1H-pyrazol-5-yl)picolinonitrile (8.77 mmol) was dissolved in 10% HCl (g) in EtOH (15 ml) and stirred at RT overnight. 20 ml of water was added to the reaction mixture, followed by addition of sat. sodium bicarbonate solution until pH was neutral. Thus resulting precipitate was filtered, washed with water and dried in vacuum to yield 1.76 g (93%) of the title compound. $^1$H-NMR (400 MHz; d6-DMSO): δ 7.22 (m, 1H), 7.98 (m, 1H), 8.99 (d, 1H), 9.50 (d, 1H), 13.5 (bs, 1H).

c) (R)-5-(1-(2-aminopropyl)-1H-pyrazol-3-yl)-3-nitropicolinonitrile (R)-5-(1-(2-aminopropyl)-1H-pyrazol-3-yl)-3-nitropicolinonitrile was prepared from 3-nitro-5-(1H-pyrazol-5-yl)picolinonitrile (0.88 g, 4.9 mmol) and (R)-tert-butyl 1-hydroxypropan-2-ylcarbamate (0.86 g, 4.9 mmol) using the method of Example 34(d). Thus, 0.62 g (56%) of the title compound was obtained. m/z [273.3+1].

d) (R)-3-acetyl-N-(1-(3-(6-cyano-5-nitropyridin-3-yl)-1H-pyrazol-1-yl)propan-2-yl)-1H-pyrazole-5-carboxamide (R)-5-(1-(2-aminopropyl)-1H-pyrazol-3-yl)-3-nitropicolinonitrile (0.62 g, 1.14 mmol) was coupled with 3-acetyl-1H-pyrazole-5-carboxylic acid (0.39 g, 2.50 mmol) using the method of Example 34(d). Crude product was purified twice by CombiFlash (1$^{st}$ column: silica, eluent: 0-10% MeOH in DCM; 2$^{nd}$ column: C-18, eluent: 0-100% MeCN in water) to yield 86 mg (19%) of the title compound. $^1$H-NMR (400 MHz; CDCl$_3$): δ 1.23 (d, 3H), 2.56 (s, 3H), 4.33 (dd, 1H), 4.55 (dd, 1H), 4.58-4.67 (m, 1H), 6.83-6.86 (m, 1H), 7.29-7.31 (broad s, 1H), 7.65 (d, 1H), 8.91-8.94 (broad s, 1H), 9.64-9.67 (m, 1H).

Example 109

(S)-3-acetyl-N-(2-(3-(3-chloro-4-cyanophenyl)-1H-pyrazol-1-yl)propyl)-1H-pyrazole-5-carboxamide a) (S)-4-(1-(1-aminopropan-2-yl)-1H-pyrazol-3-yl)-2-chlorobenzonitrile 2-Chloro-4-(1H-pyrazol-3-yl)benzonitrile (0.91 g, 3.80 mmol) was reacted with N-Boc-(S)-1-amino-2-propanol (1.00 g, 5.71 mmol) in the presence of triphenyl-phosphine and DIAD using the method of Example 99. After Boc-deprotection 0.30 g (30%) of the title compound was obtained. $^1$H-NMR (400 MHz; d6-DMSO): δ 1.43 (d, 3H), 2.91-3.40 (m 1H), 4.29-4.39 (m, 1H), 4.71-4.85 (m, 1H), 7.97 (d, 1H), 7.89 (d, 1H), 7.96 (d, 1H), 7.97 (d, 1H), 8.11 (dd, 1H). m/z [260.7+1].

b) (S)-3-acetyl-N-(2-(3-(3-chloro-4-cyanophenyl)-1H-pyrazol-1-yl)propyl)-1H-pyrazole-5-carboxamide (S)-4-(1-(1-aminopropan-2-yl)-1H-pyrazol-3-yl)-2-chlorobenzonitrile (217 mg, 0.416 mmol) was coupled with 3-acetyl-1H-pyrazole-5-carboxylic acid (128 mg, 0.832 mmol) using the method of Example 34(d). Crude product was purified by CombiFlash (column: C-18, eluent: 0-100% MeCN in water) to yield 30 mg (18%) of the title compound. $^1$H-NMR (400 MHz; CDCl$_3$): δ 1.62 (d, 3H), 2.55 (s, 3H), 3.74-3.83 (m, 1H), 3.90-3.99 (m, 1H), 4.58-4.69 (m, 1H), 6.61 (d, 1H), 7.29 (bs, 1H), 7.50 (d, 1H), 7.68 (d, 1H), 7.77 (dd, 1H), 8.09 (s, 1H), 11.1 (bs, 1H).

Example 110

(S)—N-(1-(3-(3-chloro-4-cyanophenyl)-1H-pyrazol-1-yl)propan-2-yl)-1-methyl-1H-imidazole-4-carboxamide (S)-4-(1-(2-aminopropyl)-1H-pyrazol-3-yl)-2-chlorobenzonitrile (200 mg, 0.77 mmol) was coupled with 1-methyl-1H-imidazole-4-carboxylic acid (145 mg, 1.15 mmol) using the method of Example 34(d). Crude product was purified twice by CombiFlash (1$^{st}$ column: C-18, eluent: 0-100% MeCN in water; 2$^{nd}$ column: silica, eluent 100% DCM) to yield a total of 121 mg (43%) of the title compound. $^1$H-NMR (400 MHz; CDCl$_3$): δ 1.22 (d, 3H), 3.74 (s, 3H), 4.27 (dd, 1H), 4.41 (dd, 1H), 4.50-4.62 (m, 1H), 6.61 (d, 1H), 7.43 (d, 1H), 7.48 (d, 1H), 7.50 (d, 1H), 7.66 (d, 1H), 7.78 (dd, 1H), 7.86 (d, 1H), 8.17 (d, 1H).

Example 111

(R)-3-acetyl-N-(2-(3-(3-chloro-4-cyanophenyl)-1H-pyrazol-1-yl)propyl)-1H-pyrazole-5-carboxamide a) (R)-4-(1-(1-aminopropan-2-yl)-1H-pyrazol-3-yl)-2-chlorobenzonitrile 2-Chloro-4-(1H-pyrazol-3-yl)benzonitrile (1.45 g, 7.13 mmol) was reacted with N-Boc-(R)-1-amino-2-propanol (1.50 g, 8.56 mmol) in the presence of tri-phenylphosphine and DIAD using the method of Example 99. After Boc-deprotection 843 mg (45%) of the title compound was obtained. $^1$H-NMR (400 MHz; d6-DMSO): δ 1.43 (d, 3H), 3.53-3.67 (m, 1H), 4.29-4.38 (m, 1H), 4.69-4.83 (m, 1H), 6.96 (d, 1H), 7.89 (d, 1H), 7.95 (dd, 1H), 7.97 (dd, 1H), 8.10-8.12 (m, 1H). m/z [260.7+1].

b) (R)-3-acetyl-N-(2-(3-(3-chloro-4-cyanophenyl)-1H-pyrazol-1-yl)propyl)-1H-pyrazole-5-carboxamide (R)-4-(1-(1-aminopropan-2-yl)-1H-pyrazol-3-yl)-2-chlorobenzonitrile (1.29 mmol) was coupled with 3-acetyl-1H-pyrazole-5-carboxylic acid (259 mg, 1.68 mmol) using the method of Example 34(d). Crude product was purified twice by CombiFlash (1$^{st}$ column: C-18, eluent: 0-100% MeCN in water; 2$^{nd}$ column: silica, eluent: 0-7% MeOH in DCM) to yield 288 mg (56%) of the title compound. $^1$H-NMR (400 MHz; d6-DMSO): δ 1.49 (d, 3H), 2.48 (s, 3H), 3.56-3.73 (m, 2H), 4.60-4.75 (m, 1H), 6.94 (d, 1H), 7.27 (bs, 1H), 7.87 (d, 1H), 7.91-8.01 (m, 2H), 8.08 (dd, 1H), 8.58 (bs, 1H), 14.2 (bs, 1H).

Example 112

N—((R)-2-(3-(3-chloro-4-cyanophenyl)-1H-pyrazol-1-yl)propyl)-3-(1-hydroxyethyl)-1H-pyrazole-5-carboxamide (R)-3-acetyl-N-(2-(3-(3-chloro-4-cyanophenyl)-1H-pyrazol-1-yl)propyl)-1H-pyrazole-5-carboxamide (100 mg, 0.25 mmol) was treated with sodium borohydride using the method of Example 102. Thus, 87 mg (87%) of the title compound was obtained. $^1$H-NMR (400 MHz; d6-DMSO): δ 1.37 (d, 3H), 1.46 (d, 3H), 3.52-3.72 (m, 2H), 4.63-4.84 (m, 2H), 5.40 (bs, 1H), 6.42 (bs, 1H), 6.95 (d, 1H), 7.99 (s, 2H), 8.09-8.22 (m, 2H), 13.0 (bs, 1H).

Example 113

(R)-2-(aminomethyl)-N-(1-(3-(3-chloro-4-cyanophenyl)-1H-pyrazol-1-yl)-propan-2-yl)-1H-imidazole-5-carboxamide a) (R)-tert-butyl (5-(1-(3-(3-chloro-4-cyanophenyl)-1H-pyrazol-1-yl)propan-2-ylcarbamoyl)-1H-imidazol-2-yl)methylcarbamate (R)-4-(1-(2-aminopropyl)-1H-pyrazol-3-yl)-2-chlorobenzonitrile (108 mg, 0.42 mmol) was coupled with 2-(tert-Butoxycarbonylaminomethyl)-1H-imidazole-5-carboxylic acid (100 mg, 0.42 mmol) using the method of Example 34(d). After extraction a quantitative yield of the title compound was obtained.

b) (R)-2-(aminomethyl)-N-(1-(3-(3-chloro-4-cyanophenyl)-1H-pyrazol-1-yl)propan-2-yl)-1H-imidazole-5-carboxamide (R)-tert-butyl (5-(1-(3-(3-chloro-4-cyanophenyl)-1H-pyrazol-1-yl)propan-2-ylcarbamoyl)-1H-imidazol-2-yl)methylcarbamate (0.42 mmol) was stirred with 10% HCl (g) in EtOH (30 ml) overnight. Solvent was evaporated and the residue was taken up in water (50 ml), washed with DCM (3×30 ml) and made strongly alkaline by adding 2 M NaOH solution. The water phase was extracted with DCM (3×50 ml) and combined organic phases were dried over $Na_2SO_4$ and evaporated to yield 104 mg (65%) of the title compound. $^1$H-NMR (400 MHz; d6-DMSO): δ 1.08 (d, 3H), 3.73 (s, 2H), 4.27 (dd, 1H), 4.32-4.48 (m, 2H), 6.95 (d, 1H), 7.44 (s, 1H), 7.83 (d, 1H), 7.94-8.03 (m, 2H), 8.07 (d, 1H), 8.10 (m, 1H).

Example 114

(S)—N-(1-(3-(3-chloro-4-cyanophenyl)-1H-pyrazol-1-yl)propan-2-yl)-4,5,6,7-tetrahydropyrazolo[1,5-a]pyridine-2-carboxamide The title compound was prepared as described in Example 34(d), starting from 4,5,6,7-tetrahydropyrazolo[1,5-a]pyridine-2-carboxylic acid (0.166 g, 0.997 mmol) and (S)-4-(1-(2-aminopropyl)-1H-pyrazol-3-yl)-2-chlorobenzonitrile (0.2 g, 0.767 mmol). The product was purified with flash-chromatography. Yield 56.3%. 1H-NMR (400 MHz; DMSO-d6): δ 1.09 (d, 3H), 1.74-1.82 (m, 2H), 1.94-2.03 (m, 2H), 2.71-2.78 (m, 2H), 4.11 (t, 2H), 4.27 (dd, 1H), 4.36 (dd, 1H), 4.39-4.49 (m, 1H), 6.30 (s, 1H), 6.95 (d, 1H), 7.82 (d, 1H), 7.96-8.01 (m, 2H), 8.08-8.11 (m, 1H), 8.16 (d, 1H).

Example 115

(S)—N-(1-(3-(3-chloro-4-cyanophenyl)-1H-pyrazol-1-yl)propan-2-yl)-4,5,6,7-tetrahydropyrazolo[1,5-a]pyridine-2-carboxamide a) Ethyl 2-(1H-imidazol-4-yl)thiazole-4-carboxylate 1H-Imidazole-4-carbothioamide (1 g, 7.86 mmol) and ethyl bromopyruvate (0.987 ml, 7.86 mmol) were dissolved in ethanol (20 ml). The resulting mixture was refluxed for 1.5 hours. The mixture was kept at 0° C. for an hour and filtered. Both the filtered precipitate and filtrate contained the product and both were evaporated. The filtrate was triturated twice from ethanol. In the end all precipitates were combined. LC-MS: [M+1]=224.25.

b) 2-(1H-imidazol-4-yl)thiazole-4-carboxylic Acid

Ethyl 2-(1H-imidazol-4-yl)thiazole-4-carboxylate (1.5 g, 6.72 mmol) was dissolved in THF (10 ml). Into the suspension, lithium hydroxyde monohydrate 1M solution (13.44 ml, 13.44 mmol) was added and the resulting mixture was stirred for 4 h. Then 3.36 ml of lithium hydroxide monohydrate 1M solution was added and the mixture was stirred for another hour. The mixture was evaporated, 10 ml of water added and the pH was adjusted to 1 with concentrated HCl. The precipitate was filtered. Both the filtrate and filtered precipitate contained the product. The filtrate was dissolved in toluene and evaporated twice. LC-MS: [M+1]=196.20.

c) (S)—N-(1-(3-(4-cyano-3,5-difluorophenyl)-1H-pyrazol-1-yl)propan-2-yl)-2-(1H-imidazol-4-yl)thiazole-4-carboxamide The title compound was prepared as described in Example 34(d), starting from 2-(1H-imidazol-4-yl)thiazole-4-carboxylic acid (0.097 g, 0.496 mmol) (S)-4-(1-(2-aminopropyl)-1H-pyrazol-3-yl)-2,6-difluorobenzonitrile (0.1 g, 0.381 mmol). The product was purified with flash-chromatography. Yield 44.8%. 1H-NMR (400 MHz; CDCl$_3$): δ 1.25 (d, 3H), 4.32 (dd, 1H), 4.42 (dd, 1H), 4.57-4.68 (m, 1H), 6.58 (s, 1H), 7.42 (s, 1H), 7.44 (s, 1H), 7.51 (d, 1H), 7.65 (d, 1H), 7.77 (d, 1H), 7.84 (d, 1H), 7.98 (s, 1H), 11.72 (bs, 1H).

Example 116

(S)-3-acetyl-N-(1-(3-(3-chloro-4-cyano-5-fluorophenyl)-1H-pyrazol-1-yl)propan-2-yl)-1H-pyrazole-5-carboxamide a) 4-bromo-3-chloro-5-fluoroaniline To a cooled (0° C.) solution of 3-chloro-5-fluoroaniline (5.0 g, 33 mmol) in MeCN (50 ml) was added a suspension of N-bromosuccinimide (5.9 g, 33 mmol) in MeCN (10 ml). After being stirred for 2 h at RT the reaction was quenched by adding 10% NaHSO$_3$ (50 ml). The mixture was concentrated to about half of the volume, diluted with water (50 ml) and extracted with EtOAc (3×50 ml). Combined organic phases were dried over Na$_2$SO$_4$ and evaporated to give crude product, which was purified by CombiFlash (column: silica, eluent: 0-100% EtOAc in heptane) to yield 5.5 g (74%) of the title compound. $^1$H-NMR (400 MHz; d6-DMSO): δ 5.88 (bs, 2H), 6.45 (dd, 1H), 6.64 (m, 1H).

b) 4-amino-2-chloro-6-fluorobenzonitrile

A mixture of 4-bromo-3-chloro-5-fluoroaniline (2.08 g, 9.27 mmol) and copper(I)cyanide (0.83 g, 9.27 mmol) in DMF (15 ml) was heated in microwave reactor at 190° C. for 1 h. Reaction mixture was poured into 12% ammonium hydroxide (200 ml) and stirred for 30 min. Thus formed precipitate was filtered, washed with water and dried in vacuum to obtain 1.21 g (77%) of the title compound. $^1$H-NMR (400 MHz; d6-DMSO): δ 6.44 (dd, 1H), 6.60 (m, 1H), 6.86 (bs, 2H).

c) 2-chloro-6-fluoro-4-iodobenzonitrile

To a cooled (0° C.) solution of 4-amino-2-chloro-6-fluorobenzonitrile (3.55 g, 20.8 mmol), sulfuric acid (3.33 ml, 62.4 mmol), water (30 ml) and MeCN (100 ml) was added slowly a solution of sodium nitrite (1.58 g, 22.9 mmol) in water (10 ml). A solution of potassium iodide (6.91 g, 41.6 mmol) in water (10 ml) was added slowly while maintaining temperature of the reaction mixture below 10° C. After being stirred at RT for 2 h, the reaction was quenched by adding water (100 ml) and concentrating the mixture to about half of the original volume. The mixture was extracted with DCM (3×150 ml), and combined organic fractions were dried over $Na_2SO_4$ and evaporated to yield 4.77 g, (81%) of the title compound. $^1$H-NMR (400 MHz; d6-DMSO): δ 8.06 (dd, 1H), 8.08 (m, 1H).

d) 2-chloro-6-fluoro-4-(1-(tetrahydro-2H-pyran-2-yl)-1H-pyrazol-5-yl)-benzonitrile To a solution of 2-chloro-6-fluoro-4-iodobenzonitrile (5.75 g, 20.4 mmol) and 1-(tetrahydro-2H-pyran-2-yl)-5-(4,4,5,5-tetramethyl-1,3,2-dioxaborolan-2-yl)-1H-pyrazole (7.39 g, 26.6 mmol) in THF (60 ml) was added bis(triphenylphosphine)-palladium(II) chloride (0.717 g, 1.02 mmol), sodium carbonate (5.20 g, 49.0 mmol) and water (20 ml). Reaction mixture was heated at 60° C. for 2 h, concentrated to ¼ of the volume, diluted with water (40 ml) and stirred at RT for 1 h. Thus resulting solid was filtered and suspended in EtOH (30 ml). Suspension was stirred at −10° C. for 1 h, precipitate was filtered and washed with EtOH to yield 2.90 g (46%) of the title compound. $^1$H-NMR (400 MHz; d6-DMSO): δ 1.49-1.72 (m, 3H), 1.78-2.03 (m, 2H), 2.29-2.44 (m, 1H), 3.56-3.68 (m, 1H), 3.93-4.03 (m, 1H), 5.36 (dd, 1H), 6.78 (d, 1H), 7.66 (d, 1H), 7.73 (dd, 1H), 7.81 (m, 1H).

e) 2-chloro-6-fluoro-4-(1H-pyrazol-5-yl)benzonitrile

2-Chloro-6-fluoro-4-(1-(tetrahydro-2H-pyran-2-yl)-1H-pyrazol-5-yl)benzonitrile (1.09 g, 3.55 mmol) was stirred with 10% HCl (g)/EtOH-solution (50 ml) at room temperature for 1 h. Reaction mixture was poured into water (50 ml) and made slightly alkaline with saturated $NaHCO_3$ solution. Thus resulting precipitate was filtered, washed with water and dried in vacuum to obtain 0.74 g (94%) of the title compound. $^1$H-NMR (400 MHz; d6-DMSO): δ 7.06 (d, 1H), 7.94 (dd, 1H), 8.05 (m, 1H), 13.4 (bs, 1H).

f) (S)-4-(1-(2-aminopropyl)-1H-pyrazol-3-yl)-2-chloro-6-fluorobenzonitrile

2-Chloro-6-fluoro-4-(1H-pyrazol-5-yl)benzonitrile (0.74 g, 3.3 mmol) was reacted with (S)-(−)-2-tert-butoxycarbonylamino)-1-propanol (0.88 g, 5.0 mmol) in the presence of triphenylphosphine and DIAD using the method of Example 99. After Boc-deprotection 0.45 g (49%) of the title compound was obtained. $^1$H-NMR (400 MHz; d6-DMSO): δ 0.95 (d, 3H), 3.17-3.28 (m, 1H), 4.01 (dd, 2H), 7.03 (d, 1H), 7.85-7.91 (m, 2H), 7.99 (m, 1H).

g) (S)-3-acetyl-N-(1-(3-(3-chloro-4-cyano-5-fluorophenyl)-1H-pyrazol-1-yl)propan-2-yl)-1H-pyrazole-5-carboxamide (S)-4-(1-(2-aminopropyl)-1H-pyrazol-3-yl)-2-chloro-6-fluorobenzonitrile (0.22 g, 0.55 mmol) was coupled with 3-acetyl-1H-pyrazole-5-carboxylic acid (0.17 g, 1.11 mmol) using the method of Example 34(d). Crude product was purified by CombiFlash (column: C-18, eluent: 0-100% MeCN in water) to yield 47 mg (21%) of the title compound. $^1$H-NMR (400 MHz; MeOD): δ 1.28 (d, 3H), 2.51 (s, 3H), 4.31 (dd, 1H), 4.41 (dd, 1H), 4.52-4.61 (m, 1H), 6.79 (d, 1H), 7.23 (s, 1H), 7.67 (d, 1H), 7.70 (d, 1H), 7.83 (m, 1H).

Example 117

(R)-3-acetyl-N-(2-(3-(3-chloro-4-cyano-2-methylphenyl)-1H-pyrazol-1-yl)-propyl)-1H-pyrazole-5-carboxamide a) (R)-4-(1-(1-aminopropan-2-yl)-1H-pyrazol-3-yl)-2-chloro-3-methylbenzonitrile N-t-BOC—(R)-1-Amino-2-propanol (3.22 g, 18.4 mmol) and triphenylphosphine (4.82 g, 18.4 mmol) were dissolved in EtOAc (10 ml) and added to a solution of 2-chloro-3-methyl-4-(1H-pyrazol-3-yl)benzonitrile (2.00 g, 9.2 mmol) in EtOAc (20 ml). Reaction mixture was cooled down to 0° C. and DIAD (3.62 ml, 18.4 mmol) was added slowly by syringe. After 20 h of reaction time at RT, water (10 ml) and conc. HCl (5.58 ml, 184 mmol) were added, and the reaction was stirred another 20 h. Reaction mixture was diluted with water, washed with DCM, and the organic phase was extracted twice with diluted HCl. Combined water phases were washed twice with DCM, made alkaline (pH 12) by adding 50% NaOH solution, and extracted twice with DCM. Combined organic phases were dried over $Na_2SO_4$ and evaporated to yield 0.74 g (29%) of the title compound. $^1$H-NMR (400 MHz; d6-DMSO): δ 1.43 (d, 3H), 2.57 (s, 3H), 4.29-4.38 (m, 1H), 4.70-4.85 (m, 2H), 6.63 (d, 1H), 7.69 (dd, 1H), 7.82 (dd, 1H), 7.89 (d, 1H). m/z [274.8+1].

b) (R)-3-acetyl-N-(2-(3-(3-chloro-4-cyano-2-methylphenyl)-1H-pyrazol-1-yl)propyl)-1H-pyrazole-5-carboxamide (R)-4-(1-(1-aminopropan-2-yl)-1H-pyrazol-3-yl)-2-chloro-3-methylbenzonitrile (300 mg, 1.09 mmol) was coupled with 3-acetyl-1H-pyrazole-5-carboxylic acid (202 mg, 1.31 mmol) using the method of Example 34(d). Crude product was purified by CombiFlash (column: C-18, eluent: 0-100% MeCN in water) to yield 83 mg (19%) of the title compound. $^1$H-NMR (400 MHz; $CDCl_3$): δ 1.62 (d, 3H), 2.52-2.58 (m, 6H), 3.79 (dd, 1H), 3.91 (dd, 1H), 4.60-4.71 (m, 1H), 6.92 (d, 1H), 7.25 (s, 1H), 7.27-7.29 (m, 1H), 7.52 (d, 1H), 7.54-7.60 (m, 2H).

Example 118

(R)—N-(2-(3-(3-chloro-4-cyanophenyl)-1H-pyrazol-1-yl)propyl)-1-methyl-1H-imidazole-4-carboxamide (R)-4-(1-(1-aminopropan-2-yl)-1H-pyrazol-3-yl)-2-chlorobenzonitrile (300 mg, 1.15 mmol) was coupled with 1-methyl-1H-imidazole-4-carboxylic acid (174 mg, 1.38 mmol) using the method of Example 34(d). Crude product was purified by CombiFlash (column: C-18, eluent: 0-100% MeCN in water) to yield 61 mg (14%) of the title compound. $^1$H-NMR (400 MHz; d6-DMSO): δ 1.45 (d, 3H), 3.52-3.72 (m, 4H), 3.67 (s, 3H), 4.63-4.75 (m, 1H), 6.95 (d, 1H), 7.62 (dd, 1H), 7.89 (d, 1H), 7.99 (s, 1H), 8.00 (s, 1H), 8.10 (t, 1H), 8.18 (t, 1H).

Example 119

(S)—N-(1-(3-(3-chloro-4-cyanophenyl)-1H-pyrazol-1-yl)propan-2-yl)-5-methyl-1,2,4-oxadiazole-3-carboxamide (S)-4-(1-(2-aminopropyl)-1H-pyrazol-3-yl)-2-chlorobenzonitrile (573 mg, 2.20 mmol) was coupled with 5-methyl- 1,2,4-oxadiazole-3-carboxylic acid (338 mg, 2.64 mmol) using the method of Example 34(d). Crude product was purified by CombiFlash (column: silica, eluent: 0-100% EtOAc in heptane) to yield 125 mg (15%) of the title compound. $^1$H-NMR (400 MHz; d6-DMSO): δ 1.61 (d, 3H), 2.66 (s, 3H), 4.28-4.39 (m, 2H), 4.41-4.53 (m, 1H), 6.95 (d, 1H), 6.83 (d, 1H), 7.94 (dd, 1H), 7.99 (dd, 1H), 8.09 (m, 1H), 9.02 (d, 1H).

Example 120

(S)-5-((1H-imidazol-1-yl)methyl)-N-(1-(3-(3-chloro-4-cyanophenyl)-1H-pyrazol-1-yl)propan-2-yl)thiazole-2-carboxamide a) Ethyl 5-(bromomethyl)thiazole-2-carboxylate A mixture of ethyl thiooxamate (3.00 g, 22.5 mmol) and 1,3-dibromoacetone (4.86 g, 22.5 mmol) in dry EtOH (30 ml) was refluxed for 3.5 h and stirred at RT for 20 h. Solvent was evaporated and the residue was taken up in water and extracted twice with DCM to obtain crude product, which was purified by CombiFlash (column: silica, eluent: 10-100% EtOAc in heptane) to yield 842 mg (15%) of the title compound. $^1$H-NMR (400 MHz; d6-DMSO): δ 1.34 (t, 3H), 4.39 (q, 2H), 4.83 (s, 2H), 8.16-8.17 (m, 1H).

b) Ethyl 5-((1H-imidazol-1-yl)methyl)thiazole-2-carboxylate

To a cooled (0 C) suspension of sodium hydride (60% in oil, 82 mg, 2.05 mmol) in dry DMF (2 ml) was added imidazole (93 mg, 1.37 mmol) as a solution in dry DMF (0.5 ml). Mixture was stirred at RT 45 min, cooled to 0° C. followed by addition of ethyl 5-(bromomethyl)thiazole-2-carboxylate (342 mg, 1.37 mmol) dissolved in dry DMF (2 ml). After being stirred at RT for 20 h, the reaction mixture was evaporated and the residue was taken up in DCM and washed twice with saturated NaCl solution. Thus, 143 mg (44%) of the title compound was obtained. $^1$H-NMR (400 MHz; d6-DMSO): δ 1.32 (t, 3H), 4.37 (q, 2H), 5.39 (s, 2H), 6.91 (s, 1H), 7.20 (s, 1H), 7.75 (s, 1H), 7.93 (s, 1H).

c) 5-((1H-imidazol-1-yl)methyl)thiazole-2-carboxylic Acid

A solution of ethyl 5-((1H-imidazol-1-yl)methyl)thiazole-2-carboxylate (143 mg, 0.60 mmol) and 1 M LiOH solution (1.2 ml, 1.2 mmol) in THF (2 ml) and MeOH (1 ml) was stirred at RT for 1.5 h. Some 1 M HCl was added until pH of the mixture was about 8. Solvents were evaporated and thus obtained crude product was used as such in the next synthesis step. $^1$H-NMR (400 MHz; d6-DMSO): δ 5.28 (s, 2H), 6.92 (s, 1H), 7.22 (s, 1H), 7.54 (s, 1H), 7.79 (s, 1H).

d) (S)-5-((1H-imidazol-1-yl)methyl)-N-(1-(3-(3-chloro-4-cyanophenyl)-1H-pyrazol-1-yl)propan-2-yl)thiazole-2-carboxamide (S)-4-(1-(2-aminopropyl)-1H-pyrazol-3-yl)-2-chlorobenzonitrile (157 mg, 0.60 mmol) was coupled with 5-((1H-imidazol-1-yl)methyl)thiazole-2-carboxylic acid (0.60 mmol) using the method of Example 34(d). Crude product was purified twice by CombiFlash (1$^{st}$ column: C-18, eluent: 0-100% MeCN in water; 2$^{nd}$ column: silica, eluent: 0-8% MeOH in DCM) to yield 13 mg (5%) of the title compound. $^1$H-NMR (400 MHz; d6-DMSO): δ 1.18 (d, 2H), 4.29-4.52 (m, 3H), 5.36 (s, 2H), 6.92 (s, 1H), 6.94 (dd, 1H), 7.22 (s, 1H), 7.71 (s, 1H), 7.75 (s, 1H), 7.83 (d, 1H), 7.90 (dd, 1H), 7.96 (d, 1H), 8.04 (d, 1H), 8.83 (d, 1H).

Example 121

(S)—N-(1-(3-(3-chloro-4-cyanophenyl)-1H-pyrazol-1-yl)propan-2-yl)imidazo[1,2-a]pyrazine-2-carboxamide The title compound was prepared as described in Example 34(d), starting from imidazo[1,2-a]pyrazine-2-carboxylic acid (0.163 g, 0.997 mmol) and (S)-4-(1-(2-aminopropyl)-1H-pyrazol-3-yl)-2-chlorobenzonitrile (0.2 g, 0.767 mmol). The product was purified with flash-chromatography. Yield 90%. 1H-NMR (400 MHz; CDCl$_3$): δ 1.18 (d, 3H), 4.35 (dd, 1H), 4.43 (dd, 1H), 4.47-4.57 (m, 1H), 6.93 (d, 1H), 7.85 (d, 1H), 7.94-8.00 (m, 3H), 8.03-8.06 (m, 1H), 8.47 (d, 1H), 8.60 (dd, 1H), 8.73 (d, 1H), 9.14-9.16 (m, 1H).

Example 122

(S)—N-(1-(3-(3-chloro-4-cyanophenyl)-1H-pyrazol-1-yl)propan-2-yl)-4,5,6,7-tetrahydropyrazolo[1,5-a]pyridine-3-carboxamide The title compound was prepared as described in Example 34(d), starting from 4,5,6,7-tetrahydropyrazolo[1,5-a]pyridine-3-carboxylic acid (0.127 g, 0.767 mmol) and (S)-4-(1-(2-aminopropyl)-1H-pyrazol-3-yl)-2-chlorobenzonitrile (0.2 g, 0.767 mmol). The product was purified by flash-chromatography. Yield 55.5%. 1H-NMR (400 MHz; DMSO-d6): δ 1.12 (d, 3H), 1.66-1.75 (m, 2H), 1.85-1.95 (m, 2H), 2.87 (t, 2H), 4.02 (t, 2H), 4.22-4.23 (m, 2H), 4.32-4.42 (m, 1H), 6.94 (d, 1H), 7.72 (d, 1H), 7.80 (d, 1H), 7.83 (s, 1H), 7.91 (dd, 1H), 7.97 (d, 1H), 8.06 (d, 1H).

Example 123

(S)-5-acetyl-N-(1-(3-(3-chloro-4-cyanophenyl)-1H-pyrazol-1-yl)propan-2-yl)isoxazole-3-carboxamide (S)-5-acetyl-N-(1-(3-(3-chloro-4-cyanophenyl)-1H-pyrazol-1-yl)propan-2-yl)isoxazole-3-carboxamide was prepared using the method of Example 34(d) starting from 5-acetylisoxazole-3-carboxylic acid (2.142 g, 13.81 mmol) and (S)-4-(1-(2-aminopropyl)-1H-pyrazol-3-yl)-2-chlorobenzonitrile (3 g, 2.142 g). The product was purified by Flash-chromatography with yield of 30.5%. 1H-NMR (400 MHz; CDCl$_3$): δ 1.25 (d, 3H), 2.66 (s, 3H), 4.26 (dd, 1H), 4.47 (dd, 1H), 4.56-4.66 (m, 1H), 4.65 (d, 1H), 7.30 (s, 1H), 7.50 (d, 1H), 7.71 (d, 1H), 7.84 (dd, 1H), 7.08 (d, 1H), 7.17 (d, 1H).

Example 124

N—((S)-1-(3-(3-chloro-4-cyanophenyl)-1H-pyrazol-1-yl)propan-2-yl)-5-(1-hydroxyethyl)isoxazole-3-carboxamide N—((S)-1-(3-(3-chloro-4-cyanophenyl)-1H-pyrazol-1-yl)propan-2-yl)-5-(1-hydroxyethyl)isoxazole-3-carboxamide was prepared using the method of Example 34(d) starting from 5-(1-hydroxyethyl)isoxazole-3-carboxylic acid (2.170 g, 13.81 mmol) and (S)-4-(1-(2-aminopropyl)-1H-pyrazol-3-yl)-2-chlorobenzonitrile (3 g, 11.51 mmol). The product was purified by Flash-chromatography with yield of 46.1%. 1H-NMR (400 MHz; CDCl₃): δ 1.23 (d, 3H), 1.62 (d, 3H), 2.30 (s, 1H), 4.26 (dd, 1H), 4.43 (dd, 1H), 4.53-4.64 (m, 1H), 5.06 (q, 1H), 6.63 (d, 1H), 6.64 (d, 1H), 7.48 (d, 1H), 7.69 (d, 1H), 7.84 (dd, 1H), 7.87 (d, 1H), 8.05 (d, 1H).

Example 125

(S)-2-bromo-N-(1-(3-(3-chloro-4-cyanophenyl)-1H-pyrazol-1-yl)propan-2-yl)thiazole-4-carboxamide (S)-2-bromo-N-(1-(3-(3-chloro-4-cyanophenyl)-1H-pyrazol-1-yl)propan-2-yl)thiazole-4-carboxamide was prepared using the method of Example 34(d) starting from 2-bromo-1,3-thiazole-4-carboxylic acid (0.957 g, 4.60 mmol) and (S)-4-(1-(2-aminopropyl)-1H-pyrazol-3-yl)-2-chlorobenzonitrile (1 g, 3.84 mmol). Yield 62.7%. 1H-NMR (400 MHz; CDCl₃): δ 1.32 (d, 3H), 4.36 (dd, 1H), 4.46 (dd, 1H), 4.58-4.63 (m, 1H), 6.63 (d, 1H), 7.51 (d, 1H), 7.65 (d, 1H), 7.70 (d, 1H), 7.76 (dd, 1H), 7.93 (d, 1H), 7.40 (s, 1H).

Example 126

1-(3-((S)-1-(3-(3-chloro-4-cyanophenyl)-1H-pyrazol-1-yl)propan-2-yl-carbamoyl)isoxazol-5-yl)ethyl Acetate N—((S)-1-(3-(3-chloro-4-cyanophenyl)-1H-pyrazol-1-yl)propan-2-yl)-5-(1-hydroxyethyl)isoxazole-3-carboxamide (28 mg, 0.070 mmol) and DMAP (0.864 mg, 7.00 μmol) were dissolved in pyridine under nitrogen atmosphere. The reaction mixture was cooled to 0° C., acetic anhydride (7.51 mg, 0.074 mmol) was added and the reaction mixture stirred for 2 h. The solvent was evaporated. Yield 82%. 1H-NMR (400 MHz; CDCl₃): δ 1.23 (d, 3H), δ 1.64 (d, 3H), 2.11 (s, 3H), 4.25 (dd, 1H), 4.43 (dd, 1H), 4.54-4.63 (m, 1H), 6.05 (q, 1H), 6.63 (d, 1H), 6.65 (d, 1H), 7.48 (d, 1H), 7.70 (d, 1H), 7.84 (dd, 1H), 7.89 (d, 1H), 8.06 (d, 1H).

Example 127

(S)—N-(1-(3-(3-chloro-4-cyanophenyl)-1H-pyrazol-1-yl)propan-2-yl)-2-(pyridin-4-yl)thiazole-4-carboxamide (S)—N-(1-(3-(3-chloro-4-cyanophenyl)-1H-pyrazol-1-yl)propan-2-yl)-2-(pyridin-4-yl)thiazole-4-carboxamide was prepared using the method of Example 34(d) starting from 2-(4-pyridyl)thiazole-4-carboxylic acid (0.190 g, 0.921 mmol) and (S)-4-(1-(2-aminopropyl)-1H-pyrazol-3-yl)-2-chlorobenzonitrile (0.2 g, 0.767 mmol). The product triturated using diethyl ether. Yield 47.5%. 1H-NMR (400 MHz; MeOD): δ 1.33 (d, 3H), 4.40 (dd, 1H), 4.47 (dd, 1H), 4.60-4.65 (m, 1H), 6.77 (d, 1H), 7.63 (d, 1H), 7.74 (d, 1H), 7.82 (dd, 1H), 7.93 (d, 1H), 8.00 (dd, 1H), 8.01 (dd, 1H), 8.30 (s, 1H), 8.65 (dd, 1H), 8.66 (dd, 1H).

Example 128

(S)—N-(1-(3-(3-chloro-4-cyanophenyl)-1H-pyrazol-1-yl)propan-2-yl)-2-morpholinothiazole-4-carboxamide (S)—N-(1-(3-(3-chloro-4-cyanophenyl)-1H-pyrazol-1-yl)propan-2-yl)-2-morpholinothiazole-4-carboxamide was prepared using the method of Example 34(d) starting from 2-morpholino-1,3-thiazole-4-carboxylic acid (0.454 g, 2.117 mmol) and (S)-4-(1-(2-aminopropyl)-1H-pyrazol-3-yl)-2-chlorobenzonitrile (0.5 g, 1.764 mmol. The product was purified by Flash-chromatography. Yield 5.48%. 1H-NMR (400 MHz; DMSO-d6): δ 1.13 (d, 3H), 3.38-3.43 (m, 4H), 3.67-3.72 (m, 4H), 4.27-4.45 (m, 3H), 6.95 (d, 1H), 7.40 (s, 1H), 7.83 (d, 1H), 7.92 (dd, 1H), 7.97 (d, 1H), 7.98 (dd, 1H), 8.06 (d, 1H).

Example 129

(S)-2-amino-N-(1-(3-(3-chloro-4-cyanophenyl)-1H-pyrazol-1-yl)propan-2-yl)oxazole-4-carboxamide (S)-2-amino-N-(1-(3-(3-chloro-4-cyanophenyl)-1H-pyrazol-1-yl)propan-2-yl)oxazole-4-carboxamide was prepared using the method of Example 34(d) starting from 2-amino-1,3-oxazole-4-carboxylic acid (0.037 g, 0.288 mmol) and (S)-4-(1-(2-aminopropyl)-1H-pyrazol-3-yl)-2-chlorobenzonitrile (0.05 g, 0.192 mmol). Yield 35.7%. 1H-NMR (400 MHz; MeOD): δ 1.23 (d, 3H), 4.30 (dd, 1H), 4.37 (dd, 1H), 4.46-4.54 (m, 1H), 6.77 (d, 1H), 7.65 (s, 1H), 7.69 (d, 1H), 7.79 (dd, 1H), 7.91 (dd, 1H), 8.05 (dd, 1H).

Example 130

(S)—N-(1-(3-(3-chloro-4-cyanophenyl)-1H-pyrazol-1-yl)propan-2-yl)-2-(piperidin-4-yl)thiazole-4-carboxamide a) (S)-tert-butyl 4-(4-(1-(3-(3-chloro-4-cyanophenyl)-1H-pyrazol-1-yl)propan-2-ylcarbamoyl)thiazol-2-yl)piperidine-1-carboxylate (S)-tert-butyl 4-(4-(1-(3-(3-chloro-4-cyanophenyl)-1H-pyrazol-1-yl)propan-2-ylcarbamoyl)thiazol-2-yl)piperidine-1-carboxylate was prepared using the method of Example 34(d) starting from (S)-4-(1-(2-aminopropyl)-1H-pyrazol-3-yl)-2-chlorobenzonitrile (400 mg, 1.534 mmol) and 2-[1-(tert-butoxycarbonyl)piperidin-4-yl]-1,3-thiazole-4-carboxylic acid (479 mg, 1.534 mmol). The product was purified twice by Flash-chromatography. Yield 33.9%. 1H-NMR (400 MHz; DMSO-d6): δ 1.14 (d, 3H), 1.41 (s, 9H), 1.49-1.64 (m, 2H), 1.98-2.08 (m, 2H), 2.89 (bs, 2H), 3.15-3.27 (m, 1H), 3.96-4.09 (m, 2H), 4.29-4.52 (m, 3H), 6.96 (s, 1H), 7.84 (d, 1H), 7.92 (dd, 1H), 7.97 (dd, 1H), 8.06 (dd, 1H), 8.10 (s, 1H), 8.28 (d, 1H).

b) (S)—N-(1-(3-(3-chloro-4-cyanophenyl)-1H-pyrazol-1-yl)propan-2-yl)-2-(piperidin-4-yl)thiazole-4-carboxamide (S)-tert-butyl 4-(4-(1-(3-(3-chloro-4-cyanophenyl)-1H-pyrazol-1-yl)propan-2-ylcarbamoyl)thiazol-2-yl)piperidine-1-carboxylate (0.3 g, 0.540 mmol) and TFA (0.768 g, 6.73 mmol) was dissolved in a mixture of DCM/TFA/H₂O and stirred overnight. The reaction mixture was diluted with DCM, washed with saturated Na₂CO₃ and with water. The organic layer was evaporated. Yield 82%. 1H-NMR (400 MHz; DMSO-d6): δ 1.24 (d, 3H), 1.52 (dd, 1H), 1.58 (dd, 1H), 1.91-1.97 (m, 2H), 2.54-2.62 (m, 2H), 2.97-3.03 (d, 2H), 3.04-3.11 (m, 1H), 4.33 (dd, 1H), 4.41 (dd, 1H), 4.44-4.51 (m, 1H), 6.96 (d, 1H), 7.85 (d, 1H), 7.94 (dd, 1H), 7.99 (d, 1H), 8.07 (d, 1H), 8.08 (s, 1H), 8.28 (d, 1H).

Example 131

(S)—N-(1-(3-(3-chloro-4-cyanophenyl)-1H-pyrazol-1-yl)propan-2-yl)-2-(methylamino)thiazole-4-carboxamide a) 2-(Methylamino)thiazole-4-carboxylic Acid Ethyl 2-methylamino-1,3-thiazole-4-carboxylate (300 mg, 1.611 mmol) was dissolved in THF/water mixture and 1M lithium hydroxide (3.22 ml, 3.22 mmol) was added. The reaction mixture was stirred at RT for 3 hours, pH was adjusted to acidic and the mixture was evaporated to dryness to yield the title compound. 1H-NMR (400 MHz; DMSO-d6): δ 2.84 (s, 3H), 7.46 (s, 1H), 7.90 (bs, 1H).

b) (S)—N-(1-(3-(3-chloro-4-cyanophenyl)-1H-pyrazol-1-yl)propan-2-yl)-2-(methylamino)thiazole-4-carboxamide (S)—N-(1-(3-(3-chloro-4-cyanophenyl)-1H-pyrazol-1-yl)propan-2-yl)-2-(methyl-amino)thiazole-4-carboxamide was prepared using the method of Example 34(d) starting from (S)-4-(1-(2-aminopropyl)-1H-pyrazol-3-yl)-2-chlorobenzonitrile (0.389 g, 1.343 mmol) and 2-(methylamino)thiazole-4-carboxylic acid (255 mg, 1.612 mmol). The product was purified by Flash-chromatography and triturated using diethyl ether. Yield 8.28%. 1H-NMR (400 MHz; DMSO-d6): δ 1.21 (d, 3H), 2.85 (d, 3H), 4.28-4.43 (m, 3H), 6.96 (d, 1H), 7.18 (s, 1H), 7.59 (q, 1H), 7.84 (d, 1H), 7.91 (d, 1H), 7.95-7.96 (m, 2H), 8.08 (dd, 1H).

Example 132

(R)—N-(1-(3-(3-chloro-4-cyanophenyl)-1H-pyrazol-1-yl)propan-2-yl)-2-morpholinothiazole-4-carboxamide (R)—N-(1-(3-(3-chloro-4-cyanophenyl)-1H-pyrazol-1-yl)propan-2-yl)-2-morpholinothiazole-4-carboxamide was prepared using the method of Example 34(d) starting from 2-morpholino-1,3-thiazole-4-carboxylic acid (0.229 g, 1.070 mmol) and (R)-4-(1-(2-aminopropyl)-1H-pyrazol-3-yl)-2-chlorobenzonitrile (0.25 g, 0.892 mmol). The product was purified by Flash-chromatography and triturated using diethyl ether. Yield 4.91%. 1H-NMR (400 MHz; DMSO-d6): δ 1.23 (d, 3H), 3.38-342 (m, 4H), 3.67-3.71 (m, 4H), 4.28-4.45 (m, 3H), 6.95 (d, 1H), 7.39 (s, 1H), 7.83 (d, 1H), 7.92 (dd, 1H), 7.96 (d, 1H), 7.98 (dd, 1H), 8.06 (d, 1H).

Example 133

(R)—N-(1-(3-(3-chloro-4-cyanophenyl)-1H-pyrazol-1-yl)propan-2-yl)-2-(pyridin-3-yl)thiazole-4-carboxamide (R)—N-(1-(3-(3-chloro-4-cyanophenyl)-1H-pyrazol-1-yl)propan-2-yl)-2-(pyridin-3-yl)thiazole-4-carboxamide was prepared using the method of Example 34(d) starting from 2-(3-pyridyl)-1,3-thiazole-4-carboxylic acid (0.285 g, 1.381 mmol) and (R)-4-(1-(2-aminopropyl)-1H-pyrazol-3-yl)-2-chlorobenzonitrile (0.3 g, 1.151 mmol). The product was purified by triturated using DCM. Yield 1.065%. 1H-NMR (400 MHz; CDCl$_3$): δ 1.31 (d, 3H), 4.34 (dd, 1H), 4.48 (dd, 1H), 4.60-470 (m, 1H), 6.63 (d, 1H), 7.37 (dd, 1H), 7.50-7.54 (m, 2H), 7.80 (dd, 1H), 7.88 (d, 1H), 7.98 (d, 1H), 8.13-8.18 (m, 2H), 8.73 (dd, 1H), 9.16 (d, 1H).

Example 134

(R)—N-(1-(3-(3-chloro-4-cyanophenyl)-1H-pyrazol-1-yl)propan-2-yl)-2-(pyrrolidin-1-ylmethyl)thiazole-4-carboxamide (R)—N-(1-(3-(3-chloro-4-cyanophenyl)-1H-pyrazol-1-yl)propan-2-yl)-2-(pyrrolidin-1-ylmethyl)thiazole-4-carboxamide was prepared using the method of Example 34(d) starting from 2-pyrrolidin-1-ylmethyl-thiazole-4-carboxylic acid (0.244 g, 1.151 mmol) and (R)-4-(1-(2-aminopropyl)-1H-pyrazol-3-yl)-2-chlorobenzonitrile (0.2 g, 0.767 mmol). The crude product was washed with water. Yield 55.7%. 1H-NMR (400 MHz; DMSO-d6): δ 1.23 (d, 3H), 1.72-1.76 (m, 4H), 2.57-2.61 (m, 4H), 3.95 (s, 2H), 4.32 (dd, 1H), 4.41 (dd, 1H), 4.41-4.50 (m, 1H), 6.96 (d, 1H), 7.85 (d, 1H), 7.95 (dd, 1H), 7.98 (dd, 1H), 8.09 (dd, 1H), 8.13 (s, 1H), 8.44 (d, 1H).

Example 135

(R)—N-(1-(3-(3-chloro-4-cyanophenyl)-1H-pyrazol-1-yl)propan-2-yl)-2-(1-methyl-1H-pyrazol-4-yl)thiazole-4-carboxamide (R)—N-(1-(3-(3-chloro-4-cyanophenyl)-1H-pyrazol-1-yl)propan-2-yl)-2-(1-methyl-1H-pyrazol-4-yl)thiazole-4-carboxamide was prepared using the method of Example 34(d) starting from 2-(1-methyl-1H-pyrazol-4-yl)thiazole-4-carboxylic acid (0.254 g, 1.215 mmol) and (R)-4-(1-(2-aminopropyl)-1H-pyrazol-3-yl)-2-chlorobenzonitrile (0.4 g, 1.457 mmol). The product was triturated using diethyl ether. Yield 76%. 1H-NMR (400 MHz; DMSO-d6): δ 1.17 (d, 3H), 3.90 (s, 3H), 4.35 (dd, 1H), 4.42 (dd, 1H), 4.50 (m, 1H), 6.96 (d, 1H), 7.85 (d, 1H), 7.86 (d, 1H), 7.93 (d, 1H), 7.93 (dd, 1H), 8.05 (d, 1H), 8.07 (s, 1H), 8.34 (d, 1H), 8.34 (s, 1H).

Example 136

(S)—N-(1-(3-(3-chloro-4-cyanophenyl)-1H-pyrazol-1-yl)propan-2-yl)-1H-imidazole-2-carboxamide (S)—N-(1-(3-(3-chloro-4-cyanophenyl)-1H-pyrazol-1-yl)propan-2-yl)-1H-imidazole-2-carboxamide was prepared using the method of Example 34(d) starting from 1H-imidazole-2-carboxylic acid (0.206 g, 1.841 mmol) and (S)-4-(1-(2-amino-propyl)-1H-pyrazol-3-yl)-2-chlorobenzonitrile (0.4 g, 1.534 mmol). The crude product was washed with 0.1M HCl, 1M NaCO$_3$, water and brine. Yield 76%. 1H-NMR (400 MHz; DMSO): δ 1.23 (d, 3H), 4.31 (dd, 1H), 4.38 (dd, 1H), 4.41-4.50 (m, 1H), 6.94 (d, 1H), 7.07 (s, 1H), 7.24 (dd, 1H), 7.84 (d, 1H), 7.96 (dd, 1H), 7.99 (dd, 1H), 8.17 (dd, 1H), 8.65 (d, 1H), 12.95 (s, 1H).

Example 137

(R)-2-acetyl-N-(1-(3-(3-chloro-4-cyanophenyl)-1H-pyrazol-1-yl)propan-2-yl)thiazole-4-carboxamide (R)-2-acetyl-N-(1-(3-(3-chloro-4-cyanophenyl)-1H-pyrazol-1-yl)propan-2-yl)thiazole-4-carboxamide was prepared using the method of Example 34(d) starting from 2-acetylthiazole-4-carboxylic acid (0.597 g, 3.07 mmol) and (R)-4-(1-(2-amino-propyl)-1H-pyrazol-3-yl)-2-chlorobenzonitrile (0.8 g, 3.07 mmol). The product was triturated using diethyl ether, isopropanol and DCM, respectively. Yield 24.22%. 1H-NMR (400 MHz; DMSO-d6): δ 1.19 (d, 3H), 2.30 (s, 3H), 4.37 (dd, 1H), 4.44 (dd, 1H), 4.47-4.56 (m, 1H), 6.96 (d, 1H), 7.87 (d, 1H), 7.92 (dd, 1H), 7.97 (d, 1H), 7.04 (d, 1H), 8.49 (d, 1H), 8.61 (s, 1H).

Example 138

(R)-ethyl 4-(1-(3-(3-chloro-4-cyanophenyl)-1H-pyrazol-1-yl)propan-2-yl-carbamoyl)thiazole-2-carboxylate (R)-ethyl 4-(1-(3-(3-chloro-4-cyanophenyl)-1H-pyrazol-1-yl)propan-2-yl-carbamoyl)thiazole-2-carboxylate was prepared using the method of Example 34(d) starting from 2,4-thiazoledicarboxylic acid, 2-ethyl ester (0.528 g, 2.62 mmol) and (R)-4-(1-(2-aminopropyl)-1H-pyrazol-3-yl)-2-chlorobenzonitrile (0.6 g, 2.186 mmol). The product triturated diethyl ether. Yield 66.3%. 1H-NMR (400 MHz; DMSO-d6): δ 1.17 (d, 3H), 1.34 (t, 3H), 4.34 (dd, 1H), 4.39-4.47 (m, 3H), 4.47-4.56 (m, 1H), 6.94 (d, 1H), 7.83 (d, 1H), 7.95-7.96 (m, 2H), 8.02 (dd, 1H), 8.55 (s, 1H), 8.61 (d, 1H).

Example 139

N—((R)-1-(3-(3-chloro-4-cyanophenyl)-1H-pyrazol-1-yl)propan-2-yl)-2-(1-hydroxyethyl)thiazole-4-carboxamide Sodium borohydride (29.3 mg, 0.773 mmol) was added into a flask and the atmosphere was replaced with nitrogen. Dry ethanol was added and the reaction mixture was cooled to 0° C. (R)-2-acetyl-N-(1-(3-(3-chloro-4-cyanophenyl)-1H-pyrazol-1-yl)propan-2-yl)thiazole-4-carboxamide (160 mg, 0.387 mmol) was added and the reaction mixture was warmed slowly to RT while stirring overnight. The crude product was cooled to 0° C., the pH was adjusted to 6 and the mixture was evaporated. DCM and a few drops of methanol were added and the crude product was washed with 1M Na$_2$CO$_3$ and with water. The product was triturated using diethyl ether and DCM and heptane. Yield 33.3%. 1H-NMR (400 MHz; DMSO-d6): δ 1.09-1.17 (m, 3H), 1.45 (t, 3H), 2.38-4.53 (m, 3H), 4.92-5.02 (m, 1H), 6.23 (dd, 1H), 6.96 (dd, 1H), 7.85 (dd, 1H), 7.92-7.97 (m, 2H), 8.07-8.09 (m, 1H), 8.10 (d, 1H), 8.33-8.39 (m, 1H).

Example 140

(S)—N-(1-(3-(3-chloro-4-cyanophenyl)-1H-pyrazol-1-yl)propan-2-yl)oxazole-4-carboxamide (S)—N-(1-(3-(3-chloro-4-cyanophenyl)-1H-pyrazol-1-yl)propan-2-yl)oxazole-4-carboxamide was prepared using the method of Example 34(d) starting from 4-oxazolecarboxylic acid (0.212 g, 1.841 mmol) and (S)-4-(1-(2-aminopropyl)-1H-pyrazol-3-yl)-2-chlorobenzonitrile (0.4 g, 1.534 mmol). The product was triturated using diethyl ether. Yield 32.9%. 1H-NMR (400 MHz; DMSO-d6): δ 1.11 (d, 3H), 4.31 (dd, 1H), 4.38 (dd, 1H), 4.41-4.49 (m, 1H), 6.95 (d, 1H), 7.84 (d, 1H), 7.97-8.01 (m, 2H), 8.15 (dd, 1H), 8.52 (d, 1H), 8.52 (d, 1H), 8.59 (d, 1H).

Example 141

(R)—N-(1-(3-(3-chloro-4-cyanophenyl)-1H-pyrazol-1-yl)propan-2-yl)oxazole-4-carboxamide (R)—N-(1-(3-(3-chloro-4-cyanophenyl)-1H-pyrazol-1-yl)propan-2-yl)oxazole-4-carboxamide was prepared using the method of Example 34(d) starting from 4-oxazolecarboxylic acid (0.202 g, 1.749 mmol) and (R)-4-(1-(2-amino-propyl)-1H-pyrazol-3-yl)-2-chlorobenzonitrile (0.4 g, 1.457 mmol). The product was triturated using diethyl ether. Yield 45.5%. 1H-NMR (400 MHz; DMSO-d6): δ 1.11 (d, 3H), 4.31 (dd, 1H), 4.38 (dd, 1H), 4.41-4.48 (m, 1H), 6.95 (d, 1H), 7.84 (d, 1H), 7.96-8.01 (m, 2H), 8.15 (dd, 1H), 8.50 (d, 1H), 8.54 (d, 1H), 8.58 (d, 1H).

Example 142

(R)—N-(1-(3-(3-chloro-4-cyanophenyl)-1H-pyrazol-1-yl)propan-2-yl)-2,5-dimethyloxazole-4-carboxamide (R)—N-(1-(3-(3-chloro-4-cyanophenyl)-1H-pyrazol-1-yl)propan-2-yl)-2,5-dimethyloxazole-4-carboxamide was prepared using the method of Example 34(d) starting from 2,5-dimethyl-1,3-oxazole-4-carboxylic acid (0.254 g, 1.749 mmol) and (R)-4-(1-(2-aminopropyl)-1H-pyrazol-3-yl)-2-chlorobenzonitrile (0.4 g, 1.457 mmol). The product was triturated using diethyl ether. Yield 54.7%. 1H-NMR (400 MHz; DMSO-d6): δ 1.08 (d, 3H), 2.43 (d, 6H), 4.28 (dd, 1H), 4.34-4.45 (m, 2H), 6.96 (d, 1H), 7.83 (d, 1H), 7.96-8.01 (m, 2H), 8.10 (dd, 1H), 8.23 (d, 1H).

Example 143

(S)—N-(1-(3-(3-chloro-4-cyanophenyl)-1H-pyrazol-1-yl)propan-2-yl)-2,5-dimethyloxazole-4-carboxamide (S)—N-(1-(3-(3-chloro-4-cyanophenyl)-1H-pyrazol-1-yl)propan-2-yl)-2,5-dimethyloxazole-4-carboxamide was prepared using the method of Example 34(d) starting from 2,5-dimethyl-1,3-oxazole-4-carboxylic acid (0.262 g, 1.804 mmol) and (S)-4-(1-(2-aminopropyl)-1H-pyrazol-3-yl)-2-chlorobenzonitrile (0.4 g, 1.504 mmol). The product was triturated using diethyl ether. Yield 64.7%. 1H-NMR (400 MHz; DMSO-d6): δ 1.08 (d, 3H), 2.43 (d, 6H), 4.23 (dd, 1H), 4.34-4.45 (m, 2H), 6.96 (d, 1H), 7.83 (d, 1H), 7.96-8.01 (m, 2H), 8.10 (dd, 1H), 8.23 (d, 1H).

Example 144

(R)—N-(1-(3-(3-chloro-4-cyanophenyl)-1H-pyrazol-1-yl)propan-2-yl)-2-(hydroxymethyl)thiazole-4-carboxamide Sodium borohydride (108 mg, 2.85 mmol) was added into a flask and the atmosphere was replaced with nitrogen. Dry ethanol was added and the reaction mixture was cooled to 0° C. (R)-ethyl-4-(1-(3-(3-chloro-4-cyanophenyl)-1H-pyrazol-1-yl)propan-2-ylcarbamoyl)thiazole-2-carboxylate (632.8 mg, 1.426 mmol) was added and the reaction mixture was warmed slowly to RT while stirring overnight. The crude product was cooled to 0° C., the pH was adjusted to 6 and the mixture was evaporated. DCM and a few drops of ethanol were added and the crude product was washed with 1M Na$_2$CO$_3$ and with water. The final product was triturated using diethyl ether and DCM with some heptane added dropwise. Yield 46.6%. 1H-NMR (400 MHz; DMSO-d6): δ 1.12 (d, 3H), 4.31 (dd, 1H), 4.40 (dd, 1H), 4.43-4.51 (m, 1H), 4.78 (s, 2H), 6.20 (s, 1H), 6.95 (d, 1H), 7.84 (d, 1H), 7.95 (dd, 1H), 7.98 (dd, 1H), 8.08 (dd, 1H), 8.13 (s, 1H), 8.50 (d, 1H).

Example 145

(S)-5-acetyl-N-(1-(3-(4-cyano-3-methoxyphenyl)-1H-pyrazol-1-yl)propan-2-yl)-1H-pyrazole-3-carboxamide a) (S)-4-(1-(2-Aminopropyl)-1H-pyrazol-3-yl)-2-nitrobenzonitrile (S)-4-(1-(2-aminopropyl)-1H-pyrazol-3-yl)-2-nitrobenzonitrile was prepared using the method of Example 34(c) starting from 2-nitro-4-(1H-pyrazol-5-yl)benzonitrile (2.0 g, 9.34 mmol) and (S)-tert-butyl 1-hydroxypropan-2-ylcarbamate (1.6 g, 9.13 mmol). Yield 71.0%. H-NMR (400 MHz; DMSO-d6): 0.98 (d, 3H), 3.23-3.33 (m, 1H), 4.01-4.12 (m, 2H), 7.08 (d, 1H), 7.90 (d, 1H), 8.19 (d, 1H), 8.34 (dd, 1H), 8.69 (d, 1H).

b) (S)-5-acetyl-N-(1-(3-(4-cyano-3-nitrophenyl)-1H-pyrazol-1-yl)propan-2-yl)-1H-pyrazole-3-carboxamide (S)-5-acetyl-N-(1-(3-(4-cyano-3-nitrophenyl)-1H-pyrazol-1-yl)propan-2-yl)-1H-pyrazole-3-carboxamide was prepared using the method of Example 34(d) starting from (S)-4-(1-(2-aminopropyl)-1H-pyrazol-3-yl)-2-nitrobenzonitrile (500 mg, 1.843 mmol) and 3-acetyl-1H-pyrazole-5-carboxylic acid (341 mg, 2.212 mmol). The product was triturated twice using diethyl ether. Yield 42.9%. 1H-NMR (400 MHz; DMSO-d6): δ 1.11-1.27 (m, 3H), 2.48 (s, 3H), 4.21-4.57 (m, 3H), 7.03 (d, 1H), 7.29 (s, 1H), 7.86 (d, 1H), 8.09-8.72 (m, 4H), 14.1 (bs, 1H).

c) (S)-5-acetyl-N-(1-(3-(4-cyano-3-methoxyphenyl)-1H-pyrazol-1-yl)propan-2-yl)-1H-pyrazole-3-carboxamide (S)-5-acetyl-N-(1-(3-(4-cyano-3-nitrophenyl)-1H-pyrazol-1-yl)propan-2-yl)-1H-pyrazole-3-carboxamide (0.27 g, 0.663 mmol) was added to a flask and flushed with nitrogen. Dry THF was added and tetrabutylammonium methoxide solution in methanol (1.219 ml, 0.729 mmol) was added dropwise through a septum. During the reaction 1.754 ml of tetrabutylammonium methoxide solution in methanol was added and after reacting for 6 days the reaction was stopped. The crude product was evaporated and dissolved in DCM. The mixture was washed with water, dried and evaporated. Evaporation residue was dissolved in 20% methanol/DCM-solvent and filtered through silica wetted with the same solvent. The product was triturated using a small amount of DCM. Yield 5.00%. 1H-NMR (400 MHz; DMSO-d6): δ 1.16 (d, 3H), 2.5 (s, 3H), 3.94 (s, 3H), 4.31 (s, 2H), 4.40-4.50 (m, 1H), 6.88 (d, 1H), 7.31 (s, 1H), 7.46-7.54 (m, 2H), 7.71 (d, 1H), 7.80 (d, 1H), 8.49 (s, 1H), 14.12 (s, 1H).

Example 146

(R)-methyl 4-(1-(3-(3-chloro-4-cyanophenyl)-1H-pyrazol-1-yl)propan-2-ylcarbamoyl)thiazol-2-ylcarbamate a) 2-(Methoxycarbonylamino)thiazole-4-carboxylic Acid

Methyl 2-aminothiazole-4-carboxylate (1.0 g, 6.32 mmol) was dissolved in dry pyridine and methyl chloroformate (0.733 ml, 9.48 mmol) was added slowly in RT. The reaction mixture was stirred at RT overnight and evaporated to dryness. The evaporation residue was dissolved in dry THF/methanol (9:1) mixture, 1M lithium hydroxide (3.50 ml, 3.50 mmol) was added and the reaction mixture was stirred for 4 h in RT. 1M lithium hydroxide (2.33 ml, 2.33 mmol) was added and the mixture was stirred overnight and evaporated to dryness. DCM was added and pH was adjusted to 3. The product was filtered and dried in vacuum. Yield 76%. 1H-NMR (400 MHz; DMSO-d6): δ 3.75 (s, 3H), 7.95 (s, 1H), 12.05 (s, 1H), 12.76 (bs, 1H).

b) (R)-methyl 4-(1-(3-(3-chloro-4-cyanophenyl)-1H-pyrazol-1-yl)propan-2-ylcarbamoyl)thiazol-2-ylcarbamate (R)-methyl 4-(1-(3-(3-chloro-4-cyanophenyl)-1H-pyrazol-1-yl)propan-2-yl-carbamoyl)thiazol-2-ylcarbamate was prepared using the method of Example 34(d) starting from 2-(methoxycarbonylamino)thiazole-4-carboxylic acid (0.36 g, 1.460 mmol) and (R)-4-(1-(2-aminopropyl)-1H-pyrazol-3-yl)-2-chlorobenzonitrile (0.334 g, 1.217 mmol). The product was triturated using diethyl ether and DCM, respectively. Yield 27.2%. 1H-NMR (400 MHz; DMSO-d6): δ 1.13 (d, 3H), 3.77 (s, 3H), 4.33 (d, 1H), 4.34 (d, 1H), 4.37-4.45 (m, 1H), 6.96 (d, 1H), 7.72 (s, 1H), 7.83 (d, 1H), 7.87 (d, 1H), 7.93-7.94 (m, 2H), 8.04 (t, 1H), 11.85 (s, 1H).

Example 147

(S)—N-(1-(3-(3-chloro-4-cyano-2-methylphenyl)-1H-pyrazol-1-yl)propan-2-yl)oxazole-4-carboxamide (S)—N-(1-(3-(3-chloro-4-cyano-2-methylphenyl)-1H-pyrazol-1-yl)propan-2-yl)oxazole-4-carboxamide was prepared using the method of Example 34(d) starting from 4-oxazolecarboxylic acid (0.181 g, 1.596 mmol) and (S)-4-(1-(2-aminopropyl)-1H-pyrazol-3-yl)-2-chloro-3-methylbenzonitrile (0.430 g, 1.330 mmol). The product was purified by Flash-chromatography. Yield 0.813%. 1H-NMR (400 MHz; CDCl$_3$): δ 1.27 (d, 3H), 2.57 (s, 3H), 4.31 (dd, 1H), 4.43 (dd, 1H), 4.54-4.63 (m, 1H), 6.44 (d, 1H), 7.50 (d, 1H), 7.51-7.55 (m, 2H), 7.60 (dd, 1H), 7.85 (d, 1H), 8.22 (d, 1H).

Example 148

(S)-ethyl 4-(1-(3-(3-chloro-4-cyanophenyl)-1H-pyrazol-1-yl)propan-2-yl-carbamoyl)thiazole-2-carboxylate (S)-ethyl 4-(1-(3-(3-chloro-4-cyanophenyl)-1H-pyrazol-1-yl)propan-2-yl-carbamoyl)thiazole-2-carboxylate was prepared using the method of Example 34(d) starting from 2,4-thiazoledicarboxylic acid, 2-ethyl ester (0.556 g, 2.76 mmol) and (S)-4-(1-(2-aminopropyl)-1H-pyrazol-3-yl)-2- chlorobenzonitrile (0.6 g, 2.301 mmol). The product was triturated using diethyl ether. Yield 51.9%. 1H-NMR (400 MHz; DMSO-d6): δ 1.18 (d, 3H), 1.34 (t, 3H), 4.34 (dd, 1H), 4.39-4.46 (m, 3H), 4.47-4.55 (m, 1H), 6.94 (d, 1H), 7.83 (d, 1H), 7.94-7.96 (m, 2H), 8.02 (t, 1H), 8.55 (s, 1H), 8.60 (d, 1H).

Example 149

(S)—N-(1-(3-(3-chloro-4-cyanophenyl)-1H-pyrazol-1-yl)propan-2-yl)-2-(morpholinomethyl)thiazole-4-carboxamide a) Ethyl 2-(morpholinomethyl)thiazole-4-carboxylate 2-Chloromethyl-thiazole-4-carboxylic acid ethyl ester (500 mg, 2.431 mmol) and potassium carbonate (504 mg, 3.65 mmol) were dissolved in dry DMF and morpholine (0.212 ml, 2.431 mmol) was added. The reaction mixture was stirred at RT overnight, diluted with DCM and washed with NaHCO$_3$ and water. Organic phase was evaporated to dryness to yield the title compound (93%). 1H-NMR (400 MHz; DMSO-d6): δ 1.30 (t, 3H), 2.49-2.54 (m, 4H, overlap with DMSO), 3.58-3.63 (m, 4H), 3.84 (s, 2H), 4.29 (q, 2H), 8.47 (s, 1H). m/z [256.3+1].

b) 2-(Morpholinomethyl)thiazole-4-carboxylic Acid Hydrochloride

Ethyl 2-(morpholinomethyl)thiazole-4-carboxylate (578 mg, 2.255 mmol) was dissolved in THF/methanol (9:1) mixture and 1M lithium hydroxide (4.51 ml, 4.51 mmol) was added slowly. The reaction mixture was stirred at RT for 1.5 h, pH was adjusted to 2 and the mixture was evaporated to dryness. The evaporation residue was triturated using ethanol. The precipitate was filtered and dried in vacuum. The filtrate was also evaporated to dryness to give a crude product. m/z [228+1].

c) (S)—N-(1-(3-(3-chloro-4-cyanophenyl)-1H-pyrazol-1-yl)propan-2-yl)-2-(morpholinomethyl)thiazole-4-carboxamide (S)—N-(1-(3-(3-chloro-4-cyanophenyl)-1H-pyrazol-1-yl)propan-2-yl)-2-(morpholinomethyl)thiazole-4-carboxamide was prepared using the method of Example 34(d) starting from 2-(morpholinomethyl)thiazole-4-carboxylic acid hydrochloride (260 mg, 0.982 mmol) and (S)-4-(1-(2-aminopropyl)-1H-pyrazol-3-yl)-2-chlorobenzonitrile (218 mg, 0.818 mmol). The product was purified by washing the organic phase with 1M HCl, 1M Na$_2$CO$_3$, brine and water. Yield 68.7%. 1H-NMR (400 MHz; DMSO-d6): δ 1.23 (d, 3H), 2.50 (t, 4H; overlap with DMSO), 3.61 (t, 4H), 3.85 (d, 2H), 4.32 (dd, 1H), 4.40 (dd, 1H), 4.43-4.50 (m, 1H), 6.96 (d, 1H), 7.84 (d, 1H), 7.95 (dd, 1H), 7.98 (dd, 1H), 8.02 (dd, 1H), 8.16 (s, 1H), 8.46 (d, 1H). m/z [471.0+1].

Example 150

(R)—N-(1-(3-(3-chloro-4-cyanophenyl)-1H-pyrazol-1-yl)propan-2-yl)-2-(2-methoxyethylamino)thiazole-4-carboxamide a) (R)-2-bromo-N-(1-(3-(3-chloro-4-cyanophenyl)-1H-pyrazol-1-yl)propan-2-yl)thiazole-4-carboxamide (R)-2-bromo-N-(1-(3-(3-chloro-4-cyanophenyl)-1H-pyrazol-1-yl)propan-2-yl)thiazole-4-carboxamide was prepared using the method of Example 34(d) starting from (R)-4-(1-(2-aminopropyl)-1H-pyrazol-3-yl)-2-chlorobenzonitrile (100 mg, 0.384 mmol) and 2-bromo-1,3-thiazole-4-carboxylic acid (96 mg, 0.460 mmol). The product was triturated using diethyl ether. Yield 55.8%. 1H-NMR (400 MHz; CDCl$_3$): δ 1.12 (d, 3H), 4.27-4.52 (m, 3H), 6.97 (d, 1H), 7.85 (d, 1H), 8.00 (s, 2H), 8.07 (s, 1H), 8.23 (s, 1H), 8.64 (d, 1H).

b) (R)-2-bromo-N-(1-(3-(3-chloro-4-cyanophenyl)-1H-pyrazol-1-yl)propan-2-yl)thiazole-4-carboxamide (R)-2-bromo-N-(1-(3-(3-chloro-4-cyanophenyl)-1H-pyrazol-1-yl)propan-2-yl)thiazole-4-carboxamide (71 mg, 0.158 mmol) was added into a microwave vial with dry pyridine as a solvent. The mixture was bubbled with nitrogen. 2-methoxyethylamine (0.021 ml, 0.236 mmol) was added and the mixture was heated with microwaves at 120° C. During the next few days a total of 0.133 ml of 2-methoxyethylamine was added and the reaction mixture was heated for 3-12 h at a time. The product was purified by Flash-chromatography. Yield 29.0%. 1H-NMR (400 MHz; CDCl$_3$): δ 1.23 (d, 3H), 3.40-3.46 (m, 5H), 3.58 (t, 2H), 4.29 (dd, 1H), 4.40 (dd, 1H), 4.50-4.57 (m, 1H), 5.38 (t, 1H), 6.62 (d, 1H), 7.32 (d, 1H), 7.49 (d, 1H), 7.68 (d, 1H), 7.69 (d, 1H), 7.83 (dd, 1H), 7.98 (d, 1H).

Example 151

N—((R)-1-(3-(3-chloro-4-cyanophenyl)-1H-pyrazol-1-yl)propan-2-yl)-2-(3-hydroxybutan-2-ylamino)thiazole-4-carboxamide a) Methyl 2-(3-hydroxybutan-2-ylamino)thiazole-4-carboxylate Methyl 2-aminothiazole-4-carboxylate (1.0, 6.32 mmol), 3-hydroxy-2-butanone (1.045 ml, 12.01 mmol) and acetic acid (2.278 g, 37.9 mmol) were dissolved in 1,2-dichloroethane. Sodium triacetoxy borohydride (3.75 g, 17.70 mmol) was added and the reaction mixture was stirred overnight. Sodium triacetoxy borohydride (3.1 g) was added in two portions and the reaction mixture was stirred over two nights. 1M NaHCO3 was added slowly and mixture was extracted twice with DCM. DCM phase was dried and evaporated to afford 68.1% of the title product. m/z [230.3+1].

b) 2-(3-hydroxybutan-2-ylamino)thiazole-4-carboxylic Acid

Methyl 2-(3-hydroxybutan-2-ylamino)thiazole-4-carboxylate (1.092 g, 4.75 mmol) was dissolved in THF/water (9:1) mixture and 1M lithium hydroxide (9.49 ml, 9.49 mmol) was added slowly. The reaction mixture was stirred at RT for 1 h and evaporated to dryness. DCM and water was added and pH was adjusted to 2. Acidic water phase was washed twice with DCM and evaporated to dryness. Evaporation residue was dissolved in ethanol, a precipitation was filtered and the filtrate was evaporated to dryness to give a crude product. m/z [216.3+1].

c) N—((R)-1-(3-(3-chloro-4-cyanophenyl)-1H-pyrazol-1-yl)propan-2-yl)-2-(3-hydroxybutan-2-ylamino)thiazole-4-carboxamide N—((R)-1-(3-(3-chloro-4-cyanophenyl)-1H-pyrazol-1-yl)propan-2-yl)-2-(3-hydroxybutan-2-ylamino)thiazole-4- carboxamide was prepared using the method of Example 34(d) starting from 2-(3-hydroxybutan-2-ylamino)thiazole-4-carboxylic acid (1.35 g, 6.24 mmol) and (R)-4-(1-(2-aminopropyl)-1H-pyrazol-3-yl)-2-chlorobenzonitrile (1.356 g, 5.20 mmol). The product was purified by Flash-chromatography. Yield 14.45%. 1H-NMR (400 MHz; DMSO-d6): δ 0.98-1.19 (m, 9H), 3.57-3.72 (m, 2H), 4.23-4.47 (m, 3H), 4.67 (d, 1H), 6.94-6.97 (m, 1H), 7.11-7.14 (m, 1H), 7.37-7.53 (m, 1H), 7.69-7.80 (m, 1H), 7.80-7.85 (m, 1H), 7.90-8.00 (m, 2H), 8.06-8.09 (m, 1H).

Example 152

(S)—N-(1-(3-(3-chloro-4-cyanophenyl)-1H-pyrazol-1-yl)propan-2-yl)-2-(hydroxymethyl)thiazole-4-carboxamide a) (S)-ethyl 4-(1-(3-(3-chloro-4-cyanophenyl)-1H-pyrazol-1-yl)propan-2-yl-carbamoyl)thiazole-2-carboxylate (S)-ethyl 4-(1-(3-(3-chloro-4-cyanophenyl)-1H-pyrazol-1-yl)propan-2-yl-carbamoyl)thiazole-2-carboxylate was prepared using the method of Example 34(d) starting from (S)-4-(1-(2-aminopropyl)-1H-pyrazol-3-yl)-2-chlorobenzonitrile (600 mg, 2.301 mmol) and 2,4-thiazoledicarboxylic acid, 2-ethyl ester (556 mg, 2.76 mmol). The product was triturated using diethyl ether. Yield 51.9%. 1H-NMR (400 MHz; DMSO-d6): δ 1.18 (d, 3H), 1.34 (t, 3H), 4.29-4.58 (m, 5H), 6.97 (d, 1H), 7.83 (d, 1H), 7.94-7.96 (m, 2H), 8.02 (t, 1H), 8.55 (s, 1H), 8.60 (d, 1H).

b) (S)—N-(1-(3-(3-chloro-4-cyanophenyl)-1H-pyrazol-1-yl)propan-2-yl)-2-(hydroxymethyl)thiazole-4-carboxamide Sodium borohydride (86 mg, 2.262 mmol) was added into a flask and the atmosphere was replaced with nitrogen. Dry ethanol was added and the reaction mixture was cooled to 0° C. (S)-ethyl 4-(1-(3-(3-chloro-4-cyanophenyl)-1H-pyrazol-1-yl)propan-2-ylcarbamoyl)thiazole-2-carboxylate (502 mg, 1.131 mmol) was added and the reaction mixture was warmed slowly to RT while stirring overnight. The crude product was cooled to 0° C., water was added dropwise, the pH was adjusted to 7 and the mixture was evaporated. DCM and a few drops of methanol were added and the crude product was washed with 1M $Na_2CO_3$ and with water. Yield 58.6%. 1H-NMR (400 MHz; DMSO-d6): δ 1.12 (d, 3H), 4.31 (dd, 1H), 4.40 (dd, 1H), 4.43-4.51 (m, 1H), 4.79 (d, 2H), 6.20 (t, 1H), 6.95 (d, 1H), 7.84 (d, 1H), 7.96 (dd, 1H), 7.98 (dd, 1H), 8.08 (dd, 1H), 8.13 (s, 1H), 8.50 (d, 1H).

Example 153

(S)-2-bromo-N-(1-(3-(3-chloro-4-cyanophenyl)-1H-pyrazol-1-yl)propan-2-yl)thiazole-4-carboxamide (S)-2-bromo-N-(1-(3-(3-chloro-4-cyanophenyl)-1H-pyrazol-1-yl)propan-2-yl)-thiazole-4-carboxamide was prepared using the method of Example 34(d) starting from 2-bromo-1,3-thiazole-4-carboxylic acid (0.6 g, 2.88 mmol) and (S)-4-(1-(2-aminopropyl)-1H-pyrazol-3-yl)-2-chlorobenzonitrile (0.627 g, 2.403 mmol). The product was triturated using diethyl ether. Yield 65.5%. 1H-NMR (400 MHz; DMSO-d6): δ 1.12 (d, 3H), 4.23 (dd, 1H), 4.39 (dd, 1H), 4.42-4.50 (m, 1H), 6.96 (d, 1H), 7.84 (d, 1H), 8.00-8.01 (m, 2H), 8.07 (dd, 1H), 8.23 (s, 1H), 8.64 (d, 1H).

Example 154

(R)—N-(1-(3-(3-chloro-4-cyanophenyl)-1H-pyrazol-1-yl)propan-2-yl)-2-(methylamino)thiazole-4-carboxamide (R)—N-(1-(3-(3-chloro-4-cyanophenyl)-1H-pyrazol-1-yl)propan-2-yl)-2-(methyl-amino)thiazole-4-carboxamide was prepared using the method of Example 34(d) starting from 2-(methylamino)thiazole-4-carboxylic acid (0.34 g, 2.149 mmol) and (R)-4-(1-(2-aminopropyl)-1H-pyrazol-3-yl)-2-chlorobenzonitrile (0.467 g, 1.791 mmol). The product was purified by Flash-chromatography. Yield 9.08%. 1H-NMR (400 MHz; DMSO-d6): δ 1.12 (d, 3H), 2.85 (d, 3H), 4.30-4.42 (m, 3H), 6.96 (d, 1H), 7.18 (d, 1H), 7.59 (d, 1H), 7.84 (d, 1H), 7.91 (d, 1H), 7.95-7.96 (m, 2H), 8.08 (dd, 1H).

Example 155

(S)-2-amino-N-(1-(3-(3-chloro-4-cyano-2-methyl-phenyl)-1H-pyrazol-1-yl)-propan-2-yl)oxazole-4-carboxamide (S)-2-amino-N-(1-(3-(3-chloro-4-cyano-2-methylphenyl)-1H-pyrazol-1-yl)-propan-2-yl)oxazole-4-carboxamide was prepared using the method of Example 34(d) starting from 2-amino-1,3-oxazole-4-carboxylic acid (0.196 g, 1.527 mmol) and (S)-4-(1-(2-aminopropyl)-1H-pyrazol-3-yl)-2-chloro-3-methylbenzonitrile (0.437 g, 1.272 mmol). The product was purified by Flash-chromatography. Yield 29.0%. 1H-NMR (400 MHz; $CDCl_3$): δ 1.23 (d, 3H), 2.58 (s, 3H), 4.29 (dd, 1H), 4.39 (dd, 1H), 4.54 (m, 1H), 4.59 (s, 2H), 6.44 (d, 1H), 7.31 (d, 1H), 7.50 (d, 1H), 7.53 (dd, 1H), 7.58 (dd, 1H), 7.68 (s, 1H).

Example 156

(S)-2-amino-N-(1-(3-(3-chloro-4-cyano-2-methyl-phenyl)-1H-pyrazol-1-yl)propan-2-yl)thiazole-4-carboxamide (S)-2-amino-N-(1-(3-(3-chloro-4-cyano-2-methylphenyl)-1H-pyrazol-1-yl)-propan-2-yl)thiazole-4-carboxamide was prepared using the method of Example 34(d) starting from 2-Aminothiazole-4-carboxylic acid (0.504 g 3.49 mmol) and (S)-4-(1-(2-aminopropyl)-1H-pyrazol-3-yl)-2-chloro-3-methylbenzonitrile (0.8 g, 2.91 mmol). The product was purified by Flash-chromatography. Yield 16.65%. 1H-NMR (400 MHz; $CDCl_3$): δ 1.24 (d, 3H), 2.58 (s, 3H), 4.30 (dd, 1H), 4.40 (dd, 1H), 4.53 (m, 1H), 4.86 (s, 2H), 7.44 (d, 1H), 7.35 (s, 1H), 7.51 (d, 1H), 7.54 (dd, 1H), 7.57 (d, 1H), 7.63 (d, 1H).

Example 157

(R)—N-(1-(3-(3-chloro-4-cyanophenyl)-1H-pyrazol-1-yl)propan-2-yl)-2-(1-(methylsulfonyl)piperidin-4-yl)thiazole-4-carboxamide (R)—N-(1-(3-(3-chloro-4-cyanophenyl)-1H-pyrazol-1-yl)propan-2-yl)-2-(piperidin-4-yl)thiazole-4-carboxamide (80 mg, 0.176 mmol) was added into a flask under nitrogen atmosphere. Dry pyridine was added along with methanesulfonyl chloride (20.14 mg, 0.176 mmol) and the mixture was stirred overnight. The reaction was stopped by adding water. The reaction mixture was diluted with DCM and washed with 1M $Na_2CO_3$ and water. The product was triturated using diethyl ether. Yield 35.5%. 1H-NMR (400 MHz; $CDCl_3$): δ 1.29 (d, 3H), 1.92 (m, 2H), 2.18 (m, 2H), 2.81 (dd, 1H), 2.84 (s, 3H), 3.08 (m, 1H), 3.89 (m, 2H), 4.34 (dd, 1H), 4.42 (dd, 1H), 4.59 (m, 1H), 6.63 (d, 1H), 7.50 (d, 1H), 7.67 (d, 1H), 7.68 (d, 1H), 7.77 (dd, 1H), 7.98 (d, 1H), 8.01 (s, 1H).

Example 158

(S)—N-(1-(3-(3-chloro-4-cyanophenyl)-1H-pyrazol-1-yl)propan-2-yl)-2-(2-methoxyethylamino)thiazole-4-carboxamide (S)-2-bromo-N-(1-(3-(3-chloro-4-cyanophenyl)-1H-pyrazol-1-yl)propan-2-yl)thiazole-4-carboxamide (0.2 g, 0.444 mmol) and dry pyridine were added into a microwave vial under nitrogen atmosphere. 2-methoxyethylamine (0.193 ml, 2.219 mmol) was added and the mixture was heated with microwaves at 120° C. for 10 h. Afterwards a total of 0.232 ml of 2-methoxyethylamine was added and the mixture was heated for another 10 h. The product was purified by Flash-chromatography. Yield 47.8%. 1H-NMR (400 MHz; $CDCl_3$): δ 1.22 (d, 3H), 3.41 (s, 3H), 3.44 (m, 2H), 3.57 (m, 2H), 4.29 (dd, 1H), 4.40 (dd, 1H), 4.54 (m, 1H), 5.39 (t, 1H), 6.62 (d, 1H), 7.33 (d, 1H), 7.49 (d, 1H), 7.68 (dd, 1H), 7.69 (d, 1H), 7.83 (dd, 1H), 7.98 (d, 1H).

Example 159

(S)—N-(1-(3-(3-chloro-4-cyano-5-fluorophenyl)-1H-pyrazol-1-yl)propan-2-yl)-1-(pyridin-4-yl)-1H-pyrazole-3-carboxamide The title compound was prepared as described in Example 34(d), starting from 1-(pyridin-4-yl)-1H-pyrazole-3-carboxylic acid (47.5 mg, 0.251 mmol) and (S)-4-(1-(2-aminopropyl)-1H-pyrazol-3-yl)-2-chloro-6-fluorobenzonitrile (70 mg, 0.251 mmol). The precipitate that formed during the reaction was filtered out of the reaction mixture was washed with 2×5 ml of water and dried with vacuum at 40° C. Yield 73.7%. 1H-NMR (400 MHz; DMSO-d6): δ 1.18 (d, 3H), 4.31-4.42 (m, 2H), 4.43-4.54 (m, 1H), 6.90 (d, 1H), 7.01 (dd, 1H), 7.79-8.01 (m, 5H), 8.39 (d, 1H), 8.66-8.73 (m, 2H), 8.77 (d, 1H).

Example 160

(S)-2-bromo-N-(1-(3-(3-chloro-4-cyano-2-methylphenyl)-1H-pyrazol-1-yl)-propan-2-yl)thiazole-4-carboxamide (S)-2-bromo-N-(1-(3-(3-chloro-4-cyano-2-methylphenyl)-1H-pyrazol-1-yl)-propan-2-yl)thiazole-4-carboxamide was prepared using the method of Example 34(d) starting from 2-bromo-1,3-thiazole-4-carboxylic acid (0.909 g, 4.37 mmol) and (S)-4-(1-(2-aminopropyl)-1H-pyrazol-3-yl)-2-chloro-3-methylbenzonitrile (1 g, 3.64 mmol). The product was purified by Flash-chromatography. Yield 45.0%. 1H-NMR (400 MHz; $CDCl_3$): δ 1.25 (d, 3H), 2.61 (s, 3H), 4.29 (dd, 1H), 4.45 (dd, 1H), 4.60 (m, 1H), 6.46 (d, 1H), 7.51 (d, 1H), 7.57 (dd, 1H), 7.61 (dd, 1H), 7.98 (d, 1H), 8.04 (s, 1H).

Example 161

(S)—N-(1-(3-(3-chloro-4-cyanophenyl)-1H-pyrazol-1-yl)propan-2-yl)-2-((dimethylamino)methyl)thiazole-4-carboxamide a) Ethyl 2-((dimethylamino)methyl)thiazole-4-carboxylate 2-Chloromethyl-thiazole-4-carboxylic acid ethyl ester (500 mg, 2.431 mmol) and potassium carbonate (504 mg, 3.65 mmol) were dissolved in dry DMF. Dimethylamine hydrochloride (218 mg, 2.67 mmol) in dry DMF was added slowly to the reaction mixture and stirred at RT over three nights. DCM was added and the mixture was washed with concentrated $NaHCO_3$ and water. Organic phase was evaporated to dryness and the product was purified by Flash-chromatography. Yield 34.2%. 1H-NMR (400 MHz; $CDCl_3$): δ 1.41 (t, 3H), 2.49 (s, 6H), 3.99 (s, 2H) 4.43 (q, 2H), 8.20 (s, 1H).

b) 2-((Dimethylamino)methyl)thiazole-4-carboxylic Acid

Ethyl 2-((dimethylamino)methyl)thiazole-4-carboxylate (147 mg, 0.686 mmol) was dissolved in THF/methanol mixture (9:1) and 1M lithium hydroxide (1.372 ml, 1.372 mmol) was added slowly. The reaction mixture was stirred at RT for 3 h, pH was adjusted to 2 and the mixture was evaporated to dryness to yield the title compound as a crude product. m/z [186.2+1].

c) (S)—N-(1-(3-(3-chloro-4-cyanophenyl)-1H-pyrazol-1-yl)propan-2-yl)-2-((dimethylamino)methyl)thiazole-4-carboxamide (S)—N-(1-(3-(3-chloro-4-cyanophenyl)-1H-pyrazol-1-yl)propan-2-yl)-2-((dimethylamino)methyl)thiazole-4-carboxamide was prepared using the method of Example 34(d) starting from (S)-4-(1-(2-aminopropyl)-1H-pyrazol-3-yl)-2-chlorobenzonitrile (0.149 g, 0.573 mmol) and 2-((dimethylamino)methyl)thiazole-4-carboxylic acid (128 mg, 0.687 mmol). The product was purified by Flash-chromatography. Yield 0.814%. 1H-NMR (400 MHz; $CDCl_3$): δ 1.26 (d, 3H), 2.37 (s, 6H), 3.76 (d, 2H), 4.32 (dd, 1H), 4.42 (dd, 1H), 4.59 (m, 1H), 6.62 (d, 1H), 7.50 (d, 1H), 7.67 (dd, 1H), 7.81 (dd, 1H), 7.90 (d, 1H), 7.99 (dd, 1H), 8.06 (s. 1H).

Example 162

(S)—N-(1-(3-(3-chloro-4-cyanophenyl)-1H-pyrazol-1-yl)propan-2-yl)-2-(1-(methylsulfonyl)piperidin-4-yl)oxazole-4-carboxamide a) Ethyl 2-(1-(methylsulfonyl)piperidin-4-yl)oxazole-4-carboxylate Ethyl 2-(4-piperidino)-1,3-oxazole-4-carboxylate (500 mg, 2.230 mmol) and triethylamine (0.466 ml, 3.34 mmol) were dissolved in dry DCM and cooled down to 0° C. Methanesulfonyl chloride (0.190 ml, 2.453 mmol) was added slowly at 0° C. and the reaction mixture was stirred at RT overnight. Small amount of water was added carefully and organic phase was washed with 1M $Na_2CO_3$ and water. Organic phase was dried and evaporated to yield the title compound 89%. 1H-NMR (400 MHz; $CDCl_3$): δ 1.38 (t, 3H), 1.97-2.11 (m, 2H), 2.15-2.24 (m, 2H), 2.81 (s, 3H), 2.88-3.07 (m, 3H), 3.72-3.82 (m, 2H), 4.39 (q, 2H), 8.17 (s, 1H).

b) 2-(1-(methylsulfonyl)piperidin-4-yl)oxazole-4-carboxylic Acid

Ethyl 2-(1-(methylsulfonyl)piperidin-4-yl)oxazole-4-carboxylate (590 mg, 1.951 mmol) was dissolved in THF/methanol mixture (9:1) and 1M lithium hydroxide (3.90 ml, 3.90 mmol) was added slowly. The reaction mixture was stirred at RT for 1 h, diluted with water and pH was adjusted to 1.5. The mixture was extracted three times with ethyl acetate. Ethyl acetate phases were combined and evaporated to yield the title compound (74.7%). 1H-NMR (400 MHz; DMSO): δ 1.68-1.81 (m, 2H), 2.06-2.15 (m, 2H), 2.85-2.96 (m, 5H), 2.99-3.10 (m, 1H), 3.51-3.59 (m, 2H), 8.67 (s, 1H), 13.02 (bs, 1H).

c) (S)—N-(1-(3-(3-chloro-4-cyanophenyl)-1H-pyrazol-1-yl)propan-2-yl)-2-(1-(methylsulfonyl)piperidin-4-yl)oxazole-4-carboxamide (S)—N-(1-(3-(3-chloro-4-cyanophenyl)-1H-pyrazol-1-yl)propan-2-yl)-2-(1-(methylsulfonyl)piperidin-4-yl)oxazole-4-carboxamide was prepared using the method of Example 34(d) starting from 2-(1-(methylsulfonyl)piperidin-4-yl)oxazole-4-carboxylic acid (0.4 g, 01.458 mmol) and (S)-4-(1-(2-aminopropyl)-1H-pyrazol-3-yl)-2-chlorobenzonitrile (0.317 g, 01.215 mmol). The product was purified by extracting it from DCM with 0.1 M HCl, 1 M Na$_2$CO$_3$, water and brine. Yield 87%. 1H-NMR (400 MHz; CDCl$_3$): δ 1.25 (d, 3H), 1.97 (m, 2H), 2.15 (m, 2H), 2.83 (s, 3H), 2.89 (m, 3H), 3.81 (m, 2H), 4.30 (dd, 1H), 4.41 (dd, 1H), 4.57 (m, 1H), 6.63 (d, 1H), 7.46 (d, 1H), 7.49 (d, 1H), 7.68 (dd, 1H), 7.79 (dd, 1H), 8.01 (dd, 1H), 8.11 (s, 1H).

Example 163

(S)—N-(1-(3-(3-chloro-4-cyano-5-fluorophenyl)-1H-pyrazol-1-yl)propan-2-yl)-1-(2-fluoroethyl)-2-methyl-1H-imidazole-4-carboxamide (S)—N-(1-(3-(3-chloro-4-cyano-5-fluorophenyl)-1H-pyrazol-1-yl)propan-2-yl)-2-methyl-1H-imidazole-4-carboxamide (130 mg, 0.269 mmol) was suspended in THF (5 ml). Cesium carbonate (123 mg, 0.376 mmol) and 1-iodo-2-fluoroethane (0.066 ml, 0.807 mmol) were added and the resulting mixture was stirred overnight at RT. Next day 0.2 ml of 1-iodo-2-fluoroethane was added and the mixture was left to react over the weekend. 1 ml of water was added and the reaction mixture was evaporated. The product was purified with LC/MS-trigger. Yield 27.5%. $^1$H-NMR (400 MHz; CDCl$_3$): δ 1.22 (d, 3H), 2.46 (s, 3H), 4.13-4.24 (m, 2H), 4.29 (dd, 1H), 4.40 (dd, 1H), 4.52-4.62 (m, 1H), 4.59-4.74 (m, 2H), 6.59 (d, 1H), 7.50-7.54 (m, 2H), 7.69 (d, 1H), 7.73-7.75 (m, 1H), 7.78 (bs, 1H).

Example 164

(S)—N-(1-(3-(3-chloro-4-cyano-2-methylphenyl)-1H-pyrazol-1-yl)propan-2-yl)-2-(hydroxymethyl)thiazole-4-carboxamide a) (S)-ethyl 4-(1-(3-(3-chloro-4-cyano-2-methylphenyl)-1H-pyrazol-1-yl)propan-2-ylcarbamoyl)thiazole-2-carboxylate (S)-ethyl 4-(1-(3-(3-chloro-4-cyano-2-methylphenyl)-1H-pyrazol-1-yl)propan-2-ylcarbamoyl)thiazole-2-carboxylate was prepared using the method of Example 34(d) starting from (S)-4-(1-(2-aminopropyl)-1H-pyrazol-3-yl)-2-chloro-3-methylbenzonitrile (400 mg, 1.165 mmol) and 2,4-thiazoledicarboxylic acid, 2-ethyl ester 234 mg, 1.165 mmol). The product was purified by Flash-chromatography. Yield 16.1%. 1H-NMR (400 MHz; CDCl3): δ 1.31 (d, 3H), 1.44 (t, 3H), 2.55 (s, 3H), 4.31-4-46 (m, 2H), 4.50 (q, 2H), 4.56-4.68 (m, 1H), 6.42 (d, 1H), 7.50 (d, 1H), 7.54-7.61 (m, 2H), 7.80 (bd, 1H), 8.34 (s, 1H).

c) (S)—N-(1-(3-(3-chloro-4-cyano-2-methylphenyl)-1H-pyrazol-1-yl)propan-2-yl)-2-(hydroxymethyl)thiazole-4-carboxamide Sodium borohydride (14.21 mg, 0.376 mmol) was added into a flask and the atmosphere was replaced with nitrogen. Dry ethanol was added and the reaction mixture was cooled to 0° C. (S)-ethyl 4-(1-(3-(3-chloro-4-cyano-2-methylphenyl)-1H-pyrazol-1-yl)propan-2-ylcarbamoyl)thiazole-2-carboxylate (86 mg, 0.188 mmol) was added and the reaction mixture was warmed slowly to RT while stirring overnight. The crude product was cooled to 0° C., the pH was adjusted to 7 and the mixture was evaporated. DCM and a few drops of methanol were added and the crude product was washed with 1M Na$_2$CO$_3$ and with water. Yield 89%. 1H-NMR (400 MHz; DMSO-d6): δ 1.13 (d, 3H), 2.53 (s, 3H), 4.23 (dd, 1H), 4.40 (dd, 1H), 4.49 (m, 1H), 4.75 (d, 2H), 6.21 (t, 1H), 6.62 (d, 1H), 7.64 (dd, 1H), 7.82 (dd, 1H), 7.85 (d, 1H), 8.13 (s, 1H), 8.43 (d, 1H).

Example 165

(S)—N4-(1-(3-(3-chloro-4-cyanophenyl)-1H-pyrazol-1-yl)propan-2-yl)-N2,N2-dimethylthiazole-2,4-dicarboxamide (S)—N4-(1-(3-(3-chloro-4-cyanophenyl)-1H-pyrazol-1-yl)propan-2-yl)-N2,N2-dimethylthiazole-2,4-dicarboxamide was prepared using the method of Example 34(d) starting from (S)-4-(1-(3-(3-chloro-4-cyanophenyl)-1H-pyrazol-1-yl)propan-2-ylcarbamoyl)thiazole-2-carboxylic acid (0.2 g, 0.428 mmol) and dimethylamine hydrochloride (0.029 g, 0.357 mmol). The product was purified by Flash-chromatography. Yield 23.42%. 1H-NMR (400 MHz; DMSO-d6): δ 1.18 (d, 3H), 3.05 (s, 3H), 3.45 (s, 3H), 4.37 (m, 2H), 4.46 (m, 1H), 6.94 (d, 1H), 7.84 (d, 1H), 7.89 (dd, 1H), 7.95 (d, 1H), 8.04 (d, 1H), 8.30 (d, 1H), 8.43 (s, 1H).

Example 166

(S)—N-(1-(3-(3-chloro-4-cyano-2-methylphenyl)-1H-pyrazol-1-yl)propan-2-yl)-2-(dimethylamino)thiazole-4-carboxamide (S)-2-bromo-N-(1-(3-(3-chloro-4-cyano-2-methylphenyl)-1H-pyrazol-1-yl)-propan-2-yl)thiazole-4-carboxamide (0.247 g, 0.531 mmol) was added into a microwave test tube with dry pyridine. The mixture was bubbled with nitrogen and dimethylamine 2 M in THF (1.329 ml, 2.66 mmol) was added. The reaction mixture was heated with microwaves at 120° C. for 10 h. The crude product was evaporated, diluted with DCM, washed with 1M Na$_2$CO$_3$ and water. The product was purified with Flash-chromatography. Yield 63.2%. 1H-NMR (400 MHz; CDCl$_3$): δ 1.25 (d, 3H), 2.53 (s, 3H), 3.00 (s, 6H), 4.32 (dd, 1H), 4.41 (dd, 1H), 4.55 (m, 1H), 6.41 (d, 1H), 7.30 (d, 1H), 7.52 (m, 3H), 7.74 (d, 1H).

Example 167

(S)—N-(1-(3-(3-chloro-4-cyano-2-methylphenyl)-1H-pyrazol-1-yl)propan-2-yl)-2-(trifluoromethyl)thiazole-4-carboxamide a) 2-(Trifluoromethyl)thiazole-4-carboxylic Acid Ethyl 2-(trifluoromethyl)thiazole-4-carboxylate (400 mg, 1.176 mmol) was dissolved in THF/methanol mixture (9:1) and 1M lithium hydroxide (3.55 ml, 3.55 mmol) was added slowly. The reaction mixture was stirred at RT for 1 hour, pH was adjusted to 2 and the reaction mixture was extracted three times with ethyl acetate. Ethyl acetate phases were combined, dried and evaporated to dryness. Yield 93%. m/z [197.1+1]

b) (S)—N-(1-(3-(3-chloro-4-cyano-2-methylphenyl)-1H-pyrazol-1-yl)propan-2-yl)-2-(trifluoromethyl)thiazole-4-carboxamide (S)—N-(1-(3-(3-chloro-4-cyano-2-methylphenyl)-1H-pyrazol-1-yl)propan-2-yl)-2-(trifluoromethyl)thiazole-4-carboxamide was prepared using the method of Example 34(d) starting from (S)-4-(1-(2-aminopropyl)-1H-pyrazol-3-yl)-2-chloro-3-methylbenzonitrile (376 mg, 1.370 mmol) and 2-(trifluoromethyl)thiazole-4-carboxylic acid (324 mg, 1.644 mmol). The product was triturated using DCM and heptane. Yield 13.35%. 1H-NMR (400 MHz; CDCl$_3$): δ 1.27 (d, 3H), 2.57 (s, 3H), 4.31 (dd, 1H), 4.46 (dd, 1H), 4.65 (m, 1H), 4.45 (d, 1H), 7.51 (d, 1H), 7.53 (d, 1H), 7.57 (d, 1H), 8.03 (d, 1H), 8.33 (s, 1H).

Example 168

1-(4-((S)-1-(3-(3-chloro-4-cyano-2-methylphenyl)-1H-pyrazol-1-yl)propan-2-ylcarbamoyl)thiazol-2-yl)ethyl Acetate N—((S)-1-(3-(3-chloro-4-cyano-2-methylphenyl)-1H-pyrazol-1-yl)propan-2-yl)-2-(1-hydroxyethyl)thiazole-4-carboxamide (0.1 g, 0.233 mmol) and DMAP (2.87 mg, 0.023 mmol) were added into a flask under nitrogen atmosphere. Pyridine was added, the mixture cooled to 0° C. and acetic anhydride (0.023 ml, 0.244 mmol) was added dropwise. The mixture was slowly heated to RT and stirred. After 2.5 h the mixture was evaporated. The product was purified with Flash-chromatography. Yield 80%. 1H-NMR (400 MHz; CDCl$_3$): δ 1.27 (d, 3H), 1.59 (dd, 3H), 2.15 (d, 3H), 2.56 (d, 3H), 4.33 (dd, 1H), 4.43 (dd, 1H), 4.60 (m, 1H), 6.03-6.11 (m, 1H), 6.43 (d, 1H), 7.50-7.58 (m, 3H), 7.77-7.88 (m, 1H), 8.05 (s, 1H).

Example 169

(S)-2-((1H-imidazol-1-yl)methyl)-N-(1-(3-(3-chloro-4-cyanophenyl)-1H-pyrazol-1-yl)propan-2-yl)oxazole-4-carboxamide a) 2-(Chloromethyl)oxazole-4-carboxylic Acid Methyl 2-(chloromethyl)-1,3-oxazole-4-carboxylate (1.0 g, 5.70 mmol) was dissolved in THF/methanol mixture (9:1) and 1M lithium hydroxide (11.39 ml, 11.39 mmol) was added slowly. The reaction mixture was stirred at RT for 1 h, diluted with water and pH was adjusted to 2. The reaction mixture was extracted three times with ethyl acetate. Ethyl acetate phases were combined, dried and evaporated to dryness to yield the title compound (94%). 1H-NMR (400 MHz; DMSO$_3$): δ 4.93 (s, 2H), 8.80 (s, 1H), 13.20 (bs, 1H).

b) (S)—N-(1-(3-(3-chloro-4-cyanophenyl)-1H-pyrazol-1-yl)propan-2-yl)-2-(chloromethyl)oxazole-4-carboxamide 2-(chloromethyl)oxazole-4-carboxylic acid (400 mg, 2.476 mmol) and 1,3-DCC (5110 mg, 2.476 mmol) were dissolved in dry DCM and stirred for 30 min. (S)-4-(1-(2-aminopropyl)-1H-pyrazol-3-yl)-2-chlorobenzonitrile (646 mg, 2.476 mmol) in dry DCM was added to the reaction mixture and stirred at RT overnight. The reaction mixture was diluted with DCM and washed twice with water. Organic phase was evaporated to dryness and the product was purified with Flash-chromatography. Yield 36.9%. m/z [404.3+1].

c) S)-2-((1H-imidazol-1-yl)methyl)-N-(1-(3-(3-chloro-4-cyanophenyl)-1H-pyrazol-1-yl)propan-2-yl)oxazole-4-carboxamide Sodium hydride (11.87 mg, 0.297 mmol) was added into a flask under nitrogen atmosphere. The flask was cooled to 0° C. and DMF was added through a septum. Imidazole (13.47 mg, 0.198 mmol) was added and the mixture was stirred for 60 min in RT. The mixture was again cooled to 0° C. and (S)—N-(1-(3-(3-chloro-4-cyanophenyl)-1H-pyrazol-1-yl)propan-2-yl)-2-(chloromethyl)oxazole-4-carboxamide (80 mg, 0.198 mmol) in DMF was added dropwise. The reaction mixture was stirred overnight in RT. DMF was evaporated and the resulting crude product was dissolved in DCM, washed with brine and evaporated. The product was triturated using diethyl ether and purified by Flash-chromatography. Yield 8.23%. 1H-NMR (400 MHz; CDCl$_3$): δ 1.24 (d, 3H), 4.29 (dd, 1H), 4.41 (dd, 1H), 4.58 (m, 1H), 5.26 (s, 2H), 6.64 (d, 1H), 7.00 (t, 1H), 7.11 (t, 1H), 7.49 (d, 1H), 7.60 (s, 1H), 7.61 (d, 1H), 7.68 (d, 1H), 7.78 (dd, 1H), 8.08 (d, 1H), 8.17 (s, 1H).

Example 170

(S)—N4-(1-(3-(3-chloro-4-cyano-2-methylphenyl)-1H-pyrazol-1-yl)propan-2-yl)-N2,N2-dimethylthiazole-2,4-dicarboxamide (S)—N4-(1-(3-(3-chloro-4-cyano-2-methylphenyl)-1H-pyrazol-1-yl)propan-2-yl)-N2,N2-dimethylthiazole-2,4-dicarboxamide was prepared using the method of Example 34(d) starting from (S)-4-(1-(3-(3-chloro-4-cyano-2-methylphenyl)-1H-pyrazol-1-yl)propan-2-ylcarbamoyl)thiazole-2-carboxylic acid (0.2 g, 0.340 mmol) and dimethylamine hydrochloride (0.023 g, 0.283 mmol). The product was purified by Flash-chromatography and triturated using diethyl ether, respectively. Yield 4.18%. 1H-NMR (400 MHz; CDCl$_3$): δ 1.27 (d, 3H), 2.51 (s, 3H), 3.09 (s, 3H), 3.24 (s, 3H), 4.23 (dd, 1H), 4.45 (dd, 1H), 4.62 (m, 1H), 6.41 (d, 1H), 7.48 (d, 1H), 7.51 (d, 1H), 7.54 (dd, 1H), 7.85 (d, 1H), 8.27 (s, 1H).

Example 171

(S)—N-(1-(3-(3-chloro-4-cyanophenyl)-1H-pyrazol-1-yl)propan-2-yl)-2-(2-hydroxypropan-2-yl)thiazole-4-carboxamide a) (S)-ethyl 4-(1-(3-(3-chloro-4-cyanophenyl)-1H-pyrazol-1-yl)propan-2-yl-carbamoyl)thiazole-2-carboxylate (S)-ethyl 4-(1-(3-(3-chloro-4-cyanophenyl)-1H-pyrazol-1-yl)propan-2-yl-carbamoyl)thiazole-2-carboxylate was prepared using the method of Example 34(d) starting from (S)-4-(1-(2-aminopropyl)-1H-pyrazol-3-yl)-2-chlorobenzonitrile (540 mg, 2.071 mmol) and 2,4-thiazoledicarboxylic acid, 2-ethyl ester (500 mg, 2.485 mmol). Yield 82%. 1H-NMR (400 MHz; DMSO$_3$): δ 1.18 (d, 3H), 1.35 (t, 3H), 4.35 (dd, 1H), 4.39-4.57 (m, 4H), 6.94 (d, 1H), 7.84 (d, 1H), 7.95 (m, 2H), 8.02 (m, 1H), 8.55 (s, 1H), 8.61 (d, 1H).

b) (S)—N-(1-(3-(3-chloro-4-cyanophenyl)-1H-pyrazol-1-yl)propan-2-yl)-2-(2-hydroxypropan-2-yl)thiazole-4-carboxamide (S)-ethyl 4-(1-(3-(3-chloro-4-cyanophenyl)-1H-pyrazol-1-yl)propan-2-yl-carbamoyl)thiazole-2-carboxylate (0.755 g, 1.701 mmol) was dissolved in dry THF under nitrogen atmosphere. The solution was cooled to −78° C. with acetone-dry ice-bath. Methylmagnesium bromide, 3 M solution in Et$_2$O (1.134 ml, 3.40 mmol), was added and the reaction mixture was stirred in RT. After the reaction was finished, saturated ammoniumchloride, water and DCM was added. The organic phase was washed with water. The product was purified with Flash-chromatography. Yield 4.24%. 1H-NMR (400 MHz; CDCl$_3$): δ 1.28 (d, 3H), 1.65 (d, 6H), 3.00 (s, 1H), 4.35 (dd, 1H), 4.42 (dd, 1H), 4.58 (m, 1H), 6.62 (d, 1H), 7.50 (d, 1H), 7.66 (d, 1H), 7.67 (d, 1H), 7.80 (dd, 1H), 7.91 (d, 1H), 8.00 (s, 1H).

Example 172

(R)—N-(1-(3-(3-chloro-4-cyano-2-methylphenyl)-1H-pyrazol-1-yl)butan-2-yl)-oxazole-4-carboxamide (R)—N-(1-(3-(3-chloro-4-cyano-2-methylphenyl)-1H-pyrazol-1-yl)butan-2-yl)oxazole-4-carboxamide was prepared using the method of Example 34(d) starting from 4-oxazolecarboxylic acid (0.2 g, 1.769 mmol) and (R)-4-(1-(2-aminobutyl)-1H-pyrazol-3-yl)-2-chloro-3-methylbenzonitrile (0.532 g, 1.474 mmol). The product was triturated using diethyl ether. Yield 29.9%. 1H-NMR (400 MHz; CDCl$_3$): δ 1.02 (t, 3H), 1.58 (m, 2H), 2.57 (s, 3H), 4.39 (m, 3H), 6.43 (d, 1H), 7.45 (d, 1H), 7.49 (d, 1H), 7.53 (dd, 1H), 7.58 (d, 1H), 7.85 (d, 1H), 8.22 (d, 1H).

Example 173

(S)-(4-(1-(3-(3-chloro-4-cyanophenyl)-1H-pyrazol-1-yl)propan-2-yl-carbamoyl)thiazol-2-yl)methyl 2-(dimethylamino)acetate (S)-(4-(1-(3-(3-chloro-4-cyanophenyl)-1H-pyrazol-1-yl)propan-2-yl-carbamoyl)thiazol-2-yl)methyl 2-(dimethylamino)acetate was prepared using the method of Example 34(d) starting from N,N-dimethylglycine (0.062 g, 0.597 mmol) and (S)—N-(1-(3-(3-chloro-4-cyanophenyl)-1H-pyrazol-1-yl)propan-2-yl)-2-(hydroxymethyl)thiazole-4-carboxamide (0.2 g, 0.498 mmol). The product was triturated using diethyl ether and purified by Flash-chromatography, respectively. Yield 39.5%. 1H-NMR (400 MHz; CDCl$_3$): δ 1.25 (d, 3H), 2.39 (s, 6H), 3.30 (s, 2H), 4.31 (dd, 1H), 4.43 (dd, 1H), 4.60 (m, 1H), 5.43 (d, 2H), 6.63 (d, 1H), 7.49 (d, 1H), 7.70 (d, 1H), 7.84 (dd, 1H), 7.95 (d, 1H), 7.97 (d, 1H), 8.12 (s, 1H).

Example 174

(S)—N-(1-(3-(3-chloro-4-cyanophenyl)-1H-pyrazol-1-yl)propan-2-yl)-2-(1H-pyrazol-3-yl)thiazole-4-carboxamide a) N—((S)-1-(3-(3-chloro-4-cyanophenyl)-1H-pyrazol-1-yl)propan-2-yl)-2-(1-(tetrahydro-2H-pyran-2-yl)-1H-pyrazol-5-yl)thiazole-4-carboxamide (S)-2-bromo-N-(1-(3-(3-chloro-4-cyanophenyl)-1H-pyrazol-1-yl)propan-2-yl)thiazole-4-carboxamide (300 mg, 0.666 mmol), 1-(tetrahydro-2H-pyran-2-yl)-1H-pyrazole-5-boronic acid pinacol ester (222 mg, 0.799 mmol), tetrakis(triphenyl-phosphine)palladium (23 mg, 0.020 mmol), THF and 2M Na$_2$CO$_3$ solution were added in a microwave flask and heated in microwave at 120° C. for 2 h. 1-(tetrahydro-2H-pyran-2-yl)-1H-pyrazole-5-boronic acid pinacol ester (37 mg) and tetrakis(tri-phenylphosphine)palladium (8 mg) were added and the reaction mixture was heated in 120° C. for 1 h. The reaction mixture was diluted with DCM and washed twice with Na$_2$CO$_3$ solution. Organic phase was dried and evaporated to dryness. The product was purified by Flash-chromatography. Yield 3.7%. m/z [522.0+1].

b) (S)—N-(1-(3-(3-chloro-4-cyanophenyl)-1H-pyrazol-1-yl)propan-2-yl)-2-(1H-pyrazol-3-yl)thiazole-4-carboxamide N—((S)-1-(3-(3-chloro-4-cyanophenyl)-1H-pyrazol-1-yl)propan-2-yl)-2-(1-(tetrahydro-2H-pyran-2-yl)-1H-pyrazol-5-yl)thiazole-4-carboxamide (13 mg, 0.025 mmol) was added into a flask under nitrogen atmosphere. 10% HCl/EtOH (0.028 ml, 0.062 mmol) was added and the reaction mixture was stirred in RT for 3 h. The reaction mixture was diluted with ethyl acetate and washed with 1M Na$_2$CO$_3$. The organic phase was dried, filtered and evaporated. Yield 94%. 1H-NMR (400 MHz; MeOD): δ 1.30 (d, 3H), 4.38 (dd, 1H), 4.45 (dd, 1H), 4.59 (m, 1H), 6.75 (d, 1H), 6.83 (d, 1H), 7.61 (d, 1H), 7.73 (d, 1H), 7.76 (d, 1H), 7.84 (dd, 1H), 7.95 (d, 1H), 8.06 (s, 1H).

Example 175

(S)—N-(1-(3-(3-chloro-4-cyano-5-fluorophenyl)-1H-pyrazol-1-yl)propan-2-yl)-3-(1H-imidazol-4-yl)-1,2,4-oxadiazole-5-carboxamide a) (S)—N-(1-(3-(3-chloro-4-cyano-5-fluorophenyl)-1H-pyrazol-1-yl)propan-2-yl)-3-(1-trityl-1H-imidazol-4-yl)-1,2,4-oxadiazole-5-carboxamide Into a flask containing 3-(1-trityl-1H-imidazol-4-yl)-1,2,4-oxadiazole-5-carboxylic acid (0.148 g, 0.350 mmol) and anhydrous HOBt (0.047 g; 0.350 mmol), dichloromethane (2 ml), DIPEA (0.122 ml; 0.700 mmol) and EDCI (0.067 g; 0.350 mmol) were added and stirred for 10 min at RT. (S)-4-(1-(2-aminopropyl)-1H-pyrazol-3-yl)-2-chloro-6-fluorobenzonitrile (0.100 g, 0.269 mmol) dissolved in 2 ml of dichloromethane was added and the resulting mixture stirred overnight. Next day the temperature was raised to 50° C. and more EDCI (0.067 g; 0.350 mmol) was added. The reaction mixture was allowed to react with stirring for 4 h. DCM was added and the organic layer was extracted with 1M Na$_2$CO$_3$ and water. The organic layer was then evaporated and the residue purified with flash chromatography. LC-MS: [M+1]=684.133.

b) (S)—N-(1-(3-(3-chloro-4-cyano-5-fluorophenyl)-1H-pyrazol-1-yl)propan-2-yl)-3-(1H-imidazol-4-yl)-1,2,4-oxadiazole-5-carboxamide Into a flask containing (S)—N-(1-(3-(3-chloro-4-cyano-5-fluorophenyl)-1H-pyrazol-1-yl)propan-2-yl)-3-(1-trityl-1H-imidazol-4-yl)-1,2,4-oxadiazole-5-carboxamide (0.073 g, 0.107 mmol), a mixture containing THF (9 ml), formic acid (2.459 ml, 53.4 mmol) and water (0.1 ml) was added. The resulting mixture was stirred at RT for 24 h. The solvents were evaporated. Acetonitrile (15 ml) was added and evaporated. This was repeated 3 more times. The product was purified with LC/MS-trigger. Yield 46.3%. $^1$H-NMR (400 MHz; DMSO-d6): δ 1.21 (d, 3H), 4.32-4.40 (m, 2H), 4.42-4.54 (m, 1H), 7.02 (d, 1H), 7.81-7.92 (m, 4H), 7.94 (s, 1H), 9.43 (d, 1H), 12.69 (s, 1H).

Example 176

N—((R)-1-(3-(3-chloro-4-cyano-2-methylphenyl)-1H-pyrazol-1-yl)butan-2-yl)-2-(1-hydroxyethyl)thiazole-4-carboxamide a) (R)-4-(1-(2-aminobutyl)-1H-pyrazol-3-yl)-2-chloro-3-methylbenzonitrile (R)-4-(1-(2-aminobutyl)-1H-pyrazol-3-yl)-2-chloro-3-methylbenzonitrile was prepared using the method of Example 99 starting from 2-chloro-3-methyl-4-(1H-pyrazol-3-yl)benzonitrile (2.0 g, 9.19 mmol) and (R)-tert-butyl 1-hydroxybutan-2-ylcarbamate (3.48 g, 18.38 mmol). Yield 56.5%. m/z [288.8+1].

b) (R)-2-acetyl-N-(1-(3-(3-chloro-4-cyano-2-methylphenyl)-1H-pyrazol-1-yl)butan-2-yl)thiazole-4-carboxamide (R)-2-acetyl-N-(1-(3-(3-chloro-4-cyano-2-methylphenyl)-1H-pyrazol-1-yl)butan-2-yl)thiazole-4-carboxamide was prepared using the method of Example 34(d) starting from (R)-4-(1-(2-aminobutyl)-1H-pyrazol-3-yl)-2-chloro-3-methylbenzonitrile (489 mg, 1.355 mmol) and 2-acetylthiazole-4-carboxylic acid (278 mg, 1.626 mmol). The product was purified by Flash-chromatography. Yield 11.4%. 1H-NMR (400 MHz; CDCl$_3$): δ 1.05 (t, 3H), 1.56-1.67 (m, 2H), 2.53 (s, 3H), 2.53 (s, 3H), 4.36-4.52 (m, 3H), 6.42 (d, 1H), 7.47-7.55 (m, 3H), 7.88 (d, 1H), 8.39 (s, 1H).

c) N—((R)-1-(3-(3-chloro-4-cyano-2-methylphenyl)-1H-pyrazol-1-yl)butan-2-yl)-2-(1-hydroxyethyl)thiazole-4-carboxamide Sodium borohydride (7.19 mg, 0.190 mmol) was added into a flask and the atmosphere was replaced with nitrogen. Dry ethanol was added and the reaction mixture was cooled to 0° C. (R)-2-acetyl-N-(1-(3-(3-chloro-4-cyano-2-methylphenyl)-1H-pyrazol-1-yl)butan-2-yl)thiazole-4-carboxamide (42 mg, 0.095 mmol) was added and the reaction mixture was warmed slowly to RT while stirring overnight. The crude product was cooled to 0° C., the pH was adjusted to about 3 and the mixture was evaporated. 5% DCM/MeOH was added and the crude product was washed with 1M NaHCO$_3$, water and dried. Yield 74.2%. 1H-NMR (400 MHz; CDCl$_3$): δ 1.03 (m, 3H), 1.56-1.59 (m, 3H), 2.54 & 2.55 (2× broad s, 3H), 4.34-4.46 (m, 3H), 5.07 (dd, 1H), 6.41-6.43 (m, 1H), 7.46-7.54 (m, 3H), 7.80-7.89 (m, 1H), 8.02 (s, 1H).

Example 177

N—((S)-2-(3-(3-chloro-4-cyanophenyl)-1H-pyrazol-1-yl)propyl)-5-(1-hydroxyethyl)isoxazole-3-carboxamide a) 5-Acetylisoxazole-3-carboxylic Acid Ethyl 5-acetylisoxazole-3-carboxylate (300 mg, 1.638 mmol) was dissolved in THF/methanol mixture (9:1) and 1M lithium hydroxide (3.28 ml, 3.28 mmol) was added slowly. The reaction mixture was stirred at RT for 40 min, diluted with water and pH was adjusted to 3. The reaction mixture was extracted three times with ethyl acetate. Ethyl acetate phases were combined, washed with brine, dried and evaporated to dryness to yield the title compound (29.9%). m/z [155.1+1].

b) (S)-5-acetyl-N-(2-(3-(3-chloro-4-cyanophenyl)-1H-pyrazol-1-yl)propyl)-isoxazole-3-carboxamide (S)-5-acetyl-N-(2-(3-(3-chloro-4-cyanophenyl)-1H-pyrazol-1-yl)propyl)-isoxazole-3-carboxamide was prepared using the method of Example 34(d) starting from (S)-4-(1-(1-aminopropan-2-yl)-1H-pyrazol-3-yl)-2-chlorobenzonitrile (106 mg, 0.408 mmol) and 5-acetylisoxazole-3-carboxylic acid (76 mg, 0.490 mmol). The product was purified by Flash-chromatography. Yield 24.6%. 1H-NMR (400 MHz; CDCl$_3$): δ 1.63 (d, 3H), 2.63 (s, 3H), 3.78-3.88 (m, 1H), 3.91-4.00 (m, 1H), 4.59-4.69 (m, 1H), 6.63 (d, 1H), 7.29 (s, 1H), 7.50 (s, 1H), 7.67-7.77 (m, 2H), 7.82 (dd, 1H), 8.05 (d, 1H).

c) N—((S)-2-(3-(3-chloro-4-cyanophenyl)-1H-pyrazol-1-yl)propyl)-5-(1-hydroxyethyl)isoxazole-3-carboxamide Sodium borohydride (6.41 mg, 0.169 mmol) was added into a flask and the atmosphere was replaced with nitrogen. Dry ethanol was added and the reaction mixture was cooled to 0° C. (S)-5-acetyl-N-(2-(3-(3-chloro-4-cyanophenyl)-1H-pyrazol-1-yl)propyl)isoxazole-3-carboxamide (33.7 mg, 0.085 mmol) was added and the reaction mixture was warmed slowly to RT while stirring overnight. The crude product was cooled to 0° C., the pH was adjusted to about 3 and the mixture was evaporated. 5% of DCM/MeOH was added and the crude product was washed with 1M NaHCO$_3$, water and dried. Yield 96%. 1H-NMR (400 MHz; CDCl$_3$): δ 1.57-1.65 (m, 3H) 3.75-3.84 (m, 1H), 3.87-3.95 (m, 1H), 4.57-4.67 (m, 1H), 5.03 (q, 1H), 6.61 (d, 1H), 6.62 (s, 1H), 7.50 (d, 1H), 7.56-7.63 (m, 1H), 7.65-7.69 (2×s, 1H), 7.81 (dd, 1H), 8.01 (d, 1H).

Example 178

(S)-2-acetyl-N-(1-(3-(3-chloro-4-cyano-2-methylphenyl)-1H-pyrazol-1-yl)propan-2-yl)oxazole-4-carboxamide (S)-2-acetyl-N-(1-(3-(3-chloro-4-cyano-2-methylphenyl)-1H-pyrazol-1-yl)-propan-2-yl)oxazole-4-carboxamide was prepared using the method of Example 34(d) starting from 2-acetyloxazole-4-carboxylic acid (372 mg, 2.400 mmol) and (S)-4-(1-(2-aminopropyl)-1H-pyrazol-3-yl)-2-chloro-3-methylbenzonitrile (549 mg, 2.000 mmol). The product was triturated using diethyl ether and purified by Flash-chromatography, respectively. Yield 12.47%. 1H-NMR (400 MHz; CDCl$_3$): δ 1.27 (d, 3H), 2.59 (s, 3H), 2.60 (s, 3H), 4.31 (dd, 1H), 4.45 (dd, 1H), 4.64 (m, 1H), 6.45 (d, 1H), 7.51 (d, 1H), 7.56 (m, 2H), 7.68 (d, 1H), 8.31 (s, 1H).

Example 179

(S)—N-(1-(3-(3-chloro-4-cyanophenyl)-1H-pyrazol-1-yl)propan-2-yl)picolinamide (S)-N-(1-(3-(3-chloro-4-cyanophenyl)-1H-pyrazol-1-yl)propan-2-yl)picolinamide was prepared using the method of Example 34(d) starting from picolinic acid (0.227 g, 1.841 mmol) and (S)-4-(1-(2-aminopropyl)-1H-pyrazol-3-yl)-2-chlorobenzonitrile (0.4 g, 1.534 mmol). Yield 73.7%. 1H-NMR (400 MHz; CDCl$_3$): δ 1.26 (d, 3H), 4.31 (dd, 1H), 4.45 (dd, 1H), 4.62 (m, 1H), 6.63 (d, 1H), 7.46 (m, 1H), 7.50 (d, 1H), 7.67 (d, 1H), 7.81 (dd, 1H), 7.86 (m, 1H), 8.09 (d, 1H), 8.19 (m, 1H), 8.65 (m, 1H), 8.86 (d, 1H).

Example 180

N—((S)-2-(3-(3-chloro-4-cyanophenyl)-1H-pyrazol-1-yl)propyl)-2-(1-hydroxyethyl)oxazole-4-carboxamide a) (S)-2-acetyl-N-(2-(3-(3-chloro-4-cyanophenyl)-1H-pyrazol-1-yl)-propyl)oxazole-4-carboxamide (S)-2-acetyl-N-(2-(3-(3-chloro-4-cyanophenyl)-1H-pyrazol-1-yl)propyl)oxazole-4-carboxamide was prepared using the method of Example 34(d) starting from (S)-4-(1-(1-aminopropan-2-yl)-1H-pyrazol-3-yl)-2-chlorobenzonitrile (521 mg, 2.00 mmol) and 2-acetyloxazole-4-carboxylic acid (372 mg, 2.40 mmol). The product was purified by Flash-chromatography. Yield 36.0%. 1H-NMR (400 MHz; CDCl$_3$): δ 1.62 (d, 3H), 2.61 (s, 3H), 3.75-3.98 (m, 2H), 4.59-4.71 (m, 1H), 6.62 (d, 1H), 7.45-7.53 (m, 2H), 7.71 (d, 1H), 7.86 (dd, 1H), 7.98 (d, 1H), 8.32 (s, 1H).

b) N—((S)-2-(3-(3-chloro-4-cyanophenyl)-1H-pyrazol-1-yl)propyl)-2-(1-hydroxyethyl)oxazole-4-carboxamide Sodium borohydride (0.051 g, 1.352 mmol) was added into a flask and the atmosphere was replaced with nitrogen. Dry ethanol was added and the reaction mixture was cooled to 0° C. (S)-2-acetyl-N-(2-(3-(3-chloro-4-cyanophenyl)-1H-pyrazol-1-yl)propyl)oxazole-4-carboxamide (0.269 g, 0.676 mmol) was added and the reaction mixture was warmed slowly to RT while stirring overnight. The crude product was cooled to 0° C., the pH was adjusted below 7 and the mixture was evaporated. 5% of DCM/MeOH was added and the crude product was washed with 1M NaHCO$_3$, water and dried. Yield 84%. 1H-NMR (400 MHz; CDCl$_3$): δ 1.58 (d, 3H), 1.61 (d, 3H), 2.40 (d, 1H), 3.79 (m, 1H), 3.89 (m, 1H), 4.62 (m, 1H), 4.94 (m, 1H), 6.61 (d, 1H), 7.46 (m, 1H), 7.49 (d, 1H), 7.69 (d, 1H), 7.85 (dd, 1H), 7.98 (d, 1H), 8.15 (s, 1H).

Example 181

N—((S)-1-(3-(3-chloro-4-cyano-2-methylphenyl)-1H-pyrazol-1-yl)propan-2-yl)-2-(1-hydroxyethyl)oxazole-4-carboxamide Sodium borohydride (0.037 g, 0.971 mmol) was added into a flask and the atmosphere was replaced with nitrogen. Dry ethanol was added and the reaction mixture was cooled to 0° C. (S)-2-acetyl-N-(1-(3-(3-chloro-4-cyano-2-methylphenyl)-1H-pyrazol-1-yl)propan-2-yl)oxazole-4-carboxamide (0.2 g, 0.486 mmol) was added and the reaction mixture was warmed slowly to RT while stirring overnight. The crude product was cooled to 0° C., the pH was adjusted below 7 and the mixture was evaporated. 5% of DCM/MeOH was added and the crude product was washed with 1M NaHCO$_3$, water and dried. The product was purified with Flash-chromatography. Yield 55.4%. 1H-NMR (400 MHz; CDCl$_3$): δ 1.25 (d, 3H), 1.59 (d, 3H), 2.50 (s, 1H), 2.58 (s, 3H), 4.30 (dd, 1H), 4.42 (dd, 1H), 4.59 (m, 1H), 4.94 (m, 1H), 6.44 (d, 1H), 7.54 (m, 4H), 8.14 (s, 1H).

Example 182

(S)-2-(3-(1-(3-(3-chloro-4-cyanophenyl)-1H-pyrazol-1-yl)propan-2-yl-carbamoyl)isoxazol-5-yl)propan-2-yl acetate (S)—N-(1-(3-(3-chloro-4-cyanophenyl)-1H-pyrazol-1-yl)propan-2-yl)-5-(2-hydroxypropan-2-yl)isoxazole-3-carboxamide (97 mg, 0.234 mmol) and DMAP (2.89 mg, 0.023 mmol) were dissolved in pyridine under nitrogen atmosphere. The reaction mixture was cooled to 0° C., acetic anhydride (25.1 mg, 0.246 mmol) was added and the reaction mixture stirred for 2 h in RT. The mixture was again cooled to 0° C. and 10 µl of acetic anhydride was added. The reaction mixture was stirred in RT overnight after which the solvent was evaporated. Yield 99%. 1H-NMR (400 MHz; CDCl$_3$): δ 1.22 (d, 3H), 1.80 (s, 6H), 2.05 (s, 3H), 4.25 (dd, 1H), 4.42 (dd, 1H), 4.58 (m, 1H), 6.58 (s, 1H), 6.63 (d, 1H), 7.49 (d, 1H), 7.69 (d, 1H), 7.83 (dd, 1H), 7.89 (d, 1H), 8.09 (d, 1H).

Example 183

(S)-5-acetyl-N-(1-(3-(3-chloro-4-cyano-5-fluorophenyl)-1H-pyrazol-1-yl)propan-2-yl)isoxazole-3-carboxamide (S)-5-acetyl-N-(1-(3-(3-chloro-4-cyano-5-fluorophenyl)-1H-pyrazol-1-yl)propan-2-yl)isoxazole-3-carboxamide was prepared using the method of Example 34(d) starting from 5-acetylisoxazole-3-carboxylic acid (0.200 g, 1.292 mmol) and (S)-4-(1-(2-aminopropyl)-1H-pyrazol-3-yl)-2-chloro-6-fluorobenzonitrile (0.3 g, 1.076 mmol). The product was purified by Flash-chromatography. Yield 16.09%. 1H-NMR (400 MHz; CDCl$_3$): δ 1.26 (d, 3H), 2.65 (s, 3H), 4.26 (dd, 1H), 4.46 (dd, 1H), 4.61 (m, 1H), 6.64 (d, 1H), 7.29 (s, 1H), 7.51 (d, 1H), 7.63 (dd, 1H), 7.85 (s, 1H), 8.04 (d, 1H).

Example 184

N—((S)-1-(3-(3-chloro-4-cyano-5-fluorophenyl)-1H-pyrazol-1-yl)propan-2-yl)-5-(1-hydroxyethyl)isoxazole-3-carboxamide Sodium borohydride (0.012 g, 0.308 mmol) was added into a flask and the atmosphere was replaced with nitrogen.

Dry ethanol was added and the reaction mixture was cooled to 0° C. (S)-5-acetyl-N-(1-(3-(3-chloro-4-cyano-5-fluorophenyl)-1H-pyrazol-1-yl)propan-2-yl)isoxazole-3-carboxamide (0.064 g, 0.154 mmol) was added and the reaction mixture was warmed slowly to RT while stirring overnight. The crude product was cooled to 0° C., the pH was adjusted below 7 and the mixture was evaporated. 5% of DCM/MeOH was added and the crude product was washed with 1M NaHCO$_3$, water and dried. Yield 81%. 1H-NMR (400 MHz; DMSO-d6): δ 1.16 (d, 3H), 1.40 (dd, 3H), 4.32 (d, 2H), 4.45 (m, 1H), 4.86 (m, 1H), 5.78 (dd, 1H), 6.53 (dd, 1H), 7.00 (d, 1H), 7.84 (d, 1H), 7.86 (m, 1H), 7.98 (d, 1H), 8.75 (d, 1H).

Example 185

(S)—N-(1-(3-(3-chloro-4-cyanophenyl)-1H-pyrazol-1-yl)propan-2-yl)-2-(1H-pyrazol-3-yl)oxazole-4-carboxamide a) 2-Bromooxazole-4-carboxylic Acid Ethyl 2-bromo-1,3-oxazole-4-carboxylate (2.5 g, 11.36 mmol) was dissolved in THF/methanol mixture (9:1) and 1M lithium hydroxide (22.73 ml, 22.73 mmol) was added slowly. The reaction mixture was stirred at RT for 1 h, diluted with water and pH was adjusted to 2. Formed precipitate was filtered and dried to yield the title compound (1.1 g). The filtrate was extracted three times with ethyl acetate. Ethyl acetate phases were combined, dried and evaporated to dryness to yield the title compound 0.85 g. Total yield 88%. m/z [192.0+1]

b) (S)-2-bromo-N-(1-(3-(3-chloro-4-cyanophenyl)-1H-pyrazol-1-yl)propan-2-yl)oxazole-4-carboxamide (S)-2-bromo-N-(1-(3-(3-chloro-4-cyanophenyl)-1H-pyrazol-1-yl)propan-2-yl)oxazole-4-carboxamide was prepared using the method of Example 34(d) starting from (S)-4-(1-(2-aminopropyl)-1H-pyrazol-3-yl)-2-chlorobenzonitrile (741 mg, 2.82 mmol) and 2-bromooxazole-4-carboxylic acid (850 mg, 3.41 mmol). The product was purified by Flash-chromatography. Yield 12.4%. 1H-NMR (400 MHz; CDCl$_3$): δ 1.20 (d, 3H), 4.18-4.47 (m, 2H), 4.51-4.65 (m, 1H), 6.64 (d, 1H), 7.48 (d, 1H), 7.72 (dd, 1H), 7.92-7.99 (m, 3H), 8.21 (s, 1H).

c) N—((S)-1-(3-(3-chloro-4-cyanophenyl)-1H-pyrazol-1-yl)propan-2-yl)-2-(1-(tetrahydro-2H-pyran-2-yl)-1H-pyrazol-5-yl)oxazole-4-carboxamide (S)-2-bromo-N-(1-(3-(3-chloro-4-cyanophenyl)-1H-pyrazol-1-yl)propan-2-yl)oxazole-4-carboxamide (153 mg, 0.352 mmol), 1-(tetrahydro-2H-pyran-2-yl)-1H-pyrazole-5-boronic acid pinacol ester (490 mg, 1.760 mmol), tetrakis(triphenyl-phosphine)palladium (4.07 mg, 3.52 umol), THF and 2 M Na$_2$CO$_3$ solution were added in a microwave flask and heated at 100° C. for 1 h. The reaction mixture was diluted with DCM and washed twice with NaHCO$_3$ solution. Organic phase was dried and evaporated to dryness. The product was purified twice by Flash-chromatography. Yield 31.4%. m/z [506.0+1].

d) (S)—N-(1-(3-(3-chloro-4-cyanophenyl)-1H-pyrazol-1-yl)propan-2-yl)-2-(1H-pyrazol-3-yl)oxazole-4-carboxamide N—((S)-1-(3-(3-chloro-4-cyanophenyl)-1H-pyrazol-1-yl)propan-2-yl)-2-(1-(tetrahydro-2H-pyran-2-yl)-1H-pyrazol-5-yl)oxazole-4-carboxamide (56 mg, 0.111 mmol) was added into a flask under nitrogen atmosphere. 10% HCl/EtOH (0.126 ml, 0.277 mmol) was added and the reaction mixture was stirred in RT for 2 h. The reaction mixture was diluted with ethyl acetate and washed with 1M Na$_2$CO$_3$. The organic phase was dried, filtered and evaporated. The product was triturated using acetonitrile and THF, respectively. Yield 29.6%. 1H-NMR (400 MHz; CDCl$_3$): δ 1.27 (d, 3H), 4.31 (dd, 1H), 4.43 (dd, 1H), 4.61 (m, 1H), 6.61 (d, 1H), 6.86 (d, 1H), 7.49 (d, 1H), 7.60 (d, 1H), 7.66 (d, 1H), 7.72 (d, 1H), 7.87 (dd, 1H), 7.92 (d, 1H), 8.23 (s, 1H), 10.78 (s, 1H).

Example 186

N—((S)-1-(3-(3-chloro-4-cyano-2-methylphenyl)-1H-pyrazol-1-yl)propan-2-yl)-2-(1-hydroxyethyl)thiazole-4-carboxamide Sodium borohydride (0.056 g, 1.477 mmol) was added into a flask and the atmosphere was replaced with nitrogen. Dry ethanol was added and the reaction mixture was cooled to 0° C. (S)-2-acetyl-N-(1-(3-(3-chloro-4-cyano-2-methylphenyl)-1H-pyrazol-1-yl)propan-2-yl)thiazole-4-carboxamide (0.316 g, 0.738 mmol) was added and the reaction mixture was warmed slowly to RT while stirring overnight. The crude product was cooled to 0° C., a few drops of water was added, the pH was adjusted below 7 and the mixture was evaporated. 5% of DCM/MeOH was added and the crude product was washed with 1M NaHCO$_3$, water and dried. Yield 68.1%. 1H-NMR (400 MHz; DMSO-d6): δ 1.13 (d, 3H), 1.40 (dd, 3H), 2.52 (s, 3H), 4.37 (m, 2H), 4.48 (m, 1H), 4.92 (m, 1H), 6.24 (t, 1H), 6.62 (d, 1H), 7.63 (d, 1H), 7.82 (d, 1H), 7.87 (dd, 1H), 8.10 (s, 1H), 8.37 (dd, 1H).

Example 187

(S)—N-(1-(3-(3-chloro-4-cyanophenyl)-1H-pyrazol-1-yl)propan-2-yl)-3-isopropyl-1-(3-isopropyl-1H-pyrazole-5-carbonyl)-1H-pyrazole-5-carboxamide (S)—N-(1-(3-(3-chloro-4-cyanophenyl)-1H-pyrazol-1-yl)propan-2-yl)-3-isopropyl-1-(3-isopropyl-1H-pyrazole-5-carbonyl)-1H-pyrazole-5-carboxamide was prepared using the method of Example 34(d) starting from 3-isopropyl-1H-pyrazole-5-carboxylic acid (0.284 g, 1.841 mmol) and (S)-4-(1-(2-aminopropyl)-1H-pyrazol-3-yl)-2-chlorobenzonitrile (0.4 g, 1.534 mmol). Yield 1.883%. 1H-NMR (400 MHz; CDCl$_3$): δ 1.23 (dd, 6H), 1.27 (d, 3H), 1.32 (dd, 6H), 2.94 (m, 1H), 3.81 (m, 1H), 4.32 (dd, 1H), 4.47 (dd, 1H), 4.63 (m, 1H), 6.63 (d, 1H), 6.81 (s, 1H), 7.08 (s, 1H), 7.44 (d, 1H), 7.51 (d, 1H), 7.64 (dd, 1H), 7.78 (d, 1H), 7.80 (d, 1H).

Example 188

3-Acetyl-N-(2-(3-(3-chloro-4-cyanophenyl)-1H-pyrazol-1-yl)-3-hydroxypropyl)-1H-pyrazole-5-carboxamide 3-acetyl-N-(2-(3-(3-chloro-4-cyanophenyl)-1H-pyrazol-1-yl)-3-hydroxypropyl)-1H-pyrazole-5-carboxamide was prepared using the method of Example 34(d) starting from 3-acetyl-1H-pyrazole-5-carboxylic acid (84 mg, 0.542 mmol) and 4-(1-(1-amino-3-hydroxypropan-2-yl)-1H-pyrazol-3-yl)-2-chlorobenzonitrile (125 mg, 0.452 mmol). The product was triturated using diethyl ether and acetonitrile, respectively. Yield 6.49%. 1H-NMR (400 MHz; MeOD): δ

2.51 (s, 3H), 3.88 (m, 2H), 3.97 (dd, 1H), 4.03 (dd, 1H), 4.65 (m, 1H), 6.77 (d, 1H), 7.21 (s, 1H), 7.75 (d, 1H), 7.79 (d, 1H), 7.91 (dd, 1H), 8.05 (d, 1H).

Example 189

(S)—N-(1-(3-(3-chloro-4-cyano-2-methylphenyl)-1H-pyrazol-1-yl)propan-2-yl)-2-(2-methoxyethylamino)thiazole-4-carboxamide (S)-2-bromo-N-(1-(3-(3-chloro-4-cyano-2-methylphenyl)-1H-pyrazol-1-yl)-propan-2-yl)thiazole-4-carboxamide (0.2 g, 0.430 mmol) was added into a microwave vial with dry pyridine as a solvent under nitrogen atmosphere. 2-methoxyethylamine (0.187 ml, 2.152 mmol) was added and the mixture was heated with microwaves at 120° C. Next day a total of 0.187 ml of 2-methoxyethylamine was added and the reaction mixture was heated for additional 3 h. The reaction mixture was evaporated and the crude product dissolved in DCM, washed with $Na_2CO_3$, water and brine. The product was purified by Flash-chromatography. Yield 38.5%. 1H-NMR (400 MHz; MeOD): δ 1.25 (d, 3H), 2.50 (s, 3H), 3.35 (s, 3H), 3.40-3.43 (m, 2H), 3.46-3.49 (m, 2H), 4.34 (dd, 1H), 4.41 (dd, 1H), 4.47-4.56 (m, 1H), 6.49 (d, 1H), 7.19 (s, 1H), 7.55 (d, 1H), 7.64 (dd, 1H), 7.73 (d, 1H).

Example 190

N—((S)-2-(3-(3-chloro-4-cyano-2-methylphenyl)-1H-pyrazol-1-yl)propyl)-2-(1-hydroxyethyl)oxazole-4-carboxamide a) (S)-2-acetyl-N-(2-(3-(3-chloro-4-cyano-2-methylphenyl)-1H-pyrazol-1-yl)propyl)oxazole-4-carboxamide (S)-2-acetyl-N-(2-(3-(3-chloro-4-cyano-2-methylphenyl)-1H-pyrazol-1-yl)-propyl)oxazole-4-carboxamide was prepared using the method of Example 34(d) starting from ((S)-4-(1-(1-aminopropan-2-yl)-1H-pyrazol-3-yl)-2-chloro-3-methylbenzonitrile (549 mg, 2.00 mmol) and 2-acetyloxazole-4-carboxylic acid (372 mg, 2.40 mmol). The product was purified by Flash-chromatography. Yield 33.4%. 1H-NMR (400 MHz; CDCl$_3$): δ 1.63 (d, 3H), 2.58 (d, 3H), 2.60 (s, 3H), 3.78-3.98 (m, 2H), 4.60-4.71 (m, 1H), 6.44 (d, 1H), 7.44-7.62 (m, 4H), 8.31 (s, 1H).

b) N—((S)-2-(3-(3-chloro-4-cyano-2-methylphenyl)-1H-pyrazol-1-yl)propyl)-2-(1-hydroxyethyl)oxazole-4-carboxamide Sodium borohydride (0.055 g, 1.462 mmol) was added into a flask and the atmosphere was replaced with nitrogen. Dry ethanol was added and the reaction mixture was cooled to 0° C. (S)-2-acetyl-N-(2-(3-(3-chloro-4-cyano-2-methylphenyl)-1H-pyrazol-1-yl)propyl)oxazole-4-carboxamide (0.301 g, 0.731 mmol) was added and the reaction mixture was warmed slowly to RT while stirring overnight. The crude product was cooled to 0° C., the pH was adjusted to 6 and the mixture was evaporated. 5% of methanol/DCM was added and the crude product was washed with 1M NaHCO$_3$ and with water. The mixture was dried and evaporated. Yield 94%. $^1$H-NMR (400 MHz; CDCl$_3$): δ 1.57 (d, 3H), 1.61 (d, 3H), 3.78-3.83 (m, 1H), 3.87-3.94 (m, 1H), 4.59-4.68 (m, 1H), 4.87-4.96 (m, 1H), 6.43 (d, 1H), 7.34-7.42 (m, 1H), 7.51 (d, 1H), 7.54-7.61 (m, 2H), 8.14 (s, 1H).

Example 191

(S)—N-(1-(3-(3-chloro-4-cyano-2-methylphenyl)-1H-pyrazol-1-yl)propan-2-yl)-2-(2-methoxyethylamino)oxazole-4-carboxamide a) (S)-2-bromo-N-(1-(3-(3-chloro-4-cyano-2-methylphenyl)-1H-pyrazol-1-yl)-propan-2-yl)oxazole-4-carboxamide (S)-2-bromo-N-(1-(3-(3-chloro-4-cyano-2-methylphenyl)-1H-pyrazol-1-yl)-propan-2-yl)oxazole-4-carboxamide was prepared using the method of Example 34(d) starting from ((S)-4-(1-(2-aminopropyl)-1H-pyrazol-3-yl)-2-chloro-3-methylbenzonitrile (742 mg, 2.70 mmol) and 2-bromooxazole-4-carboxylic acid (492 mg, 2.56 mmol). The product was purified by Flash-chromatography. Yield 6.2%. m/z [448.7+1].

b) (S)—N-(1-(3-(3-chloro-4-cyano-2-methylphenyl)-1H-pyrazol-1-yl)propan-2-yl)-2-(2-methoxyethylamino)oxazole-4-carboxamide (S)-2-bromo-N-(1-(3-(3-chloro-4-cyano-2-methylphenyl)-1H-pyrazol-1-yl)-propan-2-yl)oxazole-4-carboxamide (0.180 g, 0.401 mmol) was added into a microwave vial with dry pyridine as a solvent. The mixture was bubbled with nitrogen. 2-Methoxyethylamine (0.129 ml, 2.407 mmol) was added and the mixture was heated with microwaves at 120° C. for 2 h. The product was purified by Flash-chromatography. Yield 15.65%. 1H-NMR (400 MHz; CDCl$_3$): δ 1.24 (d, 3H), 2.58 (s, 3H), 3.39 (s, 3H), 3.44 (t, 2H), 3.51 (t, 2H), 4.30 (dd, 1H), 4.40 (dd, 1H), 4.51-4.60 (m, 1H), 5.07 (t, 1H), 6.44 (d, 1H), 7.40 (d, 1H), 7.51 (d, 1H), 7.52-7.58 (m, 2H), 7.67 (s, 1H).

Example 192

(R)-5-acetyl-N-(2-(3-(3-chloro-4-cyanophenyl)-1H-pyrazol-1-yl)-propyl)isoxazole-3-carboxamide (R)-5-acetyl-N-(2-(3-(3-chloro-4-cyanophenyl)-1H-pyrazol-1-yl)propyl)-isoxazole-3-carboxamide was prepared using the method of Example 34(d) starting from 5-acetyl-isoxazole-3-carboxylic acid (0.314 g, 2.025 mmol) and (R)-4-(1-(1-aminopropan-2-yl)-1H-pyrazol-3-yl)-2-chlorobenzonitrile (0.44 g, 1.688 mmol). The product was purified by Flash-chromatography. Yield 19.16%. 1H-NMR (400 MHz; CDCl$_3$): δ 1.63 (d, 3H), 2.63 (s, 3H), 3.79-3.87 (m, 1H), 3.92-3.99 (m, 1H), 4.60-4.66 (m, 1H), 6.63 (d, 1H), 7.29 (s, 1H), 7.50 (d, 1H), 7.69-7.74 (m, 2H), 7.82 (dd, 1H), 8.05 (d, 1H).

Example 193

(S)-2-acetyl-N-(1-(3-(3-chloro-4-cyano-2-methylphenyl)-1H-pyrazol-1-yl)propan-2-yl)thiazole-4-carboxamide (S)-2-acetyl-N-(1-(3-(3-chloro-4-cyano-2-methylphenyl)-1H-pyrazol-1-yl)-propan-2-yl)thiazole-4-carboxamide was prepared using the method of Example 34(d) starting from 2-acetylthiazole-4-carboxylic acid (0.680 g, 3.49 mmol) and (S)-4-(1-(2-aminopropyl)-1H-pyrazol-3-yl)-2- chloro-3-methylbenzonitrile (0.8 g, 2.91 mmol). The product was purified by Flash-chromatography. Yield 30.0%. 1H-NMR (400 MHz; CDCl$_3$): δ 1.30 (d, 3H), 2.53 (s, 3H), 2.54 (s, 3H), 4.35 (dd, 1H), 4.47 (dd, 1H), 4.61-4.69 (m, 1H), 6.44 (d, 1H), 7.49-7.54 (m, 3H), 7.95 (d, 1H), 8.39 (s, 1H).

Example 194

(S)-2-amino-N-(1-(3-(3-chloro-4-cyanophenyl)-1H-pyrazol-1-yl)butan-2-yl)oxazole-4-carboxamide (S)-2-amino-N-(1-(3-(3-chloro-4-cyanophenyl)-1H-pyrazol-1-yl)butan-2-yl)-oxazole-4-carboxamide was prepared using the method of Example 34(d) starting from 2-amino-1,3-oxazole-4-carboxylic acid (343 mg, 2.68 mmol) and (S)-4-(1-(2-aminobutyl)-1H-pyrazol-3-yl)-2-chlorobenzonitrile (613 mg, 2.231 mmol). The product was triturated using diethyl ether. Yield 4.32%. 1H-NMR (400 MHz; DMSO-d6): δ 0.86 (t, 3H), 1.41-1.51 (m, 2H), 4.18-4.39 (m, 3H), 6.78 (s, 2H), 6.93 (d, 1H), 7.74 (d, 1H), 7.76 (s, 1H), 7.79 (d, 1H), 7.94-8.00 (m, 2H), 8.08 (s, 1H).

Example 195

(S)—N-(1-(3-(3-chloro-4-cyanophenyl)-1H-pyrazol-1-yl)propan-2-yl)-2-((2,5-dioxopyrrolidin-1-yl)methyl)oxazole-4-carboxamide (S)—N-(1-(3-(3-chloro-4-cyanophenyl)-1H-pyrazol-1-yl)propan-2-yl)-2-(chloro-methyl)oxazole-4-carboxamide (0.132 g, 0.327 mmol) and potassium carbonate (0.068 g, 0.490 mmol) were dissolved in dry DMF under nitrogen atmosphere. Succinimide (0.036 g, 0.359 mmol) was added and the mixture was stirred in RT for 4.5 h. DCM was added and the organic phase was washed with water. The product was triturated using diethyl ether, DCM and finally by Flash-chromatography. Yield 16.92%. %. 1H-NMR (400 MHz; CDCl$_3$): δ 1.23 (d, 3H), 2.83 (s, 4H), 4.29 (dd, 1H), 4.39 (dd, 1H), 4.51-4.59 (m, 1H), 4.83 (s, 2H), 6.63 (d, 1H), 7.47 (d, 1H), 7.52 (d, 1H), 7.74 (d, 1H), 7.87 (dd, 1H), 7.98 (d, 1H), 8.11 (s, 1H).

Example 196

N—((S)-1-(3-(3-chloro-4-cyanophenyl)-1H-pyrazol-1-yl)propan-2-yl)-2-(1-hydroxyethyl)oxazole-4-carboxamide a) (S)-2-acetyl-N-(1-(3-(3-chloro-4-cyanophenyl)-1H-pyrazol-1-yl)propan-2-yl)oxazole-4-carboxamide (S)-2-acetyl-N-(1-(3-(3-chloro-4-cyanophenyl)-1H-pyrazol-1-yl)propan-2-yl)-oxazole-4-carboxamide was prepared using the method of Example 34(d) starting from (S)-4-(1-(2-aminopropyl)-1H-pyrazol-3-yl)-2-chlorobenzonitrile (600 mg, 2.301 mmol) and 2-acetyloxazole-4-carboxylic acid (428 mg, 2.76 mmol). The product was purified by Flash-chromatography. Yield 11.6%. 1H-NMR (400 MHz; CDCl$_3$): δ 1.26 (d, 3H), 2.68 (s, 3H), 4.26-4.33 (m, 1H), 4.40-4.47 (m, 1H), 4.55-4.68 (m, 1H), 6.63 (d, 1H), 7.49 (d, 1H), 7.67 (d, 1H), 7.72 (d, 1H), 7.88 (dd, 1H), 7.93 (d, 1H), 8.31 (s, 1H).

b) N—((S)-1-(3-(3-chloro-4-cyanophenyl)-1H-pyrazol-1-yl)propan-2-yl)-2-(1-hydroxyethyl)oxazole-4-carboxamide Sodium borohydride (0.019 g, 0.498 mmol) was added into a flask and the atmosphere was replaced with nitrogen. Dry ethanol was added and the reaction mixture was cooled to 0° C. (S)-2-acetyl-N-(1-(3-(3-chloro-4-cyanophenyl)-1H-pyrazol-1-yl)propan-2-yl)oxazole-4-carboxamide (0.099 g, 0 0.249 mmol) was added and the reaction mixture was warmed slowly to RT while stirring overnight. The crude product was cooled to 0° C., the pH was adjusted to 6 and the mixture was evaporated. 5% of DCM/MeOH was added and the crude product was washed with 1M NaHCO$_3$, water and dried. Yield 89%. 1H-NMR (400 MHz; CDCl$_3$): δ 1.22 (d, 3H), 1.63 (d, 3H), 2.51 (s, 1H), 4.25-4.31 (m, 1H), 4.41 (dd, 1H), 4.54-4.63 (m, 1H), 5.00 (q, 1H), 6.61 (d, 1H), 7.49 (d, 1H), 7.68 (d, 1H), 7.70 (d, 1H), 7.86-7.89 (m, 1H), 7.95-7.96 (m, 1H), 8.15 (s, 1H).

Example 197

(S)—N-(1-(3-(3-chloro-4-cyanophenyl)-1H-pyrazol-1-yl)propan-2-yl)-5-((2,5-dioxopyrrolidin-1-yl)methyl)isoxazole-3-carboxamide a) (S)-5-(bromomethyl)-N-(1-(3-(3-chloro-4-cyanophenyl)-1H-pyrazol-1-yl)-propan-2-yl)isoxazole-3-carboxamide 5-(Bromomethyl)isoxazole-3-carboxylic acid (1.027 g, 4.99 mmol) and DCC (1.029 g, 4.99 mmol) were dissolved in dry DCM under nitrogen atmosphere and (S)-4-(1-(2-aminopropyl)-1H-pyrazol-3-yl)-2-chlorobenzonitrile (1.0 g, 3.84 mmol) was added. The mixture was stirred overnight at RT and a precipitate was filtered. The filtrate was washed with water, dried and evaporated to dryness. The evaporation residue was purified by Flash-chromatography to give the title compound. Yield 83%. 1H-NMR (400 MHz; DMSO): δ 1.17 (d, 3H), 4.32 (d, 2H), 4.40-4.50 (m, 1H), 4.86 (s, 2H), 6.81 (s, 1H), 6.94 (d, 1H), 7.82 (d, 1H), 7.91 (dd, 1H), 7.97 (dd, 1H), 8.08 (dd, 1H). 8.85 (d, 1H)

b) (S)—N-(1-(3-(3-chloro-4-cyanophenyl)-1H-pyrazol-1-yl)propan-2-yl)-5-((2,5-dioxopyrrolidin-1-yl)methyl)isoxazole-3-carboxamide (S)—N-(1-(3-(3-chloro-4-cyanophenyl)-1H-pyrazol-1-yl)propan-2-yl)-5-((2,5-dioxopyrrolidin-1-yl)methyl)isoxazole-3-carboxamide was prepared using the method of Example 195 starting from (S)-5-(bromomethyl)-N-(1-(3-(3-chloro-4-cyanophenyl)-1H-pyrazol-1-yl)propan-2-yl) isoxazole-3-carboxamide (262 mg, 0.584 mmol). The product was purified by Flash-chromatography. Yield 89%. 1H-NMR (400 MHz; MeOD): δ 1.26 (d, 3H), 2.57 (s, 4H), 4.28-4.43 (m, 2H), 4.52-4.63 (m, 1H), 4.85 (s, 2H), 6.63 (s vai d, 1H), 6.71 (d, 1H), 7.65 (d, 1H), 7.68 (d, 1H), 7.75 (d, 1H), 7.85 (dd, 1H), 8.06 (d, 1H).

Example 198

(S)—N-(1-(3-(3-chloro-4-cyano-2-methylphenyl)-1H-pyrazol-1-yl)propan-2-yl)-2-(methylamino)thiazole-4-carboxamide (S)—N-(1-(3-(3-chloro-4-cyano-2-methylphenyl)-1H-pyrazol-1-yl)propan-2-yl)-2-(methylamino)thiazole-4-carboxamide was prepared using the method of Example 34(d) starting from (S)-4-(1-(2-aminopropyl)-1H-pyrazol-3-yl)-2-chloro-3-methylbenzonitrile (300 mg, 1.092 mmol) and 2-(methylamino)thiazole-4-carboxylic acid hydrochloride (314 mg, 1.613 mmol). The product was purified twice by Flash-chromatography (normal phase and reverse phase).

Yield 4.86%. 1H-NMR (400 MHz; CDCl3): δ 1.25 (d, 3H), 2.56 (s, 3H), 2.93 (d, 3H), 4.28-4.43 (m, 2H), 4.47-4.61 (m, 1H), 5.04-5.12 (m, 1H), 6.43 (d, 1H), 7.31 (d, 1H), 7.49-7.56 (m, 3H), 7.67 (m, 1H).

Example 199

(S)—N-(1-(3-(3-chloro-4-cyanophenyl)-1H-pyrazol-1-yl)propan-2-yl)-5-(morpholinomethyl)isoxazole-3-carboxamide (S)—N-(1-(3-(3-chloro-4-cyanophenyl)-1H-pyrazol-1-yl)propan-2-yl)-5-(morpholinomethyl)isoxazole-3-carboxamide was prepared using the method of Example 34(d) starting from (S)-4-(1-(2-aminopropyl)-1H-pyrazol-3-yl)-2-chlorobenzonitrile (200 mg, 0.690 mmol) and 5-(morpholinomethyl)isoxazole-3-carboxylic acid hydrochloride (206 mg, 0.828 mmol). The product was purified by reverse phase Flash-chromatography. Yield 16.9%. 1H-NMR (400 MHz; MeOD): δ 1.26 (d, 3H), 2.47-2.56 (m, 4H), 3.65-3.71 (m, 4H), 3.75 (d, 2H), 4.28-4.44 (m, 2H), 4.53-4.63 (m, 1H), 6.59 (t, 1H), 6.77 (d, 1H), 7.71 (d, 1H), 7.78 (dd, 1H), 7.88 (dd, 1H), 8.08 (dd, 1H).

Example 200

(S)—N-(1-(3-(3-chloro-4-cyano-2-methylphenyl)-1H-pyrazol-1-yl)propan-2-yl)-1-methyl-1H-imidazole-4-carboxamide (S)—N-(1-(3-(3-chloro-4-cyano-2-methylphenyl)-1H-pyrazol-1-yl)propan-2-yl)-1-methyl-1H-imidazole-4-carboxamide was prepared using the method of Example 34(d) starting from (S)-4-(1-(2-aminopropyl)-1H-pyrazol-3-yl)-2-chloro-3-methylbenzonitrile (300 mg, 1.092 mmol) and 1-methyl-1H-imidazole-4-carboxylic acid (207 mg, 1.638 mmol). The product was purified twice by Flash-chromatography (normal phase and reverse phase). Yield 38.7%. 1H-NMR (400 MHz; CDCl3): δ 1.26 (d, 3H), 2.56 (s, 3H), 3.74 (s, 3H), 4.30-4.43 (m, 2H), 4.49-4.61 (m, 1H), 6.41 (d, 1H), 7.35 (d, 1H), 7.39 (d, 1H), 7.49-7.56 (m, 3H), 7.60 (d, 1H).

Example 201

(S)—N-(1-(3-(3-chloro-4-cyanophenyl)-1H-pyrazol-1-yl)propan-2-yl)-5-isopropylisoxazole-3-carboxamide (S)—N-(1-(3-(3-chloro-4-cyanophenyl)-1H-pyrazol-1-yl)propan-2-yl)-5-isopropylisoxazole-3-carboxamide carboxamide was prepared using the method of Example 34(d) starting from (S)-4-(1-(2-aminopropyl)-1H-pyrazol-3-yl)-2-chlorobenzonitrile (150 mg, 0.575 mmol) and 5-isopropylisoxazole-3-carboxylic acid (98 mg, 0.633 mmol). The product was purified by Flash-chromatography and triturated using methanol. Yield 7.86%. 1H-NMR (400 MHz; CDCl3): δ 1.23 (d, 3H), 1.33 (d, 6H), 3.06-3.19 (m, 1H), 4.26 (dd, 1H), 4.43 (dd, 1H), 4.52-4.64 (m, 1H), 6.40 (d, 1H), 6.63 (d, 1H), 7.49 (d, 1H), 7.69 (d, 1H), 7.80 (d, 1H), 7.84 (dd, 1H), 8.06 (s, 1H).

Example 202

(S)-5-acetyl-N-(2-(3-(3-chloro-4-cyano-5-fluorophenyl)-1H-pyrazol-1-yl)propyl)isoxazole-3-carboxamide a) (S)-4-(1-(1-aminopropan-2-yl)-1H-pyrazol-3-yl)-2-chloro-6-fluorobenzonitrile 2-chloro-6-fluoro-4-(1H-pyrazol-3-yl)benzonitrile (5.0 g, 22.56 mmol), N-t-BOC—(R)-1-amino-2-propanol (7.91 g, 45.1 mmol) and triphenylphosphine (11.84 g, 45.1 mmol) were dissolved in dry ethyl acetate under nitrogen atmosphere and stirred. DIAD (9.12 g, 45.1 mmol) was added dropwise and the reaction flask was cooled by ice bath. The reaction was stirred at RT overnight. Water and concentrated HCl (18.53 ml, 226 mmol) were added to the reaction mixture and the reaction was stirred at RT overnight. Water and DCM were added to the reaction mixture, stirred and water phase was separated. Organic phase was extracted twice with water and water phases were combined. The combined water phase was washed twice with DCM and pH of water was adjusted to ~12 by addition of NaOH. Water phase was extracted twice with DCM and combined DCM phase was washed twice with water. Organic phase was evaporated to dryness and the product was purified by Flash-chromatography. Yield 31.8%. 1H-NMR (400 MHz; DMSO): δ 1.42 (d, 3H), 2.80-3.00 (m, 2H), 4.27-4.38 (m, 1H), 7.03 (d, 1H), 7.84-7.95 (m, 2H), 8.00 (m, 1H).

b) (S)-5-acetyl-N-(2-(3-(3-chloro-4-cyano-5-fluorophenyl)-1H-pyrazol-1-yl)propyl)isoxazole-3-carboxamide (S)-5-acetyl-N-(2-(3-(3-chloro-4-cyano-5-fluorophenyl)-1H-pyrazol-1-yl)-propyl)isoxazole-3-carboxamide was prepared using the method of Example 34(d) starting from (S)-4-(1-(1-aminopropan-2-yl)-1H-pyrazol-3-yl)-2-chloro-6-fluorobenzonitrile (500 mg, 1.794 mmol) and 5-acetylisoxazole-3-carboxylic acid (417 mg, 2.69 mmol). The product was purified twice by Flash-chromatography (normal phase and reverse phase). Yield 19.6%. 1H-NMR (400 MHz; DMSO): δ 1.51 (d, 3H), 2.57 (s, 3H), 3.56-3.77 (m, 2H), 4.65-4.77 (m, 1H), 7.01 (d, 1H), 7.56 (s, 1H), 7.89 (dd, 1H), 7.91 (d, 1H), 7.98 (s, 1H), 9.03 (t, 1H).

Example 203

(S)—N-(1-(3-(3-chloro-4-cyanophenyl)-1H-pyrazol-1-yl)propan-2-yl)-5-(5-methylfuran-2-yl)isoxazole-3-carboxamide (S)—N-(1-(3-(3-chloro-4-cyanophenyl)-1H-pyrazol-1-yl)propan-2-yl)-5-(5-methylfuran-2-yl)isoxazole-3-carboxamide was prepared using the method of Example 34(d) starting from (S)-4-(1-(2-aminopropyl)-1H-pyrazol-3-yl)-2-chlorobenzonitrile (150 mg, 0.575 mmol) and 5-(5-methylfuran-2-yl)-isoxazole-3-carboxylic acid (111 mg, 0.575 mmol). The product was purified by Flash-chromatography. Yield 41.5%. 1H-NMR (400 MHz; MeOD): δ 1.28 (d, 3H), 2.38 (dd, 3H), 4.27-4.45 (m, 2H), 4.54-4.63 (m, 1H), 6.23-

6.26 (m, 1H), 6.66 (s, 1H), 6.77 (d, 1H), 6.91 (td, 1H), 7.71 (d, 1H), 7.75 (dd, 1H), 7.86 (dd, 1H), 8.05 (dd, 1H).

Example 204

(S)—N-(2-(3-(3-chloro-4-cyano-5-fluorophenyl)-1H-pyrazol-1-yl)propyl)-2-methyl-1H-imidazole-4-carboxamide (S)—N-(2-(3-(3-chloro-4-cyano-5-fluorophenyl)-1H-pyrazol-1-yl)propyl)-2-methyl-1H-imidazole-4-carboxamide was prepared using the method of Example 34(d) starting from (S)-4-(1-(1-aminopropan-2-yl)-1H-pyrazol-3-yl)-2-chloro-6-fluorobenzonitrile (1.0 g, 3.59 mmol) and 2-methyl-1H-imidazole-4-carboxylic acid (0.498 g, 3.95 mmol). The product was purified twice by Flash-chromatography (normal phase and reverse phase). Yield 8.2%. 1H-NMR (400 MHz; DMSO): δ 1.45 (d, 3H), 2.27 (s, 3H), 3.50-3.74 (m, 2H), 4.62-4.77 (m, 1H), 7.02 (d, 1H), 7.45 (s, 1H), 7.88-8.04 (m, 4H), 12.11 (s, 1H).

Example 205

(R)—N-(1-(3-(3-chloro-4-cyanophenyl)-1H-pyrazol-1-yl)propan-2-yl)-2-(1H-pyrazol-4-yl)thiazole-4-carboxamide 1H-Pyrazole-4-carbothioic acid amide (300 mg, 2.359 mmol) and 3-bromo-2-oxopropanoic acid (433 mg, 2.60 mmol) were dissolved in dry THF under nitrogen atmosphere. The reaction mixture was heated at 60° C. for 3 h. The reaction mixture was cooled to RT and evaporated to dryness. (R)-4-(1-(2-aminopropyl)-1H-pyrazol-3-yl)-2-chlorobenzonitrile (300 mg, 1.151 mmol) and DCM were added to the reaction flask and the title compound was prepared using the method of Example 34(d). The product was purified by Flash-chromatography and triturated using methanol. Yield 13.7%. 1H-NMR (400 MHz; DMSO): δ 1.17 (d, 3H), 4.31-4.54 (m, 3H), 6.96 (d, 1H), 7.84 (d, 1H), 7.87 (d, 1H), 7.94 (dd, 1H), 8.00 (bs, 1H), 8.06 (d, 1H), 8.08 (d, 1H), 8.38 (d, 1H), 8.40 (bs, 1H), 13.38 (s, 1H).

Example 206

(S)—N-(1-(3-(3-chloro-4-cyanophenyl)-1H-pyrazol-1-yl)propan-2-yl)-2-(1H-pyrazol-4-yl)thiazole-4-carboxamide 1H-Pyrazole-4-carbothioic acid amide (1.0 g, 7.86 mmol) and 3-bromo-2-oxopropanoic acid (1.44 g, 8.65 mmol) were dissolved in dry THF under nitrogen atmosphere. The reaction mixture was heated at 60° C. for 4.5 h. The reaction mixture was cooled to RT and evaporated to dryness. (S)-4-(1-(2-aminopropyl)-1H-pyrazol-3-yl)-2-chlorobenzonitrile (1.367 g, 5.24 mmol) and DCM were added to the reaction flask and the title compound was prepared using the method of Example 34(d). The product purified by Flash-chromatography and triturated using acetonitrile. Yield 37.7%. 1H-NMR (400 MHz; DMSO): δ 1.11 (d, 3H), 4.25-4.48 (m, 3H), 6.89 (d, 1H), 7.77 (d, 1H), 7.80 (d, 1H), 7.87 (dd, 1H), 7.93 (bs, 1H), 7.99 (d, 1H), 8.01 (s, 1H), 8.31 (d, 1H), 8.33 (bs, 1H), 13.31 (bs, 1H).

Example 207

N—((S)-1-(3-(3-chloro-4-cyano-5-fluorophenyl)-1H-pyrazol-1-yl)propan-2-yl)-3-(1-hydroxyethyl)-1H-pyrazole-5-carboxamide Sodium borohydride (8.21 mg, 0.217 mmol) was added into a flask under nitrogen atmosphere. Dry ethanol was added and the mixture was stirred. (S)-3-acetyl-N-(1-(3-(3-chloro-4-cyano-5-fluorophenyl)-1H-pyrazol-1-yl)propan-2-yl)-1H-pyrazole-5-carboxamide (45 mg, 0.108 mmol) in dry ethanol was added slowly and the mixture was stirred at RT for 2.5 h. pH of the reaction mixture was adjusted to ~2 by addition of 1M HCl and the mixture was evaporated to dryness. The product was purified by Flash-chromatography. Yield 57.5%. 1H-NMR (400 MHz; DMSO): δ 1.13 (d, 3H), 1.37 (d, 3H), 4.22-4-51 (m, 3H), 4.73-4.85 (m, 1H), 5.38 (d, 1H), 6.39 (s, 1H), 6.99 (d, 1H), 7.82 (d, 1H), 7.86 (d, 1H), 7.97 (d, 1H), 8.09 (d, 1H), 13.00 (s, 1H)

Example 208

(S)—N-(1-(3-(3-chloro-4-cyanophenyl)-1H-pyrazol-1-yl)propan-2-yl)-3-methoxyisoxazole-5-carboxamide (S)—N-(1-(3-(3-chloro-4-cyanophenyl)-1H-pyrazol-1-yl)propan-2-yl)-3-methoxyisoxazole-5-carboxamide carboxamide was prepared using the method of Example 34(d) starting from (S)-4-(1-(2-aminopropyl)-1H-pyrazol-3-yl)-2-chlorobenzonitrile (350 mg, 1.342 mmol) and 3-methoxyisoxazole-5-carboxylic acid (250 mg, 1.745 mmol). The product was purified by Flash-chromatography. Yield 66.0%. 1H-NMR (400 MHz; MeOD): δ 1.28 (d, 3H), 3.98 (s, 3H), 4.26-4.42 (m, 2H), 4.49-4.60 (m, 1H), 6.50 (s, 1H), 6.77 (d, 1H), 7.69 (d, 1H), 7.77 (dd, 1H), 7.86 (dd, 1H), 8.01 (dd, 1H).

Example 209

(S)—N-(1-(3-(3-chloro-4-cyanophenyl)-1H-pyrazol-1-yl)propan-2-yl)-5-(hydroxymethyl)isoxazole-3-carboxamide (S)—N-(1-(3-(3-chloro-4-cyanophenyl)-1H-pyrazol-1-yl)propan-2-yl)-5-(hydroxymethyl)isoxazole-3-carboxamide was prepared using the method of Example 34(d) starting from (S)-4-(1-(2-aminopropyl)-1H-pyrazol-3-yl)-2-chlorobenzonitrile (200 mg, 0.675 mmol) and 5-(hydroxymethyl)isoxazole-3-carboxylic acid (126 mg, 0.878 mmol). The product purified twice by Flash-chromatography (normal phase and reverse phase) and triturated using diethyl ether. Yield 1.9%. 1H-NMR (400 MHz; MeOD): δ 1.26 (d, 3H), 4.28-4-43 (m, 2H), 4.52-4.63 (m, 1H), 4.68 (d, 2H), 6.57 (t, 1H), 6.77 (d, 1H), 7.70 (d, 1H), 7.78 (dd, 1H), 7.88 (dd, 1H), 8.07 (dd, 1H).

Example 210

(R)—N-(1-(3-(3-chloro-4-cyano-5-fluorophenyl)-1H-pyrazol-1-yl)propan-2-yl)-2-methyl-1H-imidazole-4-carboxamide a) (R)-4-(1-(2-aminopropyl)-1H-pyrazol-3-yl)-2-chloro-6-fluorobenzonitrile (R)-4-(1-(2-aminopropyl)-1H-pyrazol-3-yl)-2-chloro-6-fluorobenzonitrile was prepared using the method of Example 202 starting from 2-chloro-6-fluoro-4-(1H-pyrazol-3-yl)benzonitrile (5.0 g, 22.56 mmol) and (R)-tert-butyl (1-hydroxypropan-2-yl)carbamate (7.91 g, 45.1 mmol). The product was evaporated to dryness. Yield 70.5%. 1H-NMR (400 MHz; DMSO): δ 0.96 (d, 3H), 3.20-3.30 (m, 1H), 4.00-4.10 (m, 2H), 7.03 (d, 1H), 7.85-7.91 (m, 2H), 7.99 (m, 1H).

b) (R)—N-(1-(3-(3-chloro-4-cyano-5-fluorophenyl)-1H-pyrazol-1-yl)propan-2-yl)-2-methyl-1H-imidazole-4-carboxamide (R)—N-(1-(3-(3-chloro-4-cyano-5-fluorophenyl)-1H-pyrazol-1-yl)propan-2-yl)-2-methyl-1H-imidazole-4-carboxamide was prepared using the method of Example 34(d) starting from (R)-4-(1-(2-aminopropyl)-1H-pyrazol-3-yl)-2-chloro-6-fluorobenzonitrile (1.0 g, 3.59 mmol) and 2-methyl-1H-imidazole-4-carboxylic acid (0.50 g, 3.95 mmol). The product purified twice by Flash-chromatography (normal phase and reverse phase). Yield 10.4%. 1H-NMR (400 MHz; DMSO): δ 1.07 (d, 3H), 2.30 (s, 3H), 4.22-4.50 (m, 3H), 7.02 (d, 2H), 7.42 (d, 1H), 7.86 (d, 1H), 7.93 (dd, 1H), 8.00 (d, 1H), 8.07 (d, 1H), 12.11 (bs, 1H).

Example 211

(S)—N-(1-(3-(3-chloro-4-cyanophenyl)-1H-pyrazol-1-yl)propan-2-yl)-5-methyl-1,3,4-oxadiazole-2-carboxamide (S)—N-(1-(3-(3-chloro-4-cyanophenyl)-1H-pyrazol-1-yl)propan-2-yl)-5-methyl-1,3,4-oxadiazole-2-carboxamide was prepared using the method of Example 34(d) starting from (S)-4-(1-(2-aminopropyl)-1H-pyrazol-3-yl)-2-chlorobenzonitrile (200 mg, 0.652 mmol) and 5-methyl-1,3,4-oxadiazole-2-carboxylic acid (100 mg, 0.782 mmol). The product was purified twice by Flash-chromatography (normal phase and reverse phase). Yield 3.7%. 1H-NMR (400 MHz; MeOD): δ 1.28 (d, 3H), 2.58 (s, 3H), 4.30-4.44 (m, 2H), 4.53-4.64 (m, 1H), 6.76-6.78 (m, 1H), 7.71 (d, 1H), 7.76-7.80 (m, 1H), 7.86-7.90 (m, 1H), 8.02-8.04 (m, 1H).

Example 212

N—((S)-1-(3-(3-chloro-4-cyanophenyl)-1H-pyrazol-1-yl)propan-2-yl)-2-(1-ethoxyethyl)thiazole-4-carboxamide a) 2-(1-ethoxyethyl)thiazole-4-carboxylic Acid Potassium hydroxide (0.277 g, 4.93 mmol) and ethanol were added to a flask and stirred. 2-Bromopropionamide (0.5 g, 3.29 mmol) was added and the reaction mixture was stirred overnight. The mixture was filtrated and the filtrate was evaporated to dryness. 2,4-bis(4-methoxyphenyl)-1,3-dithia-2,4-diphosphetane-2,4-disulfide (Lawensson's reagent) (0.665 g, 1.643 mmol) and THF were added to the evaporation residue and the mixture was heated to 60° C. for 2 h. The reaction mixture was evaporated to dryness. 3-Bromopyruvic acid (0.604 g, 3.62 mmol) and THF were added to the evaporation residue and the mixture was heated to 60° C. for 3 h. The reaction mixture was cooled to RT and evaporated to dryness. The product was purified by Flash-chromatography. Yield 102%. 1H-NMR (400 MHz; DMSO): δ 1.16 (t, 3H), 1.46 (d, 3H), 3.79-3.86 (m, 2H), 4.78 (q, 1H), 8.42 (s, 1H).

b) N—((S)-1-(3-(3-chloro-4-cyanophenyl)-1H-pyrazol-1-yl)propan-2-yl)-2-(1-ethoxyethyl)thiazole-4-carboxamide N—((S)-1-(3-(3-chloro-4-cyanophenyl)-1H-pyrazol-1-yl)propan-2-yl)-2-(1-ethoxyethyl)thiazole-4-carboxamide was prepared using the method of Example 34(d) starting from (S)-4-(1-(2-aminopropyl)-1H-pyrazol-3-yl)-2-chlorobenzonitrile (350 mg, 1.342 mmol) and 2-(1-ethoxyethyl)thiazole-4-carboxylic acid (661 mg, 3.28 mmol). The product purified by Flash-chromatography (reverse phase). Yield 31.7%. 1H-NMR (400 MHz; MeOD): δ 1.19-1.24 (m, 3H), 1.26 (dd, 3H), 1.51 (t, 3H), 3.48-3.58 (m, 1H), 3.58-3.66 (m, 1H), 4.33-4.46 (m, 2H), 4.52-4.62 (m, 1H), 4.72-4.79 (m, 1H), 6.77 (dd, 1H), 7.70-7.72 (m, 1H), 7.75-7.79 (m, 1H), 7.85-7.89 (m, 1H), 8.02 (m, 1H), 8.08 (d, 1H).

Example 213

(S)—N-(1-(3-(3-chloro-4-cyanophenyl)-1H-pyrazol-1-yl)propan-2-yl)-5-(methylsulfonamidomethyl)isoxazole-3-carboxamide a) (S)-5-(aminomethyl)-N-(1-(3-(3-chloro-4-cyanophenyl)-1H-pyrazol-1-yl)propan-2-yl)isoxazole-3-carboxamide (S)—N-(1-(3-(3-chloro-4-cyanophenyl)-1H-pyrazol-1-yl)propan-2-yl)-5-(methylsulfonamidomethyl)isoxazole-3-carboxamide was prepared using the method of Example 34(d) starting from (S)-4-(1-(2-aminopropyl)-1H-pyrazol-3-yl)-2-chlorobenzonitrile (300 mg, 1.151 mmol) and 5-{[(tert-butoxycarbonyl)amino]methyl}-isoxazole-3-carboxylic acid (362 mg, 1.496 mmol). The reaction mixture was washed twice with water, dried and evaporated to dryness. 10% HCl/ethanol solution (5.2 ml) was added to this evaporation residue and the mixture was stirred at RT overnight. The reaction mixture was evaporated, DCM and water were added and pH of water phase was adjusted to ~7 by addition of 5% of NaHCO₃. Organic phase was separated, washed with water and evaporated to dryness to afford the title compound. The product was purified by Flash-chromatography. Yield 14.5%. 1H-NMR (400 MHz; MeOD): δ 1.26 (d, 3H), 3.93 (d, 2H), 4.28-4.43 (m, 2H), 4.53-4.63 (m, 1H), 6.55 (t, 1H), 6.76 (d, 1H), 7.70 (d, 1H), 7.78 (dd, 1H), 7.89 (dd, 1H), 8.07 (dd, 1H).

b) (S)—N-(1-(3-(3-chloro-4-cyanophenyl)-1H-pyrazol-1-yl)propan-2-yl)-5-(methylsulfonamidomethyl)isoxazole-3-carboxamide (S)-5-(aminomethyl)-N-(1-(3-(3-chloro-4-cyanophenyl)-1H-pyrazol-1-yl)propan-2-yl)isoxazole-3-carboxamide (25 mg, 0.065 mmol) and DCM were added to a flask and stirred under nitrogen atmosphere. Methanesulfonyl chloride (9.05 µl, 0.065 mmol) was added and the reaction mixture was stirred at RT for 1 h. Methanesulfonyl chloride (6 µl) was added and the reaction mixture was stirred at RT overnight. Methanesulfonyl chloride (16 µl) was added and the reaction mixture was stirred at RT for 3 days. The reaction mixture was evaporated to dryness and the product was triturated using acetonitrile. Yield 8.3%. 1H-NMR (400 MHz; DMSO): δ 1.16 (d, 3H), 2.94 (s, 3H), 4.26-4.53 (m, 5H), 6.64 (s, 1H), 6.94 (d, 1H), 7.82 (d, 1H), 7.86 (m, 1H), 7.92 (dd, 1H), 7.98 (d, 1H), 8.09 (d, 1H), 8.81 (d, 1H)

Example 214

(S)—N-(1-(3-(3-chloro-4-cyanophenyl)-1H-pyrazol-1-yl)propan-2-yl)-5-(1-methyl-1H-pyrazol-5-yl)isoxazole-3-carboxamide (S)—N-(1-(3-(3-chloro-4-cyanophenyl)-1H-pyrazol-1-yl)propan-2-yl)-5-(1-methyl-1H-pyrazol-5-yl)isoxazole-3-carboxamide was prepared using the method of Example 34(d) starting from (S)-4-(1-(2-aminopropyl)-1H-pyrazol-3-yl)-2-chlorobenzonitrile (200 mg, 0.69 mmol) and 5-(1-methyl-1H-pyrazol-5-yl)isoxazole-3-carboxylic acid (173 mg, 0.898 mmol). The product was purified by triturated using acetonitrile and methanol. Yield 28.2%. 1H-NMR (400 MHz; DMSO): δ 1.19 (d, 3H), 4.06 (s, 3H), 4.35 (d, 2H), 4.43-4.57 (m, 1H), 6.91 (d, 1H), 6.96 (d, 1H), 7.20 (s, 1H), 7.59 (d, 1H), 7.85 (d, 1H), 7.93 (dd, 1H), 7.97 (d, 1H), 8.09 (d, 1H), 8.94 (d, 1H).

Example 215

(S)—N-(1-(3-(3-chloro-4-cyanophenyl)-1H-pyrazol-1-yl)propan-2-yl)-5-(1-hydroxycyclopentyl)isoxazole-3-carboxamide (S)—N-(1-(3-(3-chloro-4-cyanophenyl)-1H-pyrazol-1-yl)propan-2-yl)-5-(1-hydroxycyclopentyl)isoxazole-3-carboxamide was prepared using the method of Example 34(d) starting from (S)-4-(1-(2-aminopropyl)-1H-pyrazol-3-yl)-2-chlorobenzonitrile (200 mg, 0.69 mmol) and 5-(1-hydroxycyclopentyl)isoxazole-3-carboxylic acid (173 mg, 0.878 mmol). The product purified twice by Flash-chromatography (normal phase and reverse phase). Yield 23.2%. 1H-NMR (400 MHz; MeOD): δ 1.26 (d, 3H), 1.75-2.12 (m, 8H), 4.28-4.44 (m, 2H), 4.52-4.64 (m, 1H), 6.51 (s, 1H), 6.77 (d, 1H), 7.70 (d, 1H), 7.77 (dd, 1H), 7.88 (dd, 1H), 8.09 (dd, 1H).

Example 216

(S)-5-tert-butyl-N-(1-(3-(3-chloro-4-cyanophenyl)-1H-pyrazol-1-yl)propan-2-yl)isoxazole-3-carboxamide (S)-5-tert-butyl-N-(1-(3-(3-chloro-4-cyanophenyl)-1H-pyrazol-1-yl)propan-2-yl)isoxazole-3-carboxamide was prepared using the method of Example 34(d) starting from (S)-4-(1-(2-aminopropyl)-1H-pyrazol-3-yl)-2-chlorobenzonitrile (200 mg, 0.69 mmol) and 5-tert-butylisoxazole-3-carboxylic acid (132 mg, 0.782 mmol). The product was purified by Flash-chromatography (reverse phase). Yield 53.6%. 1H-NMR (400 MHz; MeOD): δ 1.26 (d, 3H), 1.35 (s, 9H), 4.26-4.45 (m, 2H), 4.51-4.63 (m, 1H), 6.34 (s, 1H), 6.77 (d, 1H), 7.70 (d, 1H), 7.77 (dd, 1H), 7.87 (dd, 1H), 8.09 (dd, 1H).

Example 217

(S)-3-acetyl-N-(2-(3-(4-cyano-3-(trifluoromethyl)phenyl)-1H-pyrazol-1-yl)-propyl)-1H-pyrazole-5-carboxamide a) (S)-4-(1-(1-aminopropan-2-yl)-1H-pyrazol-3-yl)-2-(trifluoromethyl) benzonitrile The title compound was prepared from 4-(1H-pyrazol-5-yl)-2-(trifluoromethyl)-benzonitrile (1.4 g, 5.90 mmol), (R)-tert-butyl 2-hydroxypropylcarbamate (1.03 g, 5.90 mmol), triphenylphosphine (2.32 g, 8.85 mmol) and di-tert-butyl azodicarboxylate (2.04 g, 8.85 mmol) using the method of Example 34(c). Yield 0.429 g. $^1$H NMR (400 MHz; MeOD): δ 1.52 (d, 3H), 2.98 (dd, 1H), 3.12 (dd, 1H), 4.43 (m, 1H), 6.87 (d, 1H), 7.77 (d, 1H), 7.98 (m, 1H), 8.21 (m, 1H), 8.33 (m, 1H).

b) (S)-3-acetyl-N-(2-(3-(4-cyano-3-(trifluoromethyl)phenyl)-1H-pyrazol-1-yl)propyl)-1H-pyrazole-5-carboxamide The title compound was synthesized from (S)-4-(1-(1-aminopropan-2-yl)-1H-pyrazol-3-yl)-2-(trifluoromethyl)benzonitrile (429 mg, 1.45 mmol), 3-acetyl-1H-pyrazole-5-carboxylic acid (225 mg, 1.45 mmol), HOBt (236 mg, 1.75 mmol), DIPEA (0.305 mL, 1.75 mmol) and EDCI (335 mg, 1.75 mmol) using DCM as solvent using the method of Example 34(d) affording 483 mg of the title compound. $^1$H NMR (400 MHz; d$_6$-DMSO): δ 1.50 (d, 3H), 2.47 (s, 3H), 3.63 (m, 2H), 4.69 (m, 1H), 7.03 (d, 1H), 7.25 (bs, 1H), 7.90 (d, 1H), 8.18 (m, 2H), 8.27 (m, 1H), 14.15 (bs, 1H).

Example 218

(R)-3-acetyl-N-(2-(3-(4-cyano-3-(trifluoromethyl)phenyl)-1H-pyrazol-1-yl)-propyl)-1H-pyrazole-5-carboxamide a) (R)-4-(1-(1-aminopropan-2-yl)-1H-pyrazol-3-yl)-2-(trifluoromethyl)benzonitrile The title compound was obtained from 4-(1H-pyrazol-5-yl)-2-(trifluoromethyl)-benzonitrile (1.32 g, 5.55 mmol), (S)-tert-butyl 2-hydroxypropylcarbamate (0.97 g, 5.55 mmol), triphenyl phosphine (2.18 g, 8.33 mmol), di-tert-butyl azodicarboxylate (1.92 g, 8.33 mmol) using the method of Example 34(c). Yield 0.381 g. $^1$H NMR (400 MHz; MeOD): δ 1.52 (d, 3H), 2.98 (dd, 1H), 3.12 (dd, 1H), 4.43 (m, 1H), 6.87 (d, 1H), 7.77 (d, 1H), 7.98 (m, 1H), 8.21 (m, 1H), 8.33 (m, 1H).

b) (R)-3-acetyl-N-(2-(3-(4-cyano-3-(trifluoromethyl)phenyl)-1H-pyrazol-1-yl)propyl)-1H-pyrazole-5-carboxamide The title compound was synthesized from (R)-4-(1-(1-aminopropan-2-yl)-1H-pyrazol-3-yl)-2-(trifluoromethyl)benzonitrile (381 mg, 1.3 mmol), 3-acetyl-1H-pyrazole-5-carboxylic acid (200 mg, 1.3 mmol), HOBt (210 mg, 1.55 mmol), DIPEA (0.271 mL, 1.55 mmol) and EDCI (298 mg, 1.55 mmol) using DCM as solvent using the method of Example 34(d) affording 410 mg of the title compound. $^1$H NMR (400 MHz; d$_6$-DMSO): δ 1.50 (d, 3H), 2.47 (s, 3H), 3.63 (m, 2H), 4.69 (m, 1H), 7.03 (d, 1H), 7.25 (bs, 1H), 7.90 (d, 1H), 8.18 (m, 2H), 8.27 (m, 1H), 14.15 (bs, 1H).

Example 219

(S)-3-acetyl-N-(2-(3-(4-cyano-3,5-difluorophenyl)-1H-pyrazol-1-yl)propyl)-1H-pyrazole-5-carboxamide The title compound was synthesized from (S)-4-(1-(1-aminopropan-2-yl)-1H-pyrazol-3-yl)-2,6-difluorobenzonitrile (380 mg, 1.45 mmol) and 3-acetyl-1H-pyrazole-5-carboxylic acid (229 mg, 1.48 mmol) using the method of Example 34(d). Yield 249 mg. $^1$H NMR (400 MHz; d$_6$-DMSO): δ 1.49 (d, 3H), 2.48 (s, 3H), 3.62 (m, 2H), 4.67 (m, 1H), 6.98 (d, 1H), 7.25 (bs, 1H), 7.76 (m, 2H), 7.89 (d, 1H), 8.52 (bs, 1H), 14.18 (bs, 1H).

Example 220

N—((R)-2-(3-(4-cyano-3-(trifluoromethyl)phenyl)-1H-pyrazol-1-yl)propyl)-3-(1-hydroxyethyl)-1H-pyrazole-5-carboxamide (R)-3-acetyl-N-(2-(3-(4-cyano-3-(trifluoromethyl)phenyl)-1H-pyrazol-1-yl) propyl)-1H-pyrazole-5-carboxamide of Example 218 (0.1 g, 0.232 mmol) was reacted with sodium borohydride (0.018 g, 0.465 mmol) using the method of Example 84. Yield of the title compound 0.059 g. $^1$H NMR (400 MHz; CDCl$_3$): δ 1.55 (d, 3H), 1.61 (d, 3H), 3.77 (m, 1H), 3.90 (m, 1H), 4.64 (m, 1H), 5.03 (q, 1H), 6.60 (s, 1H), 6.65 (d, 1H), 7.44 (bs, 1H), 7.51 (d, 1H), 7.83 (d, 1H), 8.06 (dd, 1H), 8.32 (s, 1H), 10.40 (bs, 1H).

Example 221

(R)-2-amino-N-(2-(3-(4-cyano-3, 5-difluorophenyl)-1H-pyrazol-1-yl)propyl) thiazole-4-carboxamide The title compound was synthesized from (R)-4-(1-(1-aminopropan-2-yl)-1H-pyrazol-3-yl)-2,6-difluorobenzonitrile (380 mg, 1.45 mmol), 2-aminothiazole-4-carboxylic acid (217 mg, 1.5 mmol), HOBt (235 mg, 1.74 mmol), DIPEA (0.303 mL, 1.74 mmol) and EDCI (333 mg, 1.74 mmol) using DCM as solvent using the method of Example 34(d). Yield 92 mg. $^1$H NMR (400 MHz; CDCl$_3$): δ 1.60 (d, 3H), 3.81 (m, 2H), 4.61 (m, 1H), 4.91 (s, 2H), 6.60 (d, 1H), 7.37 (s, 1H), 7.50 (d, 1H), 7.58 (m, 2H), 7.80 (m, 1H).

Example 222

(R)—N-(2-(3-(4-cyano-3,5-difluorophenyl)-1H-pyrazol-1-yl)propyl)-2-(cyanomethyl)thiazole-4-carboxamide a) 2-(cyanomethyl)thiazole-4-carboxylic Acid (Cyano)thioacetamide (2 g, 19.97 mmol) was stirred in excess THF (40 mL) under nitrogen atmosphere. The solution was cooled to 0° C. and the solution of 3-bromopyruvic acid (3.33 g, 19.97 mmol) dissolved in 5 mL THF was added drop-wise. The mixture was refluxed for 3 h. Solvent was evaporated and the crude product was purified by flash chromatography (silica, eluent: 0-40% DCM-10% MeOH/DCM mixture) to yield 1.615 g of the title compound. $^1$H NMR (400 MHz; CDCl$_3$): δ 4.20 (s, 2H), 8.33 (s, 1H).

b) (R)—N-(2-(3-(4-cyano-3,5-difluorophenyl)-1H-pyrazol-1-yl)propyl)-2-(cyanomethyl)thiazole-4-carboxamide The title compound was prepared from (R)-4-(1-(1-aminopropan-2-yl)-1H-pyrazol-3-yl)-2,6-difluorobenzonitrile (380 mg, 1.45 mmol) and 2-(cyanomethyl)-thiazole-4-carboxylic acid (244 mg, 1.45 mmol) using the method of Example 34(d). Yield 70 mg. $^1$H NMR (400 MHz; d$_6$-DMSO): δ 1.47 (d, 3H), 3.29 (s, 2H), 3.67 (m, 2H), 4.74 (m, 1H), 6.99 (d, 1H), 7.77 (m, 2H), 7.92 (d, 1H), 8.25 (d, 1H), 8.44 (m, 1H).

Example 223

N—((R)-1-(3-(4-cyano-3,5-difluorophenyl)-1H-pyrazol-1-yl)propan-2-yl)-3-(1-hydroxyethyl)-1H-pyrazole-5-carboxamide a) (R)-3-acetyl-N-(1-(3-(4-cyano-3,5-difluorophenyl)-1H-pyrazol-1-yl) propan-2-yl)-1H-pyrazole-5-carboxamide The title compound was prepared from (R)-4-(1-(2-aminopropyl)-1H-pyrazol-3-yl)-2,6-difluorobenzonitrile (733 mg, 2.79 mmol) and 3-acetyl-1H-pyrazole-5-carboxylic acid (431 mg, 2.79 mmol) using the method of Example 34(d). Yield 121 mg. $^1$H NMR (400 MHz; d$_6$-DMSO): δ 1.49 (d, 3H), 2.48 (s, 3H), 3.63 (m, 2H), 4.67 (m, 1H), 6.98 (d, 1H), 7.25 (bs, 1H), 7.76 (m, 2H), 7.89 (d, 1H), 14.16 (s, 1H).

b) N—((R)-1-(3-(4-cyano-3,5-difluorophenyl)-1H-pyrazol-1-yl)propan-2-yl)-3-(1-hydroxyethyl)-1H-pyrazole-5-carboxamide The title compound was prepared from (R)-3-acetyl-N-(1-(3-(4-cyano-3,5-difluorophenyl)-1H-pyrazol-1-yl)propan-2-yl)-1H-pyrazole-5-carboxamide (90 mg, 0.226 mmol) and sodium tetrahydroborate (17 mg, 0.452 mmol) using the method of Example 84. Yield 41 mg. $^1$H NMR (400 MHz; CDCl$_3$): δ 1.57 (d, 3H), 1.59 (d, 3H), 4.26 (m, 1H), 4.45 (m, 1H), 4.58 (m, 1H), 5.06 (q, 1H), 6.61 (m, 2H), 7.50 (d, 1H), 7.58 (m, 2H), 7.73 (bs, 1H), 10.44 (s, 1H).

Example 224

(S)-3-acetyl-N-(1-(4-chloro-3-(3-chloro-4-cyanophenyl)-1H-pyrazol-1-yl)-propan-2-yl)-1H-pyrazole-5-carboxamide a) 2-chloro-4-(4-chloro-1H-pyrazol-5-yl)benzonitrile Hydrochloride 2-chloro-4-(1-(tetrahydro-2H-pyran-2-yl)-1H-pyrazol-5-yl)benzonitrile (12.0 g, 41.7 mmol) was dissolved in acetic acid (20 ml) and sodium hypochlorite solution (29.0 ml, 416 mmol) was added. The reaction mixture was stirred at RT overnight. Further again, acetic acid (120 ml) and sodium hypochlorite solution (14 ml) were added and the mixture was stirred at RT overnight. The precipitate was filtrated and washed with water and DCM. The precipitate was dried in vacuum 40° C. overnight to yield 5.8 grams of 2-chloro-4-(4-chloro-1H-pyrazol-5-yl)benzonitrile. The mixture of 2-chloro-4-(4-chloro-1H-pyrazol-5-yl)benzonitrile (5.8 g, 24.36 mmol) and 10% HCl/ethanol solution (167 ml, 365 mmol) was stirred for 2 h at RT and the precipitate was filtrated and washed with water. The precipitate was silted up with ethanol to yield 4.0 g of the raw material. The product was purified with Flash-chromatography to yield total 18% of the title compound. $^1$H NMR (400 MHz; d$_6$-DMSO): δ 8.05 (m, 2H), 8.16 (m, 2H).

b) (S)-4-(1-(2-aminopropyl)-4-chloro-1H-pyrazol-3-yl)-2-chlorobenzonitrile

The title compound was prepared from 2-chloro-4-(4-chloro-1H-pyrazol-5-yl)benzonitrile (0.690 g, 2.9 mmol), (S)-tert-butyl 1-hydroxypropan-2-ylcarbamate (0.508 g, 2.9), triphenylphosphine (1.14 g, 4.35 mmol) and di-tertbutyl azodicarboxylate (1 g, 4.35 mmol) using the method of Example 34(c). Yield 0.518 g. $^1$H NMR (400 MHz; CDCl$_3$): δ 1.16 (d, 3H), 1.32 (bs, 2H), 3.47 (m, 1H), 3.88 (dd, 1H), 4.09 (dd, 1H), 7.56 (s, 1H), 7.69 (d, 1H), 7.99 (dd, 1H), 8.13 (d, 1H).

c) (S)-3-acetyl-N-(1-(4-chloro-3-(3-chloro-4-cyanophenyl)-1H-pyrazol-1-yl)propan-2-yl)-1H-pyrazole-5-carboxamide The title compound was synthesized from (S)-4-(1-(2-aminopropyl)-4-chloro-1H-pyrazol-3-yl)-2-chlorobenzonitrile (518 mg, 1.75 mmol), 3-acetyl-1H-pyrazole-5-carboxylic acid (270 mg, 1.75 mmol), HOBt (285 mg, 2.1 mmol), DIPEA (0.367 mL, 2.1 mmol) and EDCI (404 mg, 2.1 mmol) using DCM as solvent using the method of Example 34(d) to afford 382 mg of the title compound. $^1$H NMR (400 MHz; d$_6$-DMSO): δ 1.15 (d, 3H), 2.42 (s, 3H), 4.30 (m, 2H), 4.44 (m, 1H), 6.86 (s, 1H), 8.01 (m, 3H), 8.12 (s, 1H).

Example 226

(S)—N-(2-(3-(4-cyano-3,5-difluorophenyl)-1H-pyrazol-1-yl)propyl)-3-(pyridin-3-yl)-1H-pyrazole-5-carboxamide a) Ethyl 3-(pyridin-3-yl)-1H-pyrazole-5-carboxylate Sodium (0.2 g, 13.69 mmol) was dissolved completely in 12 mL of ethanol under nitrogen atmosphere. To this solution was added 3-acetylpyridine (1.499 ml, 13.69 mmol) followed by diethyl oxalate (1.859 ml, 13.69 mmol) at RT with constant stirring. The mixture was then warmed to 75° C. for 3 h. The mixture was then cooled to RT and a solution of hydrazine hydrochloride (0.938 g, 13.69 mmol) in water (2 ml) was added. Further again the solution was warmed to 75° C. for 3 h. After the completion of the reaction as evidenced from the LC-MS, the reaction mixture was cooled and neutralized by 2 M NaOH solution. The crude product was then extracted with ethyl acetate, washed with water and brine. The organic solvent was evaporated and the residue was purified by CombiFlash (eluent: DCM: 10% MeOH/DCM). Yield 1.577 g. $^1$H NMR (400 MHz; MeOD): δ 1.40 (t, 3H), 4.39 (q, 2H), 7.29 (s, 1H), 7.51 (m, 1H), 8.24 (m, 1H), 8.51 (dd, 1H), 8.99 (d, 1H).

b) 3-(pyridin-3-yl)-1H-pyrazole-5-carboxylic Acid

Ethyl 3-(pyridin-3-yl)-1H-pyrazole-5-carboxylate (1.577 g, 7.26 mmol) in Ethanol (60 ml) and THF (60 ml) was reacted with 1M NaOH solution (40 ml, 7.26 mmol) and heated to 60° C. for 2 h. The solvents were evaporated under reduced pressure and the residue was diluted with water. The solution was made acidic by the addition of 2 N HCl solution. The resultant mixture was stirred in ice-cold bath for 4 h and the solid precipitated was filtered, dried and weighed. Yield 378 mg. $^1$H NMR (400 MHz; d$_6$-DMSO): δ 7.39 (m, 2H), 8.21 (d, 1H), 8.53 (bs, 1H), 9.06 (bs, 1H).

c) (S)—N-(2-(3-(4-cyano-3,5-difluorophenyl)-1H-pyrazol-1-yl)propyl)-3-(pyridin-3-yl)-1H-pyrazole-5-carboxamide The title compound was synthesized from (S)-4-(1-(1-aminopropan-2-yl)-1H-pyrazol-3-yl)-2,6-difluorobenzonitrile (0.277 g, 1.06 mmol), 3-(pyridin-3-yl)-1H-pyrazole-5-carboxylic acid (0.2 g, 1.06 mmol), HOBt (0.17 g, 1.27 mmol), DIPEA (0.22 mL, 1.27 mmol) and EDCI (0.243 g, 1.27 mmol) using DCM as the solvent using the method of Example 34(d). Yield 0.13 g. 1H NMR (400 MHz; d$_6$-DMSO): δ 1.50 (d, 3H), 3.66 (m, 2H), 4.72 (m, 1H), 7.00 (d, 1H), 7.20 (s, 1H), 7.48 (m, 1H), 7.78 (m, 2H), 7.93 (d, 1H), 8.13 (m, 1H), 8.55 (dd, 1H), 8.97 (s, 1H).

Example 226

(R)-5-acetyl-N-(2-(3-(4-cyano-3,5-difluorophenyl)-1H-pyrazol-1-yl)propyl) isoxazole-3-carboxamide a) (R)-4-(1-(1-aminopropan-2-yl)-1H-pyrazol-3-yl)-2,6-difluorobenzonitrile The title compound was obtained from 2,6-difluoro-4-(1H-pyrazol-5-yl)-benzonitrile (3.88 g, 18.9 mmol), (S)-tert-butyl 2-hydroxypropylcarbamate (3.31 g, 18.9 mmol), triphenyl phosphine (7.44 g, 28.4 mmol), di-tert-butyl azodicarboxylate (6.53 g, 28.4 mmol) using the method of Example 34(c). Yield 2.29 g. $^1$H NMR (400 MHz; MeOD): δ 1.51 (d, 3H), 2.98 (dd, 1H), 3.12 (m, 1H), 4.42 (m, 1H), 6.84 (d, 1H), 7.67 (m, 2H), 7.76 (d, 1H).

b) (R)-5-acetyl-N-(2-(3-(4-cyano-3,5-difluorophenyl)-1H-pyrazol-1-yl)propyl) isoxazole-3-carboxamide The title compound was synthesized from (R)-4-(1-(1-aminopropan-2-yl)-1H-pyrazol-3-yl)-2,6-difluorobenzonitrile (0.955 g, 3.64 mmol), 5-acetylisoxazole-3-carboxylic acid (0.565 g, 3.64 mmol), HOBt (0.738 g, 5.46 mmol), DIPEA (1.9 mL, 10.92 mmol) and EDCI (1.05 g, 5.46 mmol) using DMF (10 mL) as solvent using the method of Example 34(d). The product was purified with CombiFlash to afford 60 mg of pure product. $^1$H NMR (400 MHz; CDCl$_3$): δ 1.63 (d, 3H), 2.64 (s, 3H), 3.82 (m, 1H), 3.95 (m, 1H), 4.64 (m, 1H), 6.61 (d, 1H), 7.29 (s, 1H), 7.52 (m, 3H), 7.62 (m, 1H).

Example 227

(S)-3-acetyl-N-(1-(3-(3-chloro-4-cyano-2-fluorophenyl)-1H-pyrazol-1-yl)propan-2-yl)-1H-pyrazole-5-carboxamide a) 2-chloro-3-fluoro-4-(1H-pyrazol-5-yl)benzonitrile The title compound was prepared from 2-chloro-3-fluoro-4-iodobenzonitrile (0.242 g, 0.86 mmol) and 1-(tetrahydro-2H-pyran-2-yl)-1H-pyrazole-5-boronic acid pinacol ester (0.239 g, 0.86 mmol) using the method of Example 34 (a) and (b). Yield 0.075 g. $^1$H NMR (400 MHz; MeOD): δ 6.84 (dd, 1H), 7.59 (m, 2H), 7.79 (s, 1H), 8.08 (bs, 1H).

b) (S)-4-(1-(2-aminopropyl)-1H-pyrazol-3-yl)-2-chloro-3-fluorobenzonitrile

The title compound was prepared from 2-chloro-3-fluoro-4-(1H-pyrazol-5-yl)benzonitrile (0.075 g, 0.34 mmol) and (S)-tert-butyl (1-hydroxypropan-2-yl)-carbamate (0.059 g, 0.34 mmol) using the method of Example 34(c) to afford 0.051 g of the title product. $^1$H NMR (400 MHz; CDCl$_3$): δ 1.15 (d, 3H), 1.34 (bs, 2H), 3.49 (m, 1H), 3.95 (dd, 1H), 4.16 (dd, 1H), 6.79 (dd, 1H), 7.48 (m, 1H), 7.52 (d, 1H), 8.07 (m, 1H).

c) (S)-3-acetyl-N-(1-(3-(3-chloro-4-cyano-2-fluorophenyl)-1H-pyrazol-1-yl) propan-2-yl)-1H-pyrazole-5-carboxamide The title compound was synthesized from (S)-4-(1-(2-aminopropyl)-1H-pyrazol-3-yl)-2-chloro-3-fluorobenzonitrile (0.05 g, 0.18 mmol) and 3-acetyl-1H-pyrazole-5-carboxylic acid (0.028 g, 0.18 mmol) using DMF (3 mL) as solvent using the method of Example 34(d). Yield 0.056 g. $^1$H NMR (400 MHz; CDCl$_3$): δ 1.16 (d, 3H), 2.46 (s, 3H), 4.29 (m, 2H), 4.49 (m, 1H), 6.70 (dd, 1H), 7.17 (bs, 1H), 7.50 (m, 2H), 8.06 (m, 1H).

Example 228

(S)-3-acetyl-N-(1-(3-(3,5-dichloro-4-cyanophenyl)-1H-pyrazol-1-yl)propan-2-yl)-1H-pyrazole-5-carboxamide a) 4-bromo-3,5-dichloroaniline 3,5-Dichloroaniline (10 g, 61.7 mmol) in acetonitrile (100 mL) was taken in a 3-necked flask fitted with a thermometer, condenser and a dropping funnel containing N-bromosuccinimide (10.99 g, 61.7 mmol) in acetonitrile (30 mL). N-bromosuccinimide solution was added slowly to the 3,5-dichloroaniline solution in the flask at 0° C. by maintaining the internal temperature below 5° C. After the addition of NBS, the reaction mixture was warmed to RT and stirred for further 3 h. After the completion of the reaction as evidenced by LC-MS, the mixture was diluted with 10% aq. NaHSO$_3$ (150 mL). The solution was stirred for 15 min and evaporated to ⅓ of the total volume of the solvents. The resultant mixture was then diluted with water and extracted with ethyl acetate. The organic solvent was dried, evaporated and purified by CombiFlash to give pure 4-bromo-3,5-dichloroaniline. Yield 13.6 g. $^1$H NMR (400 MHz; d$_6$-DMSO): δ 5.82 (bs, 2H), 6.75 (s, 2H).

b) 4-amino-2,6-dichlorobenzonitrile

The title compound was prepared from the reaction of 4-bromo-3,5-dichloroaniline (6.88 g, 28.6 mmol) and Copper(I)cyanide (2.56 g, 28.6 mmol) in DMF (48 mL) under microwave irradiation at 190° C. for 1 h. After the completion of the reaction, the mixture was cooled to RT and quenched with 200 mL of 12% ammonia solution. The resultant mixture was stirred for 30 min at RT and the precipitate was filtered, washed with water and dried under vacuum. Yield 3.725 g. $^1$H NMR (400 MHz; d$_6$-DMSO): δ 6.70 (s, 1H), 6.79 (s, 1H).

c) 2,6-dichloro-4-iodobenzonitrile 4-amino-2,6-dichlorobenzonitrile (1.65 g, 8.82 mmol) was stirred in 7.5 mL of 12M HCl solution. The reaction mixture was cooled with ice-bath. Sodium nitrite (0.6 g, 8.82 mmol) dissolved in 6 mL of water was added drop-wise to the flask under cold condition, followed by the drop-wise addition of cold potassium iodide (5.86 g, 35.3 mmol) solution in water (12 mL). The mixture was allowed to stir at RT for a day. After the completion of the reaction, the mixture was extracted with ethyl acetate, washed with 10% Na$_2$SO$_3$ solution and brine. The organic layer was dried over anhydrous Na$_2$SO$_4$ and evaporated. The solid obtained was washed with heptane-ethyl acetate mixture (5:1) and dried under vacuum. Yield 1.09 g. $^1$H NMR (400 MHz; d$_6$-DMSO): δ 6.71 (s, 1H), 6.81 (s, 1H).

d) 2,6-dichloro-4-(1H-pyrazol-5-yl)benzonitrile Hydrochloride

The title compound was prepared from 2,6-dichloro-4-iodobenzonitrile (1.09 g, 3.66 mmol) and 1-(tetrahydro-2H-pyran-2-yl)-1H-pyrazole-5-boronic acid pinacol ester (1.32 g, 4.76 mmol) as described in Example 34 (a) and (b) until the isolation of the hydrochloride. Yield 0.824 g. $^1$H NMR (400 MHz; d$_6$-DMSO): δ 7.07 (d, 1H), 7.88 (d, 1H), 8.14 (s, 2H).

e) (S)-4-(1-(2-aminopropyl)-1H-pyrazol-3-yl)-2,6-dichlorobenzonitrile

The title compound was prepared from 2,6-dichloro-4-(1H-pyrazol-5-yl) benzonitrile (0.75 g, 3.15 mmol) and (S)-(−)-2-(tert-Butoxycarbonylamino)-1-propanol (0.552 g, 3.15 mmol) using the method of Example 34(c). Yield 0.121 g. $^1$H NMR (400 MHz; CDCl$_3$): δ 1.15 (d, 3H), 1.54 (bs, 2H), 3.49 (m, 1H), 3.93 (dd, 1H), 4.14 (dd, 1H), 6.60 (d, 1H), 7.50 (d, 1H), 7.84 (s, 2H).

f) (S)-3-Acetyl-N-(1-(3-(3,5-dichloro-4-cyanophenyl)-1H-pyrazol-1-yl)propan-2-yl)-1H-pyrazole-5-carboxamide The title compound was synthesized from (S)-4-(1-(2-aminopropyl)-1H-pyrazol-3-yl)-2,6-dichlorobenzonitrile (0.121 g, 0.41 mmol), 3-acetyl-1H-pyrazole-5-carboxylic acid (0.063 g, 0.41 mmol), HOBt (0.083 g, 0.615 mmol), DIPEA (0.214 mL, 1.23 mmol) and EDCI (0.118 g, 0.615 mmol) using DMF (10 mL) as solvent using the method of Example 34(d). Yield 6.3 mg. $^1$H NMR (400 MHz; CDCl$_3$): δ 1.29 (d, 3H), 2.55 (s, 3H), 4.36 (m, 2H), 4.57 (m, 1H), 6.64 (d, 1H), 7.40 (s, 1H), 7.58 (d, 1H), 7.83 (s, 2H).

Example 229

N—((S)-1-(3-(3-chloro-4-cyano-2-fluorophenyl)-1H-pyrazol-1-yl)propan-2-yl)-3-(1-hydroxyethyl)-1H-pyrazole-5-carboxamide (S)-3-acetyl-N-(1-(3-(3-chloro-4-cyano-2-fluorophenyl)-1H-pyrazol-1-yl) propan-2-yl)-1H-pyrazole-5-carboxamide of Example 227 (0.05 g, 0.122 mmol) was reacted with sodium borohydride (0.009 g, 0.244 mmol) using the method of Example 84. Yield of the title compound 0.015 g. $^1$H NMR (400 MHz; MeOD): δ 1.23 (d, 3H), 1.49 (d, 3H), 4.39 (m, 2H), 4.55 (m, 1H), 6.56 (s, 1H), 6.77 (dd, 1H), 7.67 (d, 1H), 7.75 (d, 1H), 8.17 (m, 1H).

Example 230

(S)—N-(1-(3-(4-cyano-3,5-difluorophenyl)-1H-pyrazol-1-yl)propan-2-yl)-3-isopropyl-1,2,4-oxadiazole-5-carboxamide a) 3-isopropyl-1,2,4-oxadiazole-5-carboxylic Acid

The title compound was prepared from ethyl 3-isopropyl-1,2,4-oxadiazole-5-carboxylate (0.4 g, 2.17 mmol) and sodium hydroxide solution (6 mL) using the method of Example 225(b). Yield 0.25 g. ¹H NMR (400 MHz; D₂O): δ 1.33 (d, 6H), 3.17 (m, 1H).

b) (S)—N-(1-(3-(4-cyano-3,5-difluorophenyl)-1H-pyrazol-1-yl)propan-2-yl)-3-isopropyl-1,2,4-oxadiazole-5-carboxamide The title compound was synthesized from (S)-4-(1-(2-aminopropyl)-1H-pyrazol-3-yl)-2,6-difluorobenzonitrile (0.168 g, 0.64 mmol), 3-isopropyl-1,2,4-oxadiazole-5-carboxylic acid (0.1 g, 0.64 mmol), HOBt (0.13 g, 0.96 mmol), DIPEA (0.335 mL, 1.92 mmol) and EDCI (0.184 g, 0.96 mmol) using DMF as solvent using the method of Example 34(d). Yield of the title compound 5 mg. ¹H NMR (400 MHz; MeOD): δ 1.27 (d, 3H), 1.36 (d, 6H), 3.16 (m, 1H), 4.39 (m, 2H), 4.58 (m, 1H), 6.80 (d, 1H), 7.62 (m, 2H), 7.72 (d, 1H).

Example 231

N—((R)-2-(3-(4-cyano-3,5-difluorophenyl)-1H-pyrazol-1-yl)propyl)-5-(1-hydroxyethyl)isoxazole-3-carboxamide (R)-5-acetyl-N-(2-(3-(4-cyano-3,5-difluorophenyl)-1H-pyrazol-1-yl)propyl) isoxazole-3-carboxamide (0.047 g, 0.136 mmol) of Example 226 was reacted with sodium borohydride (0.010 g, 0.272 mmol) using the method described in Example 84. Yield of the title compound 0.045 g. ¹H NMR (400 MHz; MeOD): δ 1.50 (dd, 3H), 1.59 (d, 3H), 3.75 (m, 2H), 4.93 (m, 1H), 6.53 (m, 1H), 6.79 (d, 1H), 7.67 (m, 2H), 7.73 (d, 1H).

Example 232

N—((R)-1-(3-(4-cyano-3,5-difluorophenyl)-1H-pyrazol-1-yl)propan-2-yl)-5-(1-hydroxyethyl)isoxazole-3-carboxamide a) (R)-5-acetyl-N-(1-(3-(4-cyano-3,5-difluorophenyl)-1H-pyrazol-1-yl)propan-2-yl)isoxazole-3-carboxamide The title compound was prepared from (R)-4-(1-(2-aminopropyl)-1H-pyrazol-3-yl)-2,6-difluorobenzonitrile (0.214 g, 0.81 mmol) and 5-acetylisoxazole-3-carboxylic acid (0.127 g, 0.81 mmol) using the method of Example 34(d). Yield 0.166 g. ¹H NMR (400 MHz; MeOD): δ 1.28 (d, 3H), 2.59 (s, 3H), 4.37 (m, 2H), 4.60 (m, 1H), 6.80 (d, 1H), 7.27 (s, 1H), 7.64 (m, 2H), 7.72 (d, 1H).

b) N—((R)-1-(3-(4-cyano-3,5-difluorophenyl)-1H-pyrazol-1-yl)propan-2-yl)-5-(1-hydroxyethyl)isoxazole-3-carboxamide Following the method described in Example 84, the starting materials (R)-5-acetyl-N-(1-(3-(4-cyano-3,5-difluorophenyl)-1H-pyrazol-1-yl)propan-2-yl)isoxazole-3-carboxamide (0.147 g, 0.4 mmol) and sodium borohydride (0.03 g, 0.8 mmol) afforded 0.135 g of the title product. ¹H NMR (400 MHz; MeOD): δ 1.26 (d, 3H), 1.51 (dd, 3H), 4.36 (m, 2H), 4.57 (m, 1H), 4.94 (m, 1H), 6.52 (m, 1H), 6.79 (d, 1H), 7.65 (m, 2H), 7.71 (d, 1H).

Example 233

(S)-5-acetyl-N-(1-(3-(3-chloro-4-cyano-2-fluorophenyl)-1H-pyrazol-1-yl)propan-2-yl)isoxazole-3-carboxamide The title compound was obtained from (S)-4-(1-(2-aminopropyl)-1H-pyrazol-3-yl)-2-chloro-3-fluorobenzonitrile (0.4 g, 1.43 mmol), 5-acetylisoxazole-3-carboxylic acid (0.223 g, 1.43 mmol), HOBt (0.291 g, 2.15 mmol), DIPEA (0.75 mL, 4.31 mmol) and EDCI (0.413 g, 2.15 mmol) using DMF (10 mL) as solvent using the method of Example 34(d). Yield 47 mg. LC-MS: m/z [M+H⁺] calculated for $C_{19}H_{15}ClFN_5O_3^+$: 415.8; found: 415.9.

Example 234

N—((S)-1-(3-(3-chloro-4-cyano-2-fluorophenyl)-1H-pyrazol-1-yl)propan-2-yl)-5-(1-hydroxyethyl)isoxazole-3-carboxamide (S)-5-acetyl-N-(1-(3-(3-chloro-4-cyano-2-fluorophenyl)-1H-pyrazol-1-yl) propan-2-yl)isoxazole-3-carboxamide (0.04 g, 0.096 mmol) of Example 233 was reacted with sodium borohydride (0.007 g, 0.192 mmol) using the method of Example 84. Yield of the title compound 0.023 g. ¹H NMR (400 MHz; MeOD): δ 1.26 (d, 3H), 1.51 (dd, 3H), 4.38 (m, 2H), 4.59 (m, 1H), 4.94 (m, 1H), 6.52 (m, 1H), 6.77 (dd, 1H), 7.63 (m, 1H), 7.74 (m, 1H), 8.12 (m, 1H).

Example 236

(S)—N-(1-(3-(3-chloro-4-cyanophenyl)-1H-pyrazol-1-yl)propan-2-yl)-3-(morpholinomethyl)-1H-pyrazole-5-carboxamide a) Ethyl 3-(morpholinomethyl)-1H-pyrazole-5-carboxylate The title compound was prepared from 1-morpholinopropan-2-one (4.192 g, 29.3 mmol), Sodium (0.43 g, 29.3 mmol), diethyl oxalate (4.28 g, 29.3 mmol) and hydrazine hydrochloride (2 g, 29.3 mmol) using the method of Example 225(a). Yield 18%. ¹H NMR (400 MHz; CDCl₃): δ 1.39 (t, 3H), 2.48 (m, 4H), 3.60 (d, 2H), 3.71 (m, 4H), 4.38 (q, 2H), 6.74 (s, 1H).

b) 3-(morpholinomethyl)-1H-pyrazole-5-carboxylic Acid

The title compound was prepared from ethyl 3-(morpholinomethyl)-1H-pyrazole-5-carboxylate (0.138 g, 0.57 mmol) and sodium hydroxide solution (2 mL) using the method of Example 225(b). Yield 0.119 g. ¹H NMR (400 MHz; MeOD): δ 3.22 (m, 2H), 3.46 (m, 2H), 3.78 (m, 2H), 4.05 (m, 2H), 4.43 (s, 2H), 7.05 (s, 1H).

c) (S)—N-(1-(3-(3-chloro-4-cyanophenyl)-1H-pyrazol-1-yl)propan-2-yl)-3-(morpholinomethyl)-1H-pyrazole-5-carboxamide The title compound was synthesized from (S)-4-(1-(2-aminopropyl)-1H-pyrazol-3-yl)-2-chlorobenzonitrile (0.147 g, 0.56 mmol), 3-(morpholinomethyl)-1H-pyrazole-5-carboxylic acid (0.119 g, 0.56 mmol), HOBt (0.114, 0.84 mmol), DIPEA (0.29 mL, 1.69 mmol) and EDCI (0.162 g, 0.84 mmol) using DMF (10 mL) as solvent using the method of Example 34(d). Yield 0.256 g. ¹H NMR (400 MHz; MeOD): δ 1.24 (d, 3H), 2.44 (m, 4H), 3.59 (s, 2H), 3.67 (m, 4H), 4.35 (m, 2H), 4.55 (m, 1H), 6.62 (bs, 1H), 6.74 (d, 1H), 7.69 (d, 1H), 7.76 (d, 1H), 7.88 (m, 1H), 8.00 (m, 1H).

Example 236

(S)—N-(1-(3-(3-chloro-4-cyano-2-fluorophenyl)-1H-pyrazol-1-yl)propan-2-yl)-5-(morpholinomethyl)isoxazole-3-carboxamide a) Ethyl 5-(morpholinomethyl)isoxazole-3-carboxylate To the solution of ethyl chlorooximidoacetate (0.588 g, 3.88 mmol) and 4-(prop-2-ynyl)morpholine (0.971 g, 7.76 mmol) in toluene (5 mL) was added solution of triethylamine (0.54 mL, 3.88 mmol) in toluene (5 mL) dropwise. The resultant mixture was stirred at RT for 5 h. After the completion of the reaction as evidenced by LC-MS, the reaction mixture was diluted with water and extracted with ethyl acetate. The organic solvent was then dried over anhydrous sodium sulfate and evaporated. The crude product was purified by Combiflash (Heptane:EtOAc eluent). Yield 0.2 g. ¹H NMR (400 MHz; MeOD): δ 1.38 (t, 3H), 2.53 (m, 4H), 3.69 (m, 4H), 3.78 (d, 2H), 4.41 (q, 2H), 6.73 (m, 1H).

b) 5-(morpholinomethyl)isoxazole-3-carboxylic Acid

The title compound was prepared from ethyl 5-(morpholinomethyl)isoxazole-3-carboxylate (0.2 g, 0.85 mmol) and sodium hydroxide solution (2 mL) using the method of Example 225(b). Yield 0.25 g. ¹H NMR (400 MHz; D₂O): δ 3.46 (m, 4H), 3.99 (m, 4H), 4.72 (s, 2H), 7.10 (m, 1H).

c) (S)—N-(1-(3-(3-chloro-4-cyano-2-fluorophenyl)-1H-pyrazol-1-yl)propan-2-yl)-5-(morpholinomethyl)isoxazole-3-carboxamide The title compound was synthesized from (S)-4-(1-(2-aminopropyl)-1H-pyrazol-3-yl)-2-chloro-3-fluorobenzonitrile (0.2 g, 0.72 mmol), 5-(morpholinomethyl)-isoxazole-3-carboxylic acid (0.15 g, 0.72 mmol), HOBt (0.145 g, 1.07 mmol), DIPEA (0.37 mL, 2.15 mmol) and EDCI (0.2 g, 1.07 mmol) using DMF (10 mL) as the solvent using the method of Example 34(d). Yield 72 mg. ¹H NMR (400 MHz; d₆-DMSO): δ 1.17 (d, 3H), 2.39 (m, 4H), 3.56 (m, 4H), 3.71 (s, 2H), 4.34 (m, 2H), 4.46 (m, 1H), 6.62 (s, 1H), 6.76 (m, 1H), 7.83 (m, 1H), 7.88 (d, 1H), 8.03 (m, 1H).

Example 237

(S)—N-(1-(3-(3-chloro-4-cyano-2-fluorophenyl)-1H-pyrazol-1-yl)propan-2-yl)-3-(pyridin-3-yl)-1,2,4-oxadiazole-5-carboxamide a) 3-(pyridin-3-yl)-1,2,4-oxadiazole-5-carboxylic Acid Following the procedure described in U.S. Pat. No. 5,578,550 for the preparation of ethyl 3-isopropyl-1,2,4-oxadiazole-5-carboxylate, the title product was prepared from (E)-N'-hydroxynicotinimidamide (2.727 g, 19.88 mmol) and ethyl oxalyl chloride (2.89 mL, 25.9 mmol) followed by subsequent ester hydrolysis with sodium hydroxide solution according to Example 225(b). Yield 1.32 g. ¹H NMR (400 MHz; d₆-DMSO): δ 7.63 (m, 1H), 8.32 (m, 1H), 8.86 (dd, 1H), 9.03 (dd, 1H).

b) (S)—N-(1-(3-(3-chloro-4-cyano-2-fluorophenyl)-1H-pyrazol-1-yl)propan-2-yl)-3-(pyridin-3-yl)-1,2,4-oxadiazole-5-carboxamide The title compound was synthesized from (S)-4-(1-(2-aminopropyl)-1H-pyrazol-3-yl)-2-chloro-3-fluorobenzonitrile (0.2 g, 0.72 mmol), 3-(pyridin-3-yl)-1,2,4-oxadiazole-5-carboxylic acid (0.137 g, 0.72 mmol), HOBt (0.145 g, 1.07 mmol), DIPEA (0.375 mL, 2.15 mmol) and EDCI (0.2 g, 1.07 mmol) using DMF as solvent using the method of Example 34(d). Yield 33.4 mg. ¹H NMR (400 MHz; d₆-DMSO): δ 1.23 (d, 3H), 4.41 (m, 2H), 4.52 (m, 1H), 6.79 (m, 1H), 7.65 (m, 1H), 7.78 (m, 1H), 7.95 (d, 1H), 8.03 (m, 1H), 8.38 (m, 1H), 8.83 (dd, 1H), 9.19 (dd, 1H), 9.51 (m, 1H).

Example 238

(S)—N-(1-(3-(3-chloro-4-cyanophenyl)-1H-pyrazol-1-yl)propan-2-yl)-3-(pyridin-3-yl)-1,2,4-oxadiazole-5-carboxamide Following the method of Example 34(d), the title compound was prepared from (S)-4-(1-(2-aminopropyl)-1H-pyrazol-3-yl)-2-chlorobenzonitrile (0.27 g, 1.05 mmol), 3-(pyridin-3-yl)-1,2,4-oxadiazole-5-carboxylic acid (0.2 g, 1.05 mmol), HOBt (0.21 g, 1.57 mmol), DIPEA (0.55 mL, 3.14 mmol) and EDCI (0.3 g, 1.57 mmol) using DMF as solvent to afford 54 mg of the title product. ¹H NMR (400 MHz; d₆-DMSO): δ 1.23 (d, 3H), 4.37 (m, 2H), 4.50 (m, 1H), 6.96 (d, 1H), 7.65 (m, 1H), 7.88 (d, 1H), 7.92 (m, 2H), 8.04 (m, 1H), 8.38 (m, 1H), 8.83 (dd, 1H), 9.19 (dd, 1H), 9.50 (m, 1H).

Example 239

(S)—N-(1-(3-(3-chloro-4-cyanophenyl)-1H-pyrazol-1-yl)propan-2-yl)-imidazo[2,1-b]thiazole-6-carboxamide a) Ethyl imidazo[2,1-b]thiazole-6-carboxylate To the cold solution of 2-aminothiazole (0.5 g, 4.99 mmol) in 10 mL of DME was added ethyl bromopyruvate (0.783 mL, 6.24 mmol). The resultant mixture was stirred at RT for 30 min. The yellow precipitate obtained was filtered. The solid residue was dissolved in 20 mL of ethanol and refluxed for 8 h. After the completion of the reaction as evidenced by LC-MS, the solvent was removed under vacuum. Residue was added to DCM and washed with sodium bicarbonate solution. The organic solvent was evaporated and the crude product was purified by Combiflash. Yield 0.285 g. ¹H NMR (400 MHz; CDCl₃): δ 1.42 (t, 3H), 4.41 (q, 2H), 6.98 (d, 1H), 7.47 (d, 1H), 8.09 (s, 1H).

b) Imidazo[2,1-b]thiazole-6-carboxylic Acid

Following the method of Example 225(b), the title compound was obtained from 0.285 g of ethyl imidazo[2,1-b]thiazole-6-carboxylate and 2 mL of sodium hydroxide solution. Yield 0.379 g. ¹H NMR (400 MHz; D₂O): δ 7.53 (d, 1H), 7.98 (d, 1H), 8.31 (s, 1H).

c) (S)—N-(1-(3-(3-chloro-4-cyanophenyl)-1H-pyrazol-1-yl)propan-2-yl) imidazo[2,1-b]thiazole-6-carboxamide The title compound was prepared from (S)-4-(1-(2-aminopropyl)-1H-pyrazol-3-yl)-2-chlorobenzonitrile (0.31 g, 1.19 mmol), imidazo[2,1-b]thiazole-6-carboxylic acid (0.2 g, 1.19 mmol), HOBt (0.24 g, 1.78 mmol), DIPEA (0.62 mL, 3.57 mmol) and EDCI (0.34 g, 1.78 mmol) using DMF (10 mL) as solvent using the method of Example 34(d) affording 232 mg of the product. $^1$H NMR (400 MHz; MeOD): δ 1.24 (d, 3H), 4.38 (m, 2H), 4.55 (m, 1H), 6.76 (d, 1H), 7.21 (d, 1H), 7.75 (m, 3H), 7.90 (dd, 1H), 8.06 (m, 1H), 8.09 (s, 1H).

Example 240

(S)—N-(1-(3-(3-chloro-4-cyano-2-fluorophenyl)-1H-pyrazol-1-yl)propan-2-yl) imidazo[1,2-a]pyrimidine-2-carboxamide The title compound was prepared using the method of Example 34(d) from (S)-4-(1-(2-aminopropyl)-1H-pyrazol-3-yl)-2-chloro-3-fluorobenzonitrile (0.3 g, 1.07 mmol), imidazo[1,2-a]pyrimidine-2-carboxylic acid (0.17 g, 1.07 mmol), HOBt (0.22 g, 1.61 mmol), DIPEA (0.56 mL, 3.23 mmol) and EDCI (0.31 g, 1.61 mmol) using DMF (10 mL) as solvent. Yield 0.29 g. $^1$H NMR (400 MHz; CDCl$_3$): δ 1.25 (d, 3H), 4.30 (dd, 1H), 4.49 (dd, 1H), 4.65 (m, 1H), 6.81 (dd, 1H), 6.98 (dd, 1H), 7.53 (d, 1H), 7.73 (dd, 1H), 8.08 (s, 1H), 8.48 (dd, 1H), 8.67 (m, 3H).

Example 241

(S)—N-(1-(3-(3-chloro-4-cyano-2-fluorophenyl)-1H-pyrazol-1-yl)propan-2-yl) imidazo[1,2-a]pyrazine-2-carboxamide Following the method described in Example 34(d), the title compound was prepared from (S)-4-(1-(2-aminopropyl)-1H-pyrazol-3-yl)-2-chloro-3-fluorobenzonitrile (0.34 g, 1.22 mmol), imidazo[1,2-a]pyrazine-2-carboxylic acid (0.2 g, 1.22 mmol), HOBt (0.25 g, 1.84 mmol), DIPEA (0.64 mL, 3.68 mmol) and EDCI (0.35 g, 1.84 mmol) using 10 mL of DMF as solvent. Yield 0.26 g. $^1$H NMR (400 MHz; MeOD): δ 1.30 (d, 3H), 4.44 (m, 2H), 4.58 (m, 1H), 6.77 (dd, 1H), 7.59 (dd, 1H), 7.78 (d, 1H), 7.90 (d, 1H), 8.14 (dd, 1H), 8.36 (d, 1H), 8.49 (dd, 1H), 9.06 (bs, 1H).

Example 242

(S)—N-(1-(3-(3-chloro-4-cyano-2-fluorophenyl)-1H-pyrazol-1-yl)propan-2-yl)-3-isopropyl-1,2,4-oxadiazole-5-carboxamide The title compound was obtained from (S)-4-(1-(2-aminopropyl)-1H-pyrazol-3-yl)-2-chloro-3-fluorobenzonitrile (0.36 g, 1.28 mmol), 3-isopropyl-1,2,4-oxadiazole-5-carboxylic acid (0.2 g, 1.28 mmol), HOBt (0.26 g, 1.92 mmol), DIPEA (0.67 mL, 3.84 mmol) and EDCI (0.37 g, 1.92 mmol) using DMF (10 mL) as solvent using the method of Example 34(d). Yield 0.144 g. $^1$H NMR (400 MHz; MeOD): δ 1.29 (d, 3H), 1.34 (d, 6H), 3.15 (m, 1H), 4.41 (m, 2H), 4.58 (m, 1H), 6.79 (dd, 1H), 7.62 (dd, 1H), 7.76 (d, 1H), 8.08 (dd, 1H).

Example 243

(S)—N-(1-(3-(3-chloro-4-cyano-2-fluorophenyl)-1H-pyrazol-1-yl)propan-2-yl)-2-(1H-imidazol-4-yl)thiazole-4-carboxamide The title compound was prepared from (S)-4-(1-(2-aminopropyl)-1H-pyrazol-3-yl)-2-chloro-3-fluorobenzonitrile (0.3 g, 1.07 mmol), 2-(1H-imidazol-4-yl)thiazole-4-carboxylic acid (0.25 g, 1.29 mmol), HOBt (0.22 g, 1.61 mmol), DIPEA (0.56 mL, 3.23 mmol) and EDCI (0.31 g, 1.61 mmol) in 10 mL DMF as solvent using the method described in Example 34(d). Yield 65 mg. $^1$H NMR (400 MHz; CDCl$_3$): δ 1.27 (d, 3H), 4.40 (m, 2H), 4.60 (m, 1H), 6.80 (dd, 1H), 7.24 (d, 1H), 7.30 (m, 1H), 7.56 (m, 2H), 7.70 (d, 1H), 8.02 (s, 1H), 8.08 (m, 1H).

Example 244

(S)—N-(1-(3-(3-chloro-4-cyano-2-fluorophenyl)-1H-pyrazol-1-yl)propan-2-yl)-2-(morpholinomethyl)thiazole-4-carboxamide The title compound was prepared from (S)-4-(1-(2-aminopropyl)-1H-pyrazol-3-yl)-2-chloro-3-fluorobenzonitrile (0.3 g, 1.07 mmol), 2-(morpholinomethyl)thiazole-4-carboxylic acid (0.29 g, 1.29 mmol), HOBt (0.22 g, 1.61 mmol), DIPEA (0.56 mL, 3.23 mmol) and EDCI (0.31 g, 1.61 mmol) in 10 mL DMF as solvent using the method of Example 34(d). Yield 0.27 g. $^1$H NMR (400 MHz; d$_6$-DMSO): δ 1.13 (d, 3H), 3.61 (m, 4H), 3.84 (d, 2H), 4.39 (m, 3H), 6.78 (dd, 1H), 7.84 (dd, 1H), 7.90 (d, 1H), 8.06 (dd, 1H), 8.15 (s, 1H), 8.45 (d, 1H).

Example 245

N—((S)-1-(3-(3,5-dichloro-4-cyanophenyl)-1H-pyrazol-1-yl)propan-2-yl)-3-(1-hydroxyethyl)-1H-pyrazole-5-carboxamide The title compound was prepared from (S)-3-acetyl-N-(1-(3-(3,5-dichloro-4-cyanophenyl)-1H-pyrazol-1-yl)propan-2-yl)-1H-pyrazole-5-carboxamide (63 mg, 0.15 mmol) and sodium borohydride (11 mg, 0.29 mmol) using the method of Example 84. Yield 15 mg. $^1$H NMR (400 MHz; CDCl$_3$): δ 1.23 (d, 3H), 1.54 (d, 3H), 4.34 (m, 2H), 4.54 (m, 1H), 4.96 (q, 1H), 6.61 (m, 2H), 7.52 (d, 1H), 7.90 (m, 2H).

Example 246

(S)—N-(1-(3-(3-chloro-4-cyano-2-fluorophenyl)-1H-pyrazol-1-yl)propan-2-yl)-5-(2-hydroxypropan-2-yl)isoxazole-3-carboxamide The title compound was prepared from (S)-4-(1-(2-aminopropyl)-1H-pyrazol-3-yl)-2-chloro-3-fluorobenzonitrile (0.3 g, 1.07 mmol), 5-(2-hydroxypropan-2-yl)-isoxazole-3-carboxylic acid (0.22 g, 1.29 mmol), HOBt (0.22 g, 1.61 mmol), DIPEA (0.56 mL, 3.23 mmol) and EDCI (0.31 g, 1.61 mmol) using DMF (10 mL) as solvent using the method of Example 34(d). Yield 40 mg. 1H NMR (400 MHz; CDCl$_3$): δ 1.23 (d, 3H), 1.62 (s, 6H), 4.36 (m, 2H), 4.59 (m, 1H), 6.57 (m, 1H), 6.82 (dd, 1H), 7.54 (m, 2H), 8.00 (m, 1H), 8.20 (m, 1H).

Example 247

(S)—N-{1-[3-(3-Chloro-4-cyanophenyl)-1H-pyrazol-1-yl]propan-2-yl}-1H-imidazole-4-carboxamide 4-Imidazolecarboxylic acid (1.00 g, 8.9 mmol) was dissolved in dry DMF (35 ml). Dry 1-(3-dimethylaminopropyl)-3-ethylcarbodiimide hydrochloride (EDCI, 2.31 g, 12.0 mmol), HOBt (1.84 g, 12.0 mmol), and DIPEA (4.7 ml, 3.46 g, 26.8 mmol) were added at RT. After stirring for 15 min (S)-4-[1-(2-aminopropyl)-1H-pyrazol-3-yl]-2-chlorobenzonitrile of Example 340 (2.44 g, 9.4 mmol) in dry DMF (15 ml) was added to the solution at RT. Then the solution was stirred for 45 h. Water was added and the product was extracted into ethyl acetate. The organic phase was washed with brine and water, dried and evaporated. The crude product was purified by triturating in hot DCM. The product was filtered and washed with heptane. $^1$H NMR (400 MHz, DMSO-$d_6$): 1.08 (3H, d), 4.30 (1H, distorted dd), 4.41 (2H, m), 6.95 (1H, d), 7.57 (1H, s), 7.75 (1H, d), 7.85 (1H, d), 8.01 (2H, m), 8.21 (1H, s), 8.30 (1H, d), 12.47 (1H, broad s).

Example 248

(S)—N-{1-[3-(3-Chloro-4-cyanophenyl)-1H-pyrazol-1-yl]propan-2-yl}-2-methyl-1H-imidazole-4-carboxamide 2-Methyl-1H-imidazole-4-carboxylic acid (1.364 g, 10.82 mmol) was suspended in N,N-Dimethyl formamide (25 ml). O-(benzotriazol-1-yl)-N,N,N',N'-tetramethyluronium-hexafluorophosphate (0.342 g, 0.901 mmol), 1-(3-dimethylaminopropyl)-3-ethylcarbodiimide hydrochloride (2.073 g, 10.82 mmol), DIPEA (3.14 ml, 18.03 mmol) and (S)-4-(1-(2-aminopropyl)-1H-pyrazol-3-yl)-2-chlorobenzonitrile (2.5 g, 9.01 mmol) were rapidly added into the mixture, respectively. The reaction mixture was stirred at RT overnight. Next day water was slowly added and the mixture was extracted twice with DCM. The combined organic phases were extracted three times with water and the DCM-layer was evaporated. The product was crystallized from acetonitrile/water mixture and finally dried with vacuum at 40° C. Yield 71.6%. $^1$H-NMR (400 MHz; d6-DMSO): δ 1.08 (d, 3H), 2.31 (s, 3H), 4.27 (dd, 1H), 4.32-4.48 (m, 2H), 6.95 (d, 1H), 7.41 (s, 1H), 7.82 (d, 1H), 7.95-8.02 (m, 2H), 8.04 (d, 1H), 8.10 (m, 1H), 12.10 (bs, 1H).

Example 249

(S)—N-{1-[3-(3-Chloro-4-cyano-5-fluorophenyl)-1H-pyrazol-1-yl]propan-2-yl}-2-methyl-1H-imidazole-4-carboxamide The title compound was prepared according to the method of Example 247 starting from 2-methyl-1H-imidazole-4-carboxylic acid and (S)-4-[1-(2-aminopropyl)-1H-pyrazol-3-yl]-2-chloro-6-fluorobenzonitrile (which can be prepared according to Example 34(c)). The crude product was purified by flash chromatography on silica gel by using $CH_2Cl_2$-MeOH as a gradient eluent (100:0-98:2) to give the product, which was triturated in diethyl ether at RT to afford the title compound. $^1$H NMR (400 MHz, DMSO-$d_6$): 1.06 (3H, d), 2.31 (3H, s), 4.28 (1H, distorted dd), 4.35-4.45 (2H, m), 7.02 (1H, d), 7.42 (1H, s), 7.86 (1H, d), 7.93 (1H, dd), 8.00 (1H, d), 8.07 (1H, d), 12.11 (1H, s).

Example 250

(S)—N-{2-[3-(3-Chloro-4-cyanophenyl)-1H-pyrazol-1-yl]propyl}-2-methyl-1H-imidazole-4-carboxamide The title compound was prepared using the method of Example 247 starting from 2-methyl-1H-imidazole-4-carboxylic acid and (S)-4-[1-(1-aminopropan-2-yl)-1H-pyrazol-3-yl]-2-chlorobenzonitrile. The crude product was purified by triturating in DCM at RT. $^1$H NMR (400 MHz, DMSO-$d_6$): 1.44 (3H, d), 2.27 (3H, s), 3.57 (1H, m), 3.67 (1H, m), 4.68 (1H, m), 6.96 (1H, d), 7.44 (1H, s), 7.89 (1H, d), 7.95-7.99 (3H, m), 8.12 (1H, s), 12.1 (1H, broad s).

Example 251

(R)—N-{2-[3-(3-Chloro-4-cyanophenyl)-1H-pyrazol-1-yl]propyl}-2-methyl-1H-imidazole-4-carboxamide a) (R)-tert-Butyl 2-hydroxypropylcarbamate Di-tert-butyl dicarbonate (10.17 g, 46.6 mmol) in DCM (30 ml) was added slowly to a solution of (R)-(-)-1-amino-2-propanol (3.67 ml, 46.6 mmol) in DCM (60 ml). After addition stirring was continued at RT overnight. The reaction mixture was then diluted with DCM (200 ml) and washed with water (2×100 ml). The organic layer was dried, filtered and evaporated to give the title compound. $^1$H NMR (400 MHz, CDCl$_3$): 1.18 (3H, d), 1.45 (9H, s), 2.47 (1H, broad s), 3.00 (1H, m), 3.26 (1H, m), 3.90 (1H, m), 4.96 (1H, broad s)

b) (R)-4-[1-(1-Aminopropan-2-yl)-1H-pyrazol-3-yl]-2-chlorobenzonitrile (R)-4-[1-(1-Aminopropan-2-yl)-1H-pyrazol-3-yl]-2-chlorobenzonitrile was prepared using the method of Example 34(c) starting from 2-chloro-4-(1H-pyrazol-3-yl)benzonitrile and (R)-tert-butyl 2-hydroxypropylcarbamate. $^1$H NMR (400 MHz, CDCl$_3$): 1.24 (2H, broad s), 1.54 (3H, d), 3.05 (1H, distorted dd), 3.17 (1H, distorted dd), 4.34 (1H, m), 6.61 (1H, d), 7.52 (1H, d), 7.66 (1H, d), 7.78 (1H, dd), 7.98 (1H, d).

c) (R)—N-{2-[3-(3-Chloro-4-cyanophenyl)-1H-pyrazol-1-yl]propyl}-2-methyl-1H-imidazole-4-carboxamide (R)—N-{2-[3-(3-Chloro-4-cyanophenyl)-1H-pyrazol-1-yl]propyl}-2-methyl-1H-imidazole-4-carboxamide was prepared using the method of Example 247 starting from 2-methyl-1H-imidazole-4-carboxylic acid and (R)-4-[1-(1-aminopropan-2-yl)-1H-pyrazol-3-yl]-2-chlorobenzonitrile. The crude product was purified by flash chromatography on silica gel by using $CH_2Cl_2$-MeOH (98:2) as an eluent. The resulting product was triturated in DCM at RT to afford the title compound. $^1$H NMR (400 MHz, CDCl$_3$): 1.61 (3H, d), 2.39 (3H, s), 3.74-3.81 (1H, m), 3.85-3.91 (1H, m), 4.63 (1H, m), 6.59 (1H, d), 7.45 (1H, d), 7.49 (1H, d), 7.62 (1H, t), 7.66 (1H, d), 7.84 (1H, dd), 8.00 (1H, d), 10.04 (1H, broad s).

Example 252

(S)—N-{1-[3-(3-Chloro-4-cyano-5-fluorophenyl)-1H-pyrazol-1-yl]propan-2-yl}-1-methyl-1H-imidazole-4-carboxamide The title compound was prepared using the method of Example 247 starting from 1-methyl-1H-imidazole-4-carboxylic acid and (S)-4-[1-(2-aminopropyl)-1H-pyrazol-3-yl]-2-chloro-6-fluorobenzonitrile (which can be prepared according to Example 34(c)). The crude product was purified by flash chromatography on silica gel by using $CH_2Cl_2$-MeOH as a gradient eluent (100:0-99:1). The resulting product was triturated in diethyl ether at RT to afford the title product. $^1$H NMR (400 MHz, DMSO-$d_6$): 1.21 (3H, d), 3.74 (3H, s), 4.26 (1H, distorted dd), 4.42 (1H, distorted dd), 4.56 (1H, m), 6.60 (1H, d), 7.43 (1H, d), 7.49 (1H, d), 7.50 (1H, d), 7.75 (1H, dd), 7.87 (1H, m), 7.97 (1H, d).

Example 253

(S)—N-{1-[3-(3-Chloro-4-cyanophenyl)-1H-pyrazol-1-yl]propan-2-yl}-1-ethyl-1H-imidazole-4-carboxamide (S)—N-{1-[3-(3-chloro-4-cyanophenyl)-1H-pyrazol-1-yl]propan-2-yl}-1H-imidazole-4-carboxamide (250 mg, 0.705 mmol) in dry DMF (3 ml) was added slowly to the mixture of dry DMF (1 ml) and 55% NaH (61.4 mg, 1.41 mmol) at 0° C. under an nitrogen atmosphere. Thereafter the reaction mixture was stirred at RT for 30 min. The reaction mixture was recooled to 0° C. Iodoethane (0.057 ml, 0.712 mmol) was slowly added at 0° C. and then the reaction mixture was stirred at RT overnight. The reaction mixture was quenched with brine (20 ml), pH was adjusted over 9 with NaOH and the product was extracted into ethyl acetate (3×30 ml). The combined organic layers were washed with water, dried and concentrated. Flash chromatography on silica gel by using $CH_2Cl_2$-MeOH as a gradient eluent (100:0-99:1) afforded the title product. $^1$H NMR (400 MHz, DMSO-$d_6$): 1.07 (3H, d), 1.34 (3H, t), 4.02 (2H, q), 4.20 (1H, distorted dd), 4.34 (2H, m), 6.95 (1H, d), 7.67 (1H, d), 7.76 (1H, d), 7.84 (1H, d), 8.00 (2H, m), 8.20 (1H, d), 8.27 (1H, d).

Example 254

(S)—N-{1-[3-(3-Chloro-4-cyanophenyl)-1H-pyrazol-1-yl]propan-2-yl}-1,2-dimethyl-1H-imidazole-4-carboxamide (S)—N-{1-[3-(3-Chloro-4-cyanophenyl)-1H-pyrazol-1-yl]propan-2-yl}-2-methyl-1H-imidazole-4-carboxamide (700 mg, 1.90 mmol), EtOH (22 ml), KOH (151 mg, 2.70 mmol) and iodomethane (0.26 ml, 593 mg, 4.18 mmol) were added to a microwave oven reaction vial. The reaction mixture was stirred at RT for 74 h. Then water was added and the solution was evaporated to dryness. Water was added again and the precipitation was filtered and washed with water and heptane. Flash chromatography on silica gel by using $CH_2Cl_2$-MeOH as a gradient eluent (100:0-99:1) afforded the product, which was recrystallized in ethyl acetate, filtered at RT and washed with heptanes to afford the title compound. $^1$H NMR (400 MHz, CDCl$_3$): 1.22 (3H, d), 2.39 (3H, s), 3.60 (3H, s), 4.29 (1H, distorted dd), 4.38 (1H, distorted dd), 4.55 (1H, m), 6.60 (1H, d), 7.41 (1H, s), 7.48 (1H, d), 7.54 (1H, d), 7.66 (1H, d), 7.85 (1H, dd), 7.99 (1H, d).

Example 255

(S)—N-{1-[3-(3-Chloro-4-cyanophenyl)-1H-pyrazol-1-yl]propan-2-yl}-1-isopropyl-2-methyl-1H-imidazole-4-carboxamide (S)—N-{1-[3-(3-Chloro-4-cyanophenyl)-1H-pyrazol-1-yl]propan-2-yl}-1-isopropyl-2-methyl-1H-imidazole-4-carboxamide was prepared using the method of Example 253 starting from (S)—N-{1-[3-(3-chloro-4-cyanophenyl)-1H-pyrazol-1-yl]propan-2-yl}-2-methyl-1H-imidazole-4-carboxamide and 2-iodopropane. $^1$H NMR (400 MHz, CDCl$_3$): 1.22 (3H, d), 1.43 (6H, d), 2.42 (3H, s), 4.29 (2H, m), 4.39 (1H, distorted dd), 4.57 (1H, m), 6.61 (1H, d), 7.49 (1H, d), 7.56 (1H, s), 7.59 (1H, d), 7.66 (1H, d), 7.86 (1H, dd), 8.00 (1H, d).

Example 256

(S)—N-{2-[3-(3-Chloro-4-cyanophenyl)-1H-pyrazol-1-yl]propyl}-1-isopropyl-2-methyl-1H-imidazole-4-carboxamide The title compound was prepared using the method of Example 253 starting from (S)—N-{2-[3-(3-chloro-4-cyanophenyl)-1H-pyrazol-1-yl]propyl}-2-methyl-1H-imidazole-4-carboxamide and 2-iodopropane. $^1$H NMR (400 MHz, CDCl$_3$): 1.42 (3H, d), 1.43 (3H, d), 1.60 (3H, d), 2.37 (3H, s), 3.77 (1H, m), 3.88 (1H, m), 4.28 (1H, m), 4.63 (1H, m), 6.58 (1H, d), 7.50 (1H, d), 7.51 (1H, t), 7.59 (1H, s), 7.66 (1H, d), 7.84 (1H, dd), 8.00 (1H, d).

Example 257

(S)—N-{1-[3-(3-Chloro-4-cyanophenyl)-1H-pyrazol-1-yl]propan-2-yl}-1-(3-oxobutyl)-1H-imidazole-4-carboxamide (S)—N-{1-[3-(3-Chloro-4-cyanophenyl)-1H-pyrazol-1-yl]propan-2-yl}-1H-imidazole-4-carboxamide (600 mg, 1.69 mmol) and methyl vinyl ketone (0.42 ml, 5.18 mmol) were added to a solution of 1-methylimidazole (7 μl, 0.085 mmol) in DMSO (6 ml). The reaction mixture was stirred at 70° C. for 11 h. Then water was added and the product was extracted into ethyl acetate. The combined organic layers were washed with water, dried and concentrated. The crude product was purified by flash chromatography on silica gel by using $CH_2Cl_2$-MeOH as a gradient eluent (100:0-98:2) to obtain the title compound. $^1$H NMR (400 MHz, CDCl$_3$): 1.21 (3H, d), 2.16 (3H, s), 2.92 (2H, t), 4.26 (2H, t), 4.28 (1H, distorted dd), 4.39 (1H, distorted dd), 4.56 (1H, m), 6.60 (1H, d), 7.48 (1H, d), 7.50 (1H, d), 7.52 (1H, d), 7.66 (1H, distorted d), 7.79 (1H, distorted dd), 7.86 (1H, d), 8.17 (1H, d).

Example 258

(S)—N-{1-[3-(3-Chloro-4-cyanophenyl)-1H-pyrazol-1-yl]propan-2-yl}-2-methyl-1-(3-oxobutyl)-1H-imidazole-4-carboxamide (S)—N-{1-[3-(3-Chloro-4-cyanophenyl)-1H-pyrazol-1-yl]propan-2-yl}-2-methyl-1H-imidazole-4- carboxamide was prepared using the method of the previous Example starting from (S)—N-{1-[3-(3-chloro-4-cyanophenyl)-1H-pyrazol-1-yl]propan-2-yl}-2-methyl-1H-imidazole-4-carboxamide and methyl vinyl ketone. $^1$H NMR (400 MHz, CDCl$_3$): 1.21 (3H, d), 2.17 (3H, s), 2.44 (3H, s), 2.89 (2H, t), 4.13 (2H, t), 4.29 (1H, distorted dd), 4.38 (1H, distorted dd), 4.55 (1H, m), 6.60 (1H, d), 7.44 (1H, s), 7.48 (1H, d), 7.58 (1H, d), 7.66 (1H, distorted d), 7.85 (1H, distorted dd), 8.00 (1H, d).

Example 259

(S)—N-{1-[3-(3-Chloro-4-cyanophenyl)-1H-pyrazol-1-yl]propan-2-yl}-1-(3-hydroxy-3-methylbutyl)-1H-imidazole-4-carboxamide (S)—N-{1-[3-(3-Chloro-4-cyanophenyl)-1H-pyrazol-1-yl]propan-2-yl}-1-(3-oxobutyl)-1H-imidazole-4-carboxamide (100 mg, 1.18 mmol) in dry THF (3 ml) was added to 3.0 M methylmagnesium bromide solution in ether (0.39 ml) at 30-40° C. Thereafter the reaction mixture was stirred at 45° C. for 3 h. The cooled reaction mixture was poured into saturated NH$_4$Cl solution. Solvents were evaporated and the product was extracted into ethyl acetate. The combined organic layers were washed with water, dried and concentrated. The crude product was purified by flash chromatography on silica gel by using EtOAc-MeOH (9:1) as an eluent. The final purification was made by preparative HPLC to obtain the title compound. $^1$H NMR (400 MHz, CDCl$_3$): 1.22 (3H, d), 1.30 (6H, s), 1.97 (2H, m), 4.14 (2H, m), 4.28 (1H, distorted dd), 4.41 (1H, distorted dd), 4.56 (1H, m), 6.60 (1H, d), 7.48 (2H, d), 7.56 (1H, d), 7.61 (1H, distorted d), 7.79 (1H, distorted dd), 7.86 (1H, d), 8.17 (1H, d).

Example 260

(S)—N-{1-[3-(3-Chloro-4-cyanophenyl)-1H-pyrazol-1-yl]propan-2-yl}-1-(3-hydroxy-3-methylbutyl)-2-methyl-1H-imidazole-4-carboxamide The title compound was prepared using the method of the previous Example starting from (S)—N-{1-[3-(3-chloro-4-cyanophenyl)-1H-pyrazol-1-yl]propan-2-yl}-2-methyl-1-(3-oxobutyl)-1H-imidazole-4-carboxamide and methylmagnesium bromide. The crude product was purified by flash chromatography on silica gel by using CH$_2$Cl$_2$-MeOH as a gradient eluent (100:1-98:2). The final purification was made by preparative HPLC to obtain the title compound. $^1$H NMR (400 MHz, CDCl$_3$): 1.22 (3H, d), 1.30 (6H, s), 1.65 (1H, broad s), 1.88 (2H, m), 2.42 (3H, s), 4.02 (2H, m), 4.30 (1H, distorted dd), 4.38 (1H, distorted dd), 4.55 (1H, m), 6.60 (1H, d), 7.47 (1H, s), 7.50 (1H, d), 7.62 (1H, d), 7.65 (1H, d), 7.84 (1H, dd), 7.99 (1H, d).

Example 261

N—{(S)-1-[3-(3-Chloro-4-cyanophenyl)-1H-pyrazol-1-yl]propan-2-yl}-1-(3-hydroxybutyl)-1H-imidazole-4-carboxamide Sodium borohydride (9.8 mg, 0.26 mmol) was added to a solution of (S)—N-{1-[3-(3-chloro-4-cyanophenyl)-1H-pyrazol-1-yl]propan-2-yl}-1-(3-oxobutyl)-1H-imidazole-4-carboxamide (100 mg, 0.24 mmol) in ethanol (3 ml) at RT. Thereafter the reaction mixture was stirred at RT for 3 h. Then water was added and the product was extracted into ethyl acetate. The combined organic layers were washed with water and dried. The solvent was evaporated to obtain the title compound. $^1$H NMR (400 MHz, CDCl$_3$): 1.21 (3H, d), 1.22 (3H, d), 1.89 (2H, m), 2.31 (1H, broad s), 3.73 (1H, m), 4.15 (2H, m), 4.28 (1H, distorted dd), 4.40 (1H, distorted dd), 4.56 (1H, m), 6.61 (1H, d), 7.51 (2H, m), 7.60 (1H, d), 7.66 (1H, distorted d), 7.79 (1H, m), 7.95 (1H, d), 8.18 (1H, d).

Example 262

N—{(S)-1-[3-(3-Chloro-4-cyanophenyl)-1H-pyrazol-1-yl]propan-2-yl}-1-(3-hydroxybutyl)-2-methyl-1H-imidazole-4-carboxamide The title compound was prepared using the method of the previous Example starting from (S)—N-{1-[3-(3-chloro-4-cyanophenyl)-1H-pyrazol-1-yl]propan-2-yl}-2-methyl-1-(3-oxobutyl)-1H-imidazole-4-carboxamide. $^1$H NMR (400 MHz, CDCl$_3$): 1.22 (6H, d), 1.81 (2H, m), 2.41 (1H, m), 2.45 (1H, broad s), 3.74 (1H, m), 4.03 (2H, m), 4.30 (1H, distorted dd), 4.38 (1H, distorted dd), 4.55 (1H, m), 6.60 (1H, d), 7.51 (1H, d), 7.53 (1H, s), 7.65 (1H, d), 7.66 (1H, d), 7.85 (1H, dd), 7.99 (1H, d).

Example 263

N—{(S)-1-[3-(3-Chloro-4-cyanophenyl)-1H-pyrazol-1-yl]propan-2-yl}-1-[(2-methyloxiran-2-yl)methyl]-1H-imidazole-4-carboxamide and 1-(3-chloro-2-hydroxy-2-methylpropyl)-N—{(S)-1-[3-(3-chloro-4-cyanophenyl)-1H-pyrazol-1-yl]propan-2-yl}-1H-imidazole-4-carboxamide A mixture of (S)—N-{1-[3-(3-chloro-4-cyanophenyl)-1H-pyrazol-1-yl]propan-2-yl}-1H-imidazole-4-carboxamide (120 mg, 0.338 mmol), 2-(chloromethyl)-2-methyl-oxirane (2.88 g, 27.1 mmol and Y(NO$_3$)$_3$×6 H$_2$O (3.6 mg, 0.0093 mmol) was stirred under MW at 120° C. for 30 min. After evaporation of oxirane the residue was purified by flash chromatography on silica gel using CH$_2$Cl$_2$-MeOH as a gradient eluent (100:0-99:1) to obtain N—{(S)-1-[3-(3-chloro-4-cyanophenyl)-1H-pyrazol-1-yl]propan-2-yl}-1-[(2-methyloxiran-2-yl)methyl]-1H-imidazole-4-carboxamide as a major product and 1-(3-chloro-2-hydroxy-2-methylpropyl)-N—{(S)-1-[3-(3-chloro-4-cyanophenyl)-1H-pyrazol-1-yl]propan-2-yl}-1H-imidazole-4-carboxamide as a minor product.

N—{(S)-1-[3-(3-Chloro-4-cyanophenyl)-1H-pyrazol-1-yl]propan-2-yl}-1-[(2-methyloxiran-2-yl)methyl]-1H-imidazole-4-carboxamide: $^1$H NMR (400 MHz, CDCl$_3$): 1.22 (3H, d), 1.31 (3H, s), 2.58 and 2.77 (two diasteromers, 1H, d), 4.08 and 4.35 (two diastereomers, 1H, distorted dd), 4.57 (1H, m), (1H, distorted dd), 6.62 (1H, d), 7.50 (1H, d), 7.51 (1H, s), 7.59 (1H, d), 7.66 (1H, distorted d), 7.79 (1H, distorted dd), 7.97 (1H, d), 8.20 (1H, d).

1-(3-Chloro-2-hydroxy-2-methylpropyl)-N—{(S)-1-[3-(3-chloro-4-cyanophenyl)-1H-pyrazol-1-yl]propan-2-yl}-1H-imidazole-4-carboxamide: $^1$H NMR (400 MHz, CDCl$_3$): 1.20 (two diastereomers, 3H, m), 1.34 and 1.35 (two diastereomers, 3H, s), 3.31-3.42 (two diastereomers, 2H, m), 3.99-4.18 (two diastereomers, 2H, m), 4.21-4.43 (two diastereomers, 3H, m), 4.54 (1H, m), 6.61 (1H, d), 7.49 (1H, d), 7.57 (1H, s), 7.66 (1H, distorted d), 7.76 (1H, s), 7.78 (1H, m), 8.15 (1H, d), 8.20 (1H, d).

Example 264

(S)—N-{1-[3-(3-Chloro-4-cyanophenyl)-1H-pyrazol-1-yl]propan-2-yl}-1-(pyridin-2-yl)-1H-imidazole-4-carboxamide A microwave oven reaction tube was charged with CuI (5.5 mg, 0.028 mmol), 1H-benzotriazole (6.7 mg, 0.056 mmol), DMSO (1 ml), 2-bromopyridine (0.054 ml, 89 mg, 0.566 mmol), (S)—N-{1-[3-(3-chloro-4-cyanophenyl)-1H-pyrazol-1-yl]propan-2-yl}-1H-imidazole-4-carboxamide (200 mg, 0.564 mmol) and KOt-Bu (89 mg, 0.789 mmol). The reaction mixture was stirred for 30 min at 150° C. in a microwave oven. Then the mixture was cooled to RT, water was added and the product was extracted into ethyl acetate. The combined organic layers were washed with water and dried. After evaporation of the solvent the residue was purified by flash chromatography on silica gel using $CH_2Cl_2$-MeOH as a gradient eluent (100:0-99:1). Trituration in diethyl ether provided the desired product. $^1$H NMR (400 MHz, CDCl$_3$): 1.26 (3H, d), 4.29 (1H, distorted dd), 4.45 (1H, distorted dd), 4.61 (1H, m), 6.62 (1H, d), 7.32 (1H, dd), 7.38 (1H, d), 7.50 (1H, d), 7.66 (1H, d), 7.81 (1H, dd), 7.88 (1H, td), 8.00 (1H, m), 8.18 (2H, m), 8.42 (1H, s), 8.53 (1H, d).

Example 265

(S)—N-{1-[3-(3-chloro-4-cyanophenyl)-1H-pyrazol-1-yl]propan-2-yl}-1-(pyridin-3-yl)-1H-imidazole-4-carboxamide Under nitrogen atmosphere, a reaction flask was charged with $K_2CO_3$ (78 mg, 0.564 mmol), CuI (10.7 mg, 0.056 mmol), 1,3-di(2-pyridyl)-1,3-propanedione (12.8 mg, 0.056 mmol), (S)—N-{1-[3-(3-chloro-4-cyanophenyl)-1H-pyrazol-1-yl]propan-2-yl}-1H-imidazole-4-carboxamide (200 mg, 0.564 mmol), dry DMF (4 ml) and 3-bromopyridine (0.054 ml, 89 mg, 0.564 mmol). The reaction mixture was stirred for 4 h at 130° C. 3-Bromopyridine (0.025 ml, 41 mg, 0.260 mmol) was added, and then heating was continued for 2 h at 130° C. Then the reaction mixture was cooled to RT and passed through a plug of Celite. After being rinsed with ethyl acetate, the combined filtrates were washed with saturated brine, dried and concentrated. The residue was purified by flash chromatography on silica gel using $CH_2Cl_2$-MeOH (98:2) as an eluent. Recrystallization in $CH_2Cl_2$-Et$_2$O provided the desired product. $^1$H NMR (400 MHz, CDCl$_3$): 1.25 (3H, d), 4.29 (1H, distorted dd), 4.46 (1H, distorted dd), 4.62 (1H, m), 6.64 (1H, d), 7.50 (1H, m), 7.51 (1H, d), 7.68 (1H, distorted d), 7.74 (1H, m), 7.80 (1H, distorted dd), 7.87 (1H, d), 7.91 (1H, d), 8.11 (1H, d), 8.24 (1H, d), 8.71 (1H, dd), 8.78 (1H, d).

Example 266

(S)—N-{1-[3-(3-Chloro-4-cyanophenyl)-1H-pyrazol-1-yl]propan-2-yl}-2-methyl-1-(pyridin-3-yl)-1H-imidazole-4-carboxamide Under nitrogen atmosphere, a reaction flask was charged with $K_2CO_3$ (94 mg, 0.678 mmol), CuI (12.9 mg, 0.068 mmol), 1,3-di(2-pyridyl)-1,3-propanedione (15.3 mg, 0.068 mmol), (S)—N-{1-[3-(3-Chloro-4-cyanophenyl)-1H-pyrazol-1-yl]propan-2-yl}-2-methyl-1H-imidazole-4-carboxamide (250 mg, 0.678 mmol), dry DMF (5 ml) and 3-bromopyridine (0.065 ml, 107 mg, 0.678 mmol). The reaction mixture was stirred for 2 h at 130° C. 3-Bromopyridine (0.070 ml, 115 mg, 0.727 mmol) was added, and then heating was continued for 4 h at 140° C. 3-Bromopyridine (0.070 ml, 115 mg, 0.727 mmol) was added again, and heating was continued for 1 h at 170° C. under microwaves. Then the reaction mixture was cooled to RT and passed through a plug of Celite. After being rinsed with ethyl acetate, the combined filtrates were washed with saturated brine, dried and concentrated. The residue was purified by flash chromatography on silica gel using $CH_2Cl_2$-MeOH as a gradient eluent (99.5:0.5-98:2). $^1$H NMR (400 MHz, CDCl$_3$): 1.25 (3H, d), 2.40 (3H, s), 4.32 (1H, distorted dd), 4.43 (1H, distorted dd), 4.61 (1H, m), 6.63 (1H, d), 7.50 (1H, m), 7.52 (1H, d), 7.64 (1H, s), 7.66 (1H, m), 7.67 (1H, d), 7.78 (1H, d), 7.87 (1H, dd), 8.03 (1H, d), 8.64 (1H, d), 8.74 (1H, dd).

Example 267

(S)—N-{1-[3-(3-Chloro-4-cyanophenyl)-1H-pyrazol-1-yl]propan-2-yl}imidazo[1,2-a]pyridine-2-carboxamide Following the method of Example 247 but substituting 4-imidazolecarboxylic acid for imidazo[1,2-a]pyridine-2-carboxylic acid (described in WO 2005/030704), the title compound was obtained. The crude product was purified by flash chromatography using $CH_2Cl_2$-MeOH as a gradient eluent (100:0-99:1) and then by trituration in diethyl ether at RT. $^1$H NMR (400 MHz, CDCl$_3$): 1.28 (3H, d), 4.33 (1H, distorted dd), 4.45 (1H, distorted dd), 4.64 (1H, m), 6.61 (1H, d), 6.87 (1H, td), 7.28 (1H, td), 7.51 (1H, d), 7.60 (1H, dd), 7.64 (1H, d), 7.84 (1H, dd), 8.02 (1H, s), 8.04 (1H, d), 8.12 (1H, d), 8.15 (1H, dt).

Example 268

(S)—N-{1-[3-(3-Chloro-4-cyanophenyl)-1H-pyrazol-1-yl]propan-2-yl}-5,6,7,8-tetrahydroimidazo[1,2-a]pyridine-2-carboxamide Following the method of Example 247 but substituting 4-imidazolecarboxylic acid for 5,6,7,8-tetrahydroimidazo[1,2-a]pyridine-2-carboxylic acid (prepared in WO 2007/108750 from imidazo[1,2-a]pyridine-2-carboxylic acid), the title compound was obtained. The crude product was purified by flash chromatography using $CH_2Cl_2$-MeOH (98:2) as an eluent. $^1$H NMR (400 MHz, CDCl$_3$): 1.22 (3H, d), 1.94-2.04 (4H, m), 2.87 (2H, m), 3.99 (2H, t), 4.30 (1H, distorted dd), 4.38 (1H, distorted dd), 4.55 (1H, m), 6.60 (1H, d), 7.40 (1H, s), 7.48 (1H, d), 7.55 (1H, d), 7.66 (1H, d), 7.86 (1H, dd), 7.99 (1H, d).

Example 269

(S)—N-{1-[3-(3-Chloro-4-cyanophenyl)-1H-pyrazol-1-yl]propan-2-yl}-3-isopropyl-1H-pyrazole-5-carboxamide Following the method of Example 247 but substituting 4-imidazolecarboxylic acid for 5-isopropyl-1H-pyrazole-3-carboxylic acid (prepared in WO 03/037432 A1), the title compound was obtained. The crude product was purified by flash chromatography using $CH_2Cl_2$-MeOH as a gradient eluent (100:0-98:2). $^1$H NMR (400 MHz, CDCl$_3$): 1.22 (3H, d), 1.30 (6H, d), 3.03 (1H, m), 4.27 (1H, distorted dd), 4.43 (1H, distorted dd), 4.58 (1H, m), 6.59 (1H, s), 6.61 (1H, d), 7.50 (1H, d), 7.67 (1H, distorted d), 7.76 (1H, distorted dd), 7.85 (1H, d), 8.19 (1H, d), 10.21 (1H, broad s).

Example 270

(S)—N-{1-[3-(3-Chloro-4-cyanophenyl)-1H-pyrazol-1-yl]propan-2-yl}-3-vinyl-1H-pyrazole-5-carboxamide Triethylamine (3.0 ml, 21.8 mmol) was added to a solution of N—{(S)-1-[3-(3-chloro-4-cyanophenyl)-1H-pyrazol-1-yl]propan-2-yl}-3-(1-hydroxyethyl)-1H-pyrazole-5-carboxamide of Example 56 (1.74 g, 4.36 mmol) in DCM (40 ml) at 0° C. Then methanesulfonyl chloride (0.675 ml, 8.73 mmol) was added slowly at 0° C. After addition stirring was continued at RT overnight. The reaction mixture was then diluted with DCM and washed with 1 M HCl. The organic layer was dried ($Na_2SO_4$), filtered and concentrated. Crystallization in DCM afforded the title compound. $^1$H NMR (400 MHz, $CDCl_3$+a drop of MeOH-d4): 1.25 (3H, d), 4.31 (1H, distorted dd), 4.39 (1H, distorted dd), 4.55 (1H, m), 5.38 (1H, d), 5.76 (1H, d), 6.60 (1H, dd), 6.63 (1H, d), 6.79 (1H, s), 7.55 (1H, d), 7.70 (1H, distorted d), 7.73 (1H, d), 7.82 (1H, distorted dd), 7.96 (1H, d).

Example 271

3-Acetyl-N-(2-(3-(3-chloro-4-cyano-2-methylphenyl) isoxazol-5-yl)ethyl)-1H-pyrazole-5-carboxamide a) 2-Chloro-4-formyl-3-methylbenzonitrile A mixture of 2-chloro-4-iodo-3-methylbenzonitrile (150 g, 0.54 mol) and THF (1200 ml) was cooled down to −32° C. A 2 M i-PrMgCl-THF-solution (541 ml, 1.08 mol) was added slowly during 1 h and the mixture was stirred at −32° C. for 2 h. DMF (83 ml, 1.08 mol) was added at −32° C. and the reaction mixture was allowed to warm to RT. After stirring overnight 10% HCl solution (1000 ml) was added at 0° C. The layers were separated and the aqueous layer was extracted with diethyl ether (2×900 ml). The combined organic layers were washed with saturated $NaHCO_3$ solution (900 ml) and brine (750 ml). The organic layer was dried with $Na_2CO_4$, filtered and evaporated. The dried crude product (95 g) was treated with hot n-heptane and activated carbon. The title compound was obtained as a yellow solid and used without further purification. $^1$H-NMR (400 MHz; $CDCl_3$): δ 2.78 (s, 3H), 7.71 (d, 1H), 7.84 (d, 1H), 10.36 (s, 1H).

b) (E)-2-Chloro-4-((hydroxyimino) methyl)-3-methylbenzonitrile 2-chloro-4-formyl-3-methylbenzonitrile (5.0 g, 27.8 mmol) was dissolved in dry THF (60 ml). Pyridine (6.7 ml, 84.0 mmol) and hydroxylamine hydrochloride (3.87 g, 55.7 mmol) were added to the solution. The mixture was heated to 70° C. and stirred for 4 h. THF was evaporated and ice water (50 ml) was added. The mixture was stirred for 1 h and the precipitate was filtered off and washed twice with cold water. After drying (5.3 g) of the title compound was obtained. $^1$H-NMR (400 MHz; d6-DMSO): δ 2.48 (s, 3H), 7.79 (m, 2H), 8.45 (s, 1H), 11.93 (s, 1H).

c) (Z)-3-Chloro-4-cyano-N-hydroxy-2-methylbenzimidoyl Chloride (E)-2-chloro-4-((hydroxyimino) methyl)-3-methylbenzonitrile (0.64 g, 3.27 mmol) was dissolved in DMF (20 ml) and cooled to 0° C. N-Chlorosuccinimide (0.48 g, 3.60 mmol) was added and the mixture was allowed to warm at RT. The mixture was stirred overnight at RT and poured into ice water (100 ml), extracted twice with EtOAc, The organic phase was washed with water and brine, dried over anhydrous $Na_2SO_4$, filtered and evaporated. The crude product (0.69 g) was used without purification. $^1$H-NMR (400 MHz; d6-DMSO): δ 2.42 (s, 3H), 7.64 (d, 1H), 7.92 (d, 1H), 12.77 (s, 1H).

d) t-Butyl (2-(3-(3-chloro-4-cyano-2-methylphenyl) isoxazol-5-yl)ethyl)-carbamate tert-Butyl but-3-yn-1-ylcarbamate (1.0 g, 4.37 mmol) was dissolved in dry DCM (10 ml) and triethylamine (0.91 ml) was added at RT. Tert-butyl (2-(3-(3-chloro-4-cyano-2-methylphenyl)isoxazol-5-yl)ethyl)carbamate (1 g, 4.37 mmol) in DCM (5 ml) was added to reaction mixture. After one hour in RT the reaction mixture was heated to reflux for 6 h. Water (30 ml) was added and the aqueous phase was extracted with dichloromethane and the combined organic phases were washed with water and brine and dried over anhydrous $Na_2SO_4$, filtered and evaporated. Crude product was purified by Flash chromatography (Toluene-EtOAc 3/1) Product fractions were combined and evaporated to give the title compound (0.71 g). $^1$H-NMR (400 MHz; d6-DMSO): δ 1.36 (s, 9H), 2.48 (s, 3H), 2.95 (t, 2H), 3.32 (m, 2H), 6.71 (s, 1H), 7.05 (bs, 1H), 7.63 (d, 1H), 7.95 (d, 1H).

e) 4-(5-(2-aminoethyl)isoxazol-3-yl)-2-chloro-3-methylbenzonitrile tert-Butyl (2-(3-(3-chloro-4-cyano-2-methylphenyl)isoxazol-5-yl)ethyl)-carbamate (0.56 g, 1.55 mmol) was dissolved to DCM (20 ml). To this mixture was added TFA (1.15 ml) and stirred at RT overnight. The reaction mixture was evaporated to dryness and dissolved to diethyl ether. 1 M HCl in diethyl ether solution was added and the mixture was stirred at RT for 2 h. The HCl salt of the title compound (0.20 g) was filtered and dried. $^1$H-NMR (400 MHz; d6-DMSO): δ 2.50 (s, 3H), 2.92 (m, 2H), 3.22 (m, 2H), 6.88 (s, 1H), 7.65 (d, 1H), 7.98 (d, 1H), 8.23 (bs, 3H).

f) 3-acetyl-N-(2-(3-(3-chloro-4-cyano-2-methylphenyl)isoxazol-5-yl)ethyl)-1H-pyrazole-5-carboxamide 3-Acetyl-1H-pyrazole-5-carboxylic acid (31 mg; 0.203 mmol) and DIPEA (0.106 ml) were dissolved in 5 ml of dry DCM. HOBt hydrate (47 mg; 0.304 mmol) and EDCI (58 mg; 0.304 mmol) were added at RT. 4-(5-(2-aminoethyl) isoxazol-3-yl)-2-chloro-3-methylbenzonitrile (53 mg; 0.203 mmol) was added and the reaction was stirred at RT for 4 h. DCM 10 ml of was added and organic layer washed with 1M HCl, saturated $NaHCO_3$ and brine. The organic phase was dried over $Na_2SO_4$, filtered and evaporated to dryness. The crude product was triturated with n-heptane to give the title product 32 mg. $^1$H-NMR (400 MHz; d6-DMSO): δ 2.44 (s, 3H), 2.51 (s, 3H), 3.12 (t, 2H), 3.63 (m, 2H), 6.75 (s, 1H), 7.30 (bs, 1H), 7.62 (d, 1H), 7.94 (d, 1H), 8.73 (bs, 1H), 14.20 (s, 1H).

Example 272

N-(2-(3-(3-chloro-4-cyano-2-methylphenyl) isoxazol-5-yl)ethyl)-3-(pyridin-3-yl)-1H-pyrazole-5-carboxamide N-(2-(3-(3-chloro-4-cyano-2-methylphenyl) isoxazol-5-yl) ethyl)-3-(pyridin-3-yl)-1H-pyrazole-5-carboxamide was prepared from 4-(5-(2-aminoethyl) isoxazol-3-yl)-2-chloro-3-methylbenzonitrile hydrochloride (54.8 g, 0.184 mmol), 3-(pyridin-3-yl)-1H-pyrazole-5-carboxylic acid (34.8 mg, 0.184 mmol), HOBt hydrate (42.2 mg, 0.276 mmol), DIPEA (0.096 ml, 0.551 mmol) and EDCI (53 mg, 0.276 mmol) using DCM as solvent as described in previous Example. The crude product was purified by preparative HPLC to give the title compound 13 mg. $^1$H-NMR (400 MHz; CDCl$_3$): δ 2.47 (s, 3H), 3.23 (t, 2H), 3.89 (m, 2H), 6.30 (s, 1H), 7.09 (bs, 1H), 7.22 (bs, 1H), 7.40 (m, 2H), 7.57 (d, 1H), 7.98 (d, 1H), 8.62 (bs, 1H), 8.95 (bs, 1H).

Example 273

(S)—N-(1-(3-(3-chloro-4-cyanophenyl)-1H-pyrazol-1-yl)propan-2-yl)-1H-pyrazole-3-carboxamide To a mixture of 1H-pyrazole-3-carboxylic acid (89 mg, 0.767 mmol) in DCM (5 ml), was added DIPEA (0.40 ml, 2.30 mmol). O-(Benzotriazol-1-yl)-N,N,N',N'-tetramethyluroniumhexafluorophosphate (HBTU, 291.0 mg, 0.767 mmol) at RT. The mixture was stirred for 15 min and solid (S)-4-(1-(2-aminopropyl)-1H-pyrazol-3-yl)-2-chlorobenzonitrile (200 mg, 0.767 mmol) was added. The reaction was stirred overnight at RT. The solvent was evaporated and water was added. The pH of the water phase was adjusted to 9-10 and the product was extracted to DCM. The organic layer was washed with water and brine, dried over Na$_2$SO$_4$ and evaporated. The crude product was purified with flash chromatography (DCM/EtOAc gradient) to give title compound 100 mg. $^1$H-NMR (400 MHz; d6-DMSO): δ 1.11 (d, 3H), 4.36 (m, 3H), 6.58 (t, 1H), 6.93 (d, 1H), 7.79 (m, 1H), 7.82 (d, 1H), 7.98 (d, 2H), 8.08 (bs, 1H), 8.25 (d, 1H), 13.20 (s, 1H).

Example 274

(S)—N-(1-(3-(3-chloro-4-cyanophenyl)-1H-pyrazol-1-yl)propan-2-yl)-4-methyl-2-(pyridin-3-yl)-1H-imidazole-5-carboxamide 4-methyl-2-(pyridin-3-yl)-1H-imidazole-5-carboxylic acid (78 mg; 0.384 mmol) and DIPEA (0.20 ml, 1.151 mmol) were dissolved in 5 ml of dry DMF. HOBt hydrate (88 mg; 0.575 mmol) and EDCI (110 mg; 0.575 mmol) were added at RT. Solid (S)-4-(1-(2-aminopropyl)-1H-pyrazol-3-yl)-2-chlorobenzonitrile (100 mg; 0.384 mmol) was added in one portion and the reaction was stirred for 2 h at 60° C. temperature and stirred at RT overnight. Water (40 ml) was added and the mixture was allowed to stir 1 h at RT. The precipitated product was filtered, dried in vacuum at 40° C. for 12 h, to give the title compound 136 mg. $^1$H-NMR (400 MHz; d6-DMSO): δ 1.12 (d, 3H), 2.49 (s, 3H), 4.40 (m, 3H), 6.97 (d, 1H), 7.48 (m, 1H), 7.88 (m, 2H), 8.02 (m, 2H), 8.07 (d, 1H), 8.21 (m, 1H), 8.58 (m, 1H), 9.13 (d, 1H), 12.85 (s, 1H).

Example 275

(S)—N-(1-(3-(3-chloro-4-cyanophenyl)-1H-pyrazol-1-yl)propan-2-yl)-5-(4-methylpyridin-3-yl)thiophene-2-carboxamide a) 5-(4-methylpyridin-3-yl) thiophene-2-carboxylic Acid Ethyl 5-(4-methylpyridin-3-yl) thiophene-2-carboxylate (0.200 g, 0.809 mmol) was dissolved in ethanol (5 ml). 2 M sodium hydroxide solution (0.809 ml, 1.617 mmol) was added and the mixture was stirred at RT overnight. Ethanol was evaporated and water (5 ml) was added. The product was precipitated during the addition of 2 M HCl. The product was filtered and dried to give 98 mg. $^1$H-NMR (400 MHz; d6-DMSO): δ 2.43 (s, 3H), 7.38 (d, 1H), 7.39 (d, 1H), 7.77 (d, 1H), 8.46 (d, 1H), 8.59 (s, 1H).

b) (S)—N-(1-(3-(3-chloro-4-cyanophenyl)-1H-pyrazol-1-yl) propan-2-yl)-5-(4-methylpyridin-3-yl) thiophene-2-carboxamide The title compound was prepared from (S)-4-(1-(2-aminopropyl)-1H-pyrazol-3-yl)-2-chlorobenzonitrile (0.116 g, 0.446 mmol), 5-(4-methylpyridin-3-yl)thiophene-2-carboxylic acid (0.098 g, 0.446 mmol), DIPEA (0.233 ml, 1.337 mmol), HOBt hydrate (0.102 g, 0.668 mmol) and EDCI (0.128 g, 0.668 mmol) as described in the previous Example affording 0.115 g of the title compound. $^1$H-NMR (400 MHz; d6-DMSO): δ 1.19 (d, 3H), 2.41 (s, 3H), 4.32 (m, 2H), 4.43 (m, 1H), 6.95 (d, 1H), 7.33 (d, 1H) 7.37 (d, 1H), 7.79 (d, 1H), 7.85 (d, 1H), 7.94 (m, 2H), 8.07 (d, 1H), 8.45 (m, 2H), 8.55 (s, 1H).

Example 276

(S)—N-(1-(3-(3-chloro-4-cyanophenyl)-1H-pyrazol-1-yl)propan-2-yl)-1-(pyridin-3-yl)-1H-pyrazole-3-carboxamide The title compound was prepared from (S)-4-(1-(2-aminopropyl)-1H-pyrazol-3-yl)-2-chlorobenzonitrile (0.058 g, 0.307 mmol), 1-(pyridin-3-yl)-1H-pyrazole-3-carboxylic acid (0.080 g, 0.307 mmol), DIPEA (0.160 ml, 0.921 mmol), HOBt hydrate (0.071 g, 0.460 mmol) and EDCI (0.088 g, 0.460 mmol) using the method of Example 274 affording 0.120 g of the title compound. $^1$H-NMR (400 MHz; d6-DMSO): δ 1.18 (d, 3H), 4.38 (m, 2H), 4.50 (m, 1H), 6.89 (d, 1H), 6.95 (d, 1H), 7.59 (m, 1H), 7.90 (m, 3H), 8.04 (d, 1H), 8.30 (m, 1H), 8.38 (d, 1H), 8.60 (d, 1H), 8.65 (d, 1H), 9.19 (d, 1H).

Example 277

(S)—N-(1-(3-(3-chloro-4-cyanophenyl)-1H-pyrazol-1-yl)propan-2-yl)-3H-imidazo[4,5-b]pyridine-5-carboxamide The title compound was prepared from (S)-4-(1-(2-aminopropyl)-1H-pyrazol-3-yl)-2-chlorobenzonitrile (0.063 g, 0.384 mmol), 3H-imidazo[4,5-b]pyridine-5-carboxylic acid (0.100 g, 0.384 mmol), DIPEA (0.200 ml, 1.151 mmol), HOBt hydrate (0.088 g, 0.575 mmol) and EDCI (0.110 g, 0.575 mmol) using the method of Example 274 affording 0.130 g of the title compound. $^1$H-NMR (400 MHz; d6-DMSO): δ 1.17 (d, 3H), 4.45 (m, 3H), 6.93 (d, 1H), 7.99 (m, 6H), 8.64 (s, 1H), 8.99 (d, 1H).

Example 278

(S)—N-(1-(3-(3-chloro-4-cyanophenyl)-1H-pyrazol-1-yl)propan-2-yl)-1-(pyridin-4-yl)-1H-pyrazole-3-carboxamide The title compound was prepared from (S)-4-(1-(2-aminopropyl)-1H-pyrazol-3-yl)-2-chlorobenzonitrile (0.058 g, 0.307 mmol), 1-(pyridin-4-yl)-1H-pyrazole-3-carboxylic acid (0.080 g, 0.307 mmol), DIPEA (0.160 ml, 0.921 mmol), HOBt hydrate (0.071 g, 0.460 mmol) and EDCI (0.088 g, 0.460 mmol) using the method of Example 274 affording 0.110 g of the title compound. $^1$H-NMR (400 MHz; d6-DMSO): δ 1.19 (d, 3H), 4.36 (m, 2H), 4.49 (m, 1H), 6.90 (d, 1H), 6.94 (d, 1H), 7.85 (d, 1H), 7.90 (m, 2H), 7.94 (m, 2H), 8.02 (s, 1H), 8.38 (d, 1H), 8.69 (m, 2H), 8.75 (d, 1H).

Example 279

(S)—N-(1-(3-(3-chloro-4-cyano-5-fluorophenyl)-1H-pyrazol-1-yl)propan-2-yl)-3H-imidazo[4,5-b]pyridine-5-carboxamide The title compound was prepared from (S)-4-(1-(2-aminopropyl)-1H-pyrazol-3-yl)-2-chloro-6-fluorobenzonitrile (0.060 g, 0.215 mmol), 3H-imidazo[4,5b]pyridine-5-carboxylic acid (0.035 g, 0.215 mmol), DIPEA (0.112 ml, 0.646 mmol), HOBt hydrate (0.050 g, 0.323 mmol) and EDCI (0.062 g, 0.323 mmol) using the method of Example 274 affording 0.050 g of the title compound. $^1$H-NMR (400 MHz; d6-DMSO): δ 1.22 (d, 3H), 4.46 (m, 3H), 6.99 (d, 1H), 7.81 (d, 1H), 7.89 (m, 3H), 8.09 (d, 1H), 8.63 (s, 1H), 8.80 (d, 1H), 13.00 (bs, 1H).

Example 280

(S)—N-(1-(3-(3-chloro-4-cyano-5-fluorophenyl)-1H-pyrazol-1-yl)propan-2-yl)-2-(pyridin-3-yl)thiazole-4-carboxamide The title compound was prepared from (S)-4-(1-(2-aminopropyl)-1H-pyrazol-3-yl)-2-chloro-6-fluorobenzonitrile (0.060 g, 0.215 mmol), 2-(pyridin-3-yl)thiazole-4-carboxylic acid (0.044 g, 0.215 mmol), DIPEA (0.112 ml, 0.646 mmol), HOBt hydrate (0.050 g, 0.323 mmol) and EDCI (0.062 g, 0.323 mmol) using the method of Example 274 affording 0.080 g of the title compound. $^1$H-NMR (400 MHz; d6-DMSO): δ 1.20 (d, 3H), 4.40 (m, 2H), 4.51 (m, 1H), 7.02 (d, 1H), 7.81 (d, 1H), 7.94 (m, 3H), 8.33 (s, 1H), 8.38 (d, 1H), 8.54 (d, 1H), 8.71 (d, 1H), 9.25 (bs, 1H).

Example 281

(S)—N-(1-(3-(3-chloro-4-cyano-5-fluorophenyl)-1H-pyrazol-1-yl)propan-2-yl)-1-(pyridin-3-yl)-1H-pyrazole-3-carboxamide The title compound was prepared from (S)-4-(1-(2-aminopropyl)-1H-pyrazol-3-yl)-2-chloro-6-fluorobenzonitrile (0.050 g, 0.179 mmol), 1-(pyridin-3-yl)-1H-pyrazole-3-carboxylic acid (0.034 g, 0.179 mmol), DIPEA (0.094 ml, 0.538 mmol l), HOBt hydrate (0.041 g, 0.269 mmol) and EDCI (0.052 g, 0.269 mmol) using the method of Example 274 affording 0.079 g of the title compound. $^1$H-NMR (400 MHz; d6-DMSO): δ 1.19 (d, 3H), 4.38 (m, 2H), 4.49 (m, 1H), 6.89 (d, 1H), 7.01 (d, 1H), 7.59 (m, 1H), 7.88 (m, 3H), 8.30 (m, 1H), 8.35 (d, 1H), 8.59 (d, 1H), 8.65 (d, 1H), 9.18 (d, 1H).

Example 282

3-Acetyl-N-(2-(3-(3-chloro-4-cyanophenyl)isoxazol-5-yl)ethyl)-1H-pyrazole-5-carboxamide a) (E)-2-Chloro-4-((hydroxyimino) benzonitrile 2-chloro-4-formylbenzonitrile (2.0 g, 12.08 mmol) was dissolved in dry THF (30 ml). Pyridine (2.9 ml, 36.2 mmol) and hydroxylamine hydrochloride (1.68 g, 24.16 mmol) was added to the solution. The mixture was heated to 70° C. and stirred for 4 h. THF was evaporated and ice water (50 ml) was added. The mixture was stirred for 1 h and the precipitate was filtered off and washed twice with cold water. After drying at 35° C. overnight (2.04 g) of the title compound was obtained. $^1$H-NMR (400 MHz; d6-DMSO): 7.75 (dd, 1H), 7.90 (d, 1H), 7.99 (d, 1H), 8.23 (s, 1H), 11.93 (s, 1H).

b) (Z)-3-Chloro-4-cyano-N-hydroxybenzimidoyl Chloride (E)-2-chloro-4-((hydroxyimino) benzonitrile (2.04 g, 11.30 mmol) was dissolved in DMF (20 ml) and cooled to 0° C. N-Chlorosuccinimide (1.66 g, 12.43 mmol) was added and the mixture was allowed to warm to RT. The reaction mixture was stirred for 2 h at RT and poured into ice water. The product was filtered and dried to give 2.26 g of the title compound. $^1$H-NMR (400 MHz; d6-DMSO): δ 7.92 (dd, 1H), 8.03 (d, 1H), 8.08 (d, 1H), 13.06 (s, 1H).

c) tert-Butyl (2-(3-(3-chloro-4-cyanophenyl)isoxazol-5-yl)ethyl)carbamate tert-Butyl but-3-yn-1-ylcarbamate (0.7 g, 4.14 mmol) was dissolved in toluene (20 ml) and triethylamine (0.87 ml) was added at RT. (Z)-3-chloro-4-cyano-N-hydroxybenzimidoyl chloride (0.98 g, 4.55 mmol) was added in DMF (2 ml) to reaction mixture. After one hour in RT the reaction mixture was heated to 40° C. for 2 h. The white precipitate was filtered and the filtrate was washed with 1 M HCl, water and brine. Dried over anhydrous $Na_2SO_4$, filtered and evaporated. The crude product was purified by Flash chromatography (Heptane-EtOAc 2:1). Product fractions were combined and evaporated to give pure title compound (0.78 g). $^1$H-NMR (400 MHz; d6-DMSO): δ 1.35 (s, 9H), 2.95 (t, 2H), 3.30 (m, 2H), 7.04 (m, 2H), 8.00 (d, 1H), 8.12 (d, 1H), 8.18 (s, 1H).

d) 4-(5-(2-Aminoethyl)isoxazol-3-yl)-2-chlorobenzonitrile Hydrochloride tert-Butyl (2-(3-(3-chloro-4-cyanophenyl)isoxazol-5-yl) ethyl)carbamate (078 g, 2.24 mmol) was stirred with 13 w-% ethylacetate HCl solution (20 ml) for 2 h at RT. The mixture was filtered and the precipitate was washed with EtOAc, dried in vacuo at 30° C. overnight. The title compound 0.53 g was obtained. $^1$H-NMR (400 MHz; d6-DMSO): δ 3.21 (m, 4H), 7.22 (s, 1H), 8.02 (d, 1H), 8.14 (d, 1H), 8.20 (s, 1H), 8.27 (bs, 3H).

e) 3-Acetyl-N-(2-(3-(3-chloro-4-cyanophenyl)isoxazol-5-yl)ethyl)-1H-pyrazole-5-carboxamide The title compound was prepared from 4-(5-(2-aminoethyl)isoxazol-3-yl)-2-chlorobenzonitrile hydrochloride (0.080 g, 0.282 mmol), 3-acetyl-1H-pyrazole-5-carboxylic acid (0.043 g, 0.282 mmol), DIPEA (0.196 ml, 1.126 mmol l), HOBt hydrate (0.065 g, 0.422 mmol) and EDCI (0.081 g, 0.422 mmol) using the method of Example 274 affording 0.013 g of the title compound after preparative HPLC purification. $^1$H-NMR (400 MHz; d6-DMSO): δ 2.53 (s, 3H), 3.20 (t, 2H), 3.83 (m, 2H), 6.54 (s, 1H), 7.33 (bs, 1H), 7.63 (bs, 1H), 7.79 (m, 1H), 7.97 (bs, 1H).

Example 283

N-(2-(3-(3-chloro-4-cyanophenyl)isoxazol-5-yl)ethyl)-5-(pyridin-3-yl)-1H-pyrazole-3-carboxamide The title compound was prepared from 4-(5-(2-aminoethyl)isoxazol-3-yl)-2-chlorobenzonitrile hydrochloride (0.080 g, 0.282 mmol), 5-(pyridin-3-yl)-1H-pyrazole-3-carboxylic acid (0.053 g, 0.282 mmol), DIPEA (0.196 ml, 1.126 mmol l), HOBt hydrate (0.065 g, 0.422 mmol) and EDCI (0.081 g, 0.422 mmol) using the method of Example 274. The title compound was converted to HCl salt by treatment of 1 M HCl ether solution for 2 h affording 0.056 g of the title compound. $^1$H-NMR (400 MHz; d6-DMSO): 3.15 (t, 2H), 3.66 (m, 2H), 7.16 (s, 1H), 7.42 (bs, 1H), 7.90 (m, 1H), 8.02 (d, 1H), 8.13 (d, 1H), 8.21 (s, 1H), 8.63 (d, 1H), 8.75 (d, 1H), 8.83 (bs, 1H), 9.19 (s, 1H).

Example 284

Pyridine-2-carboxylic Acid {(E)-2-[5-(3,4-dichlorophenyl)furan-2-yl]vinyl}amide a) 2-Bromo-5-((E)-2-nitrovinyl)furan

5-Bromo-2-furaldehyde (5.26 g, 0.0300 mol) and nitromethane (2.2 ml, 2.43 g, 0.0300 mol) in methanol (40 ml) were added to NaOH (1.20 g, 0.0300 mol) in water (40 ml) at 0° C. The resulting mixture was stirred at 0° C. for 2 h and then diluted with ice-cold water (25 ml). The resulting solution was added slowly to 10% HCl (10 ml) at <0° C. The separated precipitate was filtered off, washed with water and heptane and dried to afford the title compound. $^1$H NMR (400 MHz, DMSO-$d_6$): 6.90 (1H, d), 7.30 (1H, d), 7.77 (1H, d), 7.96 (1H, d)

b) 2-Bromo-5-(2-nitro-1-phenylsulfanylethyl)furan

2-Bromo-5-((E)-2-nitrovinyl)furan (1.50 g, 0.006880 mol), thiofenol (0.91 ml, 0.99 g, 0.008945 mol) and N-isopropylcyclohexylamine (0.1 ml, 0.085 g, 0.0006017 mol) in dry methylene chloride (150 ml) was stirred in nitrogen atmosphere at RT for 4.5 h. Then the solution was washed with water, dried with $Na_2SO_4$ and evaporated. The product was stored in a freezer. $^1$H NMR (400 MHz, DMSO-$d_6$): 4.94-5.01 (1H, m), 5.11-5.17 (2H, m), 6.37 (1H, d), 6.49 (1H, d), 7.38 (5H, m).

c) 2-(5-Bromofuran-2-yl)-2-phenylsulfanylethylamine

Zinc powder (0.80 g, 0.01224 mol) was added to 2-bromo-5-(2-nitro-1-phenyl-sulfanylethyl)furan (0.60 g, 0.001828 mol) dissolved in the mixture of glacial acetic acid (24 ml) and concentrated hydrochloric acid (2.4 ml) at 80° C. in nitrogen atmosphere. The mixture was heated at 80° C. for 2.5 h. Then, 0.40 g (0.00612 mol) of zinc powder was added and the mixture was heated for 1 h. The reaction mixture was cooled and 36 ml of water was added. pH was adjusted to 9 by 2.5 M NaOH. The product was extracted into ethyl acetate. The organic phase was washed with water, dried and evaporated. $^1$H NMR (400 MHz, DMSO-$d_6$): 2.87 (1H, distorted dd), 2.97 (1H, distorted dd), 4.41 (1H, t), 6.21 (1H, d), 6.45 (1H, d), 7.31 (5H, m).

d) Pyridine-2-carboxylic Acid [2-(5-bromofuran-2-yl)-2-phenylsulfanylethyl]amide 2-(5-Bromofuran-2-yl)-2-phenylsulfanylethylamine (0.28 g, 0.0009389 mol), 2-pyridinecarboxylic acid (0.12 g, 0.001005 mol) and EDCI were stirred in dry THF (10 ml). After disappearing of the starting material the solvent was evaporated. Then chloroform was added and the solution was washed with 1 M $Na_2CO_3$ and water, dried with $Na_2SO_4$ and evaporated. The crude product was purified by flash chromatography using heptane-EtOAc as a gradient eluent (85:15-70:30). $^1$H NMR (400 MHz, DMSO-$d_6$): 3.75-3.80 (2H, m), 4.78-4.84 (1H, m), 6.33-6.37 (2H, m), 6.44 (1H, d), 7.26-7.40 (4H, m), 7.59-7.62 (1H, m), 7.97-8.04 (2H, m), 8.62-8.64 (1H, m), 9.08 (1H, m).

e) Pyridine-2-carboxylic Acid [2-benzenesulfinyl-2-(5-bromofuran-2-yl)ethyl]-amide Sodium periodate (57 mg, 0.2677 mmol) in a small amount of water was added to pyridine-2-carboxylic acid [2-(5-bromofuran-2-yl)-2-phenylsulfanylethyl]-amide (90 mg, 0.2231 mmol) in methanol (13 ml). After refluxing for 4 h another 57 mg (0.2677 mmol) of sodium periodate was added and refluxing was continued for 4.5 h. Water (30 ml) was added and the product was extracted into EtOAc. The organic phase was washed with water, dried with $Na_2SO_4$ and evaporated. The crude product was used as such in the next step.

f) Pyridine-2-carboxylic Acid [(E)-2-(5-bromofuran-2-yl)vinyl]amide

The mixture of pyridine-2-carboxylic acid [2-benzenesulfinyl-2-(5-bromofuran-2-yl)ethyl]amide (0.11 g, 0.2623 m mol) and $Na_2CO_3$ (0.03 g, 0.2623 mmol) in toluene was refluxed in nitrogen atmosphere for 2 h. The toluene solution was washed with 1 M NaOH (25 ml), dried with $Na_2SO_4$ and evaporated. The crude product was purified by flash chromatography using heptane-EtOAc as a gradient eluent (90:10-80:20). The E isomer was used in the next step.

g) Pyridine-2-carboxylic Acid {(E)-2-[5-(3,4-dichlorophenyl)furan-2-yl]vinyl}-amide Pyridine-2-carboxylic acid [(E)-2-(5-bromofuran-2-yl)vinyl]amide (0.014 g, 0.0477 mmol) was dissolved in 1,4-dioxane (4.2 ml) in a microwave reaction vial. 3,4-Dichlorophenylboronic acid (0.0091 g, 0.0477 mmol), potassium phosphate tribasic (0.020 g, 0.0954 mmol), 0.7 ml of water and tetrakis(triphenylphosphine)-palladium(0) (0.005 g, 0.0047 mmol) were added. After removal of oxygen the reaction mixture was irradiated for 10 min at 160° C. Then water (7 ml) was added. The product was extracted into EtOAc (2×15 ml). The organic phase was washed with water, dried over $Na_2SO_4$ and evaporated. The crude product was purified by flash chromatography (eluent: heptane-EtOAc 7:3). $^1$H NMR (400 MHz, CDCl$_3$): 6.26 (1H, d), 6.29 (1H, d), 6.66 (1H, d), 7.45 (1H, distorted d), 7.48-7.52 (2H, m), 7.69-7.76 (2H, m), 7.91 (1H, td), 8.27 (1H, d), 8.61 (1H, dd), 9.88 (1H, d).

Example 285

(S)—N-(1-(3-(3-chloro-4-cyanophenyl)-1H-pyrazol-1-yl)propan-2-yl)-3-isopropyl-1,2,4-oxadiazole-5-carboxamide The title compound was prepared using the method of Example 34(d) starting from (S)-4-(1-(2-aminopropyl)-1H-pyrazol-3-yl)-2-chlorobenzonitrile (0.33 g, 1.28 mmol), 3-isopropyl-1,2,4-oxadiazole-5-carboxylic acid (0.2 g, 1.28 mmol), HOBt (0.26 g, 1.92 mmol), DIPEA (0.7 mL, 3.84 mmol) and EDCI (0.37 g, 1.92 mmol) using DMF (10 mL) as solvent. Yield 0.197 g. $^1$H NMR (400 MHz; MeOD): δ 1.24 (d, 3H), 1.33 (d, 6H), 3.15 (m, 1H), 4.38 (m, 2H), 4.57 (m, 1H), 6.78 (d, 1H), 7.71 (d, 1H), 7.77 (m, 1H), 7.87 (dd, 1H), 8.02 (dd, 1H).

Example 286

(S)—N-(1-(3-(3-chloro-4-cyano-5-fluorophenyl)-1H-pyrazol-1-yl)propan-2-yl)-2-methyl-1-(3-oxobutyl)-1H-imidazole-4-carboxamide a) (S)—N-(1-(3-(3-chloro-4-cyano-5-fluorophenyl)-1H-pyrazol-1-yl)propan-2-yl)-2-methyl-1H-imidazole-4-carboxamide The title compound was prepared using the method of Example 34 (d) starting from 2-methyl-1H-imidazole-4-carboxylic acid (0.497 g, 3.94 mmol) and (S)-4-(1-(2-aminopropyl)-1H-pyrazol-3-yl)-2-chloro-6-fluorobenzonitrile (1.2 g, 4.31 mmol) of Example 116(f). The product was purified by flash-chromatography. Yield 10.21%. 1H-NMR (400 MHz; DMSO-d6): δ 1.07 (d, 3H), 2.31 (s, 3H), 4.25-4.46 (m, 3H), 7.02 (d, 1H), 7.42 (d, 1H), 7.86 (d, 1H), 7.93 (dd, 1H), 8.00 (s, 1H), 8.07 (d, 1H), 12.11 (s, 1H).

b) (S)—N-(1-(3-(3-chloro-4-cyano-5-fluorophenyl)-1H-pyrazol-1-yl)propan-2-yl)-2-methyl-1-(3-oxobutyl)-1H-imidazole-4-carboxamide 1-Methylimidazole (1.030 µl, 0.013 mmol) and DMSO (3 ml) were added into a flask. (S)—N-(1-(3-(3-chloro-4-cyano-5-fluorophenyl)-1H-pyrazol-1-yl)propan-2-yl)-2-methyl-1H-imidazole-4-carboxamide (100 mg, 0.259 mmol) dissolved in 3 ml of DMSO was added. Lastly methyl vinyl ketone (0.065 ml, 0.776 mmol) was added and the resulting mixture was stirred in 70° C. for 2.5 h. The mixture was stirred at RT during the night and in the next morning the temperature was again raised to 70° C. for 3.5 h. During the last part of the reaction a total of 0.195 ml of methyl vinyl ketone and 16.48 µl of 1-methylimidazole were added and the mixture was stirred at 70° C. for three days. 10 ml of water was poured into the mixture and the resulting white solution was extracted with ethyl acetate. Combined ethyl acetate phases were dried, filtered and evaporated. The product was purified by flash-chromatography and recrystallization from ACN/water, respectively. Yield 42.3%. 1H-NMR (400 MHz; DMSO-d6): δ 1.05 (d, 3H), 2.09 (s, 3H), 2.35 (s, 3H), 2.97 (t, 2H), 4.04 (t, 2H), 4.23-4.45 (m, 3H), 7.01 (d, 1H), 7.48 (s, 1H), 7.85 (d, 1H), 7.93 (dd, 1H), 8.00 (s, 1H), 8.05 (d, 1H).

Example 287

(S)—N-(1-(3-(3-chloro-4-cyano-5-fluorophenyl)-1H-pyrazol-1-yl)propan-2-yl)-1-(3-hydroxy-3-methylbutyl)-2-methyl-1H-imidazole-4-carboxamide Methylmagnesium bromide 3M in Et$_2$O-solution (0.128 ml, 0.383 mmol) and dry THF (1 ml) were added into a flask and heated to 30° C. (S)—N-(1-(3-(3-chloro-4-cyano-5-fluorophenyl)-1H-pyrazol-1-yl)propan-2-yl)-2-methyl-1-(3-oxobutyl)-1H-imidazole-4-carboxamide (35 mg, 0.077 mmol) of Example 286(b) dissolved in THF (5 ml) was added very slowly. The reaction mixture was heated to 45° C. and stirred for 5 h. Another batch of methylmagnesium bromide 3M in EtO$_2$-solution (0.128 ml, 0.383 mmol) was added and the mixture was stirred at RT overnight. Next day the reaction mixture was poured into 10 ml of saturated ammonium chloride, THF was evaporated and the remaining water phase was extracted with ethyl acetate. The ethyl acetate phases were combined, dried and evaporated. The product was purified by flash-chromatography. Yield 19.32%. 1H-NMR (400 MHz; DMSO-d6): δ 1.06 (d, 3H), 1.12 (s, 6H), 1.69-1.77 (m, 2H), 2.34 (s, 3H), 3.92-3.98 (m, 2H), 4.25-4.46 (m, 4H), 7.01 (d, 1H), 7.50 (s, 1H), 7.85 (d, 1H), 7.92 (dd, 1H), 8.00 (s, 1H), 8.03 (d, 1H).

Example 288

(S)—N-(1-(3-(3-chloro-4-cyano-5-fluorophenyl)-1H-pyrazol-1-yl)propan-2-yl)imidazo[1,2-a]pyridine-2-carboxamide a) Imidazo[1,2-a]pyridine-2-carboxylic Acid Into a flask containing a mixture of ethyl imidazo[1,2-a]pyridine-2-carboxylate (1 g, 5.26 mmol), THF (5 ml) and water (5 ml), lithium hydroxide (0.378 g, 15.77 mmol) was added and stirred overnight at RT. The pH of the reaction mixture was adjusted to 2 with 2 M HCl and THF was evaporated. The remaining water phase was extracted with ethyl acetate and the combined ethyl acetate phases were dried. The product had precipitated into the water phase. Water was evaporated, and the remaining solid recrystallized from methanol. The product was used as a salt in the next step. 1H-NMR (400 MHz; DMSO-d6): δ 7.23-7.26 (m, 1H), 7.63-7.70 (m, 1H), 7.76 (dd, 1H), 8.72 (s, 1H), 8.73-8.77 (m, 1H).

b) (S)—N-(1-(3-(3-chloro-4-cyano-5-fluorophenyl)-1H-pyrazol-1-yl)propan-2-yl)imidazo[1,2-a]pyridine-2-carboxamide The title compound was prepared using the method of Example 34(d) starting from imidazo[1,2-a]pyridine-2-carboxylic acid (0.853 g, 5.26 mmol) and (S)-4-(1-(2-aminopropyl)-1H-pyrazol-3-yl)-2-chloro-6-fluorobenzonitrile (1.0 g, 3.59 mmol). The product was purified by flash chromatography and recrystallization from acetonitrile/water, respectively. Yield 39.0%. 1H-NMR (400 MHz; DMSO-d6): δ 1.13 (d, 3H), 4.35 (dd, 1H), 4.43 (dd, 1H), 4.47-4.57 (m, 1H), 6.96-7.01 (m, 1H), 7.02 (d, 1H), 7.34-7.40 (m, 1H), 7.60 (dd, 1H), 7.89 (d, 1H), 7.93 (dd, 1H), 7.97 (s, 1H), 8.32 (d, 1H), 8.55-8.58 (m, 1H), 8.61 (d, 1H).

Example 289

(S)—N-(1-(3-(3-chloro-4-cyano-5-methoxyphenyl)-1H-pyrazol-1-yl)propan-2-yl)-5-(2-hydroxypropan-2-yl)isoxazole-3-carboxamide a) (S)—N-(1-(3-(3-chloro-4-cyano-5-fluorophenyl)-1H-pyrazol-1-yl)propan-2-yl)-5-(2-hydroxypropan-2-yl)isoxazole-3-carboxamide The title compound was prepared using the method of Example 34(d) starting from 5-(2-hydroxypropan-2-yl)isoxazole-3-carboxylic acid (0.096 g, 0.560 mmol) of Example 77(a) and (S)-4-(1-(2-aminopropyl)-1H-pyrazol-3-yl)-2-chloro-6-fluorobenzonitrile (0.12 g, 0.431 mmol) of Example 116(f). The product was purified by recrystallization from ethanol. Yield 36.0%. 1H-NMR (400 MHz;

DMSO-d6): δ 1.16 (d, 3H), 1.47 (s, 6H), 4.32 (d, 2H), 4.39-4.51 (m, 1H), 5.67 (s, 1H), 6.49 (s, 1H), 7.01 (d, 1H), 7.85 (d, 1H), 7.87 (dd, 1H), 7.99 (s, 1H), 8.74 (d, 1H).

b) (S)—N-(1-(3-(3-chloro-4-cyano-5-methoxyphenyl)-1H-pyrazol-1-yl)propan-2-yl)-5-(2-hydroxypropan-2-yl)isoxazole-3-carboxamide A mixture of (S)—N-(1-(3-(3-chloro-4-cyano-5-fluorophenyl)-1H-pyrazol-1-yl)propan-2-yl)-5-(2-hydroxypropan-2-yl)isoxazole-3-carboxamide (50 mg, 0.116 mmol), 5 ml of dry methanol and cesium carbonate (75 mg, 0.232 mmol) was reacted with stirring for 6 days keeping the temperature at 60° C. during the day and at RT during the night. The mixture was evaporated dissolved in DCM, extracted with water and dried. The product was purified by flash chromatography. Yield 60.3%. 1H-NMR (400 MHz; DMSO-d6): δ 1.15 (d, 3H), 1.46 (s, 6H), 4.01 (s, 3H), 4.32 (d, 2H), 4.40-4.51 (m, 1H), 5.68 (s, 1H), 6.49 (s, 1H), 7.00 (d, 1H), 7.54 (d, 1H), 7.67 (d, 1H), 7.83 (d, 1H), 8.75 (d, 1H).

Example 290

(S)—N-(1-(3-(3-chloro-4-cyano-5-fluorophenyl)-1H-pyrazol-1-yl)propan-2-yl)-1-(pyridin-3-yl)-1H-imidazole-4-carboxamide 3-Pyridineboronic acid 1,3-propanediol ester (43.7 mg, 0.268 mmol), (S)—N-(1-(3-(3-chloro-4-cyano-5-fluorophenyl)-1H-pyrazol-1-yl)propan-2-yl)-1H-imidazole-4-carboxamide (50 mg, 0.134 mmol), anhydrous copper(II) acetate (36.5 mg, 0.201 mmol), pyridine (0.022 ml, 0.268 mmol) and DCM (1 ml) were added into a flask and stirred at RT for 47 h. The reaction mixture was extracted with ethyl acetate, dried, filtered and evaporated. The product was purified by column chromatography. Yield 16.57%. 1H-NMR (400 MHz; CDCl$_3$): δ 1.24 (d, 3H), 4.28 (dd, 1H), 4.47 (dd, 1H), 4.57-4.67 (m, 1H), 6.64 (d, 1H), 7.48-7.55 (m, 2H), 7.74-7.78 (m, 1H), 7.81 (d, 1H), 7.88 (d, 1H), 7.91-7.94 (m, 2H), 8.27 (d, 1H), 8.72 (d, 1H), 8.79 (d, 1H).

Example 291

(S)—N-(1-(3-(3-chloro-4-cyanophenyl)-1H-pyrazol-1-yl)propan-2-yl)-1H-benzo[d]imidazole-2-carboxamide The title compound was prepared using the method of Example 34(d) starting from 1H-benzo[d]imidazole-2-carboxylic acid (100 mg, 0.617 mmol) and (S)-4-(1-(2-aminopropyl)-1H-pyrazol-3-yl)-2-chlorobenzonitrile (161 mg, 0.617 mmol) using N,N-dimethyl formamide as the solvent. The product was purified by flash chromatography and recrystallized from chloroform, respectively. Yield 20.03%. 1H-NMR (400 MHz; CDCl$_3$): δ 1.33 (d, 3H), 4.32 (dd, 1H), 4.47 (dd, 1H), 4.64-4.75 (m, 1H), 6.59 (d, 1H), 7.34-7.41 (m, 2H), 7.50 (d, 1H), 7.52-7.56 (m, 1H), 7.62 (d, 1H), 7.81-7.87 (m, 2H), 8.00 (d, 1H), 8.42 (d, 1H), 10.87 (s, 1H).

Example 292

(S)—N-(1-(3-(3-chloro-4-cyanophenyl)-1H-pyrazol-1-yl)propan-2-yl)-3,3'-bipyridine-6-carboxamide The title compound was prepared using the method of Example 34(d) starting from 5-(pyridin-3-yl)picolinic acid (130 mg, 0.549 mmol) and (S)-4-(1-(2-amino-propyl)-1H-pyrazol-3-yl)-2-chlorobenzonitrile (150 mg, 0.577 mmol) using N,N-dimethyl formamide as the solvent. The product was purified by flash chromatography. Yield 45.2%. 1H-NMR (400 MHz; DMSO-d6): δ 1.18 (d, 3H), 4.38 (dd, 1H), 4.46 (dd, 1H), 4.49-4.59 (m, 1H), 6.96 (d, 1H), 7.59 (q, 1H), 7.87 (d, 1H), 7.97 (dd, 1H), 8.01 (d, 1H), 8.06-8.12 (m, 2H), 8.21-8.26 (m, 1H), 8.35 (dd, 1H), 8.69 (dd, 1H), 9.01-9.07 (m, 2H), 9.14 (d, 1H).

Example 293

1-(5-((S)-1-(3-(3-chloro-4-cyanophenyl)-1H-pyrazol-1-yl)propan-2-yl-carbamoyl)-1H-pyrazol-3-yl) ethyl Acetate A flask containing N—((S)-1-(3-(3-chloro-4-cyanophenyl)-1H-pyrazol-1-yl)-propan-2-yl)-3-(1-hydroxyethyl)-1H-pyrazole-5-carboxamide (400 mg, 1.003 mmol) and DMAP (12.25 mg, 0.100 mmol) was put under nitrogen atmosphere. Pyridine (10 ml) was added, the reaction mixture cooled down to 0° C. and acetic anhydride (0.099 ml, 108 mg) was added dropwise. The mixture was allowed to warm to RT and stirred overnight. Next day the mixture was evaporated and purified by flash chromatography. Yield 58.9%. 1H-NMR (400 MHz; DMSO-d6): δ 1.15 (d, 3H), 1.51 (d, 3H), 2.02 (s, 3H), 4.25-4.37 (m, 2H), 4.39-4.49 (m, 1H), 5.88 (q, 1H), 6.64 (s, 1H), 6.90 (dd, 1H), 7.80 (dd, 1H), 7.91-7.96 (m, 2H), 8.04-8.07 (m, 1H), 8.15 (s, 1H), 13.24 (s, 1H).

Example 294

1-(1-acetyl-3-((S)-1-(3-(3-chloro-4-cyanophenyl)-1H-pyrazol-1-yl)propan-2-ylcarbamoyl)-1H-pyrazol-5-yl)ethyl Acetate The title compound was isolated as a side product from the reaction described in Example 293. Yield 1.920%. 1H-NMR (400 MHz; DMSO-d6): δ 1.17 (d, 3H), 1.47 (dd, 3H), 2.04 (s, 3H), 2.72 (s, 3H), 4.29-4.41 (m, 2H), 4.42-4.53 (m, 1H), 6.28 (q, 1H), 6.85 (d, 1H), 6.95 (d, 1H), 7.83-7.85 (m, 1H), 7.9-7.94 (m, 1H), 7.97 (dd, 1H), 8.06 (s, 1H), 8.40 (d, 1H).

Example 295

(S)-2-acetyl-N-(1-(3-(3-chloro-4-cyanophenyl)-1H-pyrazol-1-yl)propan-2-yl)thiazole-4-carboxamide The title compound was prepared using the method of Example 34(d) starting from 2-acetylthiazole-4-carboxylic acid (1.444 g, 8.44 mmol) and (S)-4-(1-(2-amino-propyl)-1H-pyrazol-3-yl)-2-chlorobenzonitrile (2.0 g, 7.67 mmol). The product was purified by recrystallization from ethanol. Yield 93%. 1H-NMR (400 MHz; DMSO-d6): δ 1.20 (d, 3H), 2.70 (s, 3H), 4.37 (dd, 1H), 4.44 (dd, 1H), 4.48-4.56 (m, 1H), 6.96 (d, 1H), 7.87 (d, 1H), 7.92 (dd, 1H), 7.97 (dd, 1H), 8.04 (d, 1H), 8.48 (d, 1H), 8.61 (s, 1H).

Example 296

1-(4-((S)-1-(3-(3-chloro-4-cyanophenyl)-1H-pyrazol-1-yl)propan-2-yl-carbamoyl)thiazol-2-yl)ethyl acetate a) N—((S)-1-(3-(3-chloro-4-cyanophenyl)-1H-pyrazol-1-yl)propan-2-yl)-2-(1-hydroxyethyl)thiazole-4-carboxamide Into a flask containing (S)-2-acetyl-N-(1-(3-(3-chloro-4-cyanophenyl)-1H-pyrazol-1-yl)propan-2-yl)thiazole-4-carboxamide (1 g, 2.416 mmol) dissolved in ethanol (10 ml), sodium borohydride (0.137 g, 3.62 mmol) was added in small parts under nitrogen atmosphere. The following mixture was stirred overnight in RT. Next morning water (1 ml) was added dropwise and the pH of the mixture was adjusted to under 7 with 1 M HCl and the mixture was evaporated. 30 ml of ethyl acetate was added and stirred for 30 min, filtered and the filtrate was evaporated and dried in vacuum at 40° C. The product was purified by recrystallizing it twice from diethyl ether/ethanol to yield 41.6% of the title compound. 1H-NMR (400 MHz; DMSO-d6): δ 1.10-1.16 (m, 3H), 1.44-1.48 (m, 3H), 4.29-4.52 (m, 3H), 4.94-4.02 (m, 3H), 6.22-6.26 (m, 1H), 6.95-6.99 (m, 1H), 7.83-7.88 (m, 1H), 7.93-8.00 (m, 2H), 8.07-8.10 (m, 1H), 8.11 (d, 1H), 8.33-4.39 (m, 1H).

b) 1-(4-((S)-1-(3-(3-chloro-4-cyanophenyl)-1H-pyrazol-1-yl)propan-2-yl-carbamoyl)thiazol-2-yl) ethyl Acetate N—((S)-1-(3-(3-chloro-4-cyanophenyl)-1H-pyrazol-1-yl)propan-2-yl)-2-(1-hydroxy-ethyl)thiazole-4-carboxamide (250 mg, 0.601 mmol), 4-dimethylaminopyridine (7.34 mg, 0.060 mmol) and pyridine (3 ml) were added into a flask and the mixture was cooled to 0° C. Acetic anhydride (0.063 ml, 0.661 mmol) was added dropwise and the mixture was allowed to warm to RT with stirring. The reaction was left to react overnight. Next morning more acetic anhydride (10 μl, 0.106 mmol) was added and the reaction was stirred for another hour in RT. The mixture was evaporated and dried overnight in vacuum at 40° C. The product was purified by recrystallization twice from ethanol/heptanes to yield 24.09% of final product. 1H-NMR (400 MHz; DMSO-d6): δ 1.14 (d, 3H), 1.62 (dd, 3H), 2.11 (s, 3H), 4.29-4.53 (m, 3H), 6.02-6.10 (m, 1H), 6.94-6.98 (m, 1H), 7.84-7.87 (m, 1H), 7.92-8.00 (m, 2H), 8.07 (d, 1H), 8.22 (d, 1H), 8.38-4.49 (m, 1H).

Example 297

N—((S)-1-(3-(3-chloro-4-cyanophenyl)-1H-pyrazol-1-yl)propan-2-yl)-2-(1-hydroxyethyl)thiazole-4-carboxamide The following method allows preparation of pure diastereomers form optically pure 1-hydroxyl propionamides. The procedure starting from racemic starting material is described here.

a) 2-(tert-butyldiphenylsilyloxy)propanamide 2-hydroxy-propanamide (227 mg, 2.55 mmol), DMF (2 ml), tert-butylchloro-diphenyl-silane (1.0 ml, 1057 mg), imidazole (266 mg, 3.91 mmol) and 4-dimethyl-amino-pyridine (93 mg, 0.764 mmol) dissolved in DMF (2 ml) were stirred under nitrogen atmosphere over the weekend. After the weekend the temperature was raised to 90° C. and was left to react for another 4 h. The mixture was then evaporated and extracted with DCM/water and the combined organic phases were evaporated. The product was purified by column chromatography. 1H-NMR (400 MHz; DMSO-d6): δ 1.04 (d, 9H), 1.12 (d, 3H), 4.00 (q, 1H), 7.04 (bs, 1H), 7.24 (bs, 1H), 7.40-7.51 (m, 6H), 7.58-7.66 (m, 4H).

b) 2-(tert-butyldiphenylsilyloxy)propanethioamide

A flask containing 2,4-bis(4-methoxyphenyl)-1,3-dithia-2,4-diphosphetane-2,4-disulfide (387 mg, 0.957 mmol) was put under nitrogen atmosphere. 2-(tert-butyl-diphenylsilyloxy)propanamide (622 mg, 1.899 mmol) dissolved in dry THF (10 ml) was added, temperature was raised to 60° C. and the mixture was allowed to react for 3 h. The solvent was evaporated and the product was extracted from DCM/water. The product was used in the next step without further purification. LC-MS: [M+1]=344.56.

c) 2-(1-(tert-butyldiphenylsilyloxy)ethyl)thiazole-4-carboxylic Acid

A flask containing 3-bromopyruvic acid (317 mg, 1.901 mmol) was put under nitrogen atmosphere. 2-(tert-butyldiphenylsilyloxy)propanethioamide (653 mg, 1.901 mmol) was dissolved in dry THF (8 ml) and added through a septum. The following mixture was refluxed for two hours and then allowed to cool to RT. The solvent was evaporated and extracted with DCM/water and the combined organic phases were evaporated. 1H-NMR (400 MHz; DMSO-d6): δ 1.07 (s, 9H), 1.35 (d, 3H), 5.14 (q, 1H), 7.39-7.54 (m, 2H), 7.57-7.61 (m, 2H), 7.26-7.69 (m, 2H), 8.38 (s, 1H).

d) 2-(1-(tert-butyldiphenylsilyloxy)ethyl)-N—((S)-1-(3-(3-chloro-4-cyanophenyl)-1H-pyrazol-1-yl) propan-2-yl)thiazole-4-carboxamide The title compound was prepared using the method of Example 34(d) starting from 2-(1-(tert-butyldiphenylsilyloxy)ethyl)thiazole-4-carboxylic acid (326 mg, 0.792 mmol) and (S)-4-(1-(2-aminopropyl)-1H-pyrazol-3-yl)-2-chlorobenzonitrile (105 mg, 0.403 mmol). After extraction, based on the LC-MS data, the product was estimated to be pure enough for the next step. LC-MS: [M+1]=655.30.

e) N—((S)-1-(3-(3-chloro-4-cyanophenyl)-1H-pyrazol-1-yl)propan-2-yl)-2-(1-hydroxyethyl)thiazole-4-carboxamide 2-(1-(tert-butyldiphenylsilyloxy)ethyl)-N—((S)-1-(3-(3-chloro-4-cyanophenyl)-1H-pyrazol-1-yl)propan-2-yl)thiazole-4-carboxamide (264 mg, 0.403 mmol) dissolved in THF (20 ml) and tetrabutylammonium fluoride, 1.0 M solution in THF (0.41 ml, 0.410 mmol), were added into a flask and stirred at RT overnight. After reacting for an hour, more of tetrabutylammonium fluoride, 1.0 M solution in THF (0.41 ml, 0.410 mmol), was added. The crude product was dried by evaporating and extracted with DCM/water. The organic phase was isolated with phase separator and evaporated. The product was purified by flash chromatography and recrystallization from ethyl acetate/heptane, respectively. 1H-NMR (400 MHz; DMSO-d6): δ 1.10-1.15 (m, 3H), 1.46 (t, 3H), 4.29-4.52 (m, 3H), 4.93-5.01 (m, 1H), 6.24 (s, 1H), 6.94-6.98 (m, 1H), 7.83-7.87 (m, 1H), 7.92-8.00 (m, 2H), 8.08 (s, 1H), 8.10 (d, 1H), 8.33-8.39 (m, 1H).

Example 298

(S)-3-acetyl-N-(1-(3-(3,4-dichlorophenyl)-1H-pyrazol-1-yl)propan-2-yl)-1H-pyrazole-5-carboxamide a) 5-(3,4-dichlorophenyl)-1-(tetrahydro-2H-pyran-2-yl)-1H-pyrazole 1-(Tetrahydro-2H-pyran-2-yl)-1H-pyrazole-5-boronic acid pinacol ester (6.16 g, 22.13 mmol) and 4-Bromo-1,2-dichloro-benzene (2.84 ml, 22.13 mmol) were dissolved in DMF (20 ml) under nitrogen atmosphere. Bis(triphenylphosphine)-palladium(II) chloride (0.777 g, 1.107 mmol) was added along with sodium carbonate (22.13 ml, 44.3 mmol) and the resulting mixture was stirred at 50° C. for 3 h. DMF was evaporated, water was added (15 ml) and extracted with ethyl acetate. Combined organic phases were dried with $Na_2SO_4$, filtered and dried with vacuum at 40° C. The product was purified by recrystallization from diethyl ether and diethyl ether/heptane, respectively. 1H-NMR (400 MHz; DMSO-d6): δ 1.50-1.69 (m, 3H), 1.77-1.84 (m, 1H), 1.91-2.00 (m, 1H), 2.31-2.44 (m, 1H), 3.54-3.62 (m, 1H), 3.96-4.02 (m, 1H), 5.23 (dd, 1H), 6.89 (d, 1H), 7.53 (dd, 1H), 7.60 (d, 1H), 7.77-7.82 (m, 2H).

b) 5-(3,4-dichlorophenyl)-1H-pyrazole 5-(3,4-Dichlorophenyl)-1-(tetrahydro-2H-pyran-2-yl)-1H-pyrazole (2.840 g, 9.56 mmol) and 10% HCl in EtOH (1.9 mmol/ml) (10 ml) were added into a flask and stirred over the weekend at RT. The mixture was then evaporated. Water (45 ml) was added and the mixture was neutralized with saturated $NaHCO_3$. The mixture was extracted with ethyl acetate and the combined organic phases dried with $Na_2SO_4$. The drying agent was filtered off and the resulting mixture evaporated and dried with vacuum at 40° C. The product was used as such, without any further purifications. 1H-NMR (400 MHz; DMSO-d6): δ 6.83-6.86 (m, 1H), 7.65 (d, 1H), 7.72-7.86 (m, 2H), 8.05 (d, 1H), 13.06 (s, 1H).

c) (S)-1-(3-(3,4-dichlorophenyl)-1H-pyrazol-1-yl)propan-2-amine

Into a flask containing 5-(3,4-dichlorophenyl)-1H-pyrazole (1.5 g, 7.04 mmol), (S)-tert-butyl 1-hydroxypropan-2-ylcarbamate (1.357 g, 7.74 mmol) and triphenylphosphine (2.77 g, 10.56 mmol), dry THF (30 ml) was added under nitrogen atmosphere. After few minutes of stirring, DIAD (2.77 ml, 14.08 mmol) was added dropwise through a septum while using icebath to prevent the temperature from rising. The resulting mixture was stirred at RT overnight. The mixture was evaporated. The Boc-protection was removed by adding ethanol (7 ml), 10% HCl/EtOH (50 ml), concentrated HCl (5 ml) and stirring the mixture over the weekend. The mixture was evaporated, extracted with DCM/water. The pH of the water phase was adjusted to ~12 using 2 M NaOH and extracting the phase again with DCM. The combined organic phases were dried with $Na_2SO_4$, filtered and evaporated. 1H-NMR (400 MHz; DMSO-d6): δ 1.00 (d, 3H), 4.70-4.87 (m, 3H), 6.84 (d, 1H), 7.65 (d, 1H), 7.76-7.84 (m, 2H), 8.02 (d, 1H).

d) (S)-3-acetyl-N-(1-(3-(3,4-dichlorophenyl)-1H-pyrazol-1-yl)propan-2-yl)-1H-pyrazole-5-carboxamide The title compound was prepared using the method of Example 34(d) starting from 3-acetyl-1H-pyrazole-5-carboxylic acid (71.9 mg, 0.466 mmol) and (S)-1-(3-(3,4-dichlorophenyl)-1H-pyrazol-1-yl)propan-2-amine (126 mg, 0.466 mmol). The product was purified by recrystallization from acetonitrile. Yield 12.61%. 1H-NMR (400 MHz; DMSO-d6): δ 1.05-1.25 (m, 3H), 4.18-4.53 (m, 3H), 6.79 (s, 1H), 7.31 (s, 1H), 7.57-7.85 (m, 3H), 7.89-7.98 (m, 1H), 8.39-8.54 (m, 1H), 14.05&14.12 (2 broad s, 1H).

Example 299

(S,E/Z)—N-(1-(3-(4-cyano-3,5-difluorophenyl)-1H-pyrazol-1-yl)propan-2-yl)-3-(1-(hydroxyimino)ethyl)-1H-pyrazole-5-carboxamide Into a flask containing (S)-3-acetyl-N-(1-(3-(4-cyano-3,5-difluorophenyl)-1H-pyrazol-1-yl)propan-2-yl)-1H-pyrazole-5-carboxamide (50.0 mg, 0.126 mmol) of Example 78 dissolved in ethanol (3 ml) and THF (1 ml), hydroxylamine HCl (10.47 mg, 0.151 mmol) and anhydrous sodium acetate (12.36 mg, 0.151 mmol) were added. The following mixture was stirred at RT for 5 h after which 5 drops of dimethylamine was added. Stirring continued overnight. Next day the mixture was evaporated and extracted with ethyl acetate/water. The combined organic phases were dried with $Na_2SO_4$, filtered and evaporated. The crude product was dried with vacuum at 40° C. over the weekend. The product was pure enough without further purification steps. The product was obtained as a mixture of E/Z isomers of oxime. Yield 82%. 1H-NMR (400 MHz; DMSO-d6): δ 1.13-1.19 (m, 3H), 2.11 (s, 2H, E/Z), 2.16 (s, 1H, E/Z), 4.26-4.37 (m, 2H), 4.40-4.51 (m, 1H), 6.97 (d, 1H), 7.71 (s, 1H), 7.74 (s, 1H), 7.82-7.84 (m, 1H), 8.26 (bs, 1H), 11.07 (bs, ~0.5H), 11.27 (bs, ~0.5H), 13.48 (bs, 1H).

Example 300

N—((S)-1-(4-chloro-3-(3-chloro-4-cyanophenyl)-1H-pyrazol-1-yl)propan-2-yl)-3-(1-hydroxyethyl)-1H-pyrazole-5-carboxamide Into a 0° C. solution containing sodium tetrahydroborate (0.022 g, 0.580 mmol) dissolved in ethanol (1 ml), (S)-3-acetyl-N-(1-(4-chloro-3-(3-chloro-4-cyanophenyl)-1H-pyrazol-1-yl)propan-2-yl)-1H-pyrazole-5-carboxamide (0.125 g, 0.290 mmol) of Example 224 dissolved in 2 ml of ethanol was added slowly. The mixture was stirred at 0° C. for a few minutes after which the mixture was allowed to warm to RT and the stirring was continued for 4.5 h. A few drops of water was added slowly. The pH was adjusted below 4 with 2 M HCl. The solvent was evaporated and the residue extracted with DCM/water. Organic phase was isolated with phase separator and evaporated. The product was purified by recrystallization from ethanol. Yield 51.0%. 1H-NMR (400 MHz; DMSO-d6): δ 1.14 (d, 3H), 1.38 (d, 3H), 4.23-4.37 (m, 2H), 4.40-4.50 (m, 1H), 4.75-4.83 (m, 1H), 5.40 (d, 1H), 6.40 (s, 1H), 8.00 (dd, 1H), 8.04 (dd, 1H), 8.05-8.14 (m, 3H), 13.03 (s, 1H).

Example 301

(R,E/Z)—N-(2-(3-(4-cyano-3,5-difluorophenyl)-1H-pyrazol-1-yl)propyl)-3-(1-(hydroxyimino)ethyl)-1H-pyrazole-5-carboxamide a) (R)-3-acetyl-N-(2-(3-(4-cyano-3,5-difluorophenyl)-1H-pyrazol-1-yl)propyl)-1H-pyrazole-5-carboxamide The title compound was prepared using the method of Example 34(d) starting from 3-acetyl-1H-pyrazole-5-carboxylic acid (0.229 g, 1.486 mmol) and (R)-4-(1-(1-aminopropan-2-yl)-1H-pyrazol-3-yl)-2,6-difluorobenzonitrile (0.380 g, 1.449 mmol). The product was purified by flash chromatography. Yield 64.4%. 1H-NMR (400 MHz; $CDCl_3$): δ 1.62 (d, 3H), 2.55 (s, 3H), 3.74-3.83 (m, 1H), 3.90-3.98 (m, 1H), 4.60-4.69 (m, 1H), 6.59 (d, 1H), 7.31 (bs, 1H), 7.51 (d, 1H), 7.53 (s, 1H), 7.55 (s, 1H), 7.60 (bs, 1H), 10.97 (bs, 1H).

b) (R,E/Z)—N-(2-(3-(4-cyano-3,5-difluorophenyl)-1H-pyrazol-1-yl)propyl)-3-(1-(hydroxyimino)ethyl)-1H-pyrazole-5-carboxamide Into a solution containing (R)-3-acetyl-N-(2-(3-(4-cyano-3,5-difluorophenyl)-1H-pyrazol-1-yl)propyl)-1H-pyrazole- 5-carboxamide (50.2 mg, 0.126 mmol) dissolved in ethanol (3 ml), hydroxylamine hydrochloride (10.51 mg, 0.151 mmol) and anhydrous sodium acetate (12.40 mg, 0.151 mmol) were added. After stirring the resulting at RT for 5 h, 5 drops of dimethylamine was added and stirring was continued overnight. The mixture was evaporated, extracted with ethyl acetate/water, combined organic phases dried with $Na_2SO_4$, filtered and evaporated. The final product was purified by flash chromatography. The product was obtained as a mixture of E/Z isomers of oxime. Yield 81%. 1H-NMR (400 MHz; DMSO-d6): δ 1.48 (d, 3H), 2.10 (s, 2.25H, E/Z), 2.14 (s, 0.75H, E/Z), 3.56-3.72 (m, 2H), 4.62-4.76 (m, 1H), 6.98 (d, 1H), 7.76 (s, 1H), 7.79 (s, 1H), 7.90 (d, 1H), 8.19 (bs, ~0.5H), 8.55 (bs, ~0.5H), 10.98 (bs, ~0.5H), 11.31 (bs, ~0.5H), 13.48 (s, 1H).

Example 302

(S)—N-(1-(3-(3-chloro-4-cyanophenyl)-1H-pyrazol-1-yl)propan-2-yl)-3-(furan-2-yl)-1H-pyrazole-5-carboxamide The title compound was prepared using the method of Example 34(d) starting from 5-(2-furyl)-2H-pyrazole-3-carboxylic acid (3.42 g, 19.18 mmol) and (S)-4-(1-(2-aminopropyl)-1H-pyrazol-3-yl)-2-chlorobenzonitrile (5 g, 19.18 mmol). The product was purified by flash chromatography and recrystallization from acetonitrile, respectively. Yield 16.97%. 1H-NMR (400 MHz; CDCl$_3$): δ 1.26 (d, 3H), 4.30 (dd, 1H), 4.42 (dd, 1H), 4.53-4.63 (m, 1H), 6.50 (dd, 1H), 6.62 (d, 1H), 6.67 (d, 1H), 6.94 (s, 1H), 7.48 (dd, 1H), 7.53 (d, 1H), 7.68 (d, 1H), 7.73-7.84 (m, 2H), 8.02 (s, 1H), 13.70 (broad s, 1H).

Example 303

(S)—N-(1-(3-(3-chloro-4-cyanophenyl)-4-cyano-1H-pyrazol-1-yl)propan-2-yl)-1-methyl-1H-imidazole-4-carboxamide a) 4-(4-bromo-1-(tetrahydro-2H-pyran-2-yl)-1H-pyrazol-5-yl)-2-chlorobenzonitrile 2-chloro-4-(1-(tetrahydro-2H-pyran-2-yl)-1H-pyrazol-5-yl)benzonitrile (10 g, 34.8 mmol) and acetonitrile (120 ml) were added into a flask and the temperature was adjusted to 0° C. with an ice bath. N-bromosuccinimide (6.80 g, 38.2 mmol) was added in small batches keeping the temperature below 5° C. The mixture was stirred at room temperature for 3 h. 10% NaHSO$_3$ (100 ml) was added and the mixture was stirred for 15 min. The reaction mixture was extracted with DCM. The combined organic phases were dried, filtered and evaporated. The product was purified by recrystallization from ethanol. Yield 82%. 1H-NMR (400 MHz; DMSO-d6): δ 1.51-1.59 (m, 2H), 1.62-1.76 (m, 1H), 1.90-2.00 (m, 2H), 2.06-2.18 (m, 1H), 3.62-3.70 (m, 1H), 3.91-3.98 (m, 1H), 5.49 (dd, 1H), 8.02 (dd, 1H), 8.09 (d, 1H), 8.12 (d, 1H), 8.38 (s, 1H).

b) 5-(3-chloro-4-cyanophenyl)-1-(tetrahydro-2H-pyran-2-yl)-1H-pyrazole-4-carbonitrile 4-(4-bromo-1-(tetrahydro-2H-pyran-2-yl)-1H-pyrazol-5-yl)-2-chlorobenzonitrile (3 g, 8.18 mmol), copper(I) cyanide (0.733 g, 8.18 mmol) and N,N-dimethyl formamide (15 ml) were loaded in a microwave reactor tube. The mixture was heated 190° C. for 5 h. The reaction was quenched by pouring the mixture into 200 ml of 12% ammonia solution and stirred for 30 min. The precipitate was filtered, washed with water and dried in vacuum at 40° C. The product was used in the next step without further purification. LC-MS: [M+1]=313.75.

c) 5-(3-chloro-4-cyanophenyl)-1H-pyrazole-4-carbonitrile

To a solution containing 5-(3-chloro-4-cyanophenyl)-1-(tetrahydro-2H-pyran-2-yl)-1H-pyrazole-4-carbonitrile (2.686 g, 8.59 mmol) dissolved in ethanol (25 ml), 10% HCl solution in ethanol (50 ml) was added and the resulting mixture was stirred overnight. The crude product was extracted with DCM/water. The pH of the aqueous phase was adjusted to 12 by adding 2 M NaOH. The aqueous phase was again extracted with DCM. The combined organic phases were dried with $Na_2SO_4$, filtered and evaporated. The product was purified by flash chromatography. 1H-NMR (400 MHz; DMSO-d6): δ 8.00-8.05 (m, 1H), 8.13-8.19 (m, 2H), 8.75 (s, 1H), 14.24 (s, 1H).

d) (S)-1-(2-aminopropyl)-3-(3-chloro-4-cyanophenyl)-1H-pyrazole-4-carbonitrile 5-(3-chloro-4-cyanophenyl)-1H-pyrazole-4-carbonitrile (0.9 g, 3.94 mmol) dissolved in dry THF (15 ml), (S)-tert-butyl 1-hydroxypropan-2-ylcarbamate (0.690 g, 3.94 mmol) and triphenyl phosphine (1.549 g, 5.90 mmol) dissolved in dry THF (15 ml) were loaded into a flask and cooled to 0° C. with an ice bath. Di-tert-butyl azodicarboxylate (1.360 g, 5.90 mmol) was added slowly and stirred for 10 min while keeping the temperature at 0° C. The temperature was allowed to rise to RT and the mixture was stirred overnight. Next day the mixture was evaporated and the intermediate deprotected by adding 10% HCl/EtOH solution (40 ml) and stirring overnight at RT. The mixture was again evaporated and the residue extracted with DCM/water. The pH of aqueous phase was adjusted to 12 by adding 2 M NaOH and extracted again with DCM. The organic phase was isolated with phase separator and evaporated. The product was used in the next step without further purification. 1H-NMR (400 MHz; DMSO-d6): δ 1.14 (d, 3H), 4.27-4.39 (m, 3H), 6.50 (s, 2H), 8.02 (dd, 1H), 8.15-8.19 (m, 2H), 8.79 (s, 1H).

e) (S)—N-(1-(3-(3-chloro-4-cyanophenyl)-4-cyano-1H-pyrazol-1-yl)propan-2-yl)-1-methyl-1H-imidazole-4-carboxamide The title compound was prepared using the method of Example 34(d) starting from 1-methyl-1H-imidazole-4-carboxylic acid (53.0 mg, 0.420 mmol) and (S)-1-(2-aminopropyl)-3-(3-chloro-4-cyanophenyl)-1H-pyrazole-4-carbonitrile (100 mg, 0.350 mmol). The product was purified by recrystallization from diethyl ether and diethyl ether/ethanol, respectively. Finally the product was also run through flash chromatography. Yield 34.1%. 1H-NMR (400 MHz; DMSO-d6): δ 1.15 (d, 3H), 3.67 (s, 3H), 4.36-4.51 (m, 3H), 7.56 (d, 1H), 7.69 (d, 1H), 7.98 (dd, 1H), 8.04-8.10 (m, 2H), 8.15 (dd, 1H), 8.69 (s, 1H).

Example 304

(S)—N-(1-(3-(3-chloro-4-cyano-5-fluorophenyl)-1H-pyrazol-1-yl)propan-2-yl)-2-(2-hydroxypropan-2-yl)oxazole-4-carboxamide The title compound was prepared using the method of Example 34(d) starting from 2-(2-hydroxypropan-2-yl)oxazole-4-carboxylic acid (184 mg, 1.076 mmol) and (S)-4-(1-(2-aminopropyl)-1H-pyrazol-3-yl)-2-chloro-6-fluorobenzonitrile (250 mg, 0.897 mmol). The product was purified by flash chromatography. Yield 79%. 1H-NMR (400 MHz; DMSO-d6): δ 1.13 (d, 3H), 1.52 (s, 6H), 4.31 (dd, 1H), 4.41 (dd, 1H), 4.44-4.52 (m, 1H), 5.64 (s, 1H), 7.02 (d, 1H), 7.84-7.88 (m, 2H), 7.97-7.98 (m, 1H), 8.10 (d, 1H), 8.48 (s, 1H).

Example 305

(S)—N-(1-(3-(3-chloro-4-cyanophenyl)-1H-pyrazol-1-yl)propan-2-yl)-2-(2-hydroxypropan-2-yl)oxazole-4-carboxamide The title compound was prepared using the method of Example 34(d) starting from 2-(2-hydroxypropan-2-yl)oxazole-4-carboxylic acid (197 mg, 1.151 mmol) and (S)-4-(1-(2-aminopropyl)-1H-pyrazol-3-yl)-2-chlorobenzonitrile (250 mg, 0.959 mmol). The product was purified by flash chromatography. Yield 57.7%. 1H-NMR (400 MHz; DMSO-d6): δ 1.12 (d, 3H), 1.53 (s, 6H), 4.31 (dd, 1H), 4.40 (dd, 1H), 4.43-4.52 (m, 1H), 5.66 (s, 1H), 6.97 (d, 1H), 7.84 (d, 1H), 7.94-8.00 (m, 2H), 8.08-8.10 (m, 1H), 8.17 (d, 1H), 8.48 (s, 1H).

Example 306

1-(5-((S)-1-(3-(3-chloro-4-cyanophenyl)-1H-pyrazol-1-yl)propan-2-yl-carbamoyl)-1H-pyrazol-3-yl) ethyl Pivalate Into a solution containing N—((S)-1-(3-(3-chloro-4-cyanophenyl)-1H-pyrazol-1-yl)-propan-2-yl)-3-(1-hydroxyethyl)-1H-pyrazole-5-carboxamide (53 mg, 0.133 mmol) dissolved in dry pyridine (2 ml), 2,2-dimethylpropionic acid anhydride (0.031 ml, 0.153 mmol) was added dropwise under nitrogen atmosphere. The resulting mixture was stirred at RT for 2 h after which DMAP (2.5 mg, 0.020 mmol) was added and the reaction mixture was left to react overnight. Next morning more 2,2-dimethylpropionic acid anhydride (0.027 ml, 0.132 mmol) was added and the mixture was again left to react overnight with stirring. The mixture was evaporated, extracted with DCM/water and the combined organic phases were evaporated. The product was purified by column chromatography to obtain 51% yield. 1H-NMR (400 MHz; CDCl3): δ 1.18 (d, 9H), 1.21 (d, 3H), 1.65 (d, 3H), 4.25-4.32 (m, 1H), 4.38-4.46 (m, 1H), 4.55-4.65 (m, 1H), 5.85-5.91 (m, 1H), 6.61 (t, 1H), 6.81-6.82 (m, 1H), 7.51 (t, 1H), 7.64-7.68 (m, 1H), 7.73-7.77 (m, 1H), 7.99 (d, 1H), 8.17 (dd, 1H).

Example 307

N—((S)-1-(3-(4-cyano-3,5-difluorophenyl)-1H-pyrazol-1-yl)propan-2-yl)-5-(1-hydroxyethyl)-1H-pyrazole-3-carboxamide (S)-5-acetyl-N-(1-(3-(4-cyano-3,5-difluorophenyl)-1H-pyrazol-1-yl)propan-2-yl)-1H-pyrazole-3-carboxamide (200 mg, 0.50 mmol) was dissolved in ethanol (10 ml) and sodiumborohydride (95 mg, 2.51 mmol) was added. The reaction mixture was refluxed for 2 h, cooled and saturated ammonium chloride (20 ml) was added. The mixture was extracted three times with ethyl acetate and the combined organic fractions were washed with water, dried and evaporated. The residue was purified twice with reversed phase flash chromatography to afford (6.7 mg, 3%) of the title compound. 1H-NMR (400 MHz; d6-DMSO): δ 1.13 (d, 3H), 1.37 (d, 3H), 4.24-4.40 (m, 2H), 4.39-4.53 (m, 1H), 4.72-4.84 (m, 1H), 6.47 (s, 1H), 6.98 (m, 1H), 7.71-7.80 (m, 2H), 7.79-7.88 (d, 1H), 8.15 (d, 1H).

Example 308

(S)—N-(1-(3-(4-cyano-3-(trifluoromethyl)phenyl)-1H-pyrazol-1-yl)propan-2-yl)-5-methylisoxazole-3-carboxamide The title compound was prepared using the method of Example 34(d) starting from (S)-4-(1-(2-aminopropyl)-1H-pyrazol-3-yl)-2-(trifluoromethyl)-benzonitrile (120 mg, 0.408 mmol) and 5-methylisoxazole-3-carboxylic acid (62 mg, 0.489 mmol). The product was purified with flash-chromatography. Yield 88 mg (53%). 1H-NMR (400 MHz; d6-DMSO): δ 1.16 (d, 3H), 2.43 (s, 3H), 4.32-4.34 (m, 2H), 4.40-4.50 (m, 1H), 6.43 (s, 1H), 7.02 (d, 1H), 7.84 (d, 1H), 8.18 (d, 1H), 8.23-8.25 (m, 1H), 8.29 (s, 1H), 8.71 (d, 1H).

Example 309

(S)—N-(1-(3-(3-chloro-4-cyanophenyl)-1H-pyrazol-1-yl)propan-2-yl)-3-(methoxymethyl)-1H-pyrazole-5-carboxamide a) Ethyl 5-methoxy-2,4-dioxopentanoate Under nitrogen atmosphere sodium (1.61 g, 70.0 mmol) was dissolved in small pieces in a flask containing dry ethanol (150 ml). Diethyl oxalate (8.15 ml, 60 mmol) and methoxyacetone (5.52 ml, 60.0 mmol) were added with a syringe. The resulting mixture was stirred at RT for 1 h. The flask was put in an ice bath and into it a mixture of sulphuric acid and ice water was added dropwise. The resulting precipitate was filtered and washed with DCM. The ethanol/DCM filtrate was evaporated. The residue was dissolved in DCM, extracted with brine and the DCM phase dried with Na2SO4, filtered and evaporated. The product was purified with flash chromatography. 1H-NMR (400 MHz; DMSO-d6): δ 1.28 (t, 3H), 3.34 (s, 3H), 4.19-4.23 (m, 2H), 4.27 (q, 2H).

b) Ethyl 3-(methoxymethyl)-1H-pyrazole-5-carboxylate

Ethyl 5-methoxy-2,4-dioxopentanoate (2.168 g, 11.52 mmol) was dissolved in ethanol (100 ml) and hydrazine dihydrochloride (4.84 g, 46.1 mmol) was added. The resulting mixture was refluxed for 2 h. 200 ml of water was added and the pH of the mixture was neutralized with NaHCO3. The mixture was extracted with ethyl acetate. The combined organic phases were washed with brine, dried with Na2SO4, filtered and evaporated. The product was used in the next step without further purification. 1H-NMR (400 MHz; DMSO-d6): δ 1.29 (t, 3H), 3.26 (s, 3H), 4.27 (q, 2H), 4.42 (s, 2H), 6.72 (s, 1H), 13.62 (s, 1H).

c) 3-(Methoxymethyl)-1H-pyrazole-5-carboxylic Acid

Ethyl 3-(methoxymethyl)-1H-pyrazole-5-carboxylate (2.44 g, 13.25 mmol) dissolved in methanol (40 ml) and cesium carbonate (8.63 g, 26.5 mmol) dissolved in water (40 ml) were loaded into a flask and stirred overnight at RT under nitrogen atmosphere. Ethyl acetate (100 ml) and water (100 ml) were added and the pH was adjusted to 3 with 10% citric acid. Phases were separated and the water phase was extracted with more ethyl acetate. The combined organic phases were dried with $Na_2SO_4$, filtered and evaporated. The product was purified with flash chromatography. Yield 36.5%. 1H-NMR (400 MHz; DMSO-d6): δ 3.25 (s, 3H), 4.40 (s, 2H), 6.67 (s, 1H), 13.16 (bs, 2H).

d) (S)—N-(1-(3-(3-chloro-4-cyanophenyl)-1H-pyrazol-1-yl)propan-2-yl)-3-(methoxymethyl)-1H-pyrazole-5-carboxamide The title compound was prepared using the method of Example 34(d) starting from 3-(methoxymethyl)-1H-pyrazole-5-carboxylic acid (0.119 g, 0.759 mmol) and (S)-4-(1-(2-aminopropyl)-1H-pyrazol-3-yl)-2-chlorobenzonitrile (0.165 g, 0.633 mmol). The product was purified with flash-chromatography. Yield 5.07%. 1H-NMR (400 MHz; $CDCl_3$): δ 1.22 (d, 3H), 3.42 (s, 3H), 4.27 (dd, 1H), 4.43 (dd, 1H), 4.54-4.62 (m, 3H), 6.62 (d, 1H), 6.69 (s, 1H), 7.49 (d, 1H), 7.67 (d, 1H), 7.75 (dd, 1H), 7.83 (m, 1H), 8.17 (d, 1H).

Example 310

(S)-3-acetyl-N-(1-(3-(4-cyano-3-(trifluoromethyl) phenyl)-1H-pyrazol-1-yl)propan-2-yl)-1H-pyrazole-5-carboxamide The title compound was prepared using the method of Example 34(d) starting from (S)-4-(1-(2-aminopropyl)-1H-pyrazol-3-yl)-2-(trifluoromethyl)-benzonitrile (110 mg, 0.374 mmol) and 3-acetyl-1H-pyrazole-5-carboxylic acid (58 mg, 0.374 mmol). The product was purified twice with flash-chromatography. Yield 8 mg (4%). 1H-NMR (400 MHz; d6-DMSO): δ 1.17 (d, 3H), 2.48 (m, 3H), 4.29-4.38 (m, 2H), 4.41-4.50 (m, 1H), 7.01 (d, 1H), 7.29 (s, 1H), 7.84 (d, 1H), 8.15-7.19 (m, 1H), 8.24 (s, 1H), 8.44-8.50 (m, 2H), 14.13 (m, 1H).

Example 311

(R)—N-(1-(3-(3-chloro-4-cyanophenyl)-1H-pyrazol-1-yl)propan-2-yl)-5-methylisoxazole-3-carboxamide The title compound was prepared using the method of Example 34(d) starting from (R)-4-(1-(2-aminopropyl)-1H-pyrazol-3-yl)-2-chlorobenzonitrile (240 mg, 0.921 mmol) and 5-methylisoxazole-3-carboxylic acid (140 mg, 1.105 mmol). The product was purified with flash-chromatography. Yield 46 mg (13%). 1H-NMR (400 MHz; d6-DMSO): δ 1.15 (d, 3H), 4.28-4.35 (m, 2H), 4.40-4.50 (m, 1H), 6.45 (d, 1H), 6.93 (d, 1H), 7.81 (d, 1H), 7.91-7.93 (m, 1H), 7.98 (d, 1H), 8.07 (d, 1H), 8.71 (d, 1H).

Example 312

N—((S)-1-(3-(3-chloro-4-cyanophenyl)-1H-pyrazol-1-yl)propan-2-yl)-5-(2-hydroxypropyl)isoxazole-3-carboxamide a) 2-(Pent-4-yn-2-yloxy)tetrahydro-2H-pyran (+/−)-4-Pentyn-2-ol (5.58 ml, 59.4 mmol) and 3,4-dihydro-2H-pyran (8.08 ml, 89 mmol) were dissolved in DCM (100 ml). 4-Toluenesulfonic acid pyridine salt (1.494 g, 5.94 mmol) was added and the resulting mixture was stirred for 4 h at RT with $CaCl_2$-tube. The mixture was concentrated. 50 ml of diethyl ether was added, extracted with brine and dried with $MgSO_4$, filtered and evaporated. The product was used in the subsequent steps without further purifications. LC-MS: [M+1]=169.23.

b) Ethyl 5-(2-((tetrahydro-2H-pyran-2-yl)oxy)propyl)isoxazole-3-carboxylate

Ethyl chlorooximidoacetate (1 g, 6.60 mmol) and 2-(pent-4-yn-2-yloxy)tetrahydro-2H-pyran (3.33 g, 19.80 mmol) were dissolved in diethyl ether (20 ml) and the mixture was stirred vigorously. Triethylamine (0.920 ml, 6.60 mmol) diluted with diethyl ether was added dropwise. The reaction mixture was extracted with water and the organic phase dried with $MgSO_4$, filtered and evaporated. The product was used in the next step without further purifications. LC-MS: [M+1]=284.32.

c) 5-(2-((Tetrahydro-2H-pyran-2-yl)oxy)propyl) isoxazole-3-carboxylic Acid

Ethyl 5-(2-(tetrahydro-2H-pyran-2-yloxy)propyl)isoxazole-3-carboxylate (1.87 g, 6.60 mmol) was dissolved in THF (20 ml). Lithium hydroxide monohydrate 1 M (6.60 ml) was added and the resulting mixture was stirred for overnight at RT. Next day more lithium hydroxide monohydrate 1 M (3.3 ml+13.20 ml) was added and the mixture was again stirred overnight. THF was evaporated, water was added and pH was adjusted to 4 with citric acid solution. The mixture was extracted four times with ethyl acetate and the combined organic phases dried and evaporated. LC-MS: [M+1]=256.27.

d) N—((S)-1-(3-(3-chloro-4-cyanophenyl)-1H-pyrazol-1-yl)propan-2-yl)-5-(2-((tetrahydro-2H-pyran-2-yl)oxy)propyl)isoxazole-3-carboxamide The title compound was prepared using the method of Example 34(d) starting from 5-(2-(tetrahydro-2H-pyran-2-yloxy)propyl)isoxazole-3-carboxylic acid (0.392 g, 1.534 mmol) and (S)-4-(1-(2-aminopropyl)-1H-pyrazol-3-yl)-2-chlorobenzonitrile (0.2 g, 0.767 mmol). The product was purified by reverse phase flash chromatography. LC-MS: [M+1]=498.97.

e) N—((S)-1-(3-(3-chloro-4-cyanophenyl)-1H-pyrazol-1-yl)propan-2-yl)-5-(2-hydroxypropyl)isoxazole-3-carboxamide N—((S)-1-(3-(3-chloro-4-cyanophenyl)-1H-pyrazol-1-yl)propan-2-yl)-5-(2-(tetrahydro-2H-pyran-2-yloxy)propyl) isoxazole-3-carboxamide (0.1 g, 0.201 mmol), ethanol (2 ml) and hydrogen chloride, 10% in EtOH (0.5 ml, 1.350 mmol) were mixed together and stirred over the weekend at RT. The mixture was evaporated, more ethanol was added and evaporated again. The product was pure enough without further purifications. Yield 51.7%. 1H-NMR (400 MHz; DMSO-d6): δ 1.09 (dd, 3H), 1.15 (d, 3H), 2.82-2.86 (m, 2H), 3.91-3.98 (m, 1H), 4.29-4.34 (m, 2H), 4.41-4.50 (m, 1H), 6.48-6.50 (m, 1H), 6.94 (d, 1H), 7.82 (d, 1H), 7.92 (dd, 1H), 7.97 (d, 1H), 8.08-8.10 (m, 1H), 8.73 (d, 1H).

Example 313

(S)-5-((1H-imidazol-1-yl)methyl)-N-(1-(3-(3-chloro-4-cyanophenyl)-1H-pyrazol-1-yl)propan-2-yl)isoxazole-3-carboxamide (S)-5-(bromomethyl)-N-(1-(3-(3-chloro-4-cyanophenyl)-1H-pyrazol-1-yl)-propan-2-yl)isoxazole-3-carboxamide (0.328 g, 0.731 mmol) of Example 197(a) was dissolved in acetonitrile (10 ml) and imidazole (0.31 g, 4.55 mmol) dissolved in acetonitrile (3 ml) was added. The mixture was stirred at RT overnight. The mixture was evaporated, the residue dissolved in ethyl acetate and extracted with water. The organic phase was dried, filtered and evaporated. The product was purified by recrystallization from ethyl acetate. Yield 13.81%. 1H-NMR (400 MHz; DMSO-d6): δ 1.15 (d, 3H), 4.28-4.32 (m, 2H), 4.40-4.48 (m, 1H), 5.50 (s, 2H), 6.63 (s, 1H), 6.93 (d, 1H), 6.93-6.94 (m, 1H), 7.22-7.23 (m, 1H), 7.75-7.77 (m, 1H), 7.80 (d, 1H), 7.90 (dd, 1H), 7.96 (d, 1H), 8.07 (d, 1H), 8.80 (d, 1H).

Example 314

(S)-3-acetyl-4-chloro-N-(1-(3-(3-chloro-4-cyanophenyl)-1H-pyrazol-1-yl)-propan-2-yl)-1H-pyrazole-5-carboxamide a) Methyl 3-acetyl-4-chloro-1H-pyrazole-5-carboxylate Into a flask containing methyl 3-acetyl-1H-pyrazole-5-carboxylate (4.0 g, 0.0238 mol) in acetic acid (60 ml), 5% sodium hypochlorite (284 ml, 0.190 mol) was added dropwise at 10-12° C. The mixture was stirred at RT over three nights adding more 5% sodium hypochlorite (177 ml, 0.119 mol in total) during the second and third day. Water was added to the reaction mixture and the product was extracted with ethyl acetate. Organic layer was dried with anhydrous Na$_2$SO$_4$ and concentrated. The crude product was recrystallized twice from n-hexane. Yield 23%. LC-MS: [M+1] =203.5.

b) 3-Acetyl-4-chloro-1H-pyrazole-5-carboxylic Acid

To a mixture containing methyl 3-acetyl-4-chloro-1H-pyrazole-5-carboxylate (1.3 g, 0.0064 mol) in THF (30 ml), lithium hydroxide (1.35 g, 0.032 mol) in water (15 ml) was added dropwise at 5-10° C. The reaction mixture was stirred at RT for 18 h. Cold water (15 ml) was added and the pH was adjusted to ~4 with 1 N potassium bisulfate. The product was extracted with ethyl acetate, the organic layer dried with anhydrous Na$_2$SO$_4$ and concentrated. The crude product was purified by recrystallization from diethyl ether/n-hexane. Yield 56%. 1H-NMR (400 MHz; DMSO-d6): δ 2.57 (s, 3H), 13.91 (bs, 1H), 14.69 (s, 1H).

c) (S)-3-acetyl-4-chloro-N-(1-(3-(3-chloro-4-cyanophenyl)-1H-pyrazol-1-yl)propan-2-yl)-1H-pyrazole-5-carboxamide The title compound was prepared using the method of Example 34(d) starting from 3-acetyl-4-chloro-1H-pyrazole-5-carboxylic acid (0.527 g, 2.79 mmol) and (S)-4-(1-(2-aminopropyl)-1H-pyrazol-3-yl)-2-chlorobenzonitrile (0.56 g, 2.148 mmol). The product was purified by reverse phase flash chromatography. Yield 30.8%. 1H-NMR (400 MHz; DMSO-d6): δ 1.16 (d, 3H), 2.54 (s, 3H), 4.31 (dd, 1H), 4.37 (dd, 1H), 4.42-4.51 (m, 1H), 6.95 (d, 1H), 7.84 (d, 1H), 7.94 (dd, 1H), 7.98 (d, 1H), 8.06 (d, 1H), 8.27 (bs, 1H), 14.45 (s, 1H).

Example 315

(S)—N-(1-(3-(3-chloro-4-cyanophenyl)-1H-pyrazol-1-yl)propan-2-yl)-5-(2-oxopropyl)isoxazole-3-carboxamide a) Ethyl 5-(2-hydroxypropyl)isoxazole-3-carboxylate Ethyl chlorooximidoacetate (4 g, 26.4 mmol) and 4-pentyn-2-ol (10.00 ml, 107 mmol) were dissolved in diethyl ether (30 ml). A solution of triethylamine (3.68 ml, 26.4 mmol) in diethylether (20 ml) was added dropwise to the reaction mixture. After 1 h of stirring at RT the reaction mixture was washed with brine and water, dried with MgSO$_4$ and evaporated to dryness. The residue was purified with flash chromatography using a gradient of methanol in methylene chloride affording 2.51 g (48%) of the title compound. 1H-NMR (400 MHz; d6-DMSO): δ, 1.11 (d, 3H), 1.31 (t, 3H), 2.82-2.94 (m, 2H), 3.93-4.03 (m, 1H) 4.35 (q, 2H), 4.89 (d, 1H), 6.67 (s, 1H).

b) Ethyl 5-(2-oxopropyl)isoxazole-3-carboxylate

Ethyl 5-(2-hydroxypropyl)isoxazole-3-carboxylate (1.5 g, 7.53 mmol) was dissolved in acetone (40 ml) and cooled to 0° C. Jones' reagent (5.90 ml, 7.91 mmol) was added dropwise and the reaction mixture was stirred at 0 C for 30 min. Then the reaction mixture was allowed to warm up to RT and stirred 18 h. Mixture of methanol (30 ml) and water (30 ml) was added and then the volatiles were evaporated. The residue was extracted with DCM, dried with Na2SO4 and evaporated to dryness to afford 1.38 g (93%) of the title compound. 1H-NMR (400 MHz; d6-DMSO): δ, 1.32 (t, 3H), 2.22 (s, 3H), 4.29-4.44 (m, 2H), 4.22 (s, 2H), 6.67 (s, 1H).

c) 5-(2-Oxopropyl)isoxazole-3-carboxylic Acid

Ethyl 5-(2-oxopropyl)isoxazole-3-carboxylate (0.65 g, 3.30 mmol) was dissolved in ethanol (10 ml). A solution of cesium carbonate (1.611 g, 4.94 mmol) in water (5 ml) was added to the reaction mixture and it was stirred for 7 h at RT. The reaction mixture was concentrated, diluted with water and pH was adjusted to 2 with citric acid. The aqueous phase was extracted with ethyl acetate, dried with Na$_2$SO$_4$ and evaporated to dryness afforded 0.203 g (36%) of the title compound. 1H-NMR (400 MHz; d6-DMSO): δ, 2.21 (s, 3H), 4.20 (s, 2H), 6.67 (s, 1H).

d) (S)—N-(1-(3-(3-chloro-4-cyanophenyl)-1H-pyrazol-1-yl)propan-2-yl)-5-(2-oxopropyl)isoxazole-3-carboxamide The title compound was prepared using the method of Example 34(d) starting from (S)-4-(1-(2-aminopropyl)-1H-pyrazol-3-yl)-2-chlorobenzonitrile (200 mg, 0.767 mmol) and 5-(2-oxopropyl)isoxazole-3-carboxylic acid (169 mg, 0.997 mmol). The product was purified with flash chromatography using a gradient of methanol in DCM affording 101 mg (32%) of the title compound. 1H-NMR (400 MHz; CDCl$_3$): δ 1.23 (d, 3H), 1.54 (s, 3H), 3.96 (s, 2H), 4.20-4.49 (m, 2H), 4.53-4.64 (m, 1H), 6.63 (d, 1H), 6.65-6.69 (m, 1H), 7.48 (d, 1H), 7.69 (d, 1H), 7.79-7.90 (m, 2H), 8.04 (d, 1H).

Example 316

(S)—N-(1-(3-(3-chloro-4-cyanophenyl)-1H-pyrazol-1-yl)propan-2-yl)-4,5,6,7-tetrahydro-2H-indazole-3-carboxamide The title compound was prepared using the method of Example 34(d) starting from (S)-4-(1-(2-aminopropyl)-1H-pyrazol-3-yl)-2-chlorobenzonitrile (200 mg, 0.767 mmol) and 4,5,6,7-tetrahydro-2H-indazole-3-carboxylic acid (166 mg, 0.997 mmol). The product was triturated with ethanol. Yield 111 mg (35%). 1H-NMR (400 MHz; d6-DMSO): δ 1.09 (d, 3H), 1.58-1.72 (m, 4H), 2.54-2.61 (m, 4H), 4.24-4.46 (m, 3H), 6.94 (d, 1H), 7.82 (d, 1H), 7.99 (s, 2H), 8.05-8.08 (m, 2H), 12.68 (s, 1H).

Example 317

(S)—N-(1-(3-(3-chloro-4-cyanophenyl)-1H-pyrazol-1-yl)propan-2-yl)-6,7-dihydro-4H-pyrazolo[5,1-c][1,4]oxazine-2-carboxamide The title compound was prepared using the method of Example 34(d) starting from (S)-4-(1-(2-aminopropyl)-1H-pyrazol-3-yl)-2-chlorobenzonitrile (200 mg, 0.767 mmol) and 6,7-dihydro-4H-pyrazolo[5,1-c][1,4]oxazine-2-carboxylic acid (166 mg, 0.997 mmol). The product was triturated with acetonitrile. Yield 95 mg (46%). 1H-NMR (400 MHz; d6-DMSO): δ 1.09 (d, 3H), 4.09 (t, 2H), 4.18 (t, 2H), 4.26-4.39 (m, 2H), 4.42-4.49 (m, 1H), 4.79 (s, 2H), 6.38 (s, 1H), 6.95 (d, 1H), 7.82 (d, 1H), 7.97-7.99 (m, 2H), 8.09 (s, 1H), 8.26 (d, 1H).

Example 318

4-Chloro-N—((S)-1-(3-(3-chloro-4-cyanophenyl)-1H-pyrazol-1-yl)propan-2-yl)-3-(1-hydroxyethyl)-1H-pyrazole-5-carboxamide Into a mixture containing sodium borohydride (0.044 g, 1.159 mmol) in ethanol (10 ml), (S)-3-acetyl-4-chloro-N-(1-(3-(3-chloro-4-cyanophenyl)-1H-pyrazol-1-yl)propan-2-yl)-1H-pyrazole-5-carboxamide (0.5 g, 1.159 mmol) of Example 314 was slowly added and the temperature was raised to 50° C. for 10 min. The reaction mixture was stirred at RT for 19 h. Saturated ammonium chloride (30 ml) was added and the mixture was extracted with ethyl acetate, combined organic layers dried with $Na_2SO_4$, filtered and evaporated. The product was purified with flash chromatography. Yield 45.6%. 1H-NMR (400 MHz; $CDCl_3$): δ 1.24 (d, 3H), 1.58 (dd, 3H), 2.88 (bs, 1H), 4.25-4.32 (m, 1H), 4.41-4.49 (m, 1H), 4.56-4.68 (m, 1H), 5.04-5.12 (m, 1H), 6.62 (d, 1H), 7.48-7.51 (m, 1H), 7.61-7.67 (m, 2H), 7.70-7.75 (m, 1H), 8.01-8.07 (m, 1H), 11.27 (bs, 1H).

Example 319

(S)—N-(1-(3-(3-chloro-4-cyanophenyl)-1H-pyrazol-1-yl)propan-2-yl)-4,5,6,7-tetrahydrobenzo[d]isoxazole-3-carboxamide The title compound was prepared using the method of Example 34(d) starting from (S)-4-(1-(2-aminopropyl)-1H-pyrazol-3-yl)-2-chlorobenzonitrile (90 mg, 0.345 mmol) and 4,5,6,7-tetrahydrobenzo[d]isoxazole-3-carboxylic acid (75 mg, 0.449 mmol). The product was purified with flash chromatography. Yield 111 mg (78%). 1H-NMR (400 MHz; $CDCl_3$): δ 1.24 (d, 3H), 1.69-1.83 (m, 4H), 2.77-2.83 (m, 4H), 4.25-4.43 (m, 2H), 4.52-4.61 (m, 1H), 6.63 (d, 1H), 7.37 (d, 1H), 7.49 (d, 1H), 7.70 (d, 1H), 7.86 (d, 1H), 7.94 (d, 1H).

Example 320

(S)—N-(1-(3-(3-chloro-4-cyanophenyl)-1H-pyrazol-1-yl)propan-2-yl)-6,7-dihydro-4H-pyrano[3,4-d]isoxazole-3-carboxamide The title compound was prepared using the method of Example 34(d) starting from 6,7-dihydro-4H-pyrano[3,4-d]isoxazole-3-carboxylic acid (0.101 g, 0.598 mmol) and (S)-4-(1-(2-aminopropyl)-1H-pyrazol-3-yl)-2-chlorobenzonitrile (0.12 g, 0.460 mmol). The product was purified by reverse phase flash chromatography. Yield 9.50%. 1H-NMR (400 MHz; $CDCl_3$): δ 1.25 (d, 3H), 2.93 (t, 2H), 3.90 (t, 2H), 4.26 (dd, 1H), 4.42 (dd, 1H), 4.50-4.62 (m, 1H), 4.86-4.90 (m, 2H), 6.64 (d, 1H), 7.50 (d, 1H), 7.64 (d, 1H), 7.71 (d, 1H), 7.87 (dd, 1H), 7.95 (d, 1H).

Example 321

(S)—N-(1-(3-(3-chloro-4-cyanophenyl)-1H-pyrazol-1-yl)propan-2-yl)-1-(6-methylpyridin-2-yl)-1H-imidazole-4-carboxamide The title compound was prepared using the method of Example 34(d) starting from (S)-4-(1-(2-aminopropyl)-1H-pyrazol-3-yl)-2-chlorobenzonitrile (220 mg, 0.844 mmol) and 1-(6-methylpyridin-2-yl)-1H-imidazole-4-carboxylic acid (223 mg, 1.097 mmol). The product was triturated with acetonitrile. Yield 153 mg (40%). 1H-NMR (400 MHz; $CDCl_3$): δ 1.26 (d, 3H), 1.45 (s, 3H), 2.59 (s, 1H), 4.28-4.45 (m, 2H), 4.55-4.64 (m, 1H), 6.62 (d, 1H), 7.16 (d, 1H), 7.19 (d, 1H), 7.52 (d, 1H), 7.67 (d, 1H), 7.75 (t, 1H), 7.80 (m, 1H), 7.89 (d, 1H), 8.12 (d, 1H), 8.21 (d, 1H).

Example 322

(S)—N-(1-(3-(3-chloro-4-cyanophenyl)-1H-pyrazol-1-yl)propan-2-yl)imidazo[1,2-a]pyrimidine-2-carboxamide The title compound was prepared using the method of Example 34(d) starting from (S)-4-(1-(2-aminopropyl)-1H-pyrazol-3-yl)-2-chlorobenzonitrile (200 mg, 0.767 mmol) and imidazo[1,2-a]pyrimidine-2-carboxylic acid (163 mg, 0.997 mmol). The product was triturated with acetonitrile. Yield 168 mg (54%). 1H-NMR (400 MHz; d6-DMSO): δ 1.18 (d, 3H), 4.32-4.45 (m, 2H), 4.49-4.56 (m, 1H), 6.92 (d, 1H), 7.13-7.16 (m, 1H), 7.84 (d, 1H), 7.95 (d, 1H), 8.03-8.06 (m, 2H), 8.25 (s, 1H), 8.67-8.69 (m, 1H), 8.75 (d, 1H), 8.97-8.99 (m, 1H).

Example 323

(S)—N-(1-(3-(3-chloro-4-cyanophenyl)-1H-pyrazol-1-yl)propan-2-yl)-3-fluoroimidazo[1,2-a]pyridine-2-carboxamide The title compound was prepared using the method of Example 34(d) starting from (S)-4-(1-(2-aminopropyl)-1H-pyrazol-3-yl)-2-chlorobenzonitrile (200 mg, 0.767 mmol) and 3-fluoroimidazo[1,2-a]pyridine-2-carboxylic acid (180 mg, 0.997 mmol). The product was triturated with acetonitrile. Yield 217 mg (67%). 1H-NMR (400 MHz; d6-DMSO): δ 1.15 (d, 3H), 4.31-4.44 (m, 2H), 4.47-4.55 (m, 1H), 6.95 (d, 1H), 7.06 (t, 1H), 7.37 (m, 1H), 7.55-7.58 (m, 1H), 7.85 (d, 1H), 7.97 (d, 1H), 8.08 (t, 1H), 8.31 (1H, d), 8.55 (d, 1H).

Example 324

(S)—N-(1-(3-(3-chloro-4-cyano-5-fluorophenyl)-1H-pyrazol-1-yl)propan-2-yl)imidazo[1,2-a]pyrimidine-2-carboxamide The title compound was prepared using the method of Example 34(d) starting from Imidazo[1,2-a]pyrimidine-2-carboxylic acid (0.076 g, 0.466 mmol) and (S)-4-(1-(2-aminopropyl)-1H-pyrazol-3-yl)-2-chloro-6-fluorobenzonitrile (0.1 g, 0.359 mmol). The product was purified by recrystallization from acetonitrile. Yield 46.0%. 1H-NMR (400 MHz; CDCl₃): δ 1.32 (d, 3H), 4.33 (dd, 1H), 4.44 (dd, 1H), 4.57-4.67 (m, 1H), 6.57 (dd, 1H), 6.97 (dd, 1H), 7.50 (d, 1H), 7.59 (dd, 1H), 7.71 (dd, 1H), 7.80 (d, 1H), 8.08 (s, 1H), 8.47 (dd, 1H), 8.66 (dd, 1H).

Example 325

(S)—N-(1-(3-(3-chloro-4-cyano-5-fluorophenyl)-1H-pyrazol-1-yl)propan-2-yl)-3-fluoroimidazo[1,2-a]pyridine-2-carboxamide The title compound was prepared using the method of Example 34(d) starting from (S)-4-(1-(2-aminopropyl)-1H-pyrazol-3-yl)-2-chloro-6-fluorobenzonitrile (0.1 g, 0.359 mmol) and 3-fluoroimidazo[1,2-a]pyridine-2-carboxylic acid (0.084 g, 0.466 mmol). The product was purified by recrystallization from acetonitrile. Yield 37.9%. 1H-NMR (400 MHz; CDCl₃): δ 1.25 (d, 3H), 4.30 (dd, 1H), 4.46 (dd, 1H), 4.59-3.69 (m, 1H), 6.62 (d, 1H), 6.91-6.96 (m, 1H), 7.24-7.29 (m, 1H), 7.52-7.56 (m, 2H), 7.76-7.80 (m, 2H), 7.94-7.97 (m, 1H), 8.08 (d, 1H).

Example 326

(S)—N-(1-(3-(3-chloro-4-cyano-5-fluorophenyl)-1H-pyrazol-1-yl)propan-2-yl)-4,5,6,7-tetrahydro-2H-indazole-3-carboxamide The title compound was prepared using the method of Example 34(d) starting from 4,5,6,7-tetrahydro-2H-indazole-3-carboxylic acid (0.078 g, 0.466 mmol) and (S)-4-(1-(2-aminopropyl)-1H-pyrazol-3-yl)-2-chloro-6-fluorobenzonitrile (0.1 g, 0.359 mmol). The product was purified by flash chromatography. Yield 65.9%. 1H-NMR (400 MHz; DMSO-d6): δ 1.11 (d, 3H), 1.55-1.71 (m, 4H), 2.53-2.60 (m, 4H), 4.27 (dd, 1H), 4.35 (dd, 1H), 4.38-3.46 (m, 1H), 7.00 (d, 1H), 7.83-7.87 (m, 2H), 7.90-7.97 (m, 2H), 12.66 (s, 1H).

Example 327

(S)—N-(1-(3-(3-chloro-4-cyano-5-fluorophenyl)-1H-pyrazol-1-yl)propan-2-yl)-6,7-dihydro-5H-pyrazolo[5,1-b][1,3]oxazine-2-carboxamide The title compound was prepared using the method of Example 34(d) starting from 6,7-dihydro-5H-pyrazolo[5,1-b][1,3]oxazine-2-carboxylic acid (0.078 g, 0.466 mmol) and (S)-4-(1-(2-aminopropyl)-1H-pyrazol-3-yl)-2-chloro-6-fluorobenzonitrile (0.1 g, 0.359 mmol). The product was purified by recrystallization from acetonitrile and by flash-chromatography, respectively. Yield 53.3%. 1H-NMR (400 MHz; CDCl₃): δ 1.19 (d, 3H), 2.26-2.34 (m, 2H), 4.18-4.34 (m, 5H), 4.41 (dd, 1H), 4.52-4.62 (m, 1H), 6.01 (s, 1H), 6.62 (d, 1H), 7.50 (d, 1H), 7.66 (d, 1H), 7.70-7.75 (m, 2H).

Example 328

(S)—N-(1-(3-(3-chloro-4-cyano-5-fluorophenyl)-1H-pyrazol-1-yl)propan-2-yl)-2,4,6,7-tetrahydropyrano[4,3-c]pyrazole-3-carboxamide The title compound was prepared using the method of Example 34(d) starting from 2,4,6,7-tetrahydropyrano[4,3-c]pyrazole-3-carboxylic acid (0.078 g, 0.466 mmol) and (S)-4-(1-(2-aminopropyl)-1H-pyrazol-3-yl)-2-chloro-6-fluorobenzonitrile (0.1 g, 0.359 mmol). The product was purified by recrystallization from acetonitrile. Yield 32.5%. 1H-NMR (400 MHz; CDCl₃): δ 1.22 (d, 3H), 2.79 (t, 2H), 3.89-3.94 (m, 2H), 4.27 (dd, 1H), 4.39 (dd, 1H), 4.48-4.58 (m, 1H), 4.84-4.94 (m, 2H), 6.61 (d, 1H), 7.52 (d, 1H), 7.65 (dd, 1H), 7.69 (d, 1H), 7.80-7.82 (m, 1H).

Example 329

(S)—N-(1-(3-(3-chloro-4-cyanophenyl)-1H-pyrazol-1-yl)propan-2-yl)-4-hydroxypicolinamide The title compound was prepared using the method of Example 34(d) starting from 5-Hydroxy-2-pyridinecarboxylic acid (0.139 g, 0.997 mmol) and (S)-4-(1-(2-aminopropyl)-1H-pyrazol-3-yl)-2-chlorobenzonitrile (0.2 g, 0.767 mmol). The product was purified by recrystallization from ethanol/water. Yield 22.19%. 1H-NMR (400 MHz; DMSO-d6): δ 1.10 (d, 3H), 4.29-4.49 (m, 3H), 6.95 (d, 1H), 7.23 (dd, 1H), 7.83 (d, 1H), 7.85 (d, 1H), 7.98-8.00 (m, 2H), 8.11-8.13 (m, 1H), 8.17 (d, 1H), 8.82 (d, 1H).

Example 330

(S)—N-(1-(3-(3-chloro-4-cyano-5-fluorophenyl)-1H-pyrazol-1-yl)propan-2-yl)-1-(6-methylpyridin-2-yl)-1H-imidazole-4-carboxamide The title compound was prepared using the method of Example 34(d) starting from 1-(6-methylpyridin-2-yl)-1H-imidazole-4-carboxylic acid (0.190 g, 0.933 mmol) and (S)-4-(1-(2-aminopropyl)-1H-pyrazol-3-yl)-2-chloro-6-fluorobenzonitrile (0.2 g, 0.718 mmol). The product was purified by recrystallization from acetonitrile. Yield 55.3%. 1H-NMR (400 MHz; DMSO-d6): δ 1.13 (d, 3H), 2.53 (s, 3H), 4.31-4.52 (m, 3H), 7.01 (d, 1H), 7.29 (d, 1H), 7.72 (d, 1H), 7.87-7.96 (m, 3H), 8.02-8.04 (m, 1H), 8.35 (d, 1H), 8.40 (d, 1H), 8.58 (d, 1H).

Example 331

(S)—N-(1-(3-(3-chloro-4-cyanophenyl)-1H-pyrazol-1-yl)propan-2-yl)-7-methyl-5,6,7,8-tetrahydroimidazo[1,2-a]pyrazine-2-carboxamide a) (S)-tert-butyl 2-(1-(3-(3-chloro-4-cyanophenyl)-1H-pyrazol-1-yl)propan-2-ylcarbamoyl)-5,6-dihydroimidazo[1,2-a]pyrazine-7(8H)-carboxylate The title compound was prepared using the method of Example 34(d) starting from 7-(tert-butoxycarbonyl)-5,6,7,8-tetrahydroimidazo[1,2-a]pyrazine-2-carboxylic acid (0.044 g, 0.165 mmol) and (S)-4-(1-(2-aminopropyl)-1H-pyrazol-3-yl)-2-chlorobenzonitrile (0.033 g, 0.127 mmol). The product was purified by flash chromatography. LC-MS: [M+1]=510.988.

b) (S)—N-(1-(3-(3-chloro-4-cyanophenyl)-1H-pyrazol-1-yl)propan-2-yl)-5,6,7,8-tetrahydroimidazo[1,2-a]pyrazine-2-carboxamide, HCl (S)-tert-butyl 2-(1-(3-(3-chloro-4-cyanophenyl)-1H-pyrazol-1-yl)propan-2-ylcarbamoyl)-5,6-dihydroimidazo[1,2-a]pyrazine-7(8H)-carboxylate (0.029 g, 0.057 mmol) was dissolved in ethanol (2 ml) and hydrogen chloride (gas in EtOH) ~10% (0.173 ml) was added. The resulting mixture was stirred at RT for 6 days, adding more hydrogen chloride (gas in EtOH) ~10% (0.173+0.173+2 ml) during the last few days of the reaction. The solvent was evaporated, ethanol (5 ml) was added and the solvent was evaporated again. This was repeated one more time. The product was purified by recrystallization from acetonitrile. LC-MS: [M+1]=447.332.

c) (S)—N-(1-(3-(3-chloro-4-cyanophenyl)-1H-pyrazol-1-yl)propan-2-yl)-7-methyl-5,6,7,8-tetrahydroimidazo[1,2-a]pyrazine-2-carboxamide (S)—N-(1-(3-(3-chloro-4-cyanophenyl)-1H-pyrazol-1-yl)propan-2-yl)-5,6,7,8-tetrahydroimidazo[1,2-a]pyrazine-2-carboxamide (23 mg, 0.056 mmol) was dissolved in methanol (2 ml). Triethylamine (0.078 ml, 0.561 mmol), formaldehyde, 37 w-% solution in water (0.067 ml, 0.561 mmol) and sodium cyanoborohydride (35.3 mg, 0.561 mmol) were added in the solution. The resulting mixture was stirred at RT overnight. The reaction mixture was diluted with DCM, extracted with NaHCO$_3$ solution, combined organic phases were dried with Na$_2$SO$_4$, filtered and evaporated. The product was purified with LC/MS-trigger. Yield 33.6%. 1H-NMR (400 MHz; CDCl$_3$): δ 1.26 (d, 3H), 2.55 (s, 3H), 2.90 (t, 2H), 3.70 (d, 2H), 4.08 (t, 2H), 4.32 (dd, 1H), 4.40 (dd, 1H), 4.54-4.65 (m, 1H), 6.61 (d, 1H), 7.48 (s, 1H), 7.50 (d, 1H), 7.67 (d, 1H), 7.71 (d, 1H), 7.81 (dd, 1H), 8.02 (d, 1H), 8.06 (s, 1H).

Example 332

(S)—N-(1-(3-(3-chloro-4-cyano-5-fluorophenyl)-1H-pyrazol-1-yl)propan-2-yl)-6,7-dihydro-4H-pyrano[3,4-d]isoxazole-3-carboxamide The title compound was prepared using the method of Example 34(d) starting from 6,7-dihydro-4H-pyrano[3,4-d]isoxazole-3-carboxylic acid (0.174 g, 1.026 mmol) and (S)-4-(1-(2-aminopropyl)-1H-pyrazol-3-yl)-2-chloro-6-fluorobenzonitrile (0.22 g, 0.789 mmol). The product was purified by LC/MS-trigger. Yield 13.26%. 1H-NMR (400 MHz; CDCl$_3$): δ 1.23 (d, 3H), 2.93 (t, 2H), 3.91 (t, 2H), 4.27 (dd, 1H), 4.42 (dd, 1H), 4.50-4.60 (m, 1H), 4.89 (d, 2H), 6.63 (d, 1H), 7.37 (d, 1H), 7.50 (d, 1H), 7.59 (dd, 1H), 7.76-7.77 (m, 1H).

Example 333

(S)—N-(1-(3-(3-chloro-4-cyanophenyl)-1H-pyrazol-1-yl)propan-2-yl)-3-(1H-imidazol-4-yl)-1,2,4-oxadiazole-5-carboxamide a) 1H-imidazole-4-carbonitrile A mixture of 4-formylimidazole (5 g, 52.0 mmol), pyridine (30 ml) and hydroxylamine hydrochloride (4.07 g, 58.5 mmol) was stirred for 2 h at RT. In the next step the mixture was heated to 100° C. and acetic anhydride (9.29 ml, 99 mmol) was added dropwise. Finally the temperature of the reaction mixture was slowly lowered to RT with stirring. The pH of the mixture was adjusted to 7.9 with 30% NaOH. The water phase was extracted with ethyl acetate and the combined organic phases were washed with brine and evaporated. Toluene was added twice and evaporated. The remains were recrystallized from toluene, filtered and the crystals were washed with diisopropyl ether. 1H-NMR (400 MHz; DMSO-d6): δ 7.91 (s, 1H), 8.10 (s, 1H), 13.01 (s, 1H).

b) 1-trityl-1H-imidazole-4-carbonitrile

Into a mixture containing triphenylmethyl chloride (1.647 g, 5.91 mmol), 1H-imidazole-4-carbonitrile (0.5 g, 5.37 mmol) and dry acetonitrile (17 ml), triethylamine (1.295 ml, 9.29 mmol) was added dropwise and the resulting mixture stirred overnight at RT. Hexane (1.6 ml) and water (17 ml) were poured into the mixture and the stirring was continued for another 30 min. The precipitate was filtered and dried with vacuum. 1H-NMR (400 MHz; CDCl$_3$): δ 7.06-7.12 (m, 6H), 7.35-7.40 (m, 10H), 7.49 (d, 1H).

c) (Z)—N'-hydroxy-1-trityl-1H-imidazole-4-carboximidamide

A mixture containing 1-trityl-1H-imidazole-4-carbonitrile (1.6 g, 4.77 mmol), ethanol (20 ml), triethylamine (1.995 ml, 14.31 mmol) and hydroxylamine hydrochloride (0.663 g, 9.54 mmol) was heated to 70° C. and stirred 4 h. The mixture was cooled with an ice bath, some water (10 ml) was added and the precipitated product filtered and washed well with water. The product was dried with vacuum at 40° C. 1H-NMR (400 MHz; DMSO-d6): δ 5.43-5.50 (m, 2H), 7.01 (d, 1H), 7.04-7.13 (m, 6H), 7.36-7.46 (m, 10H), 9.10 (d, 1H).

d) Ethyl 3-(1-trityl-1H-imidazol-4-yl)-1,2,4-oxadiazole-5-carboxylate

A mixture containing (Z)—N'-hydroxy-1-trityl-1H-imidazole-4-carboximidamide (1.08 g, 2.93 mmol) and pyridine (20 ml) was cooled to 0° C. Ethyl oxalyl chloride (0.426 ml, 0.520 g) was added dropwise and the resulting mixture was stirred for 10 min and then let warm to RT. The reaction mixture was then heated to 70° C. and stirred for 2.5 h. The content of the flask was then poured into 50 ml of ice-water-mixture and extracted with tert-butylmethyl ether. The organic phase was dried and evaporated. The product was purified by flash chromatography. 1H-NMR (400 MHz; DMSO-d6): δ 1.33 (t, 3H), 4.41 (q, 2H), 7.14-7.19 (m, 6H), 7.39-7.48 (m, 9H), 7.53 (d, 1H), 7.72 (d, 1H).

e) 3-(1-trityl-1H-imidazol-4-yl)-1,2,4-oxadiazole-5-carboxylic Acid

Ethyl 3-(1-trityl-1H-imidazol-4-yl)-1,2,4-oxadiazole-5-carboxylate (1.1 g, 2.442 mmol) was dissolved in ethanol (60 ml) and the resulting solution was cooled to 0° C. Cesium carbonate (6.36 g, 19.53 mmol) was dissolved in water (25 ml) and added into the solution. The reaction mixture was refluxed for 1 h. Ethanol was evaporated, diluted with water, filtered and washed with water. The solid was dried in vacuum at 40° C. The product was purified by recrystallization from THF and ethyl acetate, respectively. LC-MS: [M+1]=423.435.

f) (S)—N-(1-(3-(3-chloro-4-cyanophenyl)-1H-pyrazol-1-yl)propan-2-yl)-3-(1-trityl-1H-imidazol-4-yl)-1,2,4-oxadiazole-5-carboxamide The title compound was prepared using the method of Example 34(d) starting from 3-(1-trityl-1H-imidazol-4-yl)-1,2,4-oxadiazole-5-carboxylic acid (0.211 g, 0.499 mmol) and (S)-4-(1-(2-aminopropyl)-1H-pyrazol-3-yl)-2-chlorobenzonitrile (0.1 g, 0.384 mmol). The product was purified by flash chromatography. LC-MS: [M+1]=666.142.

g) (S)—N-(1-(3-(3-chloro-4-cyanophenyl)-1H-pyrazol-1-yl)propan-2-yl)-3-(1H-imidazol-4-yl)-1,2,4-oxadiazole-5-carboxamide Into a flask containing (S)—N-(1-(3-(3-chloro-4-cyanophenyl)-1H-pyrazol-1-yl)propan-2-yl)-3-(1-trityl-1H-imidazol-4-yl)-1,2,4-oxadiazole-5-carboxamide (0.148 g, 0.223 mmol) a solution of THF (9 ml), formic acid (1 ml, 0.223 mmol) and water (0.1 ml) was added. The resulting mixture was stirred at RT. During the next 2 days 7 ml of formic acid was added. The solvents were evaporated, acetonitrile was added and evaporated, repeating this procedure twice. The product was purified with LC/MS-trigger. Yield 42.4%. 1H-NMR (400 MHz; MeOD): δ 1.33 (d, 3H), 4.36 (dd, 1H), 4.45 (dd, 1H), 4.55-4.66 (m, 1H), 6.77 (s, 1H), 7.68-7.75 (m, 2H), 7.78-7.92 (m, 3H), 8.00 (s, 1H), 8.14 (s, 1H).

Example 334

(S)—N-(1-(3-(3-chloro-4-cyanophenyl)-1H-pyrazol-1-yl)propan-2-yl)-3-ethoxy-4-methyl-1H-pyrazole-5-carboxamide a) ethyl 5-ethoxy-4-methyl-1H-pyrazole-3-carboxylate A solution of diethyl oxalpropionate (9.15 ml, 49.5 mmol) and hydrazine dihydrochloride (6.23 g, 59.3 mmol) in ethanol (50 ml) was refluxed for 1 h. The mixture was then cooled and water (150 ml) was added. The solution was neutralised with solid $NaHCO_3$ and extracted four times with EtOAc. The organic phase was washed with brine and water, dried with $Na_2SO_4$ and evaporated to dryness affording 7.81 g (80%) of the title compound. LC-MS: [M+1]=199.22.

b) 5-ethoxy-4-methyl-1H-pyrazole-3-carboxylic Acid

2 M solution of sodium hydroxide (98 ml, 197 mmol) was added to a solution of 5-ethoxy-4-methyl-1H-pyrazole-3-carboxylate (7.8 g, 39.4 mmol) in ethanol (70 ml) and THF (30 ml). The reaction mixture was refluxed for 3 h and then the solvents were evaporated and water (200 ml) was added to the residue. It was acidified to pH 1 with conc. HCl and extracted three times with EtOAc. The precipitate formed in the extraction was filtered and washed with EtOAc and the filtrate evaporated to dryness affording 4.2 g (62%) of the title compound. LC-MS: [M+1]=171.17.

c) (S)—N-(1-(3-(3-chloro-4-cyanophenyl)-1H-pyrazol-1-yl)propan-2-yl)-3-ethoxy-4-methyl-1H-pyrazole-5-carboxamide The title compound was prepared using the method of Example 34(d) starting from 3-ethoxy-4-methyl-1H-pyrazole-5-carboxylic acid (0.117 g, 0.690 mmol) and (S)-4-(1-(2-aminopropyl)-1H-pyrazol-3-yl)-2-chlorobenzonitrile (0.15 g, 0.575 mmol). The product was purified with reverse phase flash-chromatography. Yield 4.21%. 1H-NMR (400 MHz; DMSO-d6): δ 1.16 (d, 3H), 1.28 (t, 3H), 1.94 (s, 3H), 4.10-4.17 (m, 2H), 4.28-4.33 (m, 2H), 4.37-4.46 (m, 1H), 6.96 (d, 1H), 7.72 (d, 1H), 7.85 (d, 1H), 7.92 (dd, 1H), 7.98 (d, 1H), 8.07 (d, 1H), 12.08 (s, 1H).

Example 335

(S)—N-(1-(3-(3-chloro-4-cyanophenyl)-1H-pyrazol-1-yl)propan-2-yl)-5-(2-hydroxyethyl)isoxazole-3-carboxamide a) Ethyl 5-(2-((tetrahydro-2H-pyran-2-yl)oxy)ethyl)isoxazole-3-carboxylate Ethyl chlorooximidoacetate (1 g, 6.60 mmol) and 2-(but-3-ynyloxy)tetrahydro-2H-pyran (3.05 g, 19.80 mmol) were dissolved in diethyl ether (20 ml). Triethylamine (0.668 g, 6.60 mmol) was diluted with diethyl ether (10 ml) and added dropwise into previous mixture. After addition the reaction mixture was extracted with water and the organic layer was dried with $Na_2SO_4$, filtered and evaporated. LC-MS: [M+1]=172.17.

b) 5-(2-((tetrahydro-2H-pyran-2-yl)oxy)ethyl)isoxazole-3-carboxylic Acid

Ethyl 5-(2-(tetrahydro-2H-pyran-2-yloxy)ethyl)isoxazole-3-carboxylate (1.77 g, 6.57 mmol) was dissolved in THF (20 ml). 1M lithium hydroxide monohydrate (6.57 ml) was added and the resulting mixture stirred at RT for 2 h. During the same day more of 1M lithium hydroxide monohydrate (19.71 ml in total) was added and the reaction mixture was stirred overnight. THF was evaporated, water was added and the pH was adjusted to 4 with citric acid solution. The mixture was extracted four times with ethyl acetate. The combined organic layers were dried and evaporated. LC-MS: [M+1]=242.24.

c) N—((S)-1-(3-(3-chloro-4-cyanophenyl)-1H-pyrazol-1-yl)propan-2-yl)-5-(2-((tetrahydro-2H-pyran-2-yl)oxy)ethyl)isoxazole-3-carboxamide The title compound was prepared using the method of Example 34(d) starting from 5-(2-(tetrahydro-2H-pyran-2-yloxy)ethyl)isoxazole-3-carboxylic acid (0.222 g, 0.921 mmol) and (S)-4-(1-(2-aminopropyl)-1H-pyrazol-3-yl)-2-chlorobenzonitrile (0.2 g, 0.767 mmol). The product was purified with reverse phase flash-chromatography. 1H-NMR (400 MHz; DMSO-d6): δ 1.16 (d, 3H), 1.34-1.51 (m, 4H), 1.52-1.69 (m, 2H), 3.06 (t, 2H), 3.37-3.45 (m, 1H), 3.61-3.71 (m, 2H), 3.85-3.93 (m, 1H), 4.28-4.34 (m, 2H), 4.41-4.50 (m, 1H), 4.57-4.61 (m, 1H), 6.51 (d, 1H), 6.93 (d, 1H), 7.81 (d, 1H), 7.92 (dd, 1H), 7.97 (dd, 1H), 8.08 (dd, 1H), 8.74 (d, 1H).

d) (S)—N-(1-(3-(3-chloro-4-cyanophenyl)-1H-pyrazol-1-yl)propan-2-yl)-5-(2-hydroxyethyl)isoxazole-3-carboxamide Into a solution containing N—((S)-1-(3-(3-chloro-4-cyanophenyl)-1H-pyrazol-1-yl)propan-2-yl)-5-(2-(tetrahydro-2H-pyran-2-yloxy)ethyl)isoxazole-3-carboxamide (0.04 g, 0.083 mmol) and ethanol (4 ml), hydrogen chloride, 10% in EtOH (0.5 ml, 1.350 mmol) was added. The resulting mixture was stirred for 2 h at RT. The mixture was evaporated, 2 ml of diethyl ether was added and stirred. The precipitated product was filtered and washed with cold heptane. The product was pure enough without further purifications. Yield 85%. 1H-NMR (400 MHz; DMSO-d6): δ 1.16 (d, 3H), 2.92 (t, 2H), 3.69 (t, 2H), 4.29-4.34 (m, 2H), 4.41-4.50 (m, 1H), 6.51-6.53 (m, 1H), 6.94 (d, 1H), 7.82 (d, 1H), 7.92 (dd, 1H), 7.97 (dd, 1H), 8.09 (d, 1H), 8.73 (d, 1H).

Example 336

(S)—N-(1-(3-(3-chloro-4-cyanophenyl)-1H-pyrazol-1-yl)propan-2-yl)-6,7-dihydro-5H-pyrazolo[5,1-b][1,3]oxazine-2-carboxamide The title compound was prepared using the method of Example 34(d) starting from (S)-4-(1-(2-aminopropyl)-1H-pyrazol-3-yl)-2-chlorobenzonitrile (200 mg, 0.767 mmol) and 6,7-dihydro-5H-pyrazolo[5,1-b][1,3]oxazine-2-carboxylic acid (168 mg, 0.997 mmol). The product was purified with flash-chromatography. Yield 251 mg (80%). 1H-NMR (400 MHz; CDCl3): δ 1.21 (d, 3H), 2.27-2.32 (m, 2H), 4.14-4.20 (m, 2H), 4.26-4.43 (m, 4H), 4.51-4.60 (m, 1H), 6.01 (s, 1H), 6.62 (d, 1H), 7.49 (d, 1H), 7.51 (d, 1H), 7.66 (d, 1H), 7.81-7.84 (m, 1H), 8.03 (d, 1H).

Example 337

(S)—N-(1-(3-(3-chloro-4-cyano-5-fluorophenyl)-1H-pyrazol-1-yl)propan-2-yl)-5-(2-hydroxypropan-2-yl)isoxazole-3-carboxamide The title compound was prepared using the method of Example 34(d) starting from (S)-4-(1-(2-aminopropyl)-1H-pyrazol-3-yl)-2-chloro-6-fluorobenzonitrile (120 mg, 0.431 mmol) and 5-(2-hydroxypropan-2-yl)isoxazole-3-carboxylic acid (96 mg, 0.560 mmol). The product was triturated with ethanol. Yield 67 mg (36%). 1H-NMR (400 MHz; d6-DMSO): δ 1.17 (d, 3H), 1.47 (s, 6H), 4.31-4.33 (m, 2H), 4.40-4.49 (m, 1H), 6.49 (s, 1H), 7.01 (d, 1H), 7.84 (d, 1H), 7.85-7.88 (m, 1H), 7.99 (s, 1H), 8.74 (d, 1H).

Example 338

(S)—N-(1-(3-(3-chloro-4-cyanophenyl)-1H-pyrazol-1-yl)propan-2-yl)-2,4,6,7-tetrahydropyrano[4,3-c]pyrazole-3-carboxamide a) (Z)-ethyl 2-hydroxy-2-(4-oxo-2H-pyran-3(4H,5H,6H)-ylidene)acetate Lithium bis(trimethylsilyl)amide 1M solution (30.0 ml, 30.0 mmol) and diethyl ether (40 ml) were added into a flask under nitrogen atmosphere and cooled to −72° C. with dry ice/acetone-bath. Tetrahydro-4H-pyran-4-one (3 g, 30.0 mmol) was diluted with diethyl ether (10 ml) and added slowly to the previously cooled mixture. The resulting mixture was stirred at −70° C. for one hour. Diethyl oxalate (4.07 ml, 30.0 mmol) diluted with diethyl ether (10 ml) was added and the reaction mixture was allowed to warm to RT and stirred overnight. The formed yellow precipitate was filtered, washed with cold diethyl ether and dried with vacuum at 40° C. 1H-NMR (400 MHz; d6-DMSO): δ 1.16 (d, 3H), 1.92 (t, 2H), 3.68 (t, 2H), 3.98 (q, 2H), 4.19 (s, 2H).

b) Ethyl 2,4,6,7-tetrahydropyrano[4,3-c]pyrazole-3-carboxylate (Z)-ethyl 2-hydroxy-2-(4-oxo-2H-pyran-3(4H,5H,6H)-ylidene)acetate (2.5 g, 12.49 mmol) was dissolved in methanol (10 ml). Hydrazine hydrochloride (2.57 g, 37.5 mmol) was added and the resulting mixture was refluxed for one hour. The mixture was allowed to warm to RT and the solvent was evaporated. The residue was dissolved in DCM and extracted twice with water. The organic layer was dried with Na2SO4, filtered and evaporated. The product was purified with flash chromatography. 1H-NMR (400 MHz; d6-DMSO): δ 1.27 (d, 3H), 2.70 (t, 2H), 3.81 (t, 2H), 4.24 (q, 2H), 4.69 (s, 2H), 13.40 (bs, 1H).

c) 2,4,6,7-tetrahydropyrano[4,3-c]pyrazole-3-carboxylic Acid

Ethyl 2,4,6,7-tetrahydropyrano[4,3-c]pyrazole-3-carboxylate (0.97 g, 4.94 mmol) was dissolved in methanol (20 ml) and cooled to 0° C. with an ice bath. Sodium hydroxide 2 M solution (4.94 ml, 9.89 mmol) was added and the mixture was allowed to cool to RT with stirring. The mixture was stirred for 26 h during which additional 7 ml of sodium hydroxide 2 M solution was added. The solvent was evaporated and the pH adjusted to 2 with 1 M HCl. The formed precipitate was filtered and washed with water. The white solid was dried with vacuum at 40° C. 1H-NMR (400 MHz; d6-DMSO): δ 2.69 (t, 2H), 3.81 (t, 2H), 4.68 (s, 2H), 13.09 (bs, 1H).

d) (S)—N-(1-(3-(3-chloro-4-cyanophenyl)-1H-pyrazol-1-yl)propan-2-yl)-2,4,6,7-tetrahydropyrano[4,3-c]pyrazole-3-carboxamide The title compound was prepared using the method of Example 34(d) starting from 2,4,6,7-tetrahydropyrano[4,3-c]pyrazole-3-carboxylic acid (0.168 g, 0.997 mmol) and (S)-4-(1-(2-aminopropyl)-1H-pyrazol-3-yl)-2-chlorobenzonitrile (0.2 g, 0.767 mmol). The product was triturated twice with acetonitrile. Yield 65.7%. 1H-NMR (400 MHz; d6-DMSO): δ 1.11 (d, 3H), 2.70 (t, 2H), 3.72-3.80 (m, 2H), 4.23-4.46 (m, 3H), 4.56-4.68 (m, 2H), 6.94 (d, 1H), 7.82 (d, 1H), 7.97-8.00 (m, 2H), 8.07-8.09 (m, 1H), 8.21 (d, 1H). 12.98 (s, 1H).

Example 339

(S)-3-(1-benzyl-1H-imidazol-4-yl)-N-(1-(3-(3-chloro-4-cyanophenyl)-1H-pyrazol-1-yl)propan-2-yl)-1H-pyrazole-5-carboxamide a) Lithium (Z)-4-(1-benzyl-1H-imidazol-4-yl)-1-ethoxy-1,4-dioxobut-2-en-2-olate 5-acetyl-1-benzylimidazole (5 g, 24.97 mmol) was dissolved in dry diethyl ether (100 ml). The mixture was cooled to −78° C. with dry ice/acetone-bath. Lithium bis(trimethylsilyl)amide (27.5 ml, 27.5 mmol) was added dropwise and the mixture was stirred at −78° C. for 1 h. Diethyl oxalate (4.41 ml, 32.5 mmol) was added and the reaction mixture was allowed to warm to RT. The following mixture was stirred overnight at RT. The precipitated product was filtered, washed with diethyl ether and dried. 1H-NMR (400 MHz; d6-DMSO): δ, 1.22 (t, 3H), 4.11 (q, 2H), 5.62 (s, 2H), 6.18 (s, 1H), 7.16-7.31 (m, 5H), 7.49 (d, 1H), 7.89 (d, 1H).

b) Ethyl 3-(1-benzyl-1H-imidazol-4-yl)-1H-pyrazole-5-carboxylate

Into a suspension containing lithium (Z)-4-(1-benzyl-1H-imidazol-4-yl)-1-ethoxy-1,4-dioxobut-2-en-2-olate (3.0 g, 9.80 mmol) and ethanol (20 ml), hydrazine dihydrochloride (1.337 g, 12.74 mmol) was added and the resulting mixture was refluxed for 3 h with stirring. The mixture was allowed to cool to RT and the mixture was evaporated. The residue was suspended in ethanol, stirred and filtered. The precipitate was washed with cold ethanol and dried with vacuum at 40° C. 1H-NMR (400 MHz; d6-DMSO): δ, 1.31 (t, 3H), 4.33 (q, 2H), 5.82 (s, 2H), 7.18-7.37 (m, 6H), 8.19 (s, 1H), 9.42 (s, 1H), 14.53 (bs, 1H).

c) 3-(1-benzyl-1H-imidazol-4-yl)-1H-pyrazole-5-carboxylic Acid

Ethyl 3-(1-benzyl-1H-imidazol-4-yl)-1H-pyrazole-5-carboxylate (0.5 g, 1.687 mmol) was dissolved in methanol (10 ml). The mixture was cooled to 0° C. and sodium hydroxide 2 M solution (1.687 ml) was added. The reaction mixture was allowed to warm to RT with stirring. Stirring was two days during which more sodium hydroxide 2 M solution (3.4 ml in total) was added. The last hour was stirred at 40° C. Methanol was evaporated and water was added. The pH was adjusted to 1 with 1M HCl, which precipitated the product out of the solution. The mixture was filtered, precipitate washed with water and dried with vacuum at 40° C. 1H-NMR (400 MHz; d6-DMSO): δ, 5.82 (s, 2H), 7.17-7.38 (m, 6H), 8.17 (d, 1H), 9.39 (s, 1H), 14.35 (bs, 1H).

d) (S)-3-(1-benzyl-1H-imidazol-4-yl)-N-(1-(3-(3-chloro-4-cyanophenyl)-1H-pyrazol-1-yl)propan-2-yl)-1H-pyrazole-5-carboxamide The title compound was prepared using the method of Example 34(d) starting from 3-(1-benzyl-1H-imidazol-4-yl)-1H-pyrazole-5-carboxylic acid (0.268 g, 0.997 mmol) and (S)-4-(1-(2-aminopropyl)-1H-pyrazol-3-yl)-2-chlorobenzonitrile (0.2 g, 0.767 mmol). The product was purified with flash chromatography. Yield 44.9%. 1H-NMR (400 MHz; CDCl$_3$): δ 1.23 (d, 3H), 4.27 (dd, 1H), 4.41 (dd, 1H), 4.53-4.63 (m, 1H), 5.26 (s, 2H), 6.61 (d, 1H), 6.76 (s, 1H), 7.00-7.05 (m, 2H), 7.28-7.36 (m, 5H), 7.49 (d, 1H), 7.58-7.63 (m, 2H), 7.78 (dd, 1H), 8.03 (s, 1H), 11.75 (bs, 1H).

Example 340

(S)—N-(1-(3-(3-chloro-4-cyanophenyl)-1H-pyrazol-1-yl)propan-2-yl)-1-(2,2-difluoroethyl)-2-methyl-1H-imidazole-4-carboxamide (S)—N-(1-(3-(3-chloro-4-cyanophenyl)-1H-pyrazol-1-yl)propan-2-yl)-2-methyl-1H-imidazole-4-carboxamide (100 mg, 0.271 mmol) was suspended in acetonitrile (5 ml). 1,1-Difluoro-2-iodoethane (0.053 ml, 116 mg) and cesium carbonate (124 mg, 0.380 mmol) were added and the resulting mixture was stirred overnight at RT. Next day 2 ml of THF and 50 µl of 1,1-difluoro-2-iodoethane was added and the stirring was continued for three more nights. Another 0.2 ml of 1,1-difluoro-2-iodoethane was added and the reaction mixture was stirred overnight. The reaction mixture was evaporated. 3 ml of N,N-dimethyl formamide was added and the mixture filtered. Filtrate was purified with LC/MS-trigger. Yield 27.4%. $^1$H-NMR (400 MHz; CDCl$_3$): δ 1.22 (d, 3H), 2.44 (s, 3H), 4.19-4.33 (m, 3H), 4.39 (dd, 1H), 4.51-4.62 (m, 1H), 5.82-6.13 (m, 1H), 6.61 (d, 1H), 7.49 (d, 1H), 7.52 (s, 1H), 7.64-7.71 (m, 2H), 7.85 (dd, 1H), 8.00 (d, 1H).

Example 341

(S)—N-(1-(3-(3-chloro-4-cyanophenyl)-1H-pyrazol-1-yl)propan-2-yl)-1-(2-fluoroethyl)-2-methyl-1H-imidazole-4-carboxamide (S)—N-(1-(3-(3-chloro-4-cyanophenyl)-1H-pyrazol-1-yl)propan-2-yl)-2-methyl-1H-imidazole-4-carboxamide (100 mg, 0.271 mmol) suspended in acetonitrile (5 ml). Into the mixture, cesium carbonate (124 mg, 0.380 mmol) and 1-Iodo-2-fluoroethane (0.049 ml, 0.596 mmol) were added and the resulting mixture was stirred overnight at RT. Water (2 ml) was added and the mixture was evaporated. The product was purified with LC/MS-trigger. $^1$H-NMR (400 MHz; CDCl$_3$): δ 1.23 (d, 3H), 2.42 (s, 3H), 4.12-4.23 (m, 2H), 4.30 (dd, 1H), 4.39 (dd, 1H), 4.51-4.61 (m, 1H), 4.58-4.73 (m, 2H), 6.61 (d, 1H), 7.49 (d, 1H), 7.51 (d, 1H), 7.62 (d, 1H), 7.77 (dd, 1H), 7.85 (dd, 1H), 8.00 (dd, 1H).

Example 342

(S)—N-(1-(3-(3-chloro-4-cyano-2-methylphenyl)-1H-pyrazol-1-yl)propan-2-yl)-2-(2-hydroxypropan-2-yl)thiazole-4-carboxamide (S)-ethyl 4-(1-(3-(3-chloro-4-cyano-2-methylphenyl)-1H-pyrazol-1-yl)propan-2-ylcarbamoyl)thiazole-2-carboxylate (0.28 g, 0.611 mmol) was dissolved in dry THF under nitrogen atmosphere. The solution was cooled to −78° C. with acetone-dry ice-bath. Methylmagnesium bromide, 3 M solution in Et2O (0.408 ml, 1.223 mmol), was added dropwise. The reaction mixture was stirred in RT overnight. Next day the mixture was again cooled to −78° C. and 1.019 ml of methylmagnesium bromide, 3 M solution in Et$_2$O, was added. The mixture was stirred in RT overnight. Saturated ammonium chloride was added and the mixture was diluted with water and DCM. The organic phase was washed with brine and water. The product was purified by Flash-chromatography. Yield 19.08%. 1H-NMR (400 MHz; CDCl$_3$): δ 1.28 (d, 3H), 1.58 (s, 6H), 2.54 (s, 3H), 2.63 (s, 1H), 4.34 (dd, 1H), 4.44 (dd, 1H), 4.60 (m, 1H), 6.43 (d, 1H), 7.52 (m, 3H), 7.83 (d, 1H), 8.00 (s, 1H).

ABBREVIATIONS

THF=Tetrahydrofuran
TFA=Trifluoroacetic acid
TEAB=Tetraethyl ammonium bromide
DCM=Dichloromethane
DMF=Dimethylformamide
EDCI=1-(3-Dimethylaminopropyl)-3-ethylcarbodiimide hydrochloride
HOBt=1-hydroxybenzotriazole
DIAD=Diisopropyl azodicarboxylate
DIPEA=N, N-diisopropylethylamine
DMSO=Dimethyl sulfoxide
DMAP=4-Dimethylaminopyridine
TLC=Thin layer chromatography
IPA=Isopropyl alcohol
BOC=tert-Butyloxycarbonyl
RT=Room temperature
DCC=Dicyclohexylcarbodiimide

The invention claimed is:
1. A compound, which is
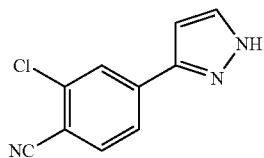 [SMILES: N#Cc1ccc(-c2cc[nH]n2)cc1Cl]
2-chloro-4-(1H-pyrazol-5-yl)benzonitrile or
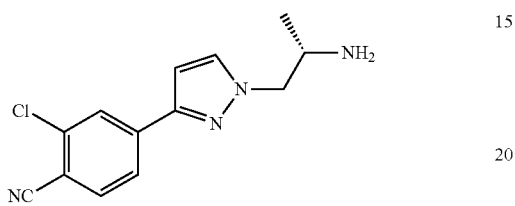
(S)-4-(1-(2-aminopropyl)-1H-pyrazol-3-yl)-2-chlorobenzonitrile.
2. The compound according to claim 1, which is 2-chloro-4-(1H-pyrazol-5-yl)benzonitrile.
3. The compound according to claim 1, which is (S)-4-(1-(2-aminopropyl)-1H-pyrazol-3-yl)-2-chlorobenzonitrile.
* * * * *